US009636336B2

(12) United States Patent
Amari et al.

(10) Patent No.: US 9,636,336 B2
(45) Date of Patent: *May 2, 2017

(54) AMINOESTER DERIVATIVES

(71) Applicant: CHIESI FARMACEUTICI S.p.A., Parma (IT)

(72) Inventors: Gabriele Amari, Parma (IT); Elisabetta Armani, Parma (IT); Wesley Blackaby, Saffron Walden (GB); Herve Van De Poeol, Saffron Walden (GB); Charles Baker-Glenn, Saffron Walden (GB); Naimisha Trivedi, Saffron Walden (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/168,425

(22) Filed: May 31, 2016

(65) Prior Publication Data

US 2016/0346268 A1 Dec. 1, 2016

(30) Foreign Application Priority Data

Jun. 1, 2015 (EP) .................................... 15170041

(51) Int. Cl.
| | |
|---|---|
| *A61K 31/4545* | (2006.01) |
| *C07D 409/14* | (2006.01) |
| *C07D 453/02* | (2006.01) |
| *A61K 31/444* | (2006.01) |
| *A61K 31/4439* | (2006.01) |
| *A61K 31/4436* | (2006.01) |
| *A61K 31/496* | (2006.01) |
| *C07D 451/02* | (2006.01) |
| *A61K 31/46* | (2006.01) |

(52) U.S. Cl.
CPC ........ *A61K 31/4545* (2013.01); *A61K 31/444* (2013.01); *A61K 31/4436* (2013.01); *A61K 31/4439* (2013.01); *A61K 31/46* (2013.01); *A61K 31/496* (2013.01); *C07D 409/14* (2013.01); *C07D 451/02* (2013.01); *C07D 453/02* (2013.01)

(58) Field of Classification Search
None
See application file for complete search history.

(56) References Cited

U.S. PATENT DOCUMENTS

| 2013/0079313 | A1* | 3/2013 | Armani | C07D 213/89 514/171 |
|---|---|---|---|---|
| 2013/0324501 | A1* | 12/2013 | Armani | C07D 401/12 514/158 |
| 2014/0155391 | A1* | 6/2014 | Armani | C07D 295/155 514/227.8 |
| 2015/0158858 | A1* | 6/2015 | Amari | C07D 409/14 514/210.2 |
| 2015/0352091 | A1* | 12/2015 | Armani | C07D 409/14 514/305 |

FOREIGN PATENT DOCUMENTS

| EP | 2 022 783 | 2/2009 |
|---|---|---|
| WO | 2012168226 | * 12/2012 |
| WO | 2013057013 | * 4/2013 |
| WO | 2013182451 | * 12/2013 |
| WO | 2014/086849 | 6/2014 |

OTHER PUBLICATIONS

Extended European Search Report issued in Application No. 15170041.6 dated Oct. 22, 2015.
Asthma: U.S. FDS approves new indication for SPIRIVA Respimat, (2016).
X. Soler et al., Curr Allergy Asthma Rep (2014) 14:484.
Clinical Trails.gov, NCT00073177 (2012).
Clinical Trails.gov, NCT00076076 (2012).
Clinical Trails.gov, NCT00163527 (2012).

* cited by examiner

*Primary Examiner* — Karl J Puttlitz
(74) *Attorney, Agent, or Firm* — Oblon, McClelland, Maier & Neustadt, L.L.P.

(57) ABSTRACT

Compounds of formula (I) defined herein are both phosphodiesterase 4 (PDE4) enzyme inhibitors and muscarinic M3 receptor antagonists and are useful for treating diseases of the respiratory tract.

17 Claims, No Drawings

AMINOESTER DERIVATIVES

CROSS REFERENCES TO RELATED APPLICATIONS

This application claims priority to European Patent Application No. 15170041.6 filed on Jun. 1, 2015, which is incorporated herein by reference in its entirety.

BACKGROUND OF THE INVENTION

Field of the Invention

The present invention relates to novel compounds which are both phosphodiesterase 4 (PDE4) enzyme inhibitors and muscarinic M3 receptor antagonists. More particularly, the present invention relates to methods of preparing such a compound, compositions which contain such a compound, and therapeutic uses of such a compound.

Discussion of the Background

Chronic obstructive pulmonary disease (COPD) is a respiratory disorder characterized by progressive, not fully reversible, airflow limitation associated with an abnormal pulmonary inflammatory response to noxious particles or gases.

For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into 2 general classes: bronchodilators, (β2-adrenoceptor agonists, antimuscarinic agents and methylxanthines) and antiinflammatory agents (glucocorticosteroids and selective phosphodiesterase-4 (PDE4) inhibitors).

Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors.

Currently, there are five known muscarinic receptor subtypes (M1 to M5); human airway smooth muscle contains M1, M2, and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells.

These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation.

Whereas dry mouth is the most common systemic anticholinergic side effect associated with the use of antimuscarinic antagonists as a result of the systemic blockade of M1 and M3 receptors, the most potentially serious systemic effect is tachycardia, which results from the blockade of cardiac M2 receptors.

Inhaled anticholinergic antimuscarinic drugs approved for the treatment of COPD include ipratropium bromide (Atrovent), oxitropium bromide (Oxivent d tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for once-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure.

Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 mL) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

WO 2014/086852, WO 2014/086849, WO 2014/086855, WO 2015/082616, and WO 2015/082619 disclose compounds which combine both bronchodilating and antiinflammatory properties in one molecule. The present invention addresses the same need by providing the compounds of the invention.

However, there remains a need for compounds which are both phosphodiesterase 4 (PDE4) enzyme inhibitors and muscarinic M3 receptor antagonists.

SUMMARY OF THE INVENTION

Accordingly, it is one object of the present invention to provide novel compounds which are both phosphodiesterase 4 (PDE4) enzyme inhibitors and muscarinic M3 receptor antagonists.

It is another object of the present invention to provide novel methods of preparing such a compound.

It is another object of the present invention to provide novel compositions which contain such a compound.

It is another object of the present invention to provide novel therapeutic uses of such a compound.

These and other objects, which will become apparent during the following detailed description, have been achieved by the inventors' discovery that compounds of formula (I):

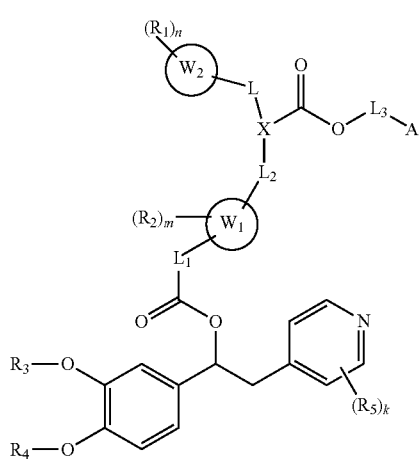

wherein
each $R_1$ is hydrogen or is independently selected from the group consisting of: halogen, $(C_1-C_4)$ alkyl, $(C_1-C_4)$ alkoxy, $(C_1-C_4)$ haloalkyl, hydroxy, $-SO_2NR_6R_7$, $-CN$, $-NR_8SO_2R_9$, $-NR_6R_7$, $-CONR_6R_7$, and $-NR_8COR_9$, wherein said $(C_1-C_4)$ alkyl is optionally substituted by one or more groups selected from $(C_3-C_7)$ cycloalkyl, hydroxy and $-NR_6R_7$ and wherein said $(C_1-C_4)$ alkoxy is optionally substituted by one or more halogens or $(C_3-C_7)$ cycloalkyl groups wherein, $R_6$ is hydrogen or $(C_1-C_6)$ alkyl;
$R_7$ is hydrogen or $(C_1-C_6)$ alkyl;
$R_8$ is hydrogen or $(C_1-C_6)$ alkyl;
$R_9$ is hydrogen or $(C_1-C_6)$ alkyl;
n is an integer ranging from 1 to 3;
each $R_2$ is hydrogen or is selected from the group consisting of halogen, $(C_1-C_4)$ alkyl, $(C_1-C_4)$ alkoxy, $(C_1-C_4)$ haloalkyl, hydroxy, $-CN$, and $-NR_{12}SO_2R_{13}$ and wherein said $(C_1-C_4)$ alkyl and said $(C_1-C_4)$ alkoxy are optionally substituted by one or more group $(C_3-C_7)$ cycloalkyl groups wherein
$R_{10}$ is hydrogen or $(C_1-C_6)$ alkyl;
$R_{11}$ is hydrogen or $(C_1-C_6)$ alkyl;
$R_{12}$ is hydrogen or $(C_1-C_6)$ alkyl;
$R_{13}$ is hydrogen or $(C_1-C_6)$ alkyl;
m is an integer ranging from 1 to 3;
$R_3$ and $R_4$ are the same or different and are independently selected from the group consisting of:
H;
$(C_3-C_7)$ cycloalkylcarbonyl;
$(C_1-C_6)$ alkyl optionally substituted by one or more substituents selected from $(C_1-C_4)$ alkoxy, $(C_3-C_7)$ cycloalkyl or $(C_5-C_7)$ cycloalkenyl;
$(C_1-C_6)$ haloalkyl;
$(C_3-C_7)$ cycloalkyl;
$(C_5-C_7)$ cycloalkenyl;
$(C_2-C_6)$ alkenyl; and
$(C_2-C_6)$ alkynyl;
each $R_5$, whenever present, is independently selected from the group consisting of: CN, $NO_2$, $CF_3$ and halogen atoms;
k is 0 or an integer ranging from 1 to 3;
$W_1$ is selected from a divalent heteroarylene group;
$W_2$ is selected from an aryl and a heteroaryl or $(C_3-C_7)$ cycloalkyl;
L is a bond or a $-(CH_2)-$ group;
$L_1$ is selected from the group consisting of:
a bond,
$-(CH_2)_p-$,
$[3]-(CH_2)_p-O-[4]$,
$[3]-(CH_2)_p-NR_{10}-(CH_2)_t[4]$,
$[3]-(CH_2)_p-OC(O)-[4]$,
$[3]-(CH_2)_p-NR_{10}C(O)-[4]$,
$[3]-(CH_2)_p-NR_{10}S(O_2)-[4]$, and
$[3]-(CH_2)_p-S(O_2)-N(R_{10})-[4]$,
wherein [3] and [4] represent, respectively the point of attachment of group $L_1$ to the carbonyl group and to the ring $W_1$ and wherein
$R_{10}$ is as described above,
p is an integer ranging from 1 to 4 and
t is an integer ranging from 1 to 4;
$L_2$ is a group selected from $-(CH_2)_q-$ wherein q is an integer ranging from 1 to 4;
$L_3$ is a $(C_1-C_4)$ alkylene;
X is a group selected from $X_1$, $X_2$ and $X_3$:

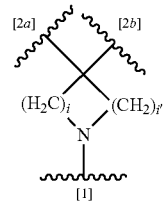

-continued $X_2$

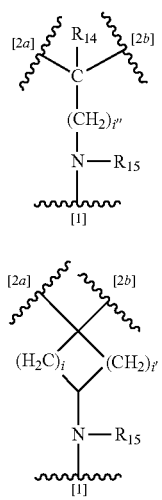

$X_3$

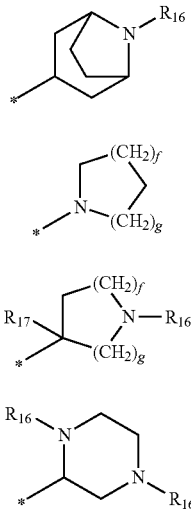

wherein [1], represents in each occurrence the point of attachment of the group X to L2, [2a] represents at each occurrence the point of attachment to L-$W_2$ and [2b] represents at each occurrence the point of attachment to the carbonyl group —$CO_2$A;

and wherein $R_{14}$ is selected from the group consisting of H, OH, ($C_1$-$C_4$) alkyl, ($C_1$-$C_4$) alkoxy, ($C_1$-$C_4$) haloalkyl, and —CN, wherein said ($C_1$-$C_4$) alkyl is optionally substituted by one or more groups selected from ($C_3$-$C_7$) cycloalkyl and hydroxyl, or, in alternative, when $R_{14}$ is ($C_1$-$C_4$) alkyl, $W_2$ is a phenyl ring, one of $R_1$ is an alkyl in ortho position with respect to L, both $R_1$ and $R_{14}$ may be connected to form with $W_2$ a condensed ring radical selected from at least 1H-cyclopropabenzene-1,1-diyl, indane-1,1-diyl (also named as 2,3-dihydro-1H-indene-1,1-diyl), indane-2,2-diyl (also named as 2,3-dihydro-1H-indene-2,2-diyl), 1,2,3,4-tetrahydronaphthalene-1,1-diyl, and 1,2,3,4-tetrahydronaphthalene-2,2-diyl;

$R_{15}$ is selected from hydrogen, ($C_1$-$C_6$) alkyl, ($C_3$-$C_7$) cycloalkyl, ($C_3$-$C_7$) heterocycloalkyl and benzyl; wherein said ($C_1$-$C_6$) alkyl is optionally substituted by hydroxyl or $NR_{18}R_{19}$; said $R_{18}$ and $R_{19}$ being independently selected from hydrogen and ($C_1$-$C_4$) alkyl, or, taken together with the nitrogen atom to which they are attached, form a nitrogen containing, saturated heterocycloalkyl group, optionally containing an additional heteroatom selected from O, S, and NH;

and wherein i is 1 or 2;

i' is 1 or 2;

i" is an integer ranging from 0 to 3;

A is selected from the groups of formula (i) to (vi):

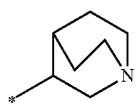 (i)

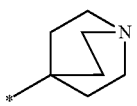 (ii)

(vi)

(iii)

(iv)

(v)

wherein $R_{16}$ is in each occurrence independently selected from ($C_1$-$C_4$) alkyl optionally substituted by one or more ($C_1$-$C_4$) alkoxy groups; $R_{17}$ is hydrogen, halogen or ($C_1$-$C_4$) alkyl; f=0, 1, 2 or 3; g=0, 1, 2 or 3; and the asterisk (*) represents the point of attachment to the group $L_3$ in formula (I);

their N-oxides on the pyridine ring, deuterated derivatives, and pharmaceutically acceptable salts, or solvates thereof exhibit the desired properties.

The present invention further provides the corresponding N-oxides on the pyridine ring of compounds of formula (I) which are represented by the formula (I)':

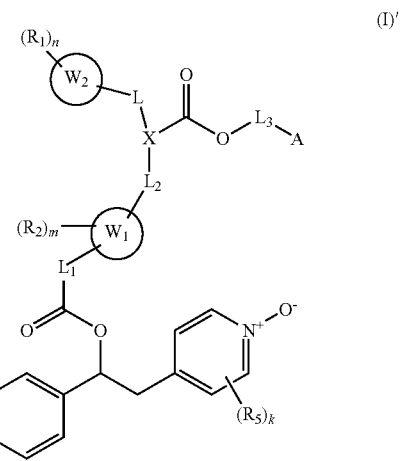

(I)' wherein $R_1$, $R_2$, $R_3$, $R_4$, $R_5$, L, $L_1$, $W_1$, $L_2$, $W_2$, X, $L_3$, A, m, n, and k are as described above.

The further invention further provides the corresponding deuterated derivatives of compounds of formula (I) wherein at least one hydrogen atom is substituted by corresponding atoms of deuterium.

In the context of the present invention, the term deuterated derivative means that the at least one position occupied by a hydrogen atom is occupied by deuterium in an amount above its natural abundance. Preferably, the percent of deuterium at that position is at least 90%, more preferably at least 95%, even more preferably 99%. Preferably deuterated derivatives according to the invention are deuterated at available positions in the substituent $R_3$.

The present invention also provides the pharmaceutically acceptable salts and/or solvates thereof.

The term "pharmaceutically acceptable salts" refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable.

Suitable examples of said salts may include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

The skilled person will appreciate that many organic compounds can form complexes with solvents in which they are reacted or from which they are precipitated or crystallized. These complexes are known as "solvates". Pharmaceutically acceptable solvates of compound of the invention are within the scope of the invention.

Included within the scope of the present invention are also polymorphs and crystalline forms of compounds of formula (I), of their N-oxides on the pyridine ring, or of pharmaceutically acceptable salts, or solvates thereof.

Hereinafter, compounds of formula (I), (IA), (IB), (IC), (ID), (Ia), (Ib), (Ic), (Id) (Ie), (If), (Ig), (Ih), (Ii), (Ik), (Im), (In), (I'), and (I)", corresponding N-oxides on the pyridine ring, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention".

The present invention further provides a process for the preparation of compounds of the invention.

The present invention also provides pharmaceutical compositions of compounds of the invention, either alone or in combination with another active ingredient, in admixture with one or more pharmaceutically acceptable carriers.

In a further aspect, the present invention provides the use of the compounds of the invention as a medicament.

In one aspect, the present invention provides the use of the compounds of the invention for the manufacture of a medicament.

In particular, the present invention provides the use of the compounds of the invention for the prevention and/or treatment of any disease wherein an inhibition of PDE4 activity along with muscarinic M3 receptor antagonism is desirable.

In particular, the compounds of the invention alone or combined with other active ingredients may be administered for the prevention and/or treatment of a disease of the respiratory tract characterized by airway obstruction such as asthma and COPD. In one embodiment, the compounds of the invention may be administered for the prevention and/or treatment of COPD.

In a further aspect, the present invention provides the use of compounds of the invention for the preparation of a medicament for the prevention and/or treatment of any disease wherein an inhibition of PDE4 activity along with muscarinic M3 receptor antagonism is desirable.

Moreover, the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

Prevention is herewith intended particularly to refer to prevention of exacerbations of the above said a disease.

A further aspect of the invention provides a suitable inhalation device, comprising a pharmaceutical composition of a compound of the invention, which may be respectively selected from a single- or multi-dose dry powder inhaler, a pressurized metered dosed inhaler or a nebulizer and in particular a soft mist nebulizer.

A further aspect of the invention provides a kit comprising the pharmaceutical compositions of a compound of the invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" includes fluorine, chlorine, bromine, and iodine, preferably chlorine.

The term "$(C_1-C_x)$ alkyl" where x is an integer greater than 1, refers to straight and branched chain alkyl groups wherein the number of constituent carbon atoms is in the range 1 to x. Particular alkyl groups are methyl, ethyl, n-propyl, i-propyl, n-butyl, sec-butyl, i-butyl, and t-butyl.

By analogy, the term "$(C_1-C_x)$alkylene" refers to a divalent $(C_1-C_x)$alkyl radical, wherein $(C_1-C_x)$alkyl is as above defined.

The term "$(C_1-C_x)$ alkoxy" where x is an integer greater than 1 refers to straight and branched chain alkoxy groups wherein the number of constituent carbon atoms is in the range 1 to x. Particular alkoxy groups are methoxy, ethoxy, n-propoxy, i-propoxy, n-butoxy, sec-butoxy, i-butoxy, and t-butoxy.

The expressions "$(C_1-C_x)$haloalkyl" refer to the above defined "$(C_1-C_x)$alkyl" groups wherein one or more hydrogen atoms are replaced by one or more halogen atoms, which can be the same or different from each other.

Examples of said $(C_1-C_6)$haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "$(C_3-C_y)$cycloalkyl", where y is an integer greater than or equal to 3, refers to saturated cyclic hydrocarbon groups containing from 3 to y ring carbon atoms. Examples include cyclopropyl, cyclobutyl, cyclopentyl, cyclohexyl, and cycloheptyl.

The expression "$(C_3-C_y)$cycloalkylcarbonyl" refers to $(C_3-C_y)$cycloalkylCO-groups wherein the group "$(C_3-C_y)$ cycloalkyl" has the meaning above defined.

The term "$(C_2-C_6)$alkenyl" refers to straight or branched, conjugated or not conjugated, carbon chains with one or more double bonds, in cis or trans configuration, wherein the number of atoms is in the range 2 to 6.

The term "($C_5$-$C_Z$) cycloalkenyl", where z is an integer greater than or equal to 5, refers to cyclic hydrocarbon groups containing from 5 to z ring carbon atoms and one or more double bonds.

The term "($C_2$-$C_6$)alkynyl" refers to straight or branched carbon chains with one or more triple bonds wherein the number of atoms is in the range 2 to 6.

The term "aryl" refers to mono or bi-cyclic systems which have 6 to 10 ring carbon atoms, wherein at least one ring is aromatic.

The expression "heteroaryl" refers to mono or bi-cyclic systems with 5 to 11 ring atoms, in which at least one ring is aromatic and in which at least one ring atom is a heteroatom (e.g. N, NH, S, or O).

Examples of suitable aryl or heteroaryl monocyclic systems with 5 to 6 ring atoms include, for instance, benzene (phenyl), thiophene (thiophenyl), pyrrole (pyrrolyl), pyrazole (pyrazolyl), imidazole (imidazolyl), triazole (triazolyl), tetrazole (tetrazolyl), isoxazole (isoxazolyl), oxazole (oxazolyl), isothiazole (isothiazolyl), thiazole (thiazolyl), pyridine (pyridinyl), furan (furanyl) derived radicals and the like.

Examples of suitable aryl or heteroaryl bicyclic systems with more than 6 ring atoms include naphthalene (naphthylenyl), biphenylene (biphenylenyl), tetrahydronaphthalene (tetrahydronaphthalenyl), purine (purinyl), pteridine (pteridinyl), benzimidazole (benzimidazolyl), benzotriazole (benzotriazolyl), quinoline (quinolinyl), isoquinoline (isoquinolinyl), indole (indolyl), isoindole (isoindolyl), indazole (indazolyl), benzothiophene (benzothiophenyl), benzofuran (benzofuranyl)), benzoxazole (benzoxazolyl), dihydrobenzo dioxin, dihydrobenzo dioxepin, benzo-oxazin radicals and the like.

The expression "arylene" refers to divalent mono or bi-cyclic systems which have 6 to 10 ring carbon atoms, wherein at least one ring is aromatic. Non limiting examples are phenylenediyl diradical at any suitable position.

The expression "heteroarylene" specifically "($C_5$-$C_6$) heteroarylene" refers to divalent monocyclic ring systems with 5 to 6 ring atoms, and in which at least one ring atom is a heteroatom (e.g. N, NH, S or O). Not limiting examples of suitable ($C_5$-$C_6$) heteroarylene systems include, for instance, thiophenediyl, furanediyl, pyrrolediyl, pyrazolediyl, imidazolediyl, triazolediyl, tetrazolediyl, isoxazolediyl, oxazolediyl, isothiazolediyl, thiazolediyl, pyridinediyl diradicals at any suitable position and the like.

The expression "heterocyclic ring system" refers to optionally substituted mono-, bi- or tri-cyclic ring systems which may be saturated or partially unsaturated, such as heterocycloalkyl groups having 3 to 11 ring atoms or specifically ($C_3$-$C_7$) heterocycloalkyl groups, in which at least one ring atom is a heteroatom (e.g. N, S or O), included in the definition are bridged mono-, bi- or tri-cyclic ring systems.

Examples of "heterocyclic ring system" are represented by: oxetan-yl, tetrahydrofuran-yl, tetrahydropyran-yl, or nitrogen containing systems including pyrrolidinyl, imidazolidinyl, piperazinyl, piperidinyl, tetrahydropyridinyl, quinuclidinyl, 8-azabicyclo[3.2.1]octanyl or dehydroxy scopine radical, all optionally substituted by ($C_1$-$C_X$) alkyl or benzyl on a nitrogen atom.

By analogy, the derived expression "heterocycloalkylene" refers to the above defined heterocyclic ring systems, e.g. ($C_3$-$C_7$) heterocycloalkylene divalent groups, when they are divalent groups bridging two parts of a molecule.

The invention is directed to a class of compounds acting both as inhibitors of the phosphodiesterase 4 (PDE4) enzyme and as muscarinic M3 receptor antagonists.

The present invention relates to derivatives of general formula (I), N-oxides on the pyridine ring, deuterated derivatives and pharmaceutically acceptable salts or solvates thereof:

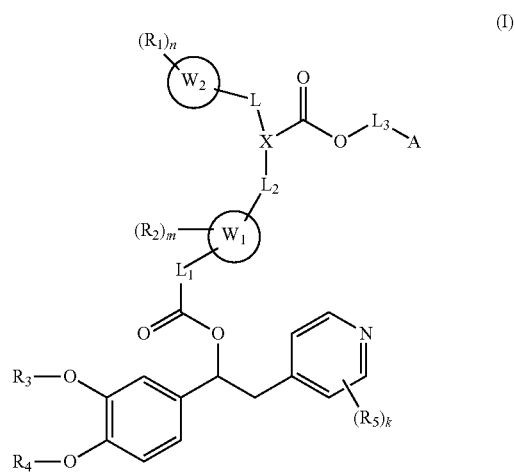

(I)

wherein $R_1$, $R_2$, $R_3$, $R_4$, $R_5$, L, $L_1$, $W_1$, $L_2$, $W_2$, X, $L_3$, A, n, m and k are as above defined.

Preferred compounds of formula (I) are those wherein the saturated heterocyclic ring system A is represented by a group of formula (i), (ii) or (iv):

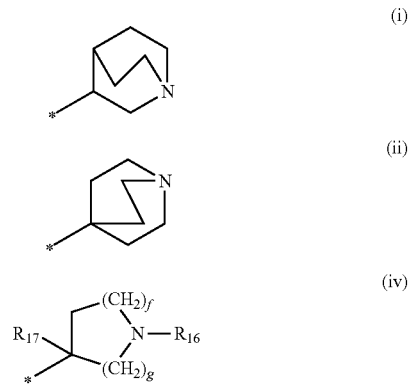

wherein f=0, 1, 2, 3; g=0, 1, 2; $R_{17}$ is hydrogen, methyl or fluorine; $R_{16}$ is methyl or ethyl and the asterisk (*) represents the point of attachment to $L_3$ in Formula (I).

It will be apparent to those skilled in the art that compounds of general formula (I) at least contain one stereogenic center, namely represented by the carbon atom (1) in formula (I)" below, and therefore exist as optical stereoisomers.

Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the invention is directed to compounds of formula (I)", which are compounds of formula (I) as above defined where the absolute configuration of carbon (1) is that shown below:

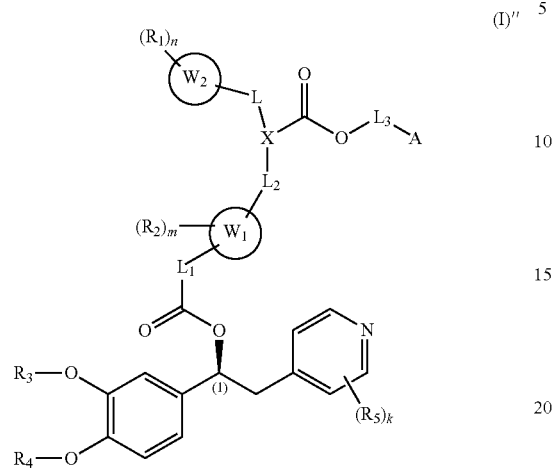
(I)″

The absolute configuration for carbon (1) is assigned on the basis of Cahn-Ingold-Prelog nomenclature based on groups' priorities.

In one preferred embodiment, for compounds of formula (I), absolute configuration at carbon (1) is (S).

In one embodiment, when A is a group of formula (i) as above defined, or a group of formula (iv) or (v) containing a stereo genic carbon atom at the point of attachment of the group A to L3 in formula (I), compounds of formula (I) may exist as at least four diastereoisomers (Ia), (Ib), (Ic), (Id), when A is (i); (Ie), (If), (Ig) and (Ih) when A is (iv) and (Ii), (Il), (Im), (In) when A is (v) as it is herebelow reported, which are comprised within the scope of the present invention. When X is the group $X_2$, or the groups $X_1$ and $X_3$ wherein i and i' are different from each other, each (Ia), (Ib), (Ic), (Id), (Ie), (If), (Ig), (Ih), (Ii), (Il), (Im) and (In) is constituted by a couple of corresponding epimers at the stereogenic center at the carbon atom of group X.

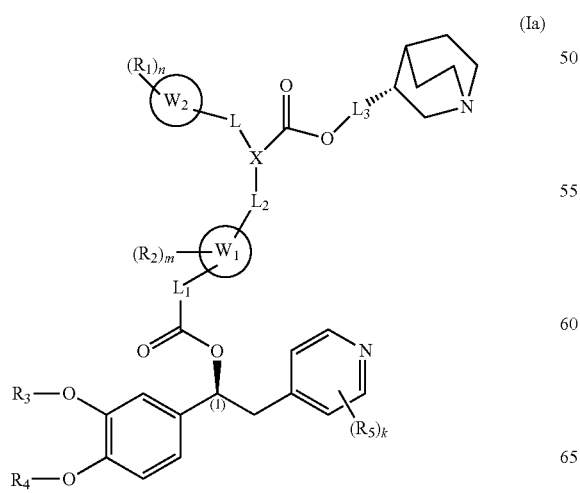
(Ia)

-continued

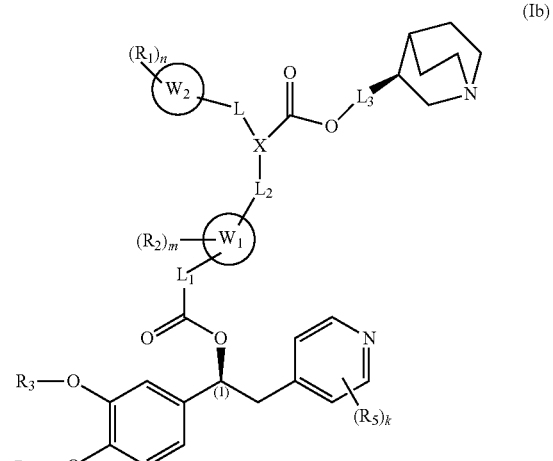
(Ib)

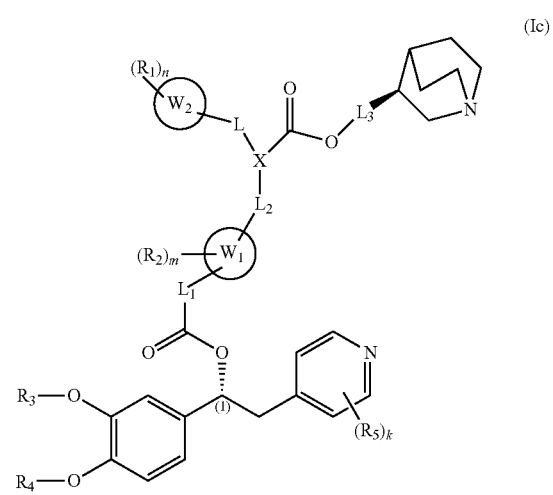
(Ic)

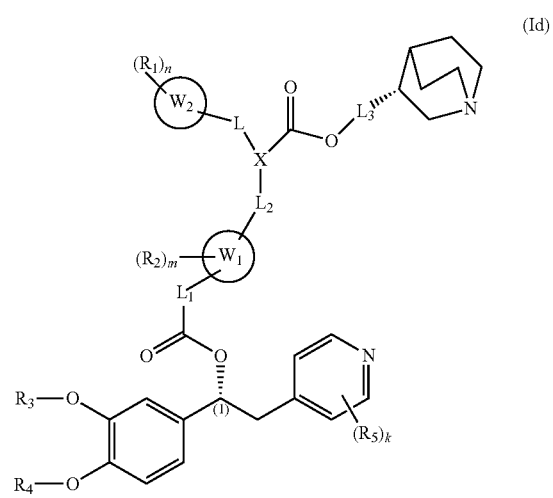
(Id)

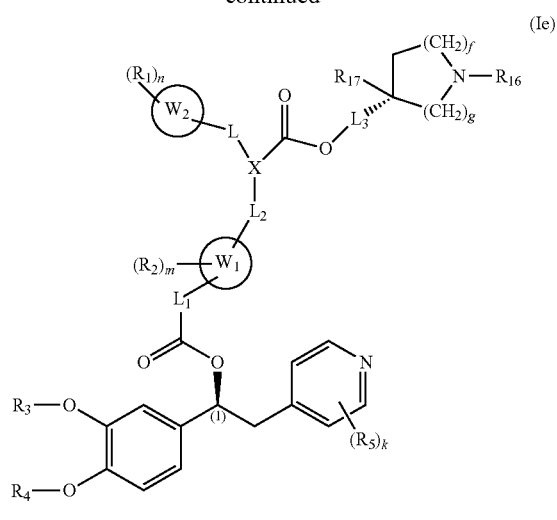
(Ie)
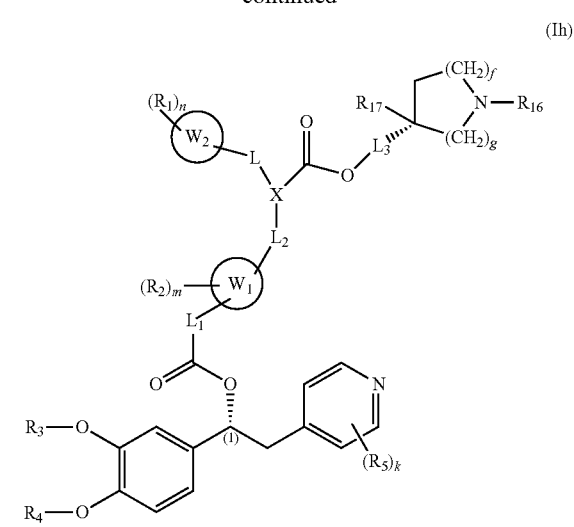
(Ih)
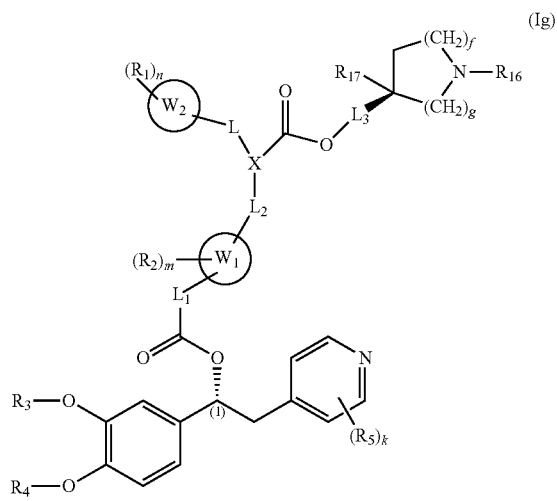
(If)
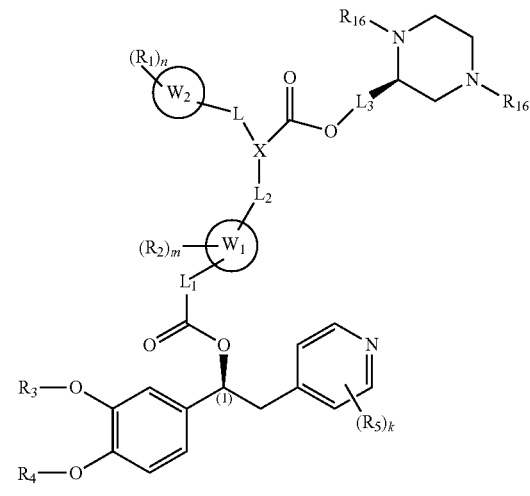
(Ii)
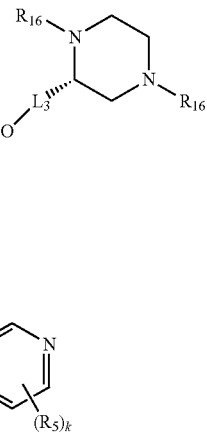
(Ig)
(Il)

(Im)

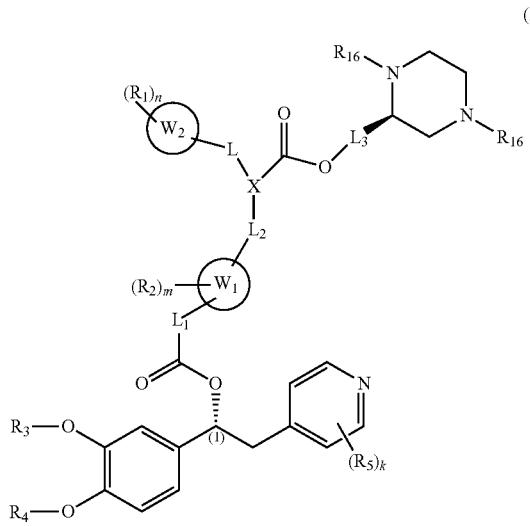

(In)

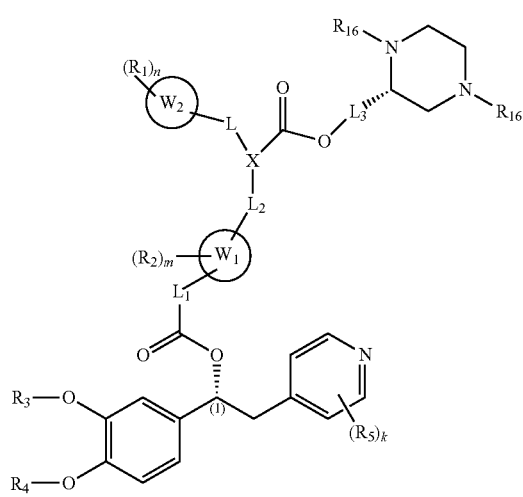

It will be apparent to the skilled person that compounds of formula (Ia), (Ib), (Ic), (Id), and (Ie), (If), (Ig), (Ih) (Ii), (Il), (Im) and (In) may be also obtained as single diastereoisomers wherein, when X contains a stereogenic centre at a carbon atom, said stereogenic centre is defined as R or S.

It is to be understood that all preferred groups or embodiments described herebelow and hereabove for compounds of formula (I) may be combined among each other and apply to compounds of formula (IA), (IB), (IC), (ID), (Ia), (Ib), (Ic), (Id), (Ie), (If), (Ig), (Ih), (Ii), (Il), (Im), (In), (I)' and (I)" as well mutatis mutandis.

In a preferred embodiment, the invention provides compounds of formula (I) wherein X is the group $X_2$.

In a further preferred embodiment, the invention provides compounds of formula (IA), which are N-oxides on the pyridine ring of compounds of formula (I) wherein X is the group $X_2$ and i" is 0, deuterated derivatives and pharmaceutically acceptable salts and solvates thereof:

(IA)

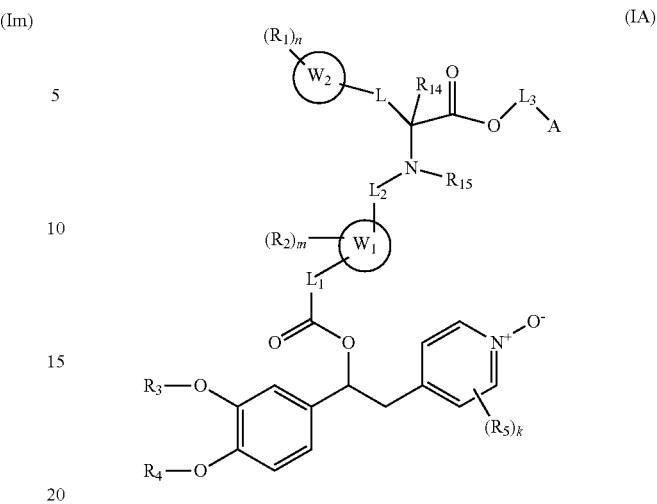

wherein $R_1$, $R_2$, $R_3$, $R_4$, $R_5$, $R_{14}$, $R_{15}$, L, $L_1$, $W_1$, $L_2$, $W_2$, A, $L_3$, m, n, and k are as described above.

In another preferred embodiment the invention provides compounds of formula (IB), which are N-oxides on the pyridine ring of compounds of formula (I) wherein L is a bond, X is the group $X_1$, deuterated derivatives and pharmaceutically acceptable salts and solvates thereof:

(IB)

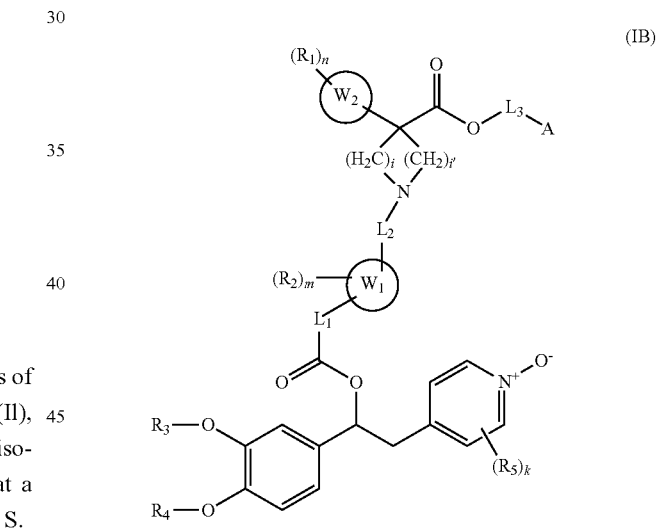

wherein $R_1$, $R_2$, $R_3$, $R_4$, $R_5$, $L_1$, $W_1$, $L_2$, $W_2$, A, i, i', $L_3$, m, n, and k are as described for formula (I).

In a preferred embodiment of formula (IA) or (IB), k is 2 and $R_5$ are halogen atoms. In a further preferred embodiment, $R_5$ are two chlorine atoms at positions 3 and 5 of the pyridine ring.

In one preferred embodiment, $R_4$ is selected from a ($C_1$-$C_6$) alkyl and $R_3$ is selected from ($C_3$-$C_7$) cycloalkyl or ($C_1$-$C_6$) alkyl; wherein said ($C_1$-$C_6$) alkyl is optionally substituted by one or more halogen or ($C_3$-$C_7$) cycloalkyl.

In another preferred embodiment, $R_4$ is methyl or difluoromethyl and $R_3$ is selected from methyl, ethyl, pentyl or cyclopropylmethyl, 2-methoxyethyl.

In another preferred embodiment, $R_3$ is ($C_1$-$C_6$) alkyl and $R_4$ is ($C_1$-$C_6$) alkyl.

In another preferred embodiment, $R_3$ and $R_4$ are both methyl.

A preferred group of compounds of formula (I) is that wherein the 4-pyridinyl ring is substituted in 3 and 5 with two atoms of chlorine, according to the general formula (IC)

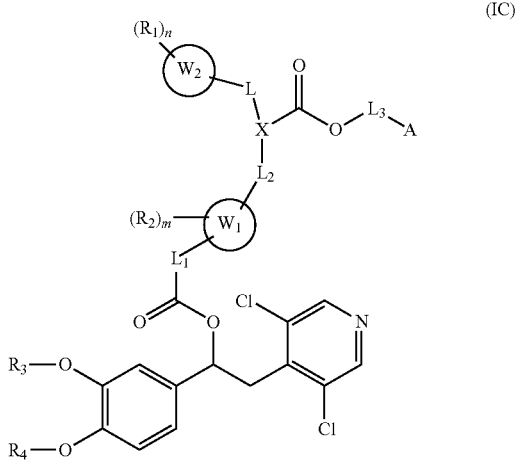

(IC)

wherein $R_1$, $R_2$, $R_3$, $R_4$, A, L, $L_1$, $W_1$, $L_2$, $W_2$, X, $L_3$, m and n are as defined above for compounds of formula (I); and the corresponding N-oxide on the pyridine ring, deuterated derivatives and pharmaceutically acceptable salts and solvates thereof.

A more preferred group of compounds is that shown below according to general formula (ID):

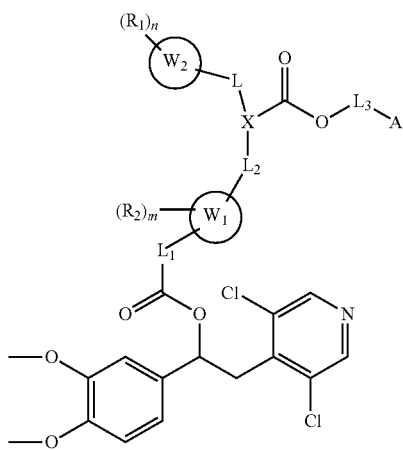

(ID)

wherein $R_1$, $R_2$, A, L, $L_1$, $W_1$, $L_2$, $W_2$, X, $L_3$, m and n are as defined above for compounds of formula (I), the corresponding N-oxide on the pyridine ring, deuterated derivatives and pharmaceutically acceptable salts and solvates thereof.

In one embodiment of formula (I), (IB), or (IC) each $R_1$ is hydrogen or is independently selected in the group consisting of: fluorine, methoxy, hydroxy; each $R_2$ is hydrogen; $R_4$ is methyl or difluoromethyl and $R_3$ is selected from methyl, ethyl, pentyl cyclopropylmethyl, or 2-methoxyethyl. Particularly preferred are compounds of formula (ID) wherein $R_4$ and $R_3$ are methyl.

In one embodiment of formula (I), (IB), (IC) or (ID) $L_1$ is a bond and $L_2$ and $L_3$ are both methylene.

In another embodiment of formula (I), (IB), (IC) or (ID) m is 0 and $W_1$ is thienylene-2,5-diyl or thienylene-2,4-diyl; alternatively named thiophene-2,5-diyl, thiophene-2,4-diyl.

In another embodiment of formula (I), (IB), (IC) or (ID) n is 0 and $W_2$ is phenyl or thienyl or cyclohexyl.

In another embodiment of formula (I), (IB), (IC) or (ID) X is a group of formula $X_1$ wherein both i and i' are 1 or 2; or X is a group of formula $X_2$ wherein i" is 0 or 1 and $R_{14}$ is selected from H, methyl, hydroxyl and hydroxymethyl, and $R_{15}$ is H or oxetan-3-yl, or $R_1$ and $R_{14}$ are connected to form with $W_2$ a condensed ring radical which is indane-1,1-diyl; or X is a group of formula $X_3$ wherein both i and i' are 1; $R_{15}$ is H or oxetan-3-yl.

In another embodiment of formula (I), (IB), (IC) or (ID), A is a group of formula (i), (ii) or (iv):

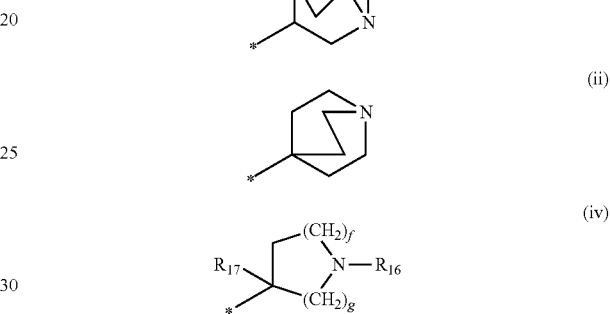

wherein f=0, 1, 2 or 3; g=0, 1, 2 or 3; $R_{17}$ is hydrogen, fluoro or methyl; $R_{16}$ is methyl, ethyl, isopropyl or 2-metoxyethyl and the asterisk (*) represents the point of attachment to $L_3$ in Formula (I)-(ID);
the corresponding N-oxide on the pyridine ring, deuterated derivatives and pharmaceutically acceptable salts and solvates thereof.

In another further preferred embodiment of formula (I), (IB), (IC) or (ID), A is a group of formula (ii) or (iv):

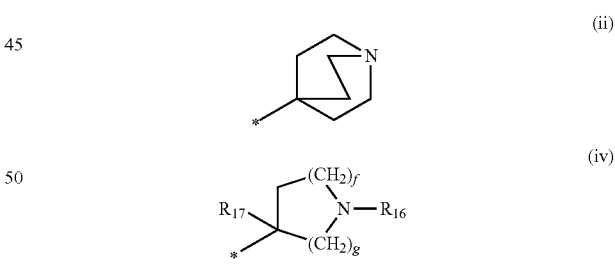

wherein f=1; g=1 or 2; $R_{17}$ is hydrogen; $R_{16}$ is methyl and the asterisk (*) represents the point of attachment to $L_3$ in Formula (I)-(ID).

According to a preferred embodiment, the present invention provides the compounds reported below:
[(1S)-2-(3,5-dichloro-1-oxido-pyridin-1-ium-4-yl)-1-(3,4-dimethoxyphenyl)ethyl]5-[[[2-hydroxy-3-[(1-methyl-4-piperidyl)methoxy]-3-oxo-2-(2-thienyl)propyl]amino]methyl]-thiophene-2-carboxylate;
[(1S)-2-(3,5-dichloro-1-oxido-pyridin-1-ium-4-yl)-1-(3,4-dimethoxyphenyl)ethyl]5-[[[2-[(1,4-dimethyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(4-fluoro-1-methyl-4-piperidyl)methoxy]-2-oxo-1-phenyl-ethyl]amino]methyl]thiophene-2-carboxylate;

Epimeric mixture 2 of [1-[3-(cyclopropylmethoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Epimeric mixture 1 of [1-[3-(cyclopentoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Epimeric mixture 2 of [1-[3-(cyclopentoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[3-[(1-methyl-4-piperidyl)methoxy]-3-oxo-2-phenyl-propyl]amino]methyl]thiophene-2-carboxylate;

Epimeric mixture 2 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-(quinuclidin-4-yl-methoxy)ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-cyclohexyl-2-[(1-methyl-4-piperidyl)methoxy]-2-oxo-ethyl]amino]methyl]-thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-[[(3S)-quinuclidin-3-yl]methoxy]ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-[[(3R)-quinuclidin-3-yl]methoxy]ethyl]amino]methyl]thiophene-2-carboxylate;

Epimeric mixture 2 of [2-(3,5-dichloro-1-oxido-pyridin-1-ium-4-yl)-1-(3-ethoxy-4-methoxy-phenyl)ethyl]5-[[[2-[(1-methyl-4-piperidyl)methoxy]-2-oxo-1-phenyl-ethyl]amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]methoxy]-2-oxo-1-phenyl-ethyl]amino]-methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2R)-1-methylpyrrolidin-2-yl]methoxy]-2-oxo-1-phenyl-ethyl]amino]-methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2S)-1-methylpyrrolidin-2-yl]methoxy]-2-oxo-1-phenyl-ethyl]amino]-methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3R)-1-methylpyrrolidin-3-yl]methoxy]-2-oxo-1-phenyl-ethyl]amino]-methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3 S)-1-methylpyrrolidin-3-yl]methoxy]-2-oxo-1-phenyl-ethyl]amino]-methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-ethyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[1-(2-methoxyethyl)-4-piperidyl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-(2-pyrrolidin-1-ylethoxy)ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-[2-(1-piperidyl)ethoxy]ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)methoxy]-2-oxo-ethyl]amino]methyl]-thiophene-2-carboxylate;

[(1S)-2-(3,5-dichloro-1-oxido-pyridin-1-ium-4-yl)-1-(3,4-dimethoxyphenyl)ethyl]5-[[[2-[(1-methylazetidin-3-yl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3S)-1-methyl-3-piperidyl]methoxy]-2-oxo-1-phenyl-ethyl]amino]methyl]-thiophene-2-carboxylate;

[(1S)-2-(3,5-dichloro-1-oxido-pyridin-1-ium-4-yl)-1-(3,4-dimethoxyphenyl)ethyl]5-[[[2-[[(2S)-1-methylazetidin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2R)-1-methylazetidin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2R)-1,4-dimethylpiperazin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2R)-1-methyl-2-piperidyl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-2-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2S)-1,4-dimethylpiperazin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-(quinuclidin-4-ylmethoxy)ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-methyl-2-[(1-methyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(hydroxymethyl)-2-[(1- methyl-4-piperidyl)methoxy]-2-oxo-1-phenyl-ethyl] amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-4-piperidyl) methoxy]-2-oxo-1-phenyl-ethyl]amino]methyl]thiophene-3-carboxylate;

[(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-(2-thienyl)ethyl] amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-[(1-methyl-4-piperidyl) methoxycarbonyl]indan-1-yl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-4-piperidyl) methoxy]-2-oxo-1-phenyl-ethyl]-(oxetan-3-yl)amino] methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-(3-hydroxyphenyl)-2-[(1-methyl-4-piperidyl) methoxy]-2-oxo-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-(3-hydroxyphenyl)-2-[(1-methyl-4-piperidyl) methoxy]-2-oxo-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(1-isopropyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(1-isopropyl-4-piperidyl)methoxy]-2-oxo-1-phenyl-ethyl]amino]methyl]thiophene-2-carboxylate;

Single diastereoisomer 1 of [(1S)-1-[3-(cyclopropyl-methoxy)-4-(difluoromethoxy)phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl] thiophene-2-carboxylate;

Single diastereoisomer 2 of [(1S)-1-[3-(cyclopropyl-methoxy)-4-(difluoromethoxy)phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl] thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(3-hydroxyphenyl)-2-[(1-methyl-4-piperidyl) methoxy]-2-oxo-ethyl]amino]methyl]thiophene-2-carboxylate;

Single diastereoisomer 1 of epimeric mixture 2 of [1-[3-(cyclopropylmethoxy)-4-methoxy-phenyl]-2-(3,5-dichloro-1-oxido-pyridin-1-ium-4-yl)ethyl]5-[[[1-(3-hydroxyphenyl)-2-[(1-methyl-4-piperidyl)methoxy]-2-oxo-ethyl]amino]methyl]thiophene-2-carboxylate;

Single diastereoisomer 2 of epimeric mixture 2 of [1-[3-(cyclopropylmethoxy)-4-methoxy-phenyl]-2-(3,5-dichloro-1-oxido-pyridin-1-ium-4-yl)ethyl]5-[[[1-(3-hydroxyphenyl)-2-[(1-methyl-4-piperidyl)methoxy]-2-oxo-ethyl]amino]methyl-thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(1,4-dimethyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(1,4-dimethyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(4-fluoro-1-methyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(4-fluoro-1-methyl-4-piperidyl)methoxy]-2-oxo-1-phenyl-ethyl]amino]methyl]thiophene-2-carboxylate;

Single diastereoisomer 1 of epimeric mixture 2 of [1-[3-(cyclopropylmethoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl] amino]methyl]thiophene-2-carboxylate;

Single diastereoisomer 2 of epimeric mixture 2 of [1-[3-(cyclopropylmethoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl] amino]methyl]thiophene-2-carboxylate;

Single diastereoisomer 1 of epimeric mixture 2 of [1-[3-(cyclopentoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl] thiophene-2-carboxylate;

Single diastereoisomer 2 of epimeric mixture 2 of [1-[3-(cyclopentoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl] thiophene-2-carboxylate;

Single diastereoisomer 1 of epimeric mixture 2 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl] thiophene-2-carboxylate;

Single diastereoisomer 2 of epimeric mixture 2 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl] thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-cyclohexyl-2-[(1-methyl-4-piperidyl)methoxy]-2-oxo-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-cyclohexyl-2-[(1-methyl-4-piperidyl)methoxy]-2-oxo-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-oxo-1-phenyl-2-[[(3S)-quinuclidin-3-yl]methoxy] ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-oxo-1-phenyl-2-[[(3S)-quinuclidin-3-yl]methoxy] ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-

[[[2-oxo-1-phenyl-2-[[(3R)-quinuclidin-3-yl]methoxy]ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-oxo-1-phenyl-2-[[(3R)-quinuclidin-3-yl]methoxy]ethyl]amino]methyl]thiophene-2-carboxylate;

Single diastereoisomer 1 of epimeric mixture 2 of [2-(3,5-dichloro-1-oxido-pyridin-1-ium-4-yl)-1-(3-ethoxy-4-methoxy-phenyl)ethyl]5-[[[2-[(1-methyl-4-piperidyl)methoxy]-2-oxo-1-phenyl-ethyl]amino]methyl]thiophene-2-carboxylate;

Single diastereoisomer 2 of epimeric mixture 2 of [2-(3,5-dichloro-1-oxido-pyridin-1-ium-4-yl)-1-(3-ethoxy-4-methoxy-phenyl)ethyl]5-[[[2-[(1-methyl-4-piperidyl)methoxy]-2-oxo-1-phenyl-ethyl]amino]methyl]thiophene-2-carboxylate;

Single diastereoisomer 1 of [(1S)-1-[3-(cyclopropylmethoxy)-4-(difluoromethoxy)phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Single diastereoisomer 2 of [(1S)-1-[3-(cyclopropylmethoxy)-4-(difluoromethoxy)phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2R)-1-methylpyrrolidin-2-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(2R)-1-methylpyrrolidin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2S)-1-methylpyrrolidin-2-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(2S)-1-methylpyrrolidin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(3R)-1-methylpyrrolidin-3-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(3R)-1-methylpyrrolidin-3-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(3S)-1-methylpyrrolidin-3-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(3S)-1-methylpyrrolidin-3-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(1-ethyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(1-ethyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[1-(2-methoxyethyl)-4-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[1-(2-methoxyethyl)-4-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-oxo-1-phenyl-2-(2-pyrrolidin-1-ylethoxy)ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-oxo-1-phenyl-2-(2-pyrrolidin-1-ylethoxy)ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-oxo-1-phenyl-2-[2-(1-piperidyl)ethoxy]ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)methoxy]-2-oxo-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)methoxy]-2-oxo-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(3S)-1-methyl-3-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(3S)-1-methyl-3-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2S)-1-methylazetidin-2-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(2S)-1-methylazetidin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2R)-1-methylazetidin-2-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(2R)-1-methylazetidin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2R)-1,4-dimethylpiperazin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2R)-1-methyl-2-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(2R)-1-methyl-2-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2S)-1-methyl-2-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(2S)-1-methyl-2-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-oxo-1-phenyl-2-(quinuclidin-4-ylmethoxy)ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-oxo-1-phenyl-2-(quinuclidin-4-ylmethoxy)ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-methyl-2-[(1-methyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-methyl-2-[(1-methyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-3-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-3-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-(2-thienyl)ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-(2-thienyl)ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-[(1-methyl-4-piperidyl)methoxycarbonyl]indan-1-yl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-[(1-methyl-4-piperidyl)methoxycarbonyl]indan-1-yl]amino]methyl]thiophene-2-carboxylate;

[(1S)-2-(3,5-dichloro-1-oxido-pyridin-1-ium-4-yl)-1-[4-(difluoromethoxy)-3-(2-methoxyethoxy)phenyl]ethyl]5-[[[2-[(1-methyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(1R,5S)-8-methyl-8-azabicyclo[3.2.1]octan-3-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(hydroxymethyl)-2-[[(3S)-1-methylpyrrolidin-3-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(hydroxymethyl)-2-[[(3R)-1-methylpyrrolidin-3-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(hydroxymethyl)-2-oxo-1-phenyl-2-(quinuclidin-4-ylmethoxy)ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-methoxyphenyl)-2-[(1-methyl-4-piperidyl)methoxy]-2-oxo-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(3-methoxyphenyl)-2-[(1-methyl-4-piperidyl)methoxy]-2-oxo-ethyl]amino]methyl]thiophene-2-carboxylate;

Epimeric mixture 2 of [2-(3,5-dichloro-1-oxido-pyridin-1-ium-4-yl)-1-(3-ethoxy-4-methoxy-phenyl)ethyl]5-[[[1-(3-hydroxyphenyl)-2-[(1-methyl-4-piperidyl)methoxy]-2-oxo-ethyl]amino]methyl]thiophene-2-carboxylate;

Diastereoisomer 1 of [(1S)-2-(3,5-dichloro-1-oxido-pyridin-1-ium-4-yl)-1-(3,4-dimethoxyphenyl)ethyl]5-[[[1-(3-methoxyphenyl)-2-[(1-methyl-4-piperidyl)methoxy]-2-oxo-ethyl]amino]methyl]thiophene-2-carboxylate;

Diastereoisomer 2 of [(1S)-2-(3,5-dichloro-1-oxido-pyridin-1-ium-4-yl)-1-(3,4-dimethoxyphenyl)ethyl]5-[[[1-(3-methoxyphenyl)-2-[(1-methyl-4-piperidyl)methoxy]-2-oxo-ethyl]amino]methyl]thiophene-2-carboxylate;

Diastereoisomer 1 of [(1S)-2-(3,5-dichloro-1-oxido-pyridin-1-ium-4-yl)-1-[4-(difluoromethoxy)-3-(2-methoxyethoxy)phenyl]ethyl]5-[[[2-[(1-methyl-4-piperidyl)methoxy]-2-oxo-1-phenyl-ethyl]amino]methyl]thiophene-2-carboxylate;

Diastereoisomer 2 of [(1S)-2-(3,5-dichloro-1-oxido-pyridin-1-ium-4-yl)-1-[4-(difluoromethoxy)-3-(2-methoxyethoxy)phenyl]ethyl]5-[[[2-[(1-methyl-4-piperidyl)methoxy]-2-oxo-1-phenyl-ethyl]amino]methyl]thiophene-2-carboxylate;

Diastereoisomer 1 of Epimeric mixture 2 of [2-(3,5-dichloro-1-oxido-pyridin-1-ium-4-yl)-1-(3-ethoxy-4-methoxy-phenyl)ethyl]5-[[[1-(3-hydroxyphenyl)-2-[(1-methyl-4-piperidyl)methoxy]-2-oxo-ethyl]amino]methyl]thiophene-2-carboxylate;

Diastereoisomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[[(3S)-1-methylpyrrolidin-3-yl]methoxy]-2-oxo-1-phenyl-ethyl]amino]methyl]thiophene-2-carboxylate;

Diastereoisomer 2 of [(1S)-2-(3,5-dichloro-1-oxido-pyridin-1-ium-4-yl)-1-(3,4-dimethoxyphenyl)ethyl]5-[[[1-(hydroxymethyl)-2-[[(3S)-1-methylpyrrolidin-3-yl]methoxy]-2-oxo-1-phenyl-ethyl]amino]methyl]thiophene-2-carboxylate;

Diastereoisomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[[(3R)-1-methylpyrrolidin-3-yl]methoxy]-2-oxo-1-phenyl-ethyl]amino]methyl]thiophene-2-carboxylate;

Diastereoisomer 2 of [(1S)-2-(3,5-dichloro-1-oxido-pyridin-1-ium-4-yl)-1-(3,4-dimethoxyphenyl)ethyl]5-[[[1-(hydroxymethyl)-2-[[(3R)-1-methylpyrrolidin-3-yl]methoxy]-2-oxo-1-phenyl-ethyl]amino]methyl]thiophene-2-carboxylate;

deuterated derivatives and pharmaceutically acceptable salts and solvates thereof.

The expression "single diastereoisomer" is reported near the chemical name of each compound of formula (I) isolated as single diastereoisomer whose absolute configuration at the stereogenic carbon atom of X was not determined.

The expression "epimeric mixture" reported near the chemical name of each compound of formula (I) refers to a mixture of two diastereoisomers that are resolved (separated and isolated) at chiral center (1) without assignment of the absolute configuration, and are not resolved at the chiral center in the group X.

The present invention also provides processes for the preparation of compounds of the invention.

Compounds of formula (IA) can be obtained according to general synthetic routes of Scheme A, below reported or following slightly modified procedures that the skilled person can easily apply.

Processes of preparation described below and reported in the following Scheme A should not be viewed as limiting the scope of the synthetic methods available for the preparation of the compounds of the invention.

In the following Scheme A, for compounds of formula (IA) and for compounds of formula (II) to (XV), wherein X is $X_2$; $R_{15}$ is hydrogen and unless otherwise indicated, $R_1$, $R_2$, $R_3$, $R_4$, $R_5$, $R_{14}$, L, $L_1$, $W_1$, $L_2$, $W_2$, A, $L_3$, n, m, k and $L_3$ are as above defined, Y is a bond or $—(CH_2)_{q'}$ wherein q' is an integer ranging from 1 to 3.

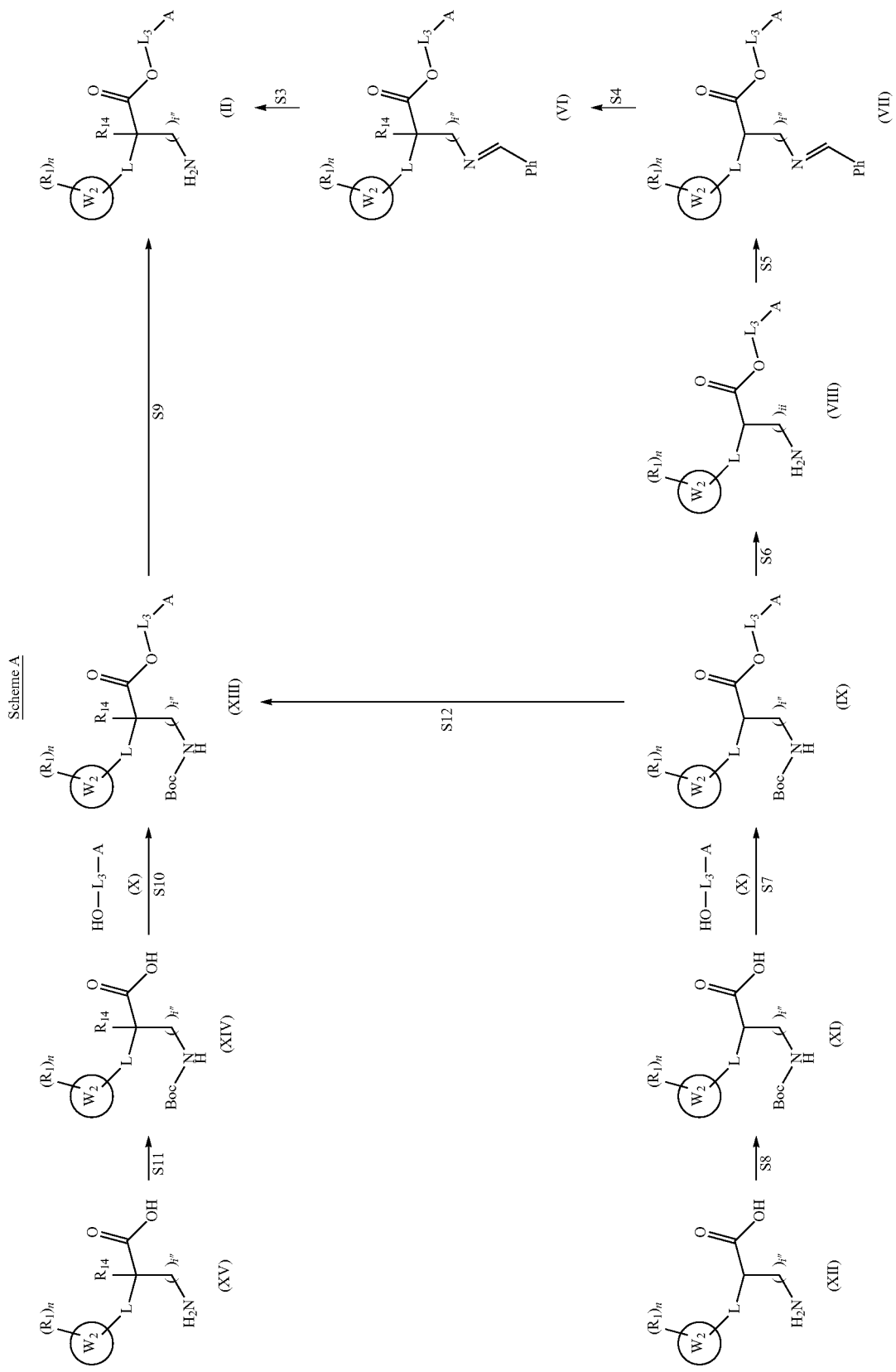

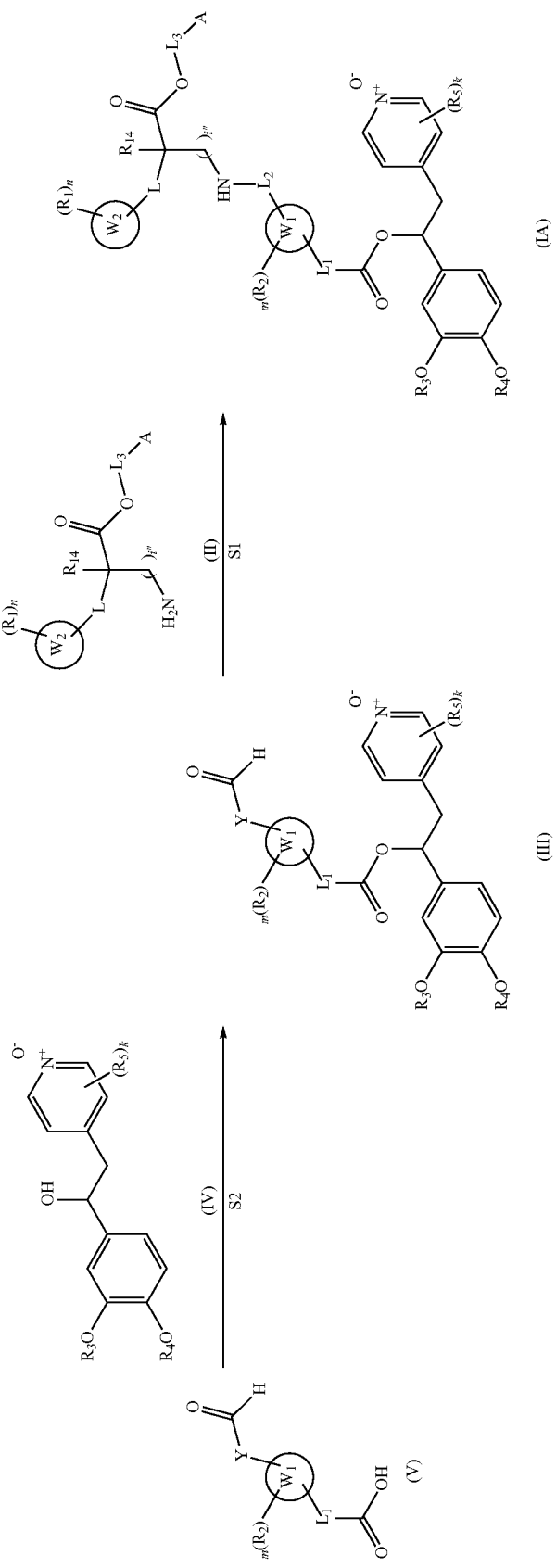

Compounds of formula (I) may be prepared according to Scheme 1/(S1) below by reaction of a compound of formula (III) with a compound of formula (II) as below reported.

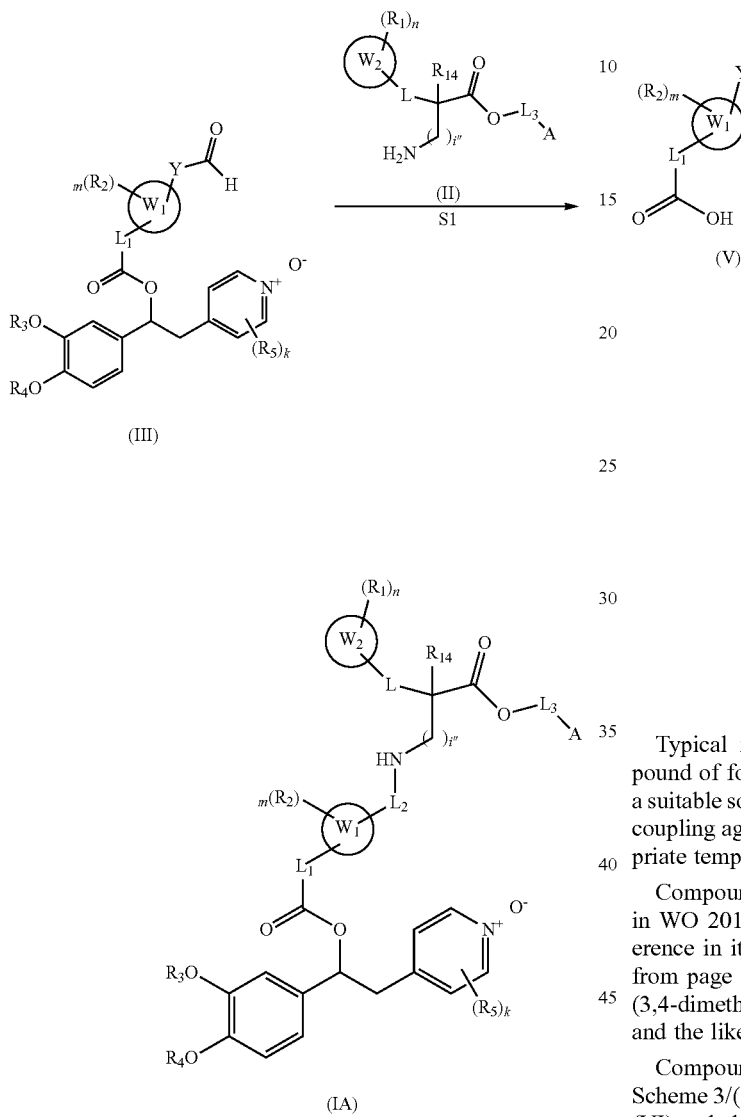

Typical reaction conditions comprise reacting a compound of formula (III) with a compound of formula (II) in a suitable solvent, such as acetonitrile, DCM, ethanol or pyridine in the presence of an optional acid, such as acetic acid, and an optional base, such as triethylamine, and a reducing agent, such as NaBH(OAc)$_3$ or NaBH$_3$CN, at an appropriate temperature, such as room (or ambient) temperature or 40° C. or 60° C.

Compounds of formula (III) may be prepared according to Scheme 2/(S2) below by reaction of a compound of formula (V) with a compound of formula (IV) as below reported.

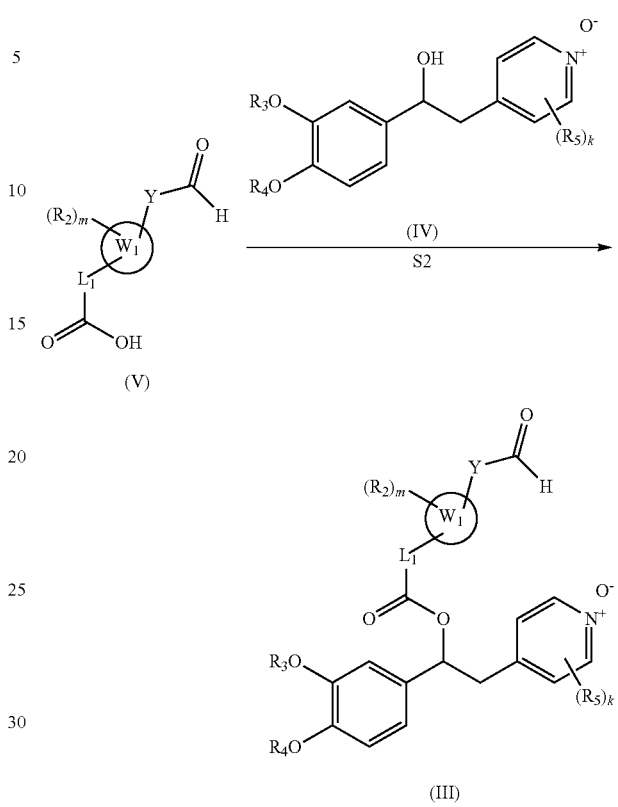

Typical reaction conditions comprise reacting a compound of formula (V) with a compound of formula (IV) in a suitable solvent, such as DCM, in the presence of a suitable coupling agent, such as EDC/DMAP or HATU, at an appropriate temperature, such as room (or ambient) temperature.

Compounds of formula (IV) may be prepared as described in WO 2014/086849, which is incorporated herein by reference in its entirety, starting at page 42 scheme 8/A, and from page 58 for Intermediate 1/A, (S)-3,5-Dichloro-4-(2-(3,4-dimethoxyphenyl)-2-hydroxyethyl)pyridine 1-oxide, and the like where R$_3$ and R$_4$ are as above defined Compounds of formula (II) may be prepared according to Scheme 3/(S3) below by reaction of a compound of formula (VI) as below reported.

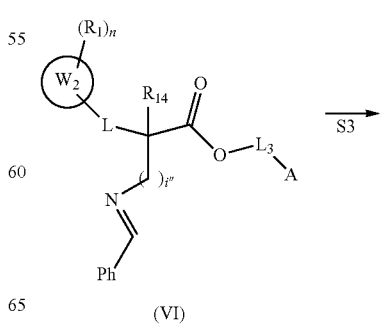

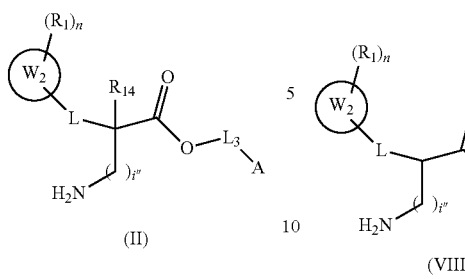

(II)

Typical reaction conditions comprise reacting a compound of formula (VI) in a suitable solvent, such as THF or 1,4-dioxane, in the presence of a suitable acid, such as hydrochloric acid, at an appropriate temperature, such as room (or ambient) temperature.

Compounds of formula (VI) may be prepared according to Scheme 4/(S4) below by reaction of a compound of formula (VII) as below reported.

Scheme 4 (S4)

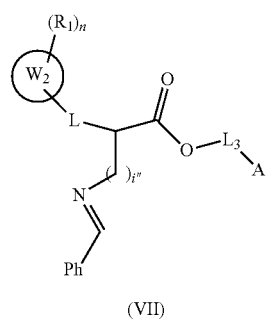

(VII)

Typical reaction conditions comprise reacting a compound of formula (VII) with an alkylating agent, such as para-formaldehyde, in a suitable solvent, such as THF or 1,4-dioxane, in the presence of a suitable base such as DBU, at an appropriate temperature, such as 0° C. or room (or ambient) temperature.

Compounds of formula (VII) may be prepared according to Scheme 5/(S5) below by reaction of a compound of formula (VIII) as below reported.

Scheme 5 (S5)

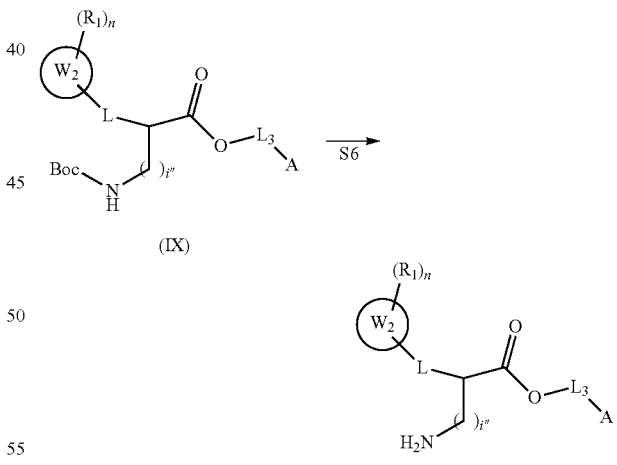

Typical reaction conditions comprise reacting a compound of formula (VIII) with an arylcarboxaldehyde (Ph-CHO), such as benzaldehyde or 4-methoxybenzaldehyde, in a suitable solvent, such as acetonitrile, DCM or ethanol in the presence of an optional base, such as triethylamine, at an appropriate temperature, such as room (or ambient) temperature or 0° C. or 40° C.

Compounds of formula (VIII) may be prepared according to Scheme 6/(S6) below by reaction of a compound of formula (IX) as below reported.

Scheme 6 (S6)

Typical reaction conditions comprise reacting a compound of formula (IX) in a suitable solvent, such as 1,4-dioxane, in the presence of a suitable acid, such as hydrochloric acid, at an appropriate temperature, such as room (or ambient) temperature.

Compounds of formula (IX) may be prepared according to Scheme 7/(S7) below by reaction of a compound of formula (XI) with a compound of formula (X) as below reported.

Scheme 7 (S7)

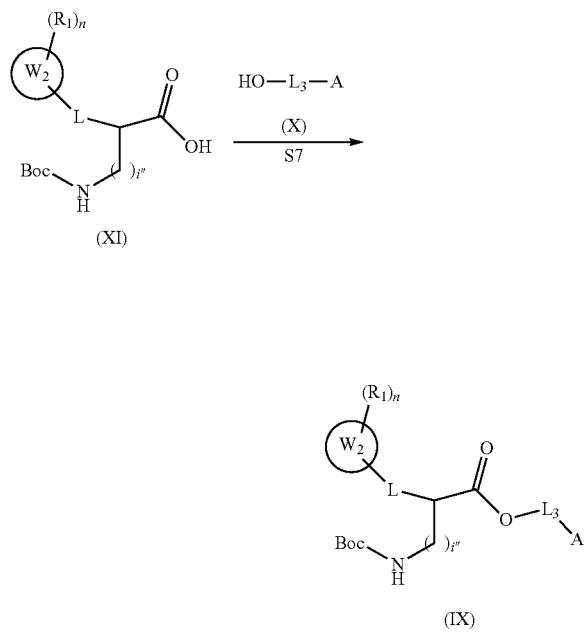

Typical reaction conditions comprise reacting a compound of formula (XI) with a compound of formula (X) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (XI) may be prepared according to Scheme 8/(S8) below by reaction of a compound of formula (XII) as below reported.

Scheme 8 (S8)

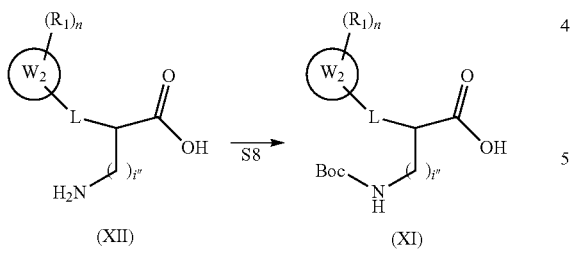

Typical reaction conditions comprise reacting a compound of formula (XII) with di-tert-butyl dicarbonate, in a suitable solvent, such as 1,4-dioxane/water, in the presence of a suitable base such as sodium hydroxide, at an appropriate temperature, such as 0° C. or room (or ambient) temperature.

Compounds of formula (II) may also be prepared according to Scheme 9/(S9) below by deprotection of a compound of formula (XIII).

Scheme 9 (S9)

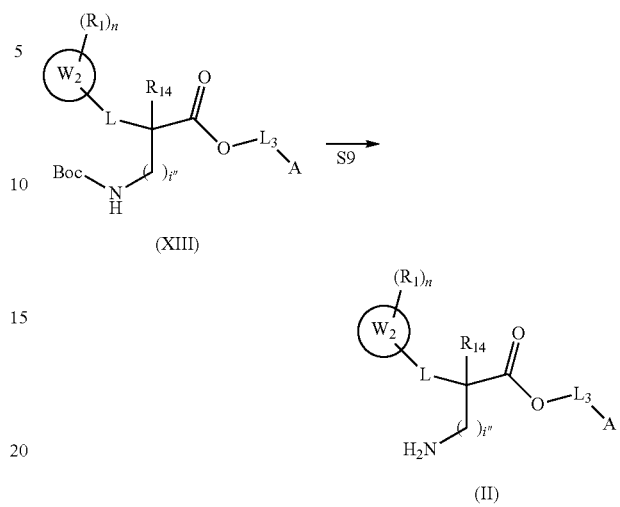

Typical reaction conditions comprise reacting a compound of formula (XIII) in a suitable solvent, such as 1,4-dioxane, in the presence of a suitable acid, such as hydrochloric acid, at an appropriate temperature, such as room (or ambient) temperature.

Compounds of formula (XIII) may be prepared according to Scheme 10/(S10) below by reaction of a compound of formula (XIV) with a compound of formula (X) as below reported.

Scheme 10 (S10)

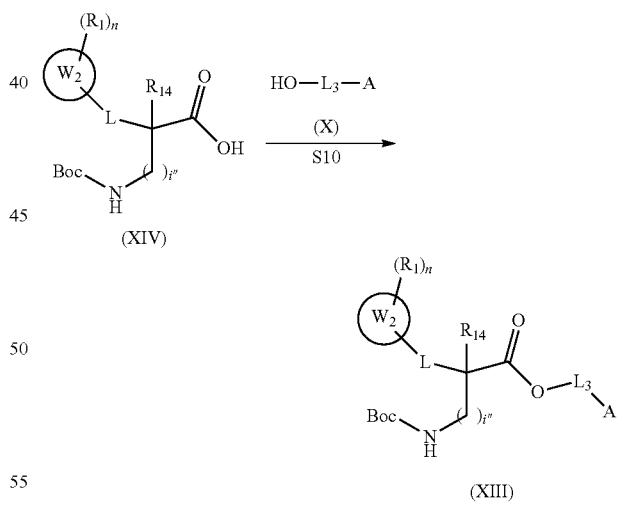

Typical reaction conditions comprise reacting a compound of formula (XIV) with a compound of formula (X) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (XIV) may be prepared according to Scheme 11/(S11) below by reaction of a compound of formula (XV) as below reported.

Scheme 11 (S11)

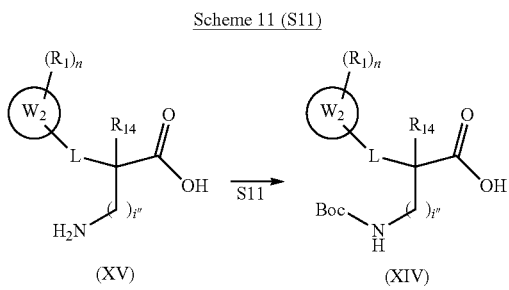

Typical reaction conditions comprise reacting a compound of formula (XII) with di-tert-butyl dicarbonate, in a suitable solvent, such as 1,4-dioxane/water, in the presence of a suitable base such as sodium hydroxide, at an appropriate temperature, such as 0° C. or room (or ambient) temperature.

Compounds of formula (XIII) may also be prepared according to Scheme 12/(S12) below by reaction of a compound of formula (IX) as below reported.

Scheme 12 (S12)

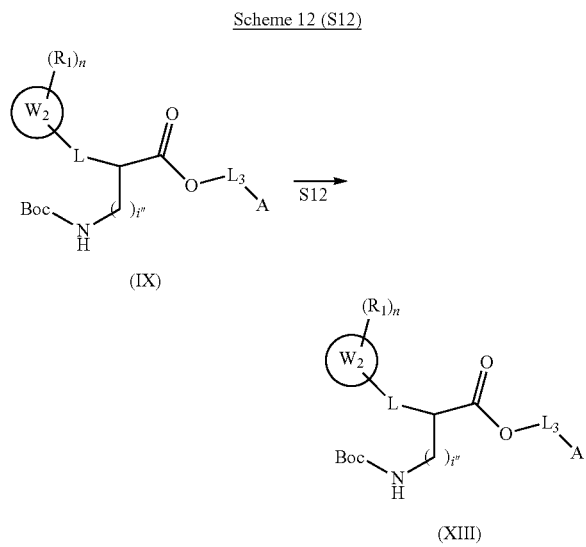

Typical reaction conditions comprise reacting a compound of formula (IX) with an alkylating agent, such as para-formaldehyde, in a suitable solvent, such as THF or 1,4-dioxane, in the presence of a suitable base such as DBU, at an appropriate temperature, such as 0° C. or room (or ambient) temperature.

The processes described are particularly advantageous as they are susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form.

In particular, functional groups which may be present in the intermediate compounds and reactants depicted in Scheme A or Scheme B and which could generate unwanted side reactions and by-products, need to be properly protected before the relevant reaction takes place. Likewise, subsequent deprotection of those same protected groups may follow upon completion of the said reactions.

According to the present invention, unless otherwise indicated, the term "protecting group" designates a protective group (PG) adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known (see, for a general reference, T.W. Green; Protective Groups in Organic Synthesis (Wiley, N.Y. 1999) which is incorporated herein by reference in its entirety).

Likewise, selective protection and deprotection of any of the said groups, for instance including carbonyl, hydroxy or amino groups, may be accomplished according to well-known methods commonly employed in organic synthetic chemistry.

Optional salification of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the invention, including aqueous and non-aqueous solutions, emulsions, suspensions, syrups, and elixirs. Such dosage forms can also contain known suitable inert diluents such as water and known suitable excipients such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, known suitable carriers.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metered aerosols or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (FINE) inhibitors, phosphodiesterase 4 (PDE4) inhibitors, leukotriene modulators, non-steroidal anti-inflammatory agents (NSAIDs) and mucus regulators.

The present invention also provides combinations of a compound of the invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, GSK 870086.

The present invention also provides combinations of a compound of the invention, with an antimuscarinic agent selected from the group consisting of aclidinium, tiotropium, ipratropium, trospium, glycopyrronium and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414 and RPL-554.

The present invention also provides combinations of a compound of the invention, with a P38 MAP kinase inhibitor selected from the group consisting of semapimod, talmapimod, pirfenidone, PH-797804, GSK-725, minokine and losmapimod and salts thereof.

In a preferred embodiment, the present invention provides combinations of a compound of the invention with an IKK2 inhibitor.

The present invention also provides combinations of a compound of the invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The present invention also provides combinations of a compound of the invention with a leukotriene modulator selected from the group consisting of montelukast, zafirlukast, and pranlukast.

The present invention also provides combinations of a compound of the invention with a NSAID selected from the group consisting of ibuprofen and ketoprofen.

The present invention also provides combinations of a compound of the invention with a mucus regulator selected from the group consisting of INS-37217, diquafosol, sibenadet, CS-003, talnetant, DNK-333, MSI-1956, and gefitinib.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

The compounds of the invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behcet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolateroslerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations
-Boc=terbutoxycarbonyl;
-Cbz=Benzyloxycarbonyl;
DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy) methaniminium hexafluorophosphate;
EDC=1-ethyl-3-(3-dimethylaminopropyl) carbodiimide hydrochloride;
DBU=1,8-diazabicyclo[5.4.0]undec-7-ene; DMAP=4-dimethylaminopyridine;
DMF=dimethylformamide;
DMSO=dimethyl sulfoxide;
EtOAc=ethyl acetate;
RT=room temperature;
THF=tetrahydrofuran;
DCM=dichloromethane;
MeOH=methyl alcohol;
EtOH=ethyl alcohol;
LHMDS=lithium bis(trimethylsilyl)amide;
m-CPBA=meta-chloroperoxybenzoic acid;
TFA=trifluoroacetic acid;
LC-MS=liquid chromatography/mass spectrometry;
NMR=nuclear magnetic resonance;
HPLC=high pressure liquid chromatography;
MPLC=medium pressure liquid chromatography;
SFC=supercritical fluid chromatography
General Experimental Details
Analytical Methods
Liquid Chromatography-Mass Spectrometry
Method 1

LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 μm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2

LC-MS was performed on a Waters 2795 Alliance HT HPLC with Waters 2996 Diode Array Detector coupled to a Micromass ZQ, single quadrapole mass spectrometer using a Waters Xterra MS C18 column (5 μm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.
Method 3

UPLC-MS was performed on a Waters Acquity I-Class with Waters Diode Array Detector coupled to a Waters SQD2 single quadrapole mass spectrometer using an Waters HSS C18 column (1.8 μM, 100×2.1 mm) being initially held at 5% acetonitrile/water (with 0.1% formic acid in each mobile phase) for 1.2 minutes, followed by a linear gradient of 5-100% within 3.5 minutes and then held at 100% for 1.5 minutes (F=0.5 mL/min).
Method 4

UPLC-MS was performed on a Waters Acquity I-Class with Waters Diode Array Detector coupled to a Waters SQD2 single quadrapole mass spectrometer using an Waters BEH Shield RP18 column (1.7 μm, 100×2.1 mm) being initially held at 5% acetonitrile/water (with 10 mM ammonium bicarbonate in each mobile phase) for 1.2 minutes, followed by a linear gradient of 5-100% within 3.5 minutes and then held at 100% for 1.5 minutes (F=0.5 mL/min).
Method 24

UPLC-MS was performed on a Waters Acquity I-Class with Waters Diode Array Detector coupled to a Waters SQD2 single quadrapole mass spectrometer using an Waters HSS T3 column (1.8 μm, 100×2.1 mm) being initially held at 5% acetonitrile/water (with 0.1% formic acid in each mobile phase) for 2.5 minutes, followed by a linear gradient of 4-100% within 2.4 minutes and then held at 100% for 0.1 minutes (F=0.5 mL/min).
Supercritical Fluid Chromatography—Mass Spectrometry Analytical Conditions
Method 5

SFC-MS was performed on a Waters/Thar SFC systems with Waters SQD using a Lux Cellulose-4 column with a 35% iso-propyl alcohol/$CO_2$ (with 0.1% diethylamine) isocratic run at 5 mL/min, 120 bar backpressure, 40° C. column temperature.
Method 6

SFC-MS was performed on a Waters/Thar SFC systems with Waters SQD using a Lux Cellulose-4 column with a 50% ethyl alcohol/$CO_2$ (with 0.1% diethylamine) isocratic run at 5 mL/min, 120 bar backpressure, 40° C. column temperature.
Method 7

SFC-MS was performed on a Waters/Thar SFC systems with Waters SQD using a YMC Amylose-C column with a 30% ethyl alcohol/$CO_2$ (with 0.1% diethylamine) isocratic run at 5 mL/min, 120 bar backpressure, 40° C. column temperature.
Method 8

SFC-MS was performed on a Waters/Thar SFC systems with Waters SQD using a YMC Amylose-C column with a 35% ethyl alcohol/$CO_2$ (with 0.1% diethylamine) isocratic run at 5 mL/min, 120 bar backpressure, 40° C. column temperature.
Method 9

SFC-MS was performed on a Waters/Thar SFC systems with Waters SQD using a YMC Amylose-C column with a 40% ethyl alcohol/$CO_2$ (with 0.1% diethylamine) isocratic run at 5 mL/min, 120 bar backpressure, 40° C. column temperature.
Method 10

SFC-MS was performed on a Waters/Thar SFC systems with Waters SQD using a YMC Amylose-C column with a 55% ethyl alcohol/$CO_2$ (with 0.1% diethylamine) isocratic run at 5 mL/min, 120 bar backpressure, 40° C. column temperature.

Method 11

SFC-MS was performed on a Waters/Thar SFC systems with Waters SQD using a YMC Amylose-C column with a 30% iso-propyl alcohol/$CO_2$ (with 0.1% diethylamine) isocratic run at 5 mL/min, 120 bar backpressure, 40° C. column temperature.

Method 12

SFC-MS was performed on a Waters/Thar SFC systems with Waters SQD using a YMC Amylose-C column with a 35% iso-propyl alcohol/$CO_2$ (with 0.1% diethylamine) isocratic run at 5 mL/min, 120 bar backpressure, 40° C. column temperature.

Method 13

SFC-MS was performed on a Waters/Thar SFC systems with Waters SQD using a YMC Amylose-C column with a 40% iso-propyl alcohol/$CO_2$ (with 0.1% diethylamine) isocratic run at 5 mL/min, 120 bar backpressure, 40° C. column temperature.

Method 14

SFC-MS was performed on a Waters/Thar SFC systems with Waters SQD using a YMC Amylose-C column with a 45% iso-propyl alcohol/$CO_2$ (with 0.1% diethylamine) isocratic run at 5 mL/min, 120 bar backpressure, 40° C. column temperature.

Method 15

SFC-MS was performed on a Waters/Thar SFC systems with Waters SQD using a YMC Amylose-C column with a 55% iso-propyl alcohol/$CO_2$ (with 0.1% diethylamine) isocratic run at 5 mL/min, 120 bar backpressure, 40° C. column temperature.

Method 16

SFC-MS was performed on a Waters/Thar SFC systems with Waters SQD using a YMC Cellulose-C column with a 35% ethyl alcohol/$CO_2$ (with 0.1% diethylamine) isocratic run at 5 mL/min, 120 bar backpressure, 40° C. column temperature.

Method 17

SFC-MS was performed on a Waters/Thar SFC systems with Waters SQD using a YMC cellulose-C column with a 30% iso-propyl alcohol/$CO_2$ (with 0.1% diethylamine) isocratic run at 5 mL/min, 120 bar backpressure, 40° C. column temperature.

Method 18

SFC-MS was performed on a Waters/Thar SFC systems with Waters SQD using a Chiralpak IC column with a 55% iso-propyl alcohol/$CO_2$ (with 0.1% diethylamine) isocratic run at 5 mL/min, 120 bar backpressure, 40° C. column temperature.

Method 19

SFC-MS was performed on a Waters/Thar SFC systems with Waters SQD using a Lux Cellulose-C column with a 15% methyl alcohol/$CO_2$ (with 0.1% diethylamine) isocratic run at 5 mL/min, 120 bar backpressure, 40° C. column temperature.

Chiral HPLC-Analytical Conditions

Method 20

Chiral HPLC was performed on an Agilent 1200 series HPLC system using a YMC Amylose-C column with 50% ethyl alcohol/heptane (with 0.1% diethylamine) at 1 mL/min.

Method 21

Chiral HPLC was performed on an Agilent 1200 series HPLC system using a YMC Amylose-C column with 50% iso-propyl alcohol/heptane (with 0.1% diethylamine) at 1 mL/min.

Method 22

Chiral HPLC was performed on an Agilent 1200 series HPLC system using a YMC Cellulose-C column with 50% iso-propyl alcohol/heptane (with 0.1% diethylamine) at 1 mL/min.

Method 23

Chiral HPLC was performed on an Agilent 1200 series HPLC system using a YMC Cellulose-C column with 30% iso-propyl alcohol/heptane (with 0.1% diethylamine) at 1 mL/min.

NMR $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector.

The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column.

Appropriate focused gradients were selected based on acetonitrile and methanol solvent systems under either acidic or basic conditions.

The modifiers used under acidic/basic conditions were formic acid or trifluoroacetic acid (0.1% V/V) and ammonium bicarbonate (10 mM) respectively.

The purification was controlled by Waters Fractionlynx software through monitoring at 210-400 nm, and triggered a threshold collection value at 260 nm and, when using the Fractionlynx, the presence of target molecular ion as observed under API conditions. Collected fractions were analysed by LCMS (Waters Acquity systems with Waters SQD).

Chiral Separation Protocol

The diastereomeric separation of compounds was achieved either by chiral High Performance Liquid Chromatography (HPLC) using a Gilson Trilution preparative HPLC system (322 pump, 155 UVNIS, GX281 liquid handler and fraction collector) or by Supercritical Fluid Chromatography (SFC) using a Waters Thar Prep100 preparative SFC system (P200 $CO_2$ pump, 2545 modifier pump, 2998 UVNIS detector, 2767 liquid handler with Stacked Injection Module). The Waters 2767 liquid handler acted as both auto-sampler and fraction collector.

The column used for the preparative purification of the compounds was a Diacel Chiralpak IA/IB/IC, a Phenomenex Lux Cellulose-4, an YMC Amylose-C or an YMC Cellulose-C at 5 μm 250×20–21.2 mm ID.

Appropriate isocratic methods were selected based on methanol, ethanol or isopropanol solvent systems under un-modified or basic conditions.

The standard SFC method used was modifier, CO₂, 100 mL/min, 120 Bar backpressure, 40° C. column temperature. The standard HPLC method used was modifier, heptane, 5 mL/min and room temperature.

The modifier used under basic conditions was diethylamine (0.1% V/V). The modifier used under acidic conditions was either formic acid (0.1% V/V) or trifluoroacetic acid (0.1% V/V).

The SFC purification was controlled by Waters Fractionlynx software through monitoring at 210-400 nm and triggered at a threshold collection value, typically 260 nm. Collected fractions were analysed by SFC (Waters/Thar SFC systems with Waters SQD). The fractions that contained the desired product were concentrated by vacuum centrifugation.

HPLC purification was controlled by Gilson Trilution software monitoring two wavelengths and triggered at a threshold collection value, typically 260 nm. Collected fractions were analysed by HPLC (Agilent 1200 series HPLC system). The fractions that contained the desired product were concentrated by vacuum centrifugation.

Compounds Preparation

Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Flash chromatography refers to silica gel chromatography and is carried out using an Isolera MPLC system (manufactured by Biotage); pre-packed silica gel cartridges (supplied by Biotage); or using conventional glass column chromatography.

In the procedures that follow, after each starting material, reference to a compound number may be provided. This is provided merely for assistance to the skilled chemist. The starting material may not necessarily have been prepared from the batch referred to.

Many of the compounds described in the following Examples have been prepared from stereochemically pure starting materials, for example 95% enantiomeric excess (ee).

The stereochemistry of the compounds in the Examples, where indicated, has been assigned on the assumption that absolute configuration at resolved stereogenic centers of starting materials is maintained throughout any subsequent reaction conditions. Compounds of general formula (I) that were isolated as single diastereoisomers whose absolute configuration at the stereogenic center at the carbon atom of group X was not determined, are herebelow and above referred to as Single Diastereoisomers without mention in their chemical name of absolute configuration (S) or (R) for the unassigned stereogenic center.

The term epimeric mixture herewith refers to a mixture of two diastereoisomers that are resolved (separated and isolated) at the chiral center (1) without assignment of the absolute configuration, and are not resolved at the chiral center in the group X.

Intermediate 1

[(1S)-2-(3,5-Dichloro-1-oxido-pyridin-1-ium-4-yl)-1-(3,4-dimethoxyphenyl)ethyl]5-formylthiophene-2-carboxylate

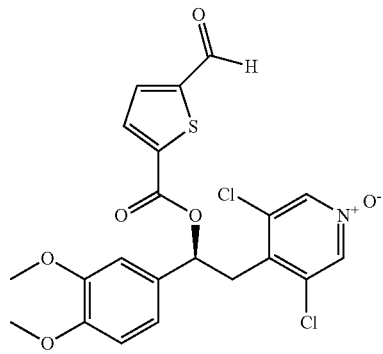

To a stirred solution of 5-formyl-2-thiophenecarboxylic acid (400 mg, 2.56 mmol) in DCM (20 mL) was added (1S)-2-(3,5-dichloro-1-oxido-pyridin-1-ium-4-yl)-1-(3,4-dimethoxyphenyl)ethanol, obtained as described in the co-pending international application WO 2014/086849, which is incorporated herein by reference in its entirety, page 58 (881 mg, 2.56 mmol) followed by 4-(dimethylamino)-pyridine (156 mg, 1.28 mmol) and N-(3-dimethylaminopropyl)-N'-ethylcarbodiimide hydrochloride (983 mg, 5.12 mmol). The resulting mixture was stirred at room temperature for 18 hours. The reaction was partitioned between DCM and saturated aqueous sodium bicarbonate solution. The organic layer was washed with brine, passed through a hydrophobic fit and the solvent was removed in vacuo. The crude material was purified by silica gel column chromatography, eluting with 0-100% EtOAc in DCM, to afford the title compound (488 mg, 39%) as yellow oil.

¹H NMR (400 MHz, CDCl3): δ 9.97 (s, 1 H), 8.15 (s, 2 H), 7.81 (d, J=3.6 Hz, 1 H), 7.72 (d, J=3.6 Hz, 1 H), 7.03-6.99 (m, 2 H), 6.87 (d, J=8.7 Hz, 1 H), 6.26 (dd, J=4.4, 10.0 Hz, 1 H), 3.91 (s, 3 H), 3.88 (s, 3 H), 3.72 (dd, J=10.0, 14.0 Hz, 1 H), 3.33 (dd, J=4.4, 14.0 Hz, 1 H). LCMS (Method 2): [MH+]=482 at 3.38 min.

The following intermediates were synthesized via the same procedure by reacting the suitable carboxylic acid intermediate, commercially available, with the suitable alcohol intermediate, obtained as described in the co-pending international application WO 2014/086849, which is incorporated herein by reference in its entirety, pages 62-75.

| Structure | Intermediate number | Analytical Data |
|---|---|---|
| 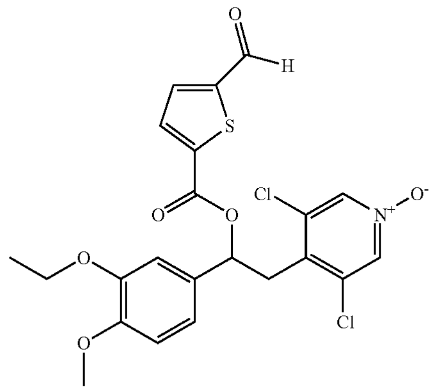 [SMILES: CCOc1cc(C(Cc2c(Cl)c[n+]([O-])cc2Cl)OC(=O)c2ccc(C=O)s2)ccc1OC] | Intermediate 2 | LCMS (Method 1): [MH+] = 496 at 3.71 min. |
| 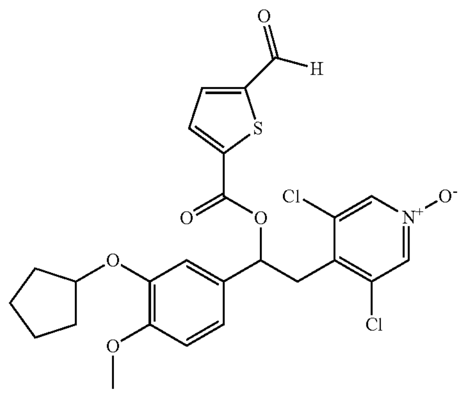 [SMILES: COc1ccc(C(Cc2c(Cl)c[n+]([O-])cc2Cl)OC(=O)c2ccc(C=O)s2)cc1OC1CCCC1] | Intermediate 3 | LCMS (Method 1): [MH+] = 536 at 4.15 min |
| 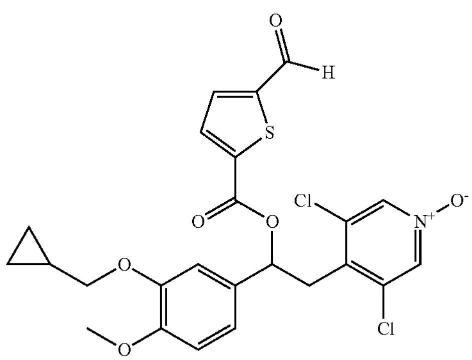 [SMILES: COc1ccc(C(Cc2c(Cl)c[n+]([O-])cc2Cl)OC(=O)c2ccc(C=O)s2)cc1OCC1CC1] | Intermediate 4 | LCMS (Method 1): [MH+] = 522 at 3.95 min. |
| 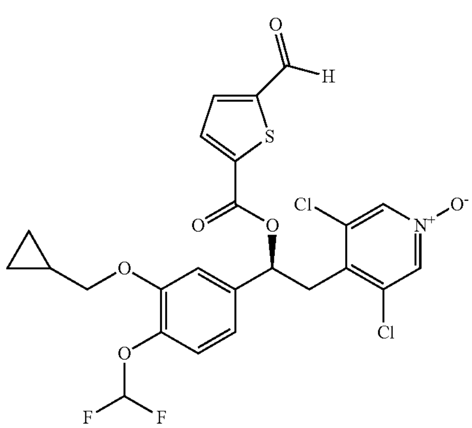 [SMILES: O=Cc1ccc(C(=O)O[C@@H](Cc2c(Cl)c[n+]([O-])cc2Cl)c2ccc(OC(F)F)c(OCC3CC3)c2)s1] | Intermediate 5 | LCMS (Method 1): [MH+] = 558 at 4.17 min. |

-continued

| Structure | Intermediate number | Analytical Data |
|---|---|---|
| (structure of Intermediate 6) | Intermediate 6 | LCMS (Method 1): [MH+] = 482 at 3.52 min. |

The following intermediates were obtained by SFC purification of the appropriate racemic mixture hereabove described:

| Structure | Intermediate number | Analytical Data |
|---|---|---|
| (structure) Enantiomer 1 of Intermediate 2 | Intermediate 7 | LCMS (Method 1): [MH+] = 496 at 3.27 min. SFC/MS (Method 5): [MH + NHEt$_2$]$^+$ = 569 at 6.10 min. |
| (structure) Enantiomer 2 of Intermediate 2 | Intermediate 8 | LCMS (Method 1): [MH+] = 496 at 3.71 min. SFC/MS (Method 5): [MH + NHEt$_2$]$^+$ = 569 at 7.70 min. |

-continued

| Structure | Intermediate number | Analytical Data |
|---|---|---|
| 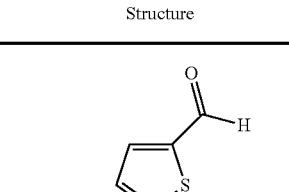<br>Enantiomer 1 of Intermediate 3 | Intermediate 9 | LCMS (Method 1): [MH+] = 536 at 4.15 min.<br>SFC/MS (Method 17): [MH + NHEt$_2$]$^+$ = 609 at 3.84 min. |
| Enantiomer 2 of Intermediate 3 | Intermediate 10 | LCMS (Method 1): [MH+] = 536 at 4.15 min.<br>SFC/MS (Method 17): [MH + NHEt$_2$]$^+$ = 609 at 4.62 min. |
| Enantiomer 1 of Intermediate 4 | Intermediate 11 | LCMS (Method 2): [MH+] = 522 at 3.26 min.<br>SFC/MS (Method 18): [MH + NHEt$_2$]$^+$ = 595 at 7.10 min. |

| Structure | Intermediate number | Analytical Data |
|---|---|---|
| 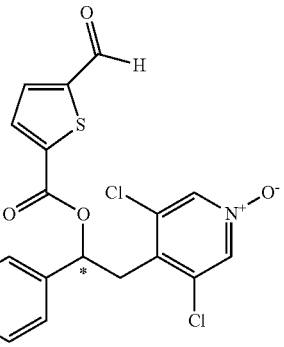<br>Enantiomer 2 of Intermediate 4 | Intermediate 12 | LCMS (Method 2): [MH+] = 522 at 3.26 min.<br>SFC/MS (Method 18): [MH + NHEt$_2$]$^+$ = 595 at 9.00 min. |

Intermediate 94

(1S)-2-(3,5-dichloro-1-oxido-pyridin-1-ium-4-yl)-1-[4-(difluoromethoxy)-3-(2-methoxyethoxy)phenyl]ethanol

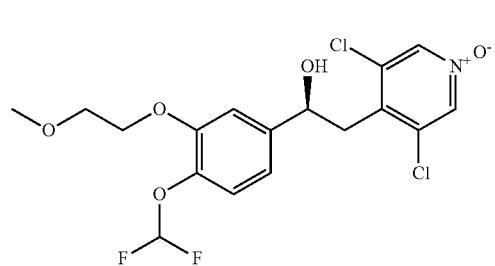

5-[(1S)-2-(3,5-dichloro-1-oxido-pyridin-1-ium-4-yl)-1-hydroxy-ethyl]-2-(difluoromethoxy)phenol (I-32/I from US2014155427A1, which is incorporated herein by reference in its entirety) (1.0 g, 2.74 mmol) was dissolved in DMF (10 mL). KI (454 mg, 2.74 mmol), K$_2$CO$_3$ (567 mg, 4.11 mmol) and 1-bromo-2-methoxyethane (0.51 mL, 5.48 mmol) were then added. The dark brown slurry was stirred at room temperature for 18 hours before being diluted with EtOAc and water (1:1, 50 mL). The layers were separated and the organic phase dried over magnesium sulfate, filtered and the solvent removed in vacuo. The residue was purified by silica gel column chromatography, eluting with 0-20% MeOH in EtOAc to afford the title compound (535 mg, 46%) as a white solid.

$^1$H NMR (400 MHz, CDCl$_3$): δ 8.10 (s, 2 H), 7.15-7.09 (m, 2 H), 6.91 (dd, J=1.9, 8.2 Hz, 1 H), 6.62 (t, J=75.3 Hz, 1 H), 5.05-4.99 (m, 1 H), 4.20-4.15 (m, 2 H), 3.76 (dd, J=4.7, 4.7 Hz, 2 H), 3.43 (s, 3 H), 3.35 (dd, J=8.9, 13.4 Hz, 1 H), 3.12 (dd, J=4.8, 13.7 Hz, 1 H), OH not observed. LCMS [(Method 3)]: [MH+]=424 at 2.92 min.

Intermediate 95

[(1S)-2-(3,5-dichloro-1-oxido-pyridin-1-ium-4-yl)-1-[4-(difluoromethoxy)-3-(2-methoxyethoxy)phenyl]ethyl]5-formylthiophene-2-carboxylate

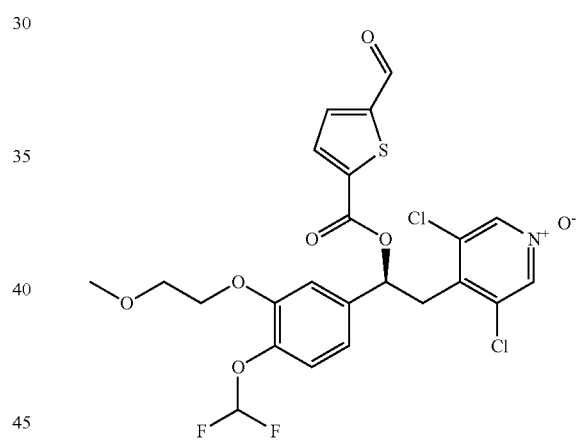

A stirred solution of 5-formyl-2-thiophenecarboxylic acid (179 mg, 1.15 mmol) in DCM (20 mL) was added with (1S)-2-(3,5-dichloro-1-oxido-pyridin-1-ium-4-yl)-1-[4-(difluoromethoxy)-3-(2-methoxyethoxy)phenyl]ethanol (535 mg, 1.26 mmol) followed by 4-(dimethylamino)-pyridine (70 mg, 0.58 mmol) and N-(3-dimethylaminopropyl)-N'-ethylcarbodiimide hydrochloride (330 mg, 1.72 mmol). The resulting mixture was stirred at room temperature for 18 hours. The reaction was partitioned between DCM and saturated aqueous sodium bicarbonate solution. The organic layer was washed with brine, passed through a hydrophobic frit and the solvent was removed in vacuo. The crude material was purified by silica gel column chromatography, eluting with 0-100% EtOAc in DCM, to afford the title compound (495 mg, 77%) as a white solid.

$^1$H NMR (400 MHz, CDCl$_3$): δ 9.98 (s, 1 H), 8.15 (s, 2 H), 7.82 (d, J=3.8 Hz, 1 H), 7.72 (d, J=4.0 Hz, 1 H), 7.19 (d, J=8.3 Hz, 1 H), 7.11 (d, J=1.8 Hz, 1 H), 7.05 (dd, J=2.0, 8.1 Hz, 1 H), 6.62 (t, J=74.8 Hz, 1 H), 6.24 (dd, J=4.3, 10.1 Hz, 1 H), 4.23 (dd, J=4.6, 10.3 Hz, 1 H), 4.18 (dd, J=4.6, 10.3

Hz, 1 H), 3.77 (t, J=4.7 Hz, 2 H), 3.68 (dd, J=10.4, 14.0 Hz, 1 H), 3.44 (s, 3 H), 3.31 (dd, J=4.3, 14.1 Hz, 1 H). LCMS [(Method 3)]: [MH+]=563 at 3.29 min.

Intermediate 13

[(3R)-1-methyl-3-piperidyl]methanol

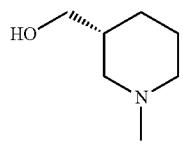

A solution of tert-butyl (3R)-3-(hydroxymethyl)piperidine-1-carboxylate (1.07 g, 4.98 mmol) in dry THF (10 mL) was stirred under $N_2$ and cooled in an ice-water bath. A 2 M solution of $LiAlH_4$ in THF (3.0 mL, 5.97 mmol) was added dropwise over a period of 10 minutes. The mixture was stirred at 0° C. and gradually allowed to warm to room temperature over 3 hours. After stirring at room temperature overnight the mixture was cooled in an ice-bath and a 1 N solution of NaOH (1 mL) was added dropwise over a period of 10 minutes followed by water (0.5 mL). The mixture was stirred at room temperature for 3 hours, filtered through a Celite® cartridge which was then washed through with THF and the combined filtrates were concentrated in vacuo to give the title product as a yellow oil (0.61 g, 95%).

LCMS (Method 2): [MH+]=130 at 0.69 min

The following intermediates were synthesized via the same procedure.

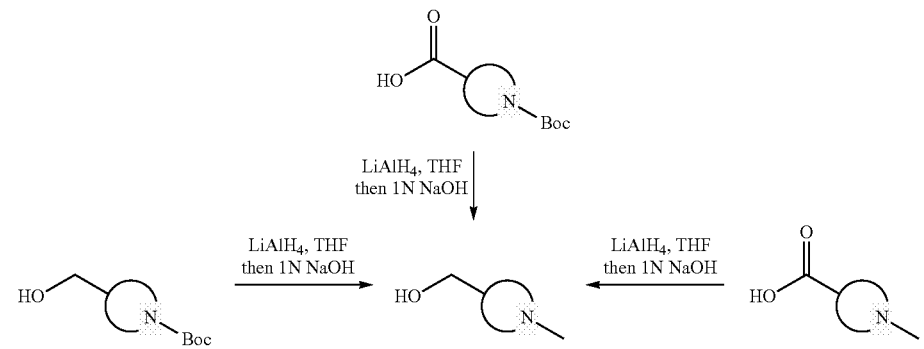

| Structure | Intermediate number | Precursor | Analytical Data |
|---|---|---|---|
| HO—⧗⟨N⟩ | Intermediate 14 | tert-butyl 3-(hydroxymethyl)azetidine-1-carboxylate | LCMS (Method 1): [MH+] = 102 at 1.66 min |
| HO—⧗⟨N⟩ | Intermediate 15 | tert-butyl (3S)-3-(hydroxymethyl)piperidine-1-carboxylate | LCMS (Method 1): [MH+] = 130 at 1.90 min |
| HO—⧗⟨N⟩ | Intermediate 16 | (2R)-1-tert-butoxycarbonylazetidine-2-carboxylic acid | LCMS (Method 2): [MH+] = 102 at 0.71 min |
| HO—⧗⟨N⟩ | Intermediate 17 | (2S)-1-tert-butoxycarbonylazetidine-2-carboxylic acid | LCMS (Method 2): [MH+] = 102 at 0.66 min |
| HO—⧗⟨N⟩ | Intermediate 18 | (2R)-1,4-bis(tert-butoxycarbonyl)piperazine-2-carboxylic acid | LCMS (Method 2): [MH+] = 145 at 0.70 min |

| Structure | Intermediate number | Precursor | Analytical Data |
|---|---|---|---|
| (structure: HO-CH2-piperidine-N-Me, 2R) | Intermediate 19 | (2R)-1-tert-butoxycarbonylpiperidine-2-carboxylic acid | LCMS (Method 1): [MH+] = 130 at 0.66 min |
| (structure: HO-CH2-piperidine-N-Me) | Intermediate 20 | 1-methylpiperidine-2-carboxylic acid hydrochloride | LCMS (Method 1): [MH+] = 130 at 0.60 min |
| (structure: HO-CH2-piperazine-N,N-diMe, 2S) | Intermediate 21 | di-tert-butyl (2S)-2-(hydroxymethyl)piperazine-1,4-dicarboxylate | LCMS (Method 3): [MH+] = 145 at 0.43 min |
| (structure: HO-CH2-8-methyl-8-azabicyclo[3.2.1]octane, 1R,5S) | Intermediate 96 | (1R,5S)-8-tert-butoxycarbonyl-8-azabicyclo[3.2.1]octane-3-carboxylic acid | LCMS (Method 24): [MH+] = 156 at 0.56 min |

Intermediate 22 and Intermediate 23

[(3S)-quinuclidin-3-yl]methanol (I-22) and [(3R)-quinuclidin-3-yl]methanol (I-23)

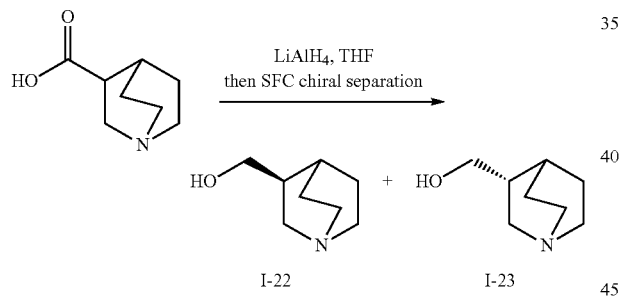

A solution of quinuclidine-3-carboxylic acid (665 mg, 4.28 mmol) in dry THF (7 mL) was stirred under $N_2$ and cooled in an ice-water bath. A 2 M solution of $LiAlH_4$ in $Et_2O$ (4.3 mL, 8.56 mmol) was added dropwise over a period of 10 minutes. The mixture was stirred in an ice bath for one hour then allowed to warm to room temperature and stirred for 72 hours. The mixture was cooled in an ice-bath and a 1 N solution of NaOH (1 mL) was added dropwise over a period of 10 minutes followed by water (0.5 mL). The mixture was stirred at room temperature for one hour and then filtered through a Celite® cartridge which was then washed through with a small amount of THF and water. The combined filtrates were concentrated in vacuo to give a racemic mixture of the title product as a colourless oil. (792 mg, 76%).

LCMS (Method 2): [MH+]=142 at 0.60 min.

Purification of the mixture of enantiomers by chiral preparative SFC afforded the single enantiomer.

Title compound (Intermediate 22, single enantiomer 1) was obtained as a light brown gum (235 mg, 59%). LCMS (Method 4): [MH+]=142 at 0.62 min. Chiral analysis (Method 19) at 9.56 min. $[\alpha]_D^{20}$=−51.17° (c=0.3 g/100 mL, $CH_3OH$).

Title compound (intermediate 23, single enantiomer 2) was obtained as a light brown gum (203 mg, 51%). LCMS (Method 4): [MH+]=142 at 0.61 min. Chiral analysis (Method 19) at 11.28 min. $[\alpha]_D^{20}$=+36.33° (c=0.3 g/100 mL, $CH_3OH$).

Intermediate 24

2-(tert-butoxycarbonylamino)-2-phenyl-propanoic acid

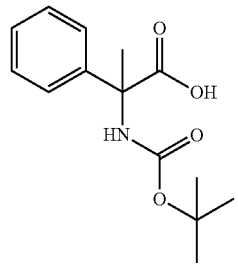 [SMILES: CC(C)(C)OC(=O)NC(C)(C(=O)O)c1ccccc1]

To a stirred mixture of 2-amino-2-phenylpropanoic acid (1.03 g, 6.24 mmol) and di-tert-butyl dicarbonate (1.63 g, 7.40 mmol) in 1,4-dioxane (35 mL) was added $Et_3N$ (1.74 mL, 12.48 mmol) and the resulting white suspension was stirred at room temperature overnight. Saturated aqueous $NaHCO_3$ solution (30 mL) was added followed by additional di-tert-butyl dicarbonate (1.42 g, 6.51 mmol) and the mixture was stirred at room temperature for 24 hours. The reaction mixture was acidified to pH 4 with 1 N HCl and extracted with EtOAc (3×100 mL), the combined organic extracts were filtered through a phase separator and the solvent was removed in vacuo to give the title compound as a colourless gum (990 mg, 60%). The aqueous phase was saturated with NaCl and further extracted with EtOAc (2×75 mL). The combined organic extracts were filtered through a phase separator and the solvent was removed in vacuo to give a second batch of the title compound as a white gum (600 mg, 36%).

LCMS (Method 2): [MH⁻]=264 at 2.45 min.

Intermediate 25

[(3R)-1-methyl-3-piperidyl]methyl-2-(tert-butoxycarbonylamino)-2-phenyl-acetate

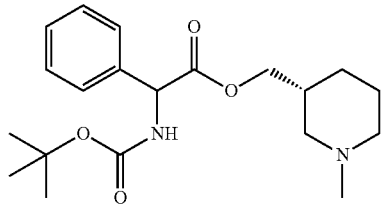 [SMILES: CN1CCC[C@@H](COC(=O)C(NC(=O)OC(C)(C)C)c2ccccc2)C1]

A mixture of 2-((tert-butoxycarbonyl)amino)-2-phenylacetic acid (0.5 g, 2.0 mmol), N,N-dicyclohexylcarbodiimide (0.82 g, 3.98 mmol) and 1-hydroxybenzotriazole hydrate (0.54 g, 3.98 mmol) in THF (10 mL) was stirred at room temperature. After one hour a solution of [(3R)-1-methyl-3-piperidyl]methanol (0.51 g, 3.98 mmol) in THF (5 mL) was added and the mixture was stirred at room temperature for 72 hours. The reaction mixture was filtered through a pad of Celite® and concentrated in vacuo. The residue was taken up into EtOAc (30 mL) and washed with 2 M aqueous sodium carbonate solution (2×30 mL), then with brine (30 mL). The organic phase was collected, filtered through a phase separator and the solvent was removed in vacuo to give the title compound as a pale yellow gum (716 mg, 99%).

LCMS (Method 1): [MH+]=363 at 2.57 min.

The following intermediates were synthesized via the same procedure.

| Structure | Intermediate number | Precursor | Analytical Data |
|---|---|---|---|
| 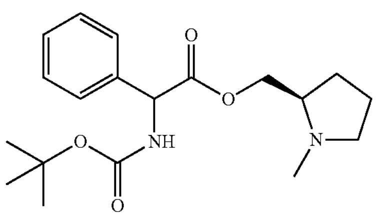 [SMILES: CN1CCC[C@@H]1COC(=O)C(NC(=O)OC(C)(C)C)c1ccccc1] | Intermediate 26 | 2-((tert-butoxycarbonyl)amino)-2-phenylacetic acid and [(2R)-1-methylpyrrolidin-2-yl]methanol | LCMS (Method 2): [MH+] = 349 at 3.21 min. |
| 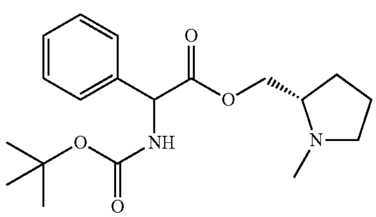 [SMILES: CN1CCC[C@H]1COC(=O)C(NC(=O)OC(C)(C)C)c1ccccc1] | Intermediate 27 | 2-((tert-butoxycarbonyl)amino)-2-phenylacetic acid and [(2S)-1-methylpyrrolidin-2-yl]methanol | LCMS (Method 1): [MH+] = 349 at 2.50 min. |
| 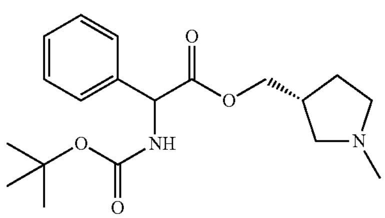 [SMILES: CN1CC[C@@H](COC(=O)C(NC(=O)OC(C)(C)C)c2ccccc2)C1] | Intermediate 28 | 2-((tert-butoxycarbonyl)amino-2-phenylacetic acid and [(3R)-1-methylpyrrolidin-3-yl]methanol | LCMS (Method 1): [MH+] = 349 at 2.50 min. |
| 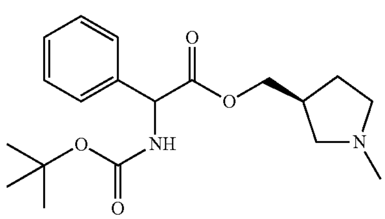 [SMILES: CN1CC[C@H](COC(=O)C(NC(=O)OC(C)(C)C)c2ccccc2)C1] | Intermediate 29 | 2-((tert-butoxycarbonyl)amino)-2-phenylacetic acid and [(3S)-1-methylpyrrolidin-3-yl]methanol | LCMS (Method 3): [MH+] = 349 at 2.63 min. |

-continued

| Structure | Intermediate number | Precursor | Analytical Data |
|---|---|---|---|
| 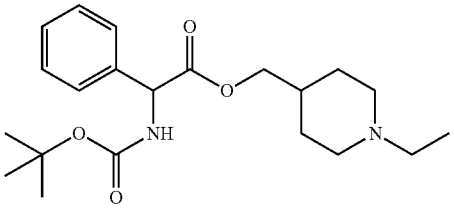 [SMILES: CCN1CCC(COC(=O)C(NC(=O)OC(C)(C)C)c2ccccc2)CC1] | Intermediate 30 | 2-((tert-butoxycarbonyl)amino)-2-phenylacetic acid and (1-ethyl-4-piperidyl)methanol | LCMS (Method 4): [MH+] = 377 at 3.19 min. |
| 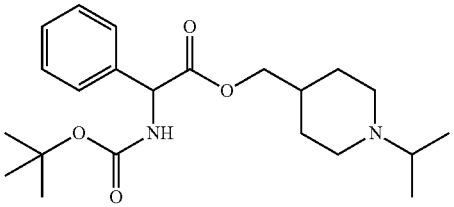 [SMILES: CC(C)N1CCC(COC(=O)C(NC(=O)OC(C)(C)C)c2ccccc2)CC1] | Intermediate 31 | 2-((tert-butoxycarbonyl)amino)-2-phenylacetic acid and (1-isopropyl-4-piperidyl)methanol | LCMS (Method 4): [MH+] = 391 at 3.16 min. |
| 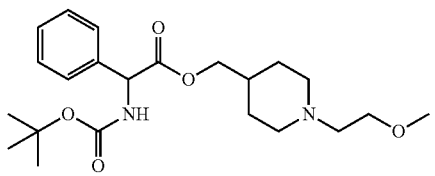 [SMILES: COCCN1CCC(COC(=O)C(NC(=O)OC(C)(C)C)c2ccccc2)CC1] | Intermediate 32 | 2-((tert-butoxycarbonyl)amino)-2-phenylacetic acid and [1-(2-methoxyethyl)-4-piperidyl]methanol | LCMS (Method 3): [MH+] = 407 at 2.80 min. |
| 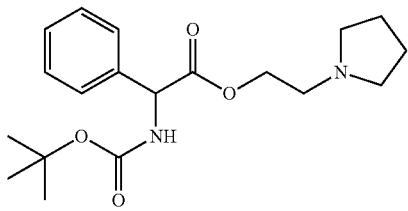 [SMILES: CC(C)(C)OC(=O)NC(C(=O)OCCN1CCCC1)c1ccccc1] | Intermediate 33 | 2-((tert-butoxycarbonyl)amino)-2-phenylacetic acid and 2-pyrrolidin-1-ylethanol | LCMS (Method 2): [MH+] = 349 at 3.19 min. |
| 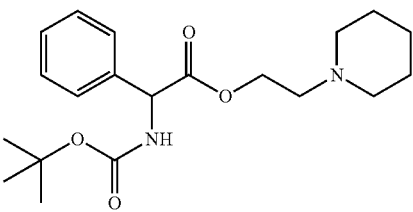 [SMILES: CC(C)(C)OC(=O)NC(C(=O)OCCN1CCCCC1)c1ccccc1] | Intermediate 34 | 2-((tert-butoxycarbonyl)amino)-2-phenylacetic acid and 2-(1-piperidyl)ethanol | LCMS (Method 2): [MH+] = 363 at 3.46 min. |
| 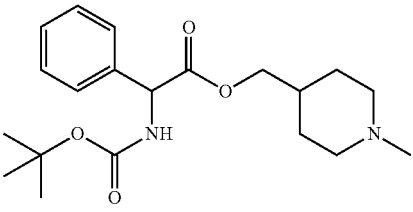 [SMILES: CN1CCC(COC(=O)C(NC(=O)OC(C)(C)C)c2ccccc2)CC1] | Intermediate 35 | 2-((tert-butoxycarbonyl)amino)-2-phenylacetic acid and (1-methyl-4-piperidyl)-methanol | LCMS (Method 1): [MH+] = 363 at 2.54 min. |
| 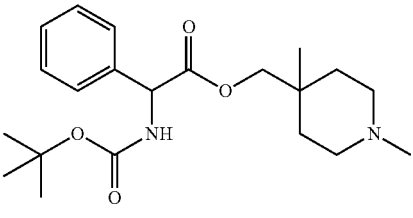 [SMILES: CN1CCC(C)(COC(=O)C(NC(=O)OC(C)(C)C)c2ccccc2)CC1] | Intermediate 36 | 2-((tert-butoxycarbonyl)amino)-2-phenylacetic acid and (1,4-dimethyl-4-piperidyl)methanol | LCMS (Method 2): [MH+] = 377 at 3.68 min. |

-continued

| Structure | Intermediate number | Precursor | Analytical Data |
|---|---|---|---|
| 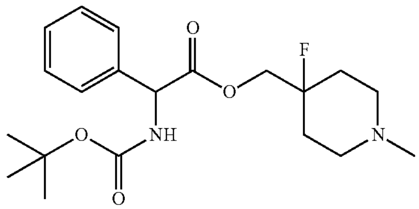 | Intermediate 37 | 2-((tert-butoxycarbonyl)amino-2-phenylacetic acid and (4-fluoro-1-methyl-4-piperidyl)methanol | LCMS (Method 2): [MH+] = 381 at 3.65 min. |
| 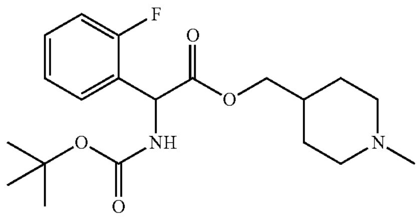 [SMILES: CN1CCC(COC(=O)C(NC(=O)OC(C)(C)C)c2ccccc2F)CC1] | Intermediate 38 | 2-(tert-butoxycarbonylamino)-2-(2-fluorophenyl)-acetic acid and (1-methyl-4-piperidyl)-methanol | LCMS (Method 1): [MH+] = 381 at 2.57 min. |
| 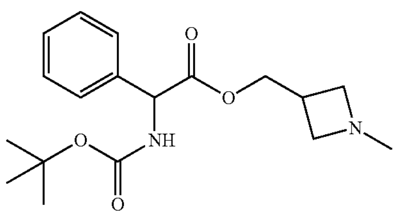 [SMILES: CN1CC(COC(=O)C(NC(=O)OC(C)(C)C)c2ccccc2)C1] | Intermediate 39 | 2-((tert-butoxycarbonyl)amino)-2-phenylacetic acid and Intermediate 14 | LCMS (Method 2): [MH+] = 335 at 2.63 min. |
| 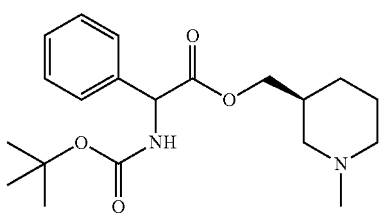 | Intermediate 40 | 2-((tert-butoxycarbonyl)amino)-2-phenylacetic acid and Intermediate 15 | LCMS (Method 2): [MH+] = 363 at 3.06 min. |
| 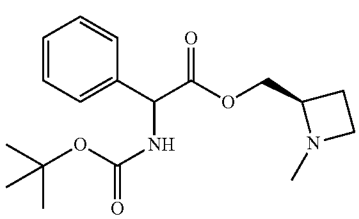 [SMILES: CN1CC[C@@H]1COC(=O)C(NC(=O)OC(C)(C)C)c1ccccc1] | Intermediate 41 | 2-((tert-butoxycarbonyl)amino)-2-phenylacetic acid and Intermediate 16 | LCMS (Method 1): [MH+] = 335 at 2.47 min. |
| 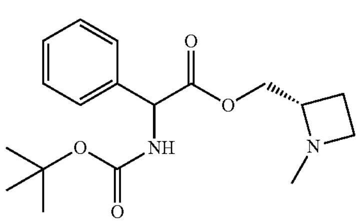 [SMILES: CN1CC[C@H]1COC(=O)C(NC(=O)OC(C)(C)C)c1ccccc1] | Intermediate 42 | 2-((tert-butoxycarbonyl)amino)-2-phenylacetic acid and Intermediate 17 | LCMS (Method 2): [MH+] = 335 at 3.50 min. |
| 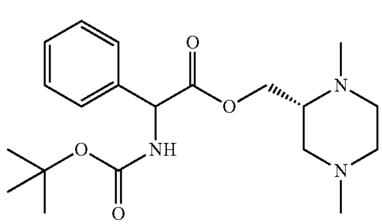 [SMILES: CN1CCN(C)[C@@H](COC(=O)C(NC(=O)OC(C)(C)C)c2ccccc2)C1] | Intermediate 43 | 2-((tert-butoxycarbonyl)amino)-2-phenylacetic acid and Intermediate 18 | LCMS (Method 1): [MH+] = 378 at 2.44 min. |

-continued

| Structure | Intermediate number | Precursor | Analytical Data |
|---|---|---|---|
| 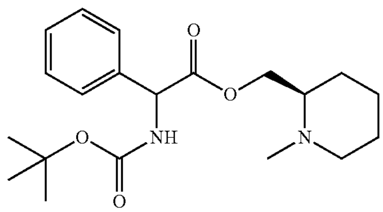 [SMILES: CN1CCCC[C@@H]1COC(=O)C(NC(=O)OC(C)(C)C)c1ccccc1] | Intermediate 44 | 2-((tert-butoxycarbonyl)amino)-2-phenylacetic acid and Intermediate 19 | LCMS (Method 1): [MH+] = 363 at 2.53 min. |
| 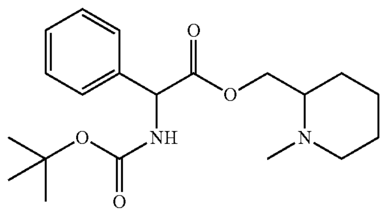 [SMILES: CN1CCCCC1COC(=O)C(NC(=O)OC(C)(C)C)c1ccccc1] | Intermediate 45 | 2-((tert-butoxycarbonyl)amino)-2-phenylacetic acid and Intermediate 20 | LCMS (Method 1): [MH+] = 363 at 2.53 min. |
| 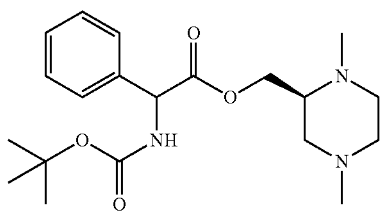 [SMILES: CN1CCN(C)[C@H](COC(=O)C(NC(=O)OC(C)(C)C)c2ccccc2)C1] | Intermediate 46 | 2-((tert-butoxycarbonyl)amino)-2-phenylacetic acid and Intermediate 21 | LCMS (Method 4): [MH+] = 378 at 3.01 min. |
| 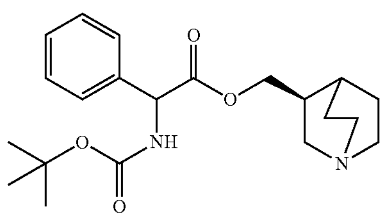 [SMILES: CC(C)(C)OC(=O)NC(C(=O)OC[C@@H]1CN2CCC1CC2)c1ccccc1] | Intermediate 47 | 2-((tert-butoxycarbonyl)amino)-2-phenylacetic acid and Intermediate 22 | LCMS (Method 4): [MH+] = 375 at 3.06 min. |
| 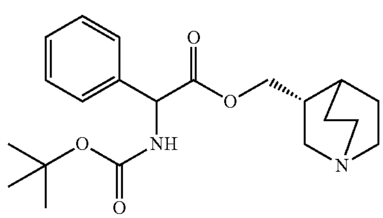 [SMILES: CC(C)(C)OC(=O)NC(C(=O)OC[C@H]1CN2CCC1CC2)c1ccccc1] | Intermediate 48 | 2-((tert-butoxycarbonyl)amino)-2-phenylacetic acid and Intermediate 23 | LCMS (Method 4): [MH+] = 375 at 3.07 min. |
| 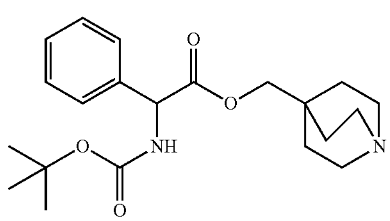 [SMILES: CC(C)(C)OC(=O)NC(C(=O)OCC12CCN(CC1)CC2)c1ccccc1] | Intermediate 49 | 2-((tert-butoxycarbonyl)amino)-2-phenylacetic acid and quinuclidin-4-ylmethanol | LCMS (Method 1): [MH+] = 375 at 2.56 min. |
| 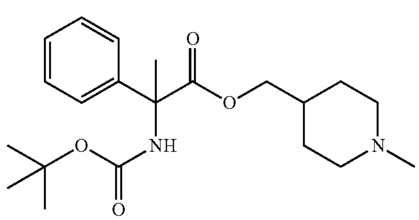 [SMILES: CN1CCC(COC(=O)C(C)(NC(=O)OC(C)(C)C)c2ccccc2)CC1] | Intermediate 50 | Intermediate 24 and (1-methyl-4-piperidyl)-methanol | LCMS (Method 1): [MH+] = 377 at 2.61 min. |

-continued

| Structure | Intermediate number | Precursor | Analytical Data |
|---|---|---|---|
| 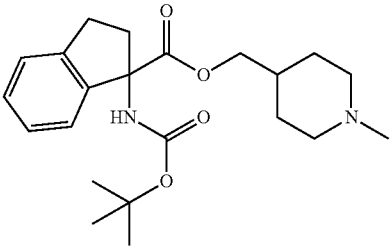 [SMILES: CN1CCC(COC(=O)C2(NC(=O)OC(C)(C)C)CCc3ccccc32)CC1] | Intermediate 51 | 1-(tert-butoxycarbonylamino) indane-1-carboxylic acid and (1-methyl-4-piperidyl)-methanol | LCMS (Method 2): [MH+] = 389 at 3.04 min. |
| 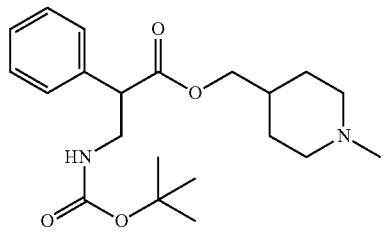 [SMILES: CN1CCC(COC(=O)C(CNC(=O)OC(C)(C)C)c2ccccc2)CC1] | Intermediate 52 | 3-(tert-butoxycarbonylamino)-2-phenyl-propanoic acid and (1-methyl-4-piperidyl)-methanol | LCMS (Method 1): [MH+] = 377 at 2.58 min. |
| 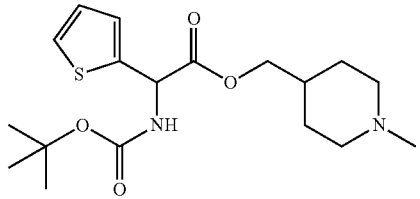 [SMILES: CN1CCC(COC(=O)C(NC(=O)OC(C)(C)C)c2cccs2)CC1] | Intermediate 53 | 2-(tert-butoxycarbonylamino)-2-(2-thienyl)acetic acid and (1-methyl-4-piperidyl)-methanol | LCMS (Method 1): [MH+] = 369 at 2.52 min. |
| 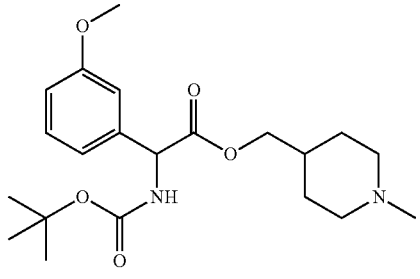 [SMILES: COc1cccc(C(NC(=O)OC(C)(C)C)C(=O)OCC2CCN(C)CC2)c1] | Intermediate 54 | 2-((tert-butoxycarbonyl)amino)-2-(3-methoxyphenyl)-acetic acid and (1-methyl-4-piperidyl)-methanol | LCMS (Method 4): [MH+] = 393 at 3.20 min. |
| 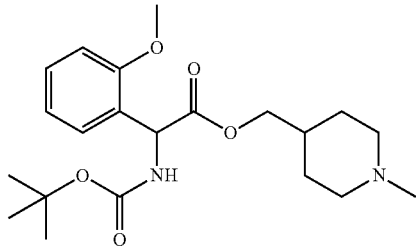 [SMILES: COc1ccccc1C(NC(=O)OC(C)(C)C)C(=O)OCC1CCN(C)CC1] | Intermediate 97 | 2-((tert-butoxycarbonyl)amino)-2-(2-methoxyphenyl)-acetic acid and (1-methyl-4-piperidyl)-methanol | LCMS (Method 3): [MH+] = 393 at 2.66 min. |
| 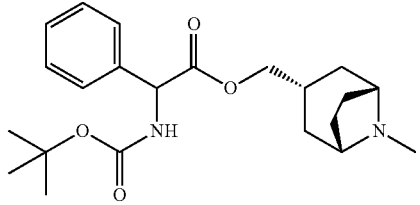 [SMILES: CN1[C@@H]2CC[C@H]1C[C@H](COC(=O)C(NC(=O)OC(C)(C)C)c1ccccc1)C2] | Intermediate 98 | 2-((tert-butoxycarbonyl)amino)-2-phenylacetic acid and Intermediate 96 | LCMS (Method 3): [MH+] = 389 at 2.68 min. |

| Structure | Intermediate number | Precursor | Analytical Data |
|---|---|---|---|
| ![structure] | Intermediate 99 | 2-((tert-butoxycarbonyl)amino)-2-phenylacetic acid and 1-(1-methylpiperidin-4-yl)ethan-1-ol | LCMS (Method 3): [MH+] = 377 at 2.66 min. |

Intermediate 100

[(3S)-1-methylpyrrolidin-3-yl]methyl 2-(tert-butoxycarbonylamino)-3-hydroxy-2-phenyl-propanoate his hydrochloride

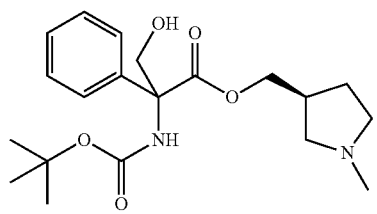 [SMILES: CN1CC[C@H](COC(=O)C(CO)(NC(=O)OC(C)(C)C)c2ccccc2)C1]

To a solution of [(3S)-1-methylpyrrolidin-3-yl]methyl 2-(tert-butoxycarbonylamino)-2-phenyl-acetate (0.87 g, 2.50 mmol) in dry THF (6 mL) was added DBU (0.76 mL, 5.12 mmol) followed by paraformaldehyde (100 mg, 3.25 mmol) and the resulting mixture was heated at 40° C. After one hour the reaction mixture was cooled and the solvent was removed by evaporation under reduced pressure, the residue was suspended in EtOAc (35 mL) and washed with water (2×30 mL). The organic phase was collected, filtered through a phase separator and the solvent was removed in vacuo to give the title compound as a pale yellow gum (780 mg, 82%).

LCMS (Method 3): [MH+]=379 at 2.63 min.

The following intermediate was synthesized via the same method.

Intermediate 55

[(3R)-1-methyl-3-piperidyl]methyl 2-amino-2-phenyl-acetate, bis-hydrochloride

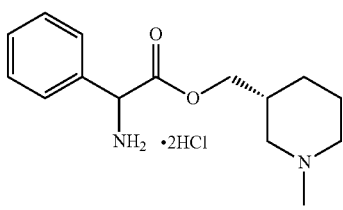 [SMILES: CN1CCC[C@@H](COC(=O)C(N)c2ccccc2)C1]

A solution of [(3R)-1-methyl-3-piperidyl]methyl-2-(tert-butoxycarbonylamino)-2-phenyl-acetate (1.28 g, 3.54 mmol) in a 4 N solution of HCl in dioxane (4.4 mL, 17.7 mmol)) was stirred at room temperature overnight. The solvent was removed by evaporation under reduced pressure, co-evaporated with diethyl ether and dried in vacuo to give the title compound as a white solid (918 mg, 99%).

LCMS (Method 2): [MH+]=263 at 2.55 min

The following intermediates were synthesized via the same method.

| Structure | Intermediate number | Precursor | Analytical Data |
|---|---|---|---|
| ![structure] | Intermediate 101 | Intermediate 28 | LCMS (Method 3): [MH+] = 379 at 2.63 min. |

| Structure | Intermediate number | Precursor | Analytical Data |
| --- | --- | --- | --- |
| 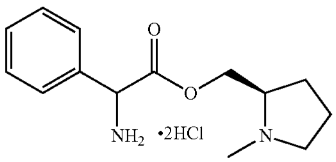 [SMILES: CN1CCC[C@@H]1COC(=O)C(N)c1ccccc1] | Intermediate 56 | Intermediate 26 | LCMS (Method 2): [MH+] = 249 at 2.13 min |
| 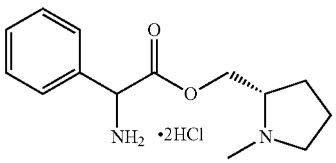 [SMILES: CN1CCC[C@H]1COC(=O)C(N)c1ccccc1] | Intermediate 57 | Intermediate 27 | LCMS (Method 2): [MH+] = 249 at 2.15 min |
| 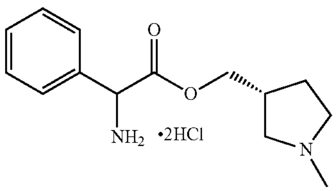 [SMILES: CN1CC[C@@H](COC(=O)C(N)c2ccccc2)C1] | Intermediate 58 | Intermediate 28 | LCMS (Method 2): [MH+] = 249 at 2.33 min |
| 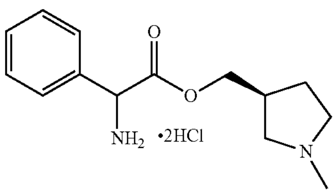 [SMILES: CN1CC[C@H](COC(=O)C(N)c2ccccc2)C1] | Intermediate 59 | Intermediate 29 | LCMS (Method 4): [MH+] = 249 at 2.47 min |
| 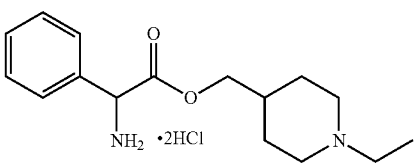 [SMILES: CCN1CCC(COC(=O)C(N)c2ccccc2)CC1] | Intermediate 60 | Intermediate 30 | LCMS (Method 4): [MH+] = 277 at 2.55 min |
| 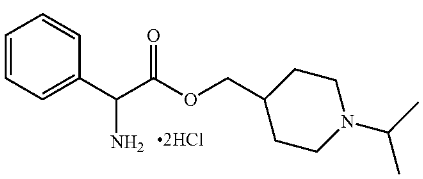 [SMILES: CC(C)N1CCC(COC(=O)C(N)c2ccccc2)CC1] | Intermediate 61 | Intermediate 31 | LCMS (Method 4): [MH+] = 291 at 2.55 min |
| 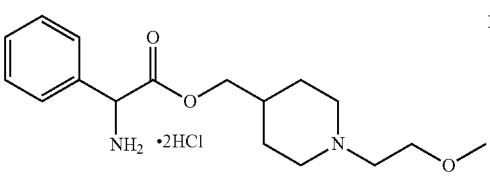 [SMILES: COCCN1CCC(COC(=O)C(N)c2ccccc2)CC1] | Intermediate 62 | Intermediate 32 | LCMS (Method 4): [MH+] = 307 at 2.67 min |
| 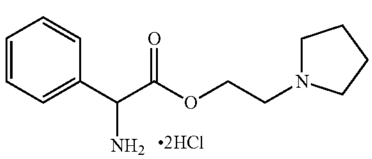 [SMILES: NC(C(=O)OCCN1CCCC1)c1ccccc1] | Intermediate 63 | Intermediate 33 | LCMS (Method 2): [MH+] = 249 at 2.55 min |
| 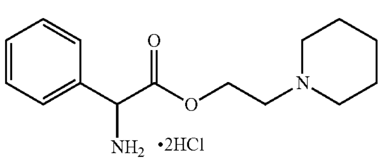 [SMILES: NC(C(=O)OCCN1CCCCC1)c1ccccc1] | Intermediate 64 | Intermediate 34 | LCMS (Method 2): [MH+] = 263 at 2.82 min |

-continued

| Structure | Intermediate number | Precursor | Analytical Data |
|---|---|---|---|
| Phenyl-CH(NH₂)-C(=O)-O-CH₂-(1-methylpiperidin-4-yl) · 2HCl | Intermediate 65 | Intermediate 35 | LCMS (Method 2): [MH+] = 263 at 1.89 min |
| 2-Fluorophenyl-CH(NH₂)-C(=O)-O-CH₂-(1-methylpiperidin-4-yl) · 2HCl | Intermediate 66 | Intermediate 38 | LCMS (Method 2): [MH+] = 281 at 2.49 min. |
| Phenyl-CH(NH₂)-C(=O)-O-CH₂-(1-methylazetidin-3-yl) · 2HCl | Intermediate 67 | Intermediate 39 | LCMS (Method 2): [MH+] = 235 at 2.71/2.82 min |
| Phenyl-CH(NH₂)-C(=O)-O-CH₂-(1-methylpiperidin-3-yl) · 2HCl | Intermediate 68 | Intermediate 40 | LCMS (Method 2): [MH+] = 263 at 2.63 min |
| Phenyl-CH(NH₂)-C(=O)-O-CH₂-(1-methylazetidin-2-yl) · 2HCl | Intermediate 69 | Intermediate 41 | LCMS (Method 2): [MH+] = 235 at 2.32 min |
| Phenyl-CH(NH₂)-C(=O)-O-CH₂-(1-methylazetidin-2-yl) · 2HCl | Intermediate 70 | Intermediate 42 | LCMS (Method 1): [MH+] = 235 at 0.56 min |
| Phenyl-CH(NH₂)-C(=O)-O-CH₂-(1,4-dimethylpiperazin-2-yl) · 3HCl | Intermediate 71 | Intermediate 43 | LCMS (Method 2): [MH+] = 278 at 2.27 min |
| Phenyl-CH(NH₂)-C(=O)-O-CH₂-(1-methylpiperidin-2-yl) · 2HCl | Intermediate 72 | Intermediate 44 | LCMS (Method 4): [MH+] = 263 at 2.74 min |

-continued

| Structure | Intermediate number | Precursor | Analytical Data |
|---|---|---|---|
| (phenyl-CH(NH₂)-C(O)-O-CH₂-(1-methylpiperidin-2-yl)) ·2HCl | Intermediate 73 | Intermediate 45 | LCMS (Method 4): [MH+] = 263 at 2.74 min |
| (phenyl-CH(NH₂)-C(O)-O-CH₂-(1,4-dimethylpiperazin-2-yl)) ·3HCl | Intermediate 74 | Intermediate 46 | LCMS (Method 4): [MH+] = 278 at 2.42 min |
| (phenyl-CH(NH₂)-C(O)-O-CH₂-quinuclidin-3-yl) ·2HCl | Intermediate 75 | Intermediate 47 | LCMS (Method 4): [MH+] = 275 at 2.35 min |
| (phenyl-CH(NH₂)-C(O)-O-CH₂-quinuclidin-3-yl, other stereo) ·2HCl | Intermediate 76 | Intermediate 48 | LCMS (Method 4): [MH+] = 275 at 2.34 min |
| (phenyl-CH(NH₂)-C(O)-O-CH₂-(1-azabicyclo[2.2.1]) ·2HCl | Intermediate 77 | Intermediate 49 | LCMS (Method 4): [MH+] = 275 at 2.35 min. |
| (phenyl-C(CH₃)(NH₂)-C(O)-O-CH₂-(1-methylpiperidin-4-yl)) ·2HCl | Intermediate 78 | Intermediate 50 | LCMS (Method 2): [MH+] = 277 at 2.63 min. |
| (1-amino-indan-1-yl-C(O)-O-CH₂-(1-methylpiperidin-4-yl)) ·2HCl | Intermediate 79 | Intermediate 51 | LCMS (Method 2): [MH+] = 289 at 2.06 min. |
| (thiophen-2-yl-CH(NH₂)-C(O)-O-CH₂-(1-methylpiperidin-4-yl)) ·2HCl | Intermediate 80 | Intermediate 53 | LCMS (Method 2): [MH+] = 269 at 2.37 min. |

-continued

| Structure | Intermediate number | Precursor | Analytical Data |
|---|---|---|---|
| 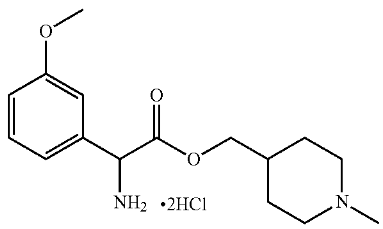 | Intermediate 102 | Intermediate 54 | LCMS [(Method 4)]: [MH+] = 281 at 2.49 min. |
| 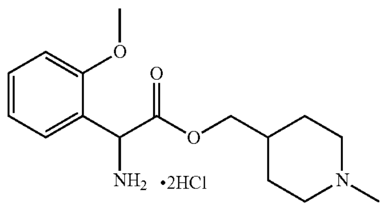 [SMILES: COc1ccccc1C(N)C(=O)OCC1CCN(C)CC1] | Intermediate 103 | Intermediate 97 | LCMS (Method 4): [MH+] = 293 at 2.53 min. |
| 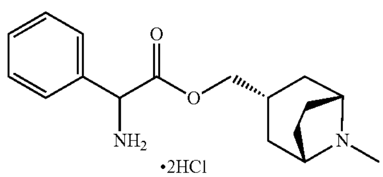 [SMILES: CN1[C@@H]2CC[C@H]1C[C@H](COC(=O)C(N)c1ccccc1)C2] | Intermediate 104 | Intermediate 98 | LCMS (Method 4): [MH+] = 289 at 2.57 min. |
| 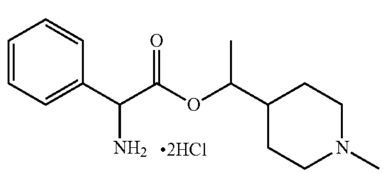 [SMILES: CC(OC(=O)C(N)c1ccccc1)C1CCN(C)CC1] | Intermediate 105 | Intermediate 99 | LCMS (Method 4): [MH+] = 277 at 2.59 and 2.67 min. |
| 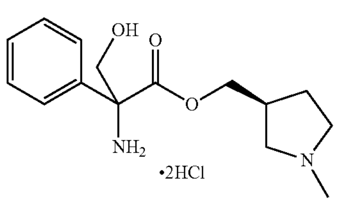 [SMILES: CN1CC[C@H](COC(=O)C(N)(CO)c2ccccc2)C1] | Intermediate 106 | Intermediate 100 | LCMS (Method 4): [MH+] = 279 at 2.65 min. |
| 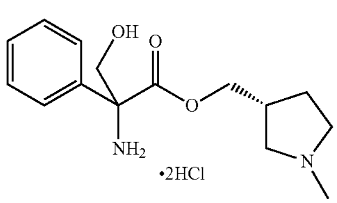 [SMILES: CN1CC[C@@H](COC(=O)C(N)(CO)c2ccccc2)C1] | Intermediate 107 | Intermediate 101 | LCMS (Method 4): [MH+] = 279 at 2.65 min. |

Intermediate 81

(1-methyl-4-piperidyl)methyl 2-[(E)-benzylideneamino]-2-phenyl-acetate

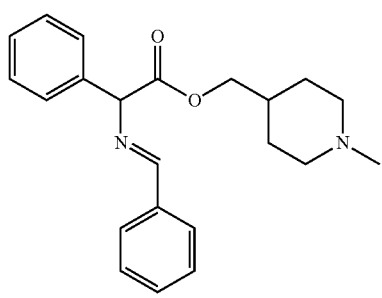 [SMILES: CN1CCC(COC(=O)C(/N=C/c2ccccc2)c2ccccc2)CC1]

To a stirred solution of (1-methyl-4-piperidyl)methyl 2-amino-2-phenyl-acetate bis hydrochloride (0.48 g, 1.43 mmol) and Et$_3$N (0.4 mL, 2.86 mmol) in dry DCM (10 mL) was added MgSO$_4$ and the resulting mixture was stirred at room temperature. After one hour benzaldehyde (0.15 mL, 1.43 mmol) was added and the mixture was stirred at room temperature for 48 hours. The mixture was filtered and the solid was washed through with DCM. The filtrate was washed with water and the organic phase was isolated by passing through a phase separator and the solvent was removed in vacuo to give the title compound as a yellow gum (0.36 g, 72%). LCMS (Method 2): [MH+]=351 at 3.69 min.

Intermediate 82

(1-methyl-4-piperidyl)methyl 2-amino-3-hydroxy-2-phenyl-propanoate, bis hydrochloride

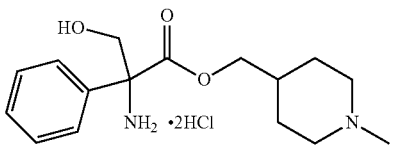 [SMILES: CN1CCC(COC(=O)C(N)(CO)c2ccccc2)CC1]

To a mixture of (1-methyl-4-piperidyl)methyl 2-[(E)-benzylideneamino]-2-phenyl-acetate (357 mg, 1.02 mmol) and para-formaldehyde (61 mg, 2.04 mmol) in dry dioxane (6 mL) was added DBU (0.18 mL, 1.24 mmol). The mixture was stirred at room temperature for four hours. The solvent was removed in vacuo, the residue was dissolved in EtOAc (25 mL) and washed with water (2×25 mL) and the combined aqueous washes were back-extracted with EtOAc (25 mL). The organic phases were combined, filtered through a phase separator and the solvent was removed in vacuo to give a yellow gum. The residue was suspended in a 1:1 mixture of 1 N HCl/THF (10 mL) and stirred at room temperature for 72 hours. The solvent was removed in vacuo, the residue was taken up in 1 N HCl (5 mL) and washed with EtOAc (2×10 mL). The organic phases were combined, washed with 1 N HCl (5 mL), filtered through a phase separator and the solvent was removed in vacuo. The residue was co-evaporated with toluene (2×10 mL) to give the title compound as a light brown solid (274 mg, 74%). LCMS (Method 2): [MH+]=293 at 2.34 min

Intermediate 83

2-Amino-2-(3-(benzyloxy)phenyl)acetonitrile

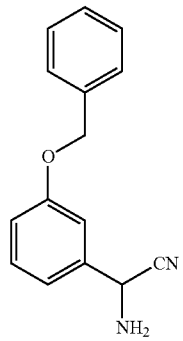 [SMILES: N#CC(N)c1cccc(OCc2ccccc2)c1]

To a stirred solution of 3-benzyloxybenzaldehyde (2.12 g, 10 mmol) in a 7 N ammonia solution in MeOH (50 mL) at 0° C. was added trimethylsilyl cyanide (1.11 mL, 15 mmol) dropwise. The resulting mixture was stirred at 0° C. for 10 minutes, warmed to 45° C. for 18 hours and then concentrated to dryness. The crude material was purified by silica gel column chromatography, eluting with 0-100% DCM/10% MeOH in DCM, to afford the title compound (1.26 g, 53%) as an orange oil.
$^1$H NMR (400 MHz, CDCl$_3$): δ 7.44-7.29 (m, 6 H), 7.16 (t, J=2.1 Hz, 1 H), 7.11 (d, J=7.6 Hz, 1 H), 6.97 (dd, J=2.4, 8.2 Hz, 1 H), 5.08 (s, 2 H), 4.86 (s, 1 H), 1.92 (brs, 2 H). LCMS (Method 2): [MH+]=238 at 3.65 min.

Intermediate 84

Methyl 2-amino-2-(3-(benzyloxy)phenyl)acetate

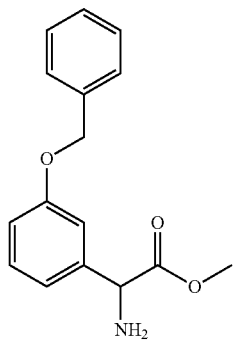 [SMILES: COC(=O)C(N)c1cccc(OCc2ccccc2)c1]

To a stirred solution of 2-amino-2-(3-(benzyloxy)phenyl)acetonitrile (1.22 g, 5.3 mmol) in MeOH (10 mL) at room temperature was added 2 N HCl in ether (10 mL, 20 mmol). The resulting mixture was heated under reflux for 18 hours and concentrated to dryness. The crude material was taken up in EtOAc (200 mL) and washed with saturated aqueous sodium bicarbonate (100 mL). The layers were separated and the organic phase was dried over magnesium sulfate, filtered and the solvent was removed in vacuo. The residue was loaded onto a SCX cartridge eluting with DCM/MeOH followed by 7 N ammonia in MeOH to afford the title compound (1.0 g, 70%) as a thick orange oil.

Intermediate 85

Methyl 2-(benzyloxycarbonylamino)-2-(3-benzyloxyphenyl)acetate

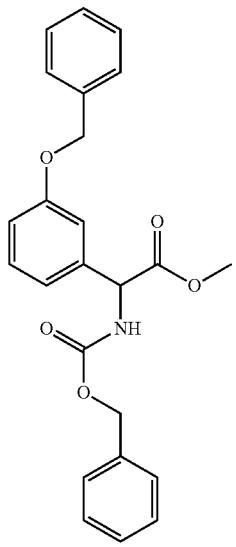 [SMILES: COC(=O)C(NC(=O)OCc1ccccc1)c1cccc(OCc2ccccc2)c1]

To a solution of methyl 2-amino-2-(3-(benzyloxy)phenyl)acetate (1.09 g, 4 mmol) in a mixture of THF and water (1:1, 90 mL) at 0° C. was added benzyl chloroformate (0.57 mL, 4 mmol) and a 4 N aqueous solution of sodium hydroxide (1 mL, 4 mmol) simultaneously. The mixture was stirred at 0° C. for one hour. The ice bath was removed and the reaction mixture was stirred at room temperature for 16 hours. The solvent was removed in vacuo and EtOAc (100 mL) and water (30 mL) were added. The layers were separated and the aqueous phase was re-extracted with EtOAc (2×50 mL). The combined organic fractions were dried over magnesium sulfate, filtered and the solvent was removed in vacuo. The residue was purified by silica gel column chromatography, eluting with 0-40% EtOAc in iso-hexane to afford the title compound (900 mg, 56%) as a brown oil.

$^1$H NMR (400 MHz, CDCl$_3$): δ 7.47-7.20 (m, 11 H), 7.04-6.90 (m, 3 H), 5.88 (d, J=7.1 Hz, 1 H), 5.35 (d, J=7.3 Hz, 1 H), 5.13 (d, J=12.9 Hz, 1 H), 5.06 (d, J=12.0 Hz, 1 H), 5.02 (s, 2 H), 3.68 (s, 3 H). LCMS (Method 2): [MH+]=406 at 3.67 min.

Intermediate 86

2-(((Benzyloxy)carbonyl)amino)-2-(3-(benzyloxy)phenyl)acetic acid

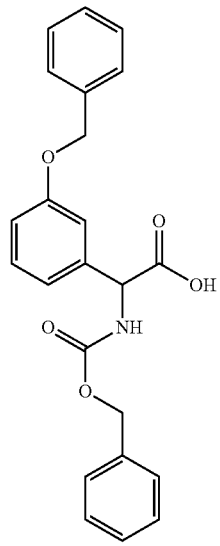 [SMILES: O=C(NC(C(=O)O)c1cccc(OCc2ccccc2)c1)OCc1ccccc1]

A mixture of methyl 2-(benzyloxycarbonylamino)-2-(3-benzyloxyphenyl)acetate (640 mg, 1.75 mmol) and 1 N aqueous lithium hydroxide solution (3.50 mL, 3.50 mmol) in MeOH (5 mL) and THF (5 mL) was stirred at room temperature for one hour. The mixture was concentrated in vacuo and the residue was diluted with DCM (30 mL) and acidified to pH 0.5 with 2 N HCl. The aqueous phase was re-extracted with DCM (2×50 mL). The combined organic fractions were filtered through a phase separator and the solvent was removed in vacuo to give the title compound as a light brown oil (460 mg, 67%). The residue was used in the next step without further purification.

$^1$H NMR (400 MHz, CDCl$_3$): δ 7.37-7.24 (m, 9 H), 7.21-7.12 (m, 2 H), 7.01-6.90 (m, 2 H), 6.86 (dd, J=1.6, 8.2 Hz, 1 H), 5.91 (d, J=7.1 Hz, 1 H), 5.32 (d, J=7.1 Hz, 1 H), 5.18 (d, J=5.6 Hz, 1 H), 5.01-4.87 (m, 4 H). LCMS (Method 2): [MH+]=391 at 2.4 min.

---

(Preceding text, column 83:)

$^1$H NMR (400 MHz, CDCl$_3$): δ 7.44-7.20 (m, 6 H), 7.01 (dd, J=2.0, 2.0 Hz, 1 H), 6.95 (d, J=7.8 Hz, 1 H), 6.89 (dd, J=1.9, 8.2 Hz, 1 H), 5.03 (s, 2 H), 4.57 (s, 1 H), 3.65 (s, 3 H), 2.17 (s, 2 H). LCMS (Method 2): [MH+]=272 at 3.53 min.

Intermediate 87

(1-Methyl-4-piperidyl)methyl 2-(benzyloxycarbonylamino)-2-(3-benzyloxyphenyl)acetate

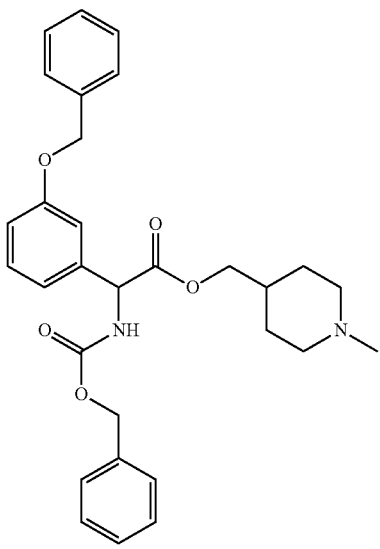 [SMILES: CN1CCC(COC(=O)C(NC(=O)OCc2ccccc2)c2cccc(OCc3ccccc3)c2)CC1]

A solution of 2-(((benzyloxy)carbonyl)amino)-2-(3-(benzyloxy)phenyl)acetic acid (1.20 g, 3.07 mmol), N,N'-dicyclohexylcarbodiimide (759 mg, 3.68 mmol), 1-hydroxybenzotriazole hydrate (500 mg, 3.68 mmol) and (1-methyl-4-piperidyl)methanol (593 mg, 4.60 mmol) in dry THF (23 mL) was stirred at room temperature for 18 hours. Additional (1-methyl-4-piperidyl)methanol (0.60 g, 4.6 mmol), N,N'-dicyclohexylcarbodiimide (0.6 g, 2.9 mmol), and 1-hydroxybenzotriazole hydrate (370 mg, 2.74 mmol) were then added to the mixture and stirred for 4 days. The white slurry was then filtered through a pad of Celite®, rinsed with EtOAc (100 mL) and the solvent was removed in vacuo. The residue was partitioned between EtOAc (100 mL) and saturated aqueous sodium carbonate solution (50 mL). The layers were separated and the aqueous phase was back-extracted with EtOAc (2×50 mL). The combined organic fractions were dried over magnesium sulfate, filtered and the solvent was removed in vacuo. The residue was purified by silica gel column chromatography, eluting with 0-40% EtOAc/10% methanolic ammonia solution in EtOAc to afford the title compound (1.5 g, 97%) as a clear thick oil.

LCMS (Method 1): [MH+]=503 at 2.93 min.

Intermediate 88

(1-Methyl-4-piperidyl)methyl 2-amino-2-(3-hydroxyphenyl)acetate

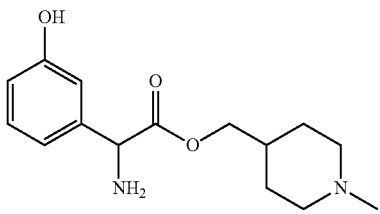 [SMILES: CN1CCC(COC(=O)C(N)c2cccc(O)c2)CC1]

To a solution of (1-methyl-4-piperidyl)methyl 2-(benzyloxycarbonylamino)-2-(3-benzyloxyphenyl)acetate (544 mg, 1.09 mmol) in EtOAc (20 mL) was added ammonium formate (200 mg, 3.2 mmol) and 10% Pd/C (200 mg). The mixture was heated to 80° C. for 4 hours. After cooling the slurry to room temperature and filtration through a pad of Celite®, the solids were washed with EtOAc (100 mL). The solvent was removed in vacuo to yield the title compound as a thick yellow oil (410 mg, 100%) which was used in the next step without further purification.

LCMS (Method 2): [MH+]=279 at 1.33 min.

Intermediate 89

(1-Methyl-4-piperidyl)methyl 2-amino-2-(3-hydroxyphenyl)acetate bis hydrobromide

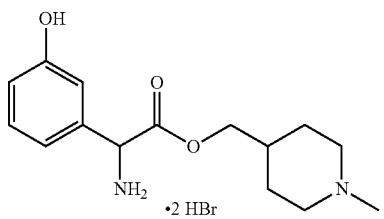 [SMILES: CN1CCC(COC(=O)C(N)c2cccc(O)c2)CC1]

To a solution of (1-methyl-4-piperidyl)methyl 2-(tert-butyloxycarbonylamino)-2-(3-methoxyphenyl)acetate (1.4 g, 3.6 mmol) in dry DCM (30 mL) at −78° C. was added a 1 N solution of boron tribromide in DCM (18 mL, 18 mmol). The reaction mixture was allowed to warm to room temperature and was stirred for 4 hours. After cooling the mixture back to −78° C., methanol (30 mL) was cautiously added. The reaction mixture was then warmed to room temperature and concentrated in vacuo to give the title compound as a brown foam (1.3 g, 82%) which was used in the next step without further purification.

LCMS (Method 2): [MH+]=279 at 1.33 min.

Intermediate 90

2-oxo-2-(2-thienyl) acetic acid

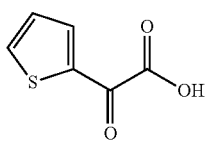

To a solution of thiophenyl ethylglyoxylate (4 mL, 27.17 mmol) in EtOH (60 mL) was added a 4 N aqueous NaOH solution (10.2 mL, 40.76 mmol) and the resulting mixture was stirred at room temperature for 18 hours. The reaction solution was acidified with 2 N aqueous HCl until pH~2 and the solvents were removed in vacuo to give the title compound as a yellow solid (Quantitative yield). The residue was used in the next step without purification.

LCMS (Method 2): [MH−]=155 at 0.71 min.

Intermediate 91

(1-Methyl-4-piperidyl)methyl-2-oxo-2-(2-thienyl) acetate

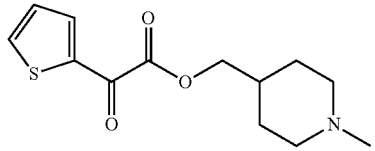 [SMILES: CN1CCC(COC(=O)C(=O)c2cccs2)CC1]

To a solution of 2-oxo-2-(2-thienyl)acetic acid (2.00 g, 12.8 mmol) in THF (80 mL) was added (1-methyl-4-piperidyl)methanol (2.03 mL, 15.4 mmol), N,N'-dicyclohexylcarbodiimide (3.17 g, 15.4 mmol) and 1-hydroxybenzotriazole hydrate (2.08 g, 15.4 mmol). The resulting mixture was stirred at room temperature for 18 hours. The reaction mixture was filtered through a pad of Celite® and the filtrate concentrated in vacuo. The residue was partitioned between EtOAc (30 mL) and saturated aqueous sodium carbonate solution (2×30 mL). The organic phase was filtered through a phase separator and the solvent was removed in vacuo to give the title compound as an orange oil (2.04 g, 60%). The material was used in the next step without purification.

LCMS (Method 3): [MH+]=268 at 2.33 min.

Intermediate 92

(1-Methyl-4-piperidyl)methyl 2-hydroxy-3-nitro-2-(2-thienyl)propanoate

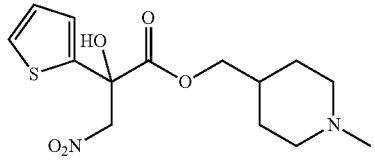 [SMILES: CN1CCC(COC(=O)C(O)(C[N+](=O)[O-])c2cccs2)CC1]

To a solution of (1-methyl-4-piperidyl)methyl 2-oxo-2-(2-thienyl)acetate (2.04 g, 7.64 mmol) in nitromethane (10 mL) was added Et₃N (213 μL, 1.53 mmol). The mixture was stirred at room temperature for 72 hours. The solvent was removed in vacuo and the residue was co-evaporated with EtOAc and MeCN to give the title compound (2.5 g, quantitative yield) as a brown oil.

LCMS (Method 3): [MH+]=329 at 1.29 min.

Intermediate 93

(1-methyl-4-piperidyl)methyl 3-amino-2-hydroxy-2-(2-thienyl)propanoate bis acetate

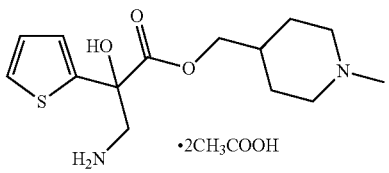 [SMILES: CN1CCC(COC(=O)C(O)(CN)c2cccs2)CC1]

To a solution of (1-methyl-4-piperidyl)methyl 2-hydroxy-3-nitro-2-(2-thienyl)propanoate (2.5 g, 7.62 mmol) in acetic acid (40 mL) was added zinc dust (5.44 g, 76.2 mmol) portionwise. The mixture was stirred at room temperature for 18 hours. The solvent was removed in vacuo to give the title compound (quantitative yield) as a brown oil.

LCMS (Method 4): [MH+]=299 at 2.26 min.

Example 1

[(1S)-2-(3,5-dichloro-1-oxido-pyridin-1-ium-4-yl)-1-(3,4-dimethoxyphenyl)ethyl]5-[[[2-hydroxy-3-[(1-methyl-4-piperidyl)methoxy]-3-oxo-2-(2-thienyl)propyl]amino]methyl]-thiophene-2-carboxylate

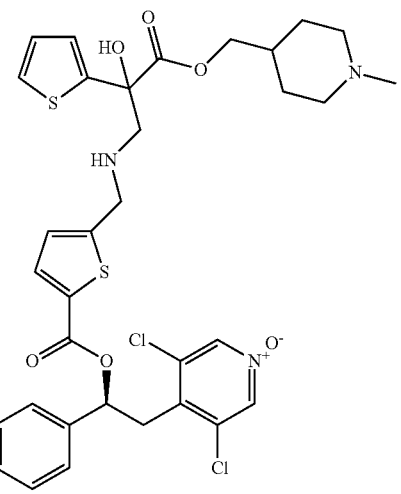

To a solution of (1-methyl-4-piperidyl)methyl 3-amino-2-hydroxy-2-(2-thienyl)propanoate bis acetate (Intermediate 93, 2.3 g, 7.62 mmol) in EtOH (410 mL) was added [(1S)-2-(3,5-dichloro-1-oxido-pyridin-1-ium-4-yl)-1-(3,4-dimethoxyphenyl)ethyl]5-formylthiophene-2-carboxylate (Intermediate 1, 1.75 g, 3.63 mmol). The mixture was stirred at room temperature for 30 minutes. NaBH₃CN (0.96 g, 15.24 mmol) was added and the solution was stirred at room temperature for 18 hours. The reaction solvent was removed in vacuo and the residue was partitioned between EtOAc and H₂O. The organic phases were combined, filtered through a phase separator and concentrated in vacuo. Purification of the crude material by preparative HPLC afforded the title compound (10 mg, 0.2%) as an off-white solid.

¹H NMR (400 MHz, CD₃CN): δ 8.19*ᵒʳ† (s, 2 H), 8.18*ᵒʳ† (s, 2 H), 7.67 (t, J=4.0 Hz, 1 H), 7.33-7.30 (m, 1 H), 7.09-6.90 (m, 6 H), 6.15 (dd, J=4.8, 9.4 Hz, 1 H), 4.08-3.86 (m, 4 H), 3.81*ᵒʳ† (s, 3 H), 3.80*ᵒʳ† (s, 3 H), 3.79 (s, 3 H), 3.69-3.61 (m, 1 H), 3.36-3.28 (m, 2 H), 3.01 (dd, J=2.2, 12.2 Hz, 1 H), 2.71-2.64 (m, 2 H), 2.10 (d, J=7.8 Hz, 2 H), 1.79-1.70 (m, 3 H), 1.57-1.48 (m, 3 H), 1.24-1.13 (m, 2 H). † and * refer to different isomers (arbitrarily assigned), NH and OH not observed. LCMS (Method 4): [MH+]=764 at 3.18 min.

Example 2

[(1S)-2-(3,5-dichloro-1-oxido-pyridin-1-ium-4-yl)-1-(3,4-dimethoxyphenyl)ethyl]5-[[[2-[(1,4-dimethyl-4-piperidyl)methoxy]-2-oxo-1-phenyl-ethyl]amino]methyl]thiophene-2-carboxylate

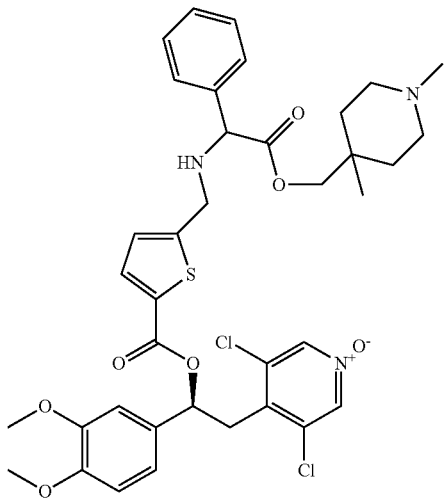

A solution of (1,4-dimethyl-4-piperidyl)methyl 2-(tert-butoxycarbonylamino)-2-phenylacetate (Intermediate 36, 1.26 g, 3.35 mmol) in 4N HCl in dioxane (4.19 mL, 16.76 mmol) was stirred at room temperature for 18 hours. The reaction solvent was removed in vacuo to give a white solid. The residue was diluted with DCM (20 mL) and to the solution was added [(1S)-2-(3,5-dichloro-1-oxido-pyridin-1-ium-4-yl)-1-(3,4-dimethoxyphenyl)ethyl]5-formylthiophene-2-carboxylate (Intermediate 1, 1.61 g, 3.35 mmol), Et$_3$N (932 µL, 6.70 mmol) and acetic acid (384 µl, 6.70 mmol). The mixture was stirred at room temperature for 18 hours. NaBH(OAc)$_3$ (1.42 g, 6.70 mmol) was then added and the solution was stirred for 72 hours. The reaction mixture was concentrated in vacuo and the residue was partitioned between EtOAc and H$_2$O. The aqueous phase was concentrated in vacuo. The residue was washed with saturated aqueous NaHCO$_3$ (20 mL) and extracted with EtOAc (3×20 mL). The organic phases were combined, filtered through a phase separator and concentrated in vacuo. Purification of the crude material by preparative HPLC afforded the title compound (220 mg, 9%) as a light brown solid.

$^1$H NMR (400 MHz, CDCl$_3$): δ 8.15$^{*or\dagger}$ (s, 2 H), 8.14$^{*or\dagger}$ (s, 2 H), 7.65 (d, J=3.7 Hz, 1 H), 7.39-7.31 (m, 5 H), 7.01-6.96 (m, 2 H), 6.88 (d, J=3.9 Hz, 1 H), 6.85 (d, J=8.1 Hz, 1 H), 6.24-6.22$^{*or\dagger}$ (m, 1 H), 6.22-6.19$^{*or\dagger}$ (m, 1 H), 4.44 (d, J=3.2 Hz, 1 H), 3.98-3.91 (m, 3 H), 3.91$^{*or\dagger}$ (s, 3 H), 3.90$^{*or\dagger}$ (s, 3 H), 3.88 (s, 3 H), 3.84 (dd, J=3.9, 11.0 Hz, 1 H), 3.67 (dd, J=10.6, 14.0 Hz, 1 H), 3.35-3.31$^{*or\dagger}$ (m, 1 H), 3.31-3.28$^{*or\dagger}$ (m, 1 H), 2.46-2.32 (m, 2 H), 2.24 (s, 3 H), 2.20-2.15 (m, 2 H), 1.60 (s, 1 H), 1.53-1.44 (m, 1 H), 1.43-1.35 (m, 1 H), 1.34-1.27 (m, 1 H), 1.26-1.18 (m, 1 H), 0.78$^{*or\dagger}$ (s, 3 H), 0.78$^{*or\dagger}$ (s, 3 H). † and * refer to different isomers (arbitrarily assigned). LCMS (Method 1): [MH+]=742 at 2.6 min.

The following compounds were synthesized via a similar method as a mixture of diastereoisomers.

| Structure | Example Number | Precursor | Analytical Data |
| --- | --- | --- | --- |
| [(1S)-2-(3,5-dichloro-1-oxido-pyridin-1-ium-4-yl)-1-(3,4-dimethoxyphenyl)ethyl]5-[[[2-[(4-fluoro-1-methyl-4-piperidyl)methoxy]-2-oxo-1-phenyl-ethyl]amino]methyl]thiophene-2-carboxylate | Example 3 | Intermediate 1 and Intermediate 37 | $^1$H NMR (400 MHz, CDCl$_3$): δ 8.15$^{*or\dagger}$ (s, 2 H), 8.14$^{*or\dagger}$ (s, 2 H), 7.65 (d, J = 3.6 Hz, 1 H), 7.39-7.30 (m, 5 H), 7.02-6.96 (m, 2 H), 6.88 (d, J = 4.0 Hz, 1 H), 6.86 (d, J = 8.1 Hz, 1 H), 6.23$^{*or\dagger}$ (dd, J = 2.4, 4.4 Hz, 1 H), 6.20$^{*or\dagger}$ (dd, J = 2.7, 4.3 Hz, 1 H), 4.49 (d, J = 2.1 Hz, 1 H), 4.18-4.16 (m, 1 H), 4.13-4.10 (m, 1 H), 3.96-3.93 (m, 2 H), 3.91$^{*or\dagger}$ (s, 3 H), 3.96$^{*or\dagger}$ (s, 3 H), 3.88 (s, 3 H), 3.67 (dd, J = 10.1, 14.4 Hz, 1 H), 3.33$^{*or\dagger}$ (dd, J = 2.3, 4.4 Hz, 1 H), 3.29$^{*or\dagger}$ (dd, J = 2.3, 4.5 Hz, 1H), 2.63-2.52 (m, 2 H), 2.26 (s, 3 H), 2.21 (d, J = 23.3 Hz, 2 H), 1.78-1.43 (m, 5 H). † and * refer to different isomers (arbitrarily assigned). LCMS (Method 1): [MH+] = 746 at 2.6 min. |

| Structure | Example Number | Precursor | Analytical Data |
|---|---|---|---|
| Epimeric mixture 2 of [1-[3-(cyclopropylmethoxy)-4-methoxy-phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate 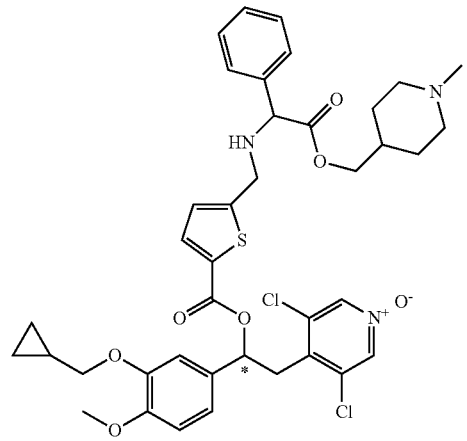 | Example 4 | Intermediate 12 and Intermediate 35 | $^1$H NMR (400 MHz, CD$_3$CN): δ 8.21*$^{or\dagger}$ (s, 2 H), 8.20*$^{or\dagger}$ (s, 2 H), 7.68 (d, J = 3.9 Hz, 1 H), 7.40-7.34 (m, 5 H), 7.05-7.00 (m, 2 H), 6.97-6.93 (m, 2 H), 6.15 (dd, J = 4.6, 9.6 Hz, 1 H), 4.43 (s, 1 H), 3.95-3.84 (m, 6 H), 3.83 (s, 3 H), 3.66 (dd, J = 9.8, 14.3 Hz, 1 H), 3.36-3.30 (m, 1 H), 2.74 (d, J = 11.9 Hz, 2 H), 2.15 (s, 3 H), 1.86-1.78 (m, 2 H), 1.53-1.47 (m, 3 H), 1.25-1.13 (m, 3 H), 0.63-0.57 (m, 2 H), 0.35-0.30 (m, 2 H). Note NH not visible. † and * refer to different isomers (arbitrarily assigned). LCMS (Method 4): [MH+] = 768 at 3.52 min. |
| Epimeric mixture 1 of [1-[3-(cyclopentoxy)-4-methoxy-phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate 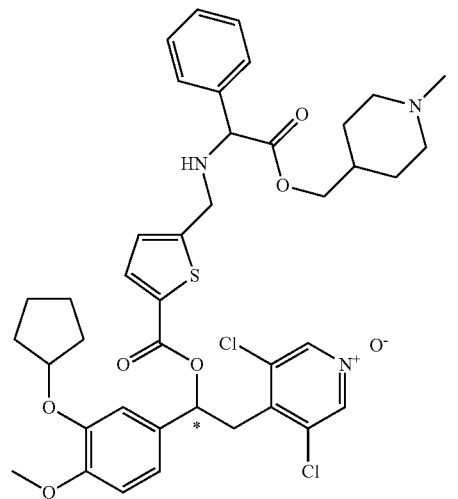 | Example 5 | Intermediate 9 and Intermediate 35 | $^1$H NMR (400 MHz, CD$_3$CN): δ 8.21 (s, 2 H), 7.69 (d, J = 3.8 Hz, 1 H), 7.41-7.32 (m, 5 H), 7.00 (dd, J = 1.9, 5.9 Hz, 2 H), 6.97-6.92 (m, 2 H), 6.15 (dd, J = 4.8, 9.3 Hz, 1 H), 4.84-4.79 (m, 1 H), 4.43 (s, 1 H), 3.99-3.87 (m, 4 H), 3.79 (s, 3 H), 3.65 (dd, J = 9.3, 13.9 Hz, 1 H), 3.39-3.32 (m, 1 H), 2.74 (d, J = 11.1 Hz, 2 H), 2.15-2.12 (m, 3 H), 1.89-1.71 (m, 8 H), 1.63-1.59 (m, 2 H), 1.52-1.47 (m, 3 H), 1.24-1.12 (m, 2 H). Note: NH not visible. LCMS (Method 1): [MH+] = 782 at 2.8 min. |

| Structure | Example Number | Precursor | Analytical Data |
|---|---|---|---|
| Epimeric mixture 2 of [1-[3-(cyclopentoxy)-4-methoxy-phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate 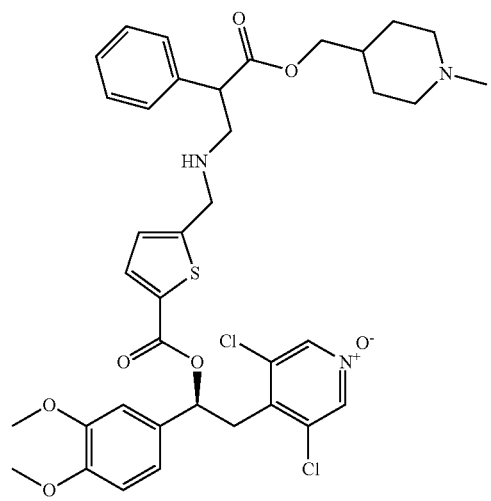 | Example 6 | Intermediate 10 and Intermediate 35 | $^1$H NMR (400 MHz, CD$_3$CN): δ 8.21 (s, 2 H), 7.69 (d, J = 3.8 Hz, 1 H), 7.41-7.32 (m, 5 H), 7.00 (dd, J = 1.9, 5.9 Hz, 2 H), 6.97-6.91 (m, 2 H), 6.15 (dd, J = 4.9, 9.2 Hz, 1 H), 4.83-4.79 (m, 1 H), 4.43 (s, 1 H), 3.99-3.87 (m, 4 H), 3.79 (s, 3 H), 3.65 (dd, J = 9.3, 14.1 Hz, 1 H), 3.39-3.32 (m, 1 H), 2.73 (d, J = 11.6 Hz, 2 H), 2.14 (s, 3 H), 1.90-1.67 (m, 8 H), 1.62-1.58 (m, 2 H), 1.53-1.47 (m, 3 H), 1.24-1.12 (m, 2 H). Note: NH not visible. LCMS (Method 1): [MH+] = 782 at 2.8 min. |

Example 7

[(1S)-2-(3,5-dichloro-1-oxido-pyridin-1-ium-4-yl)-1-(3,4-dimethoxyphenyl)ethyl]5-[[[3-[(1-methyl-4-piperidyl)methoxy]-3-oxo-2-phenyl-propyl]amino]methyl]thiophene-2-carboxylate A solution of (1-methyl-4-piperidyl)methyl 3-(tert-butoxycarbonylamino)-2-phenylpropanoate (Intermediate 52, 1.20 g, 3.19 mmol) in 4 N HCl in dioxane (4 mL, 15.96 mmol) was stirred at room temperature for 18 hours. The reaction solvent was removed in vacuo to give a white solid. The residue was diluted with EtOAc (12 mL), and Et$_3$N was added (889 µL, 6.38 mmol). The resultant mixture was stirred at room temperature for one hour. The solids were filtered off and the filtrate was concentrated in vacuo to give an orange oil. The residue was diluted with MeCN (10 mL) and [(1S)-2-(3,5-dichloro-1-oxido-pyridin-1-ium-4-yl)-1-(3,4-dimethoxyphenyl)ethyl]5-formylthiophene-2-carboxylate (Intermediate 1, 1.54 g, 3.19 mmol) and acetic acid (183 µL, 3.19 mmol) were added. The resultant solution was stirred at room temperature for 18 hours. NaBH(OAc)$_3$ (2.03 g, 9.57 mmol) was then added and the reaction solution was stirred at room temperature for 72 hours. The solvent was removed in vacuo and the residue was partitioned between EtOAc and H$_2$O. The aqueous phase was concentrated in vacuo. The residue was diluted with CHCl$_3$ (20 mL) and washed with brine (30 mL). The organic phase was filtered through a phase separator and concentrated in vacuo. Purification of the crude material by preparative HPLC afforded the title compound (300 mg, 13%) as a brown solid.

$^1$H NMR (400 MHz, DMSO): δ 8.59 (s, 2 H), 7.72 (d, J=3.8 Hz, 1 H), 7.38-7.30 (m, 5 H), 7.08-7.02 (m, 4 H), 6.18 (dd, J=4.4, 9.5 Hz, 1 H), 4.02-3.91 (m, 4 H), 3.85 (dd, J=6.0, 10.0 Hz, 1 H), 3.82 (s, 3 H), 3.80 (s, 3 H), 3.63 (dd, J=9.6, 14.1 Hz, 1 H), 3.35 (dd, J=4.3, 14.1 Hz, 1 H), 3.20 (dd, J=9.6, 11.6 Hz, 1 H), 2.83 (dd, J=5.4, 11.7 Hz, 1 H), 2.76-2.69 (m, 2 H), 2.15 (s, 3 H), 1.82-1.81 (m, 2 H), 1.57-1.48 (m, 3 H), 1.22-1.12 (m, 2 H). NH not observed LCMS (Method 1): [MH+]=742 at 2.33 min.

The following compound was synthesized via a similar method as a mixture of diastereoisomers.

| Structure | Example Number | Precursor | Analytical Data |
|---|---|---|---|
| Epimeric mixture 2 of [1-[3-(cyclopropylmethoxy)-4-methoxy-phenyl]-2-(3,5-dichloro-1-oxido-pyridin-1-ium-4-yl)ethyl] 5-[[[2-oxo-1-phenyl-2-(quinuclidin-4-ylmethoxy)ethyl]amino]methyl]thiophene-2-carboxylate | Example 8 | Intermediate 12 and Intermediate 77 | $^1$H NMR (400 MHz, CD$_3$CN): δ 8.15*$^{or\dagger}$ (s, 2 H), 8.15*$^{or\dagger}$ (s, 2 H), 7.66 (d, J = 3.7 Hz, 1 H), 7.40-7.37 (m, 4 H), 7.36-7.30 (m, 1 H), 7.03-6.97 (m, 2 H), 6.95-6.91 (m, 2 H), 6.13 (dd, J = 4.7, 9.7 Hz, 1 H), 4.45-4.40 (m, 1 H), 3.98-3.85 (m, 2 H), 3.83-3.81 (m, 1 H), 3.82-3.79 (m, 4 H), 3.76 (dd, J = 2.7, 10.6 Hz, 1 H), 3.71-3.67 (m, 1 H), 3.63 (dd, J = 9.7, 14.2 Hz, 1 H), 3.30 (ddd, J = 1.4, 4.8, 14.4 Hz, 1 H), 2.87 (br s, 1 H), 2.70 (t, J = 7.7 Hz, 6 H), 1.28-1.14 (m, 7 H), 0.61-0.55 (m, 2 H), 0.33-0.28 (m, 2 H). † and * refer to different isomers (arbitrarily assigned). LCMS (Method 3): [MH+] = 780 at 2.86 min. |

Example 9

[(1S)-2-(3,5-dichloro-1-oxido-pyridin-1-ium-4-yl)-1-(3,4-dimethoxyphenyl)ethyl]5-[[[1-cyclohexyl-2-[(1-methyl-4-piperidyl)methoxy]-2-oxo-ethyl]amino]methyl]thiophene-2-carboxylate

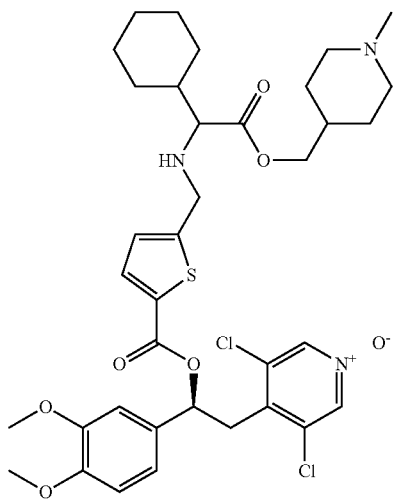

To a solution of 2-(tert-butoxycarbonylamino)-2-cyclohexyl-acetic acid (600 mg, 2.33 mmol) in THF (25 mL) was successively added (1-methyl-4-piperidyl)methanol (361 mg, 2.8 mmol), N,N'-dicyclohexylcarbodiimide (580 mg, 2.8 mmol) and 1-hydroxybenzotriazole hydrate (380 mg, 2.8 mmol). The resulting mixture was stirred at room temperature for 18 hours. The reaction mixture was filtered through a pad of Celite® and concentrated in vacuo. The residue was taken up in EtOAc (30 mL) and washed with 2 M aqueous sodium carbonate solution (2×30 mL), then with brine (30 mL). The organic phase was separated, filtered through a phase separator and the solvent was removed in vacuo. The residue was taken up into 1,4-dioxane (5 mL) and a 4 N solution of HCl in dioxane (10 mL, 40 mmol) was added. The resulting solution was stirred at room temperature for 18 hours. The solvent was removed by evaporation under reduced pressure, co-evaporated with diethyl ether and dried in vacuo. The residue was taken up into DCM (25 mL), and Et$_3$N (650 µL, 4.6 mmol) was added followed by [(1S)-2-(3,5-dichloro-1-oxido-pyridin-1-ium-4-yl)-1-(3,4-dimethoxyphenyl)ethyl]5-formylthiophene-2-carboxylate (Intermediate 1, 880 mg, 1.84 mmol) and acetic acid (110 µL, 1.84 mmol). The resulting mixture was stirred at room temperature for 18 hours. NaBH(OAc)$_3$ (2.0 g, 9.2 mmol) was added and the reaction mixture was stirred at room temperature 24 hours. The mixture was diluted with DCM (10 mL) and washed successively with saturated aqueous NaHCO$_3$ solution (2×20 mL), brine (20 mL) and 1 N aqueous HCl (2×25 mL). The organic phase was filtered through a phase separator and the solvent was removed in vacuo. Purification by preparative HPLC gave the title compound (mixture of diastereoisomers) as a yellow solid (480 mg, 28%).

$^1$H NMR (400 MHz, CDCl$_3$) δ 8.14*$^{or\dagger}$ (s, 2 H), 8.13*$^{or\dagger}$ (s, 2 H), 7.64-7.62 (m, 1 H), 7.00-6.97 (m, 2 H), 6.87-6.83 (m, 2 H), 6.25-6.19 (m, 1 H), 4.10-3.97 (m, 3 H), 3.91*$^{or\dagger}$ (s, 3 H), 3.90*$^{or\dagger}$ (s, 3 H), 3.87 (s, 3 H), 3.75-3.63 (m, 2 H), 3.33*$^{or\dagger}$ (dd, J=2.7, 4.5 Hz, 1 H), 3.29*$^{or\dagger}$ (dd, J=2.7, 4.6 Hz, 1 H), 3.07 (dd, J=3.3, 6.1 Hz, 1 H), 2.90-2.84 (m, 2 H), 2.27 (s, 3 H), 1.97-1.53 (m, 11 H), 1.42-0.99 (m, 7 H). * and † refer to different isomers. NH not observed. LCMS (Method 1): [MH+]=734 at 2.53 min.

Example 10

[(1S)-2-(3,5-dichloro-1-oxido-pyridin-1-ium-4-yl)-1-(3,4-dimethoxyphenyl)ethyl]5-[[[2-oxo-1-phenyl-2-[[(3S)-quinuclidin-3-yl]methoxy]ethyl]amino]methyl]thiophene-2-carboxylate

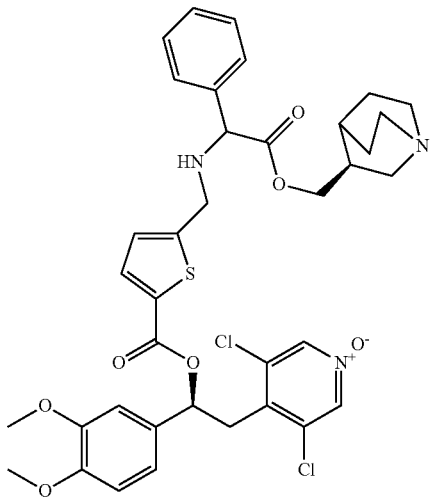

A mixture of [(1S)-2-(3,5-dichloro-1-oxido-pyridin-1-ium-4-yl)-1-(3,4-dimethoxyphenyl)ethyl]5-formylthiophene-2-carboxylate (Intermediate 1, 100 mg, 0.21 mmol), [(3S)-quinuclidin-3-yl]methyl 2-amino-2-phenyl-acetate bis-hydrochloride (100 mg, 0.29 mmol) and NaBH$_3$CN (10 mg, 0.16 mmol) in ethanol (6 mL) was stirred at room temperature for 18 hours. The solvent was removed in vacuo and the residue was partitioned between EtOAc (20 mL) and 1 N HCl (20 mL). The aqueous phase was extracted with EtOAc (2×20 mL) then basified with solid NaHCO$_3$ and extracted with EtOAc (3×10 mL). The combined organic extracts were filtered through a phase separator and the solvent was removed in vacuo. Purification by preparative HPLC gave the title compound as a colourless gum (70 mg, 45%).

$^1$H NMR (400 MHz, CD$_3$CN): δ 8.19$^{*or†}$ (s, 2 H), 8.18$^{*or†}$ (s, 2 H), 7.69 (d, J=3.8 Hz, 1 H), 7.42-7.38 (m, 5 H), 7.07-7.02 (m, 2 H), 6.97-6.94 (m, 2 H), 6.19 (dd, J=4.5, 9.6 Hz, 1 H), 4.44 (s, 1 H), 4.15-4.03 (m, 2 H), 4.00-3.89 (m, 2 H), 3.84$^{*or†}$ (s, 3 H), 3.83$^{*or†}$ (s, 3 H), 3.82 (s, 3 H), 3.71-3.64 (m, 1 H), 3.35 (dd, J=4.5, 14.1 Hz, 1 H), 2.89-2.80 (m, 2 H), 2.76-2.64 (m, 4 H), 2.30-2.19 (m, 1 H), 1.91-1.85 (m, 1 H), 1.59-1.50 (m, 3 H), 1.46-1.39 (m, 1 H), 1.32-1.23 (m, 1 H). † and * refer to different isomers (arbitrarily assigned).

LCMS (Method 4): [MH+]=740 at 3.19 min.

The following compounds were synthesized via a similar method as a mixture of diastereoisomers.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-oxo-1-phenyl-2-[[(3R)-quinuclidin-3-yl]methoxyethyl]amino]methyl]thiophene-2-carboxylate | Example 11 | Intermediate 1 and Intermediate 76 | $^1$H NMR (400 MHz, CD$_3$CN): δ 8.19*$^{or†}$ (s, 2 H), 8.18*$^{or†}$ (s, 2 H), 7.69 (d, J = 3.8 Hz, 1 H), 7.40-7.38 (m, 5 H), 7.07-7.01 (m, 2 H), 6.97-6.93 (m, 2 H), 6.18 (dd, J = 4.5, 9.6 Hz, 1 H), 4.43 (s, 1 H), 4.15-4.02 (m, 2 H), 3.99-3.89 (m, 2 H), 3.84*$^{or†}$ (s, 3 H), 3.83*$^{or†}$ (s, 3 H), 3.82 (s, 3 H), 3.67 (dd, J = 9.5, 14.0 Hz, 1 H), 3.34 (dd, J = 4.5, 14.1 Hz, 1 H), 2.86-2.80 (m, 2 H), 2.75-2.63 (m, 4 H), 2.29-2.16 (m, 1 H), 1.89-1.86 (m, 1 H), 1.58-1.49 (m, 3 H), 1.44-1.39 (m, 1 H), 1.34-1.23 (m, 1 H). † and * refer to different isomers (arbitrarily assigned). LCMS (Method 4): [MH+] = 740 at 3.18 min. |

| Structure | Example number | Precursor | Analytical Data |
|---|---|---|---|
| Epimeric mixture 2 of [2-(3,5-dichloro-1-oxido-pyridin-1-ium-4-yl)-1-(3-ethoxy-4-methoxy-phenyl)ethyl] 5-[[[2-[(1-methyl-4-piperidyl)methoxy]-2-oxo-1-phenyl-ethyl]amino]methyl]thiophene-2-carboxylate 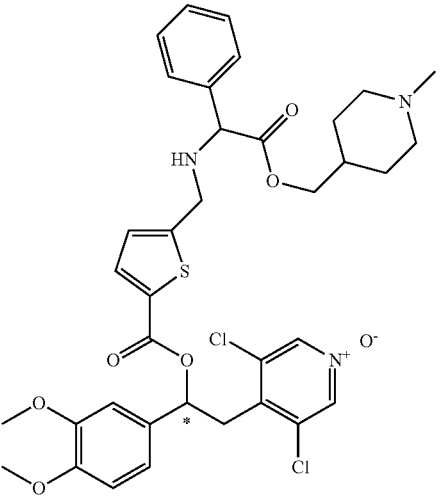 | Example 12 | Intermediate 8 and Intermediate 65 | $^1$H NMR (400 MHz, CD3CN): δ 8.18*$^{or\dagger}$ (s, 2 H), 8.17*$^{or\dagger}$ (s, 2 H), 7.70-7.68 (m, 1 H), 7.41-7.36 (m, 5 H), 7.06-7.00 (m, 2 H), 6.97-6.92 (m, 2 H), 6.17 (dd, J = 4.5, 9.6 Hz, 1 H), 4.45-4.44 (m, 1 H), 4.13-4.04 (m, 2 H), 3.96-3.91 (m, 4 H), 3.82 (s, 3 H), 3.66 (dd, J = 9.3, 14.1 Hz, 1 H), 3.36-3.31 (m, 1 H), 2.85-2.84 (m, 1 H), 2.75-2.70 (m, 2 H), 2.15 (s, 3 H), 1.81-1.74 (m, 2 H), 1.53-1.48 (m, 3 H), 1.40-1.35 (m, 3 H), 1.23-1.11 (m, 2 H). *and † refer to different isomers (arbitrarily assigned). LCMS (Method 3): [MH+] = 742 at 2.74 min. |
| [(1S)-1-[3-(cyclopropylmethoxy)-4-(difluoromethoxy)phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate 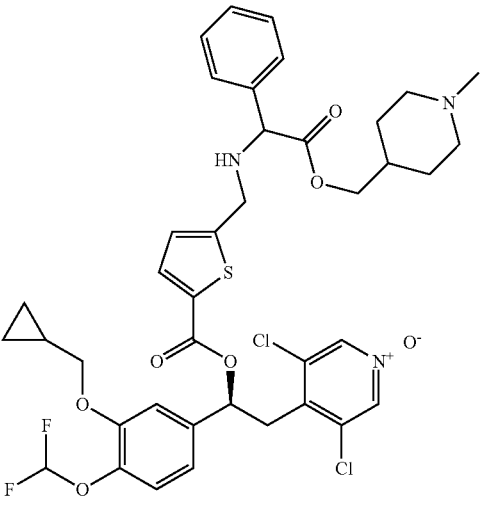 | Example 13 | Intermediate 5 and Intermediate 65 | $^1$H NMR (400 MHz, CD3CN): δ 8.19*$^{or\dagger}$ (s, 2 H), 8.19*$^{or\dagger}$ (s, 2 H), 7.71 (d, J = 3.8 Hz, 1 H), 7.43-7.33 (m, 5 H), 7.20-7.14 (m, 2 H), 7.07 (dd, J = 1.9, 8.2 Hz, 1 H), 6.96 (d, J = 4.8 Hz, 1 H), 6.78 (t, J = 75.4 Hz, 1 H), 6.17 (dd, J = 4.8, 9.3 Hz, 1 H), 4.45 (dd, J = 1.5, 8.8 Hz, 1 H), 4.00-3.89 (m, 6 H), 3.64 (dd, J = 9.3, 14.1 Hz, 1 H), 3.38-3.32 (m, 1 H), 2.91-2.85 (m, 1 H), 2.75-2.69 (m, 2 H), 2.15 (s, 3 H), 1.83-1.11 (m, 7 H), 0.65-0.60 (m, 2 H), 0.39-0.35 (m, 2 H). * and † refer to different diastereomers, NH not visible. LCMS (Method 3): [MH+] = 804 at 2.98 min. |

Example 14

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]methoxy]-2-oxo-1-phenyl-ethyl]amino]methyl]thiophene-2-carboxylate

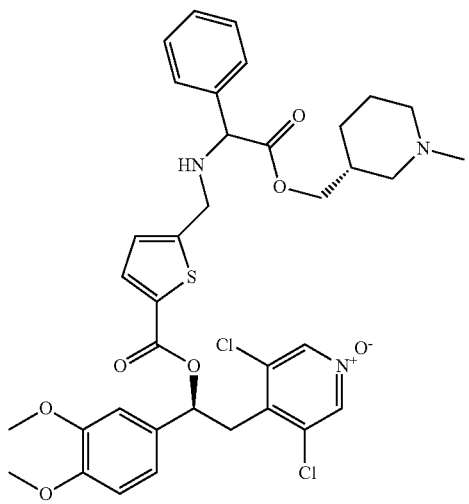

A mixture of [(1S)-2-(3,5-dichloro-1-oxido-pyridin-1-ium-4-yl)-1-(3,4-dimethoxyphenyl)ethyl]5-formylthiophene-2-carboxylate (Intermediate 1, 0.54 g, 1.11 mmol) and [(3R)-1-methyl-3-piperidyl]methyl 2-amino-2-phenyl-acetate, bis-hydrochloride (Intermediate 55, 0.45 g, 1.34 mmol) in DCM (10 mL) was stirred at room temperature and $Et_3N$ (0.37 mL, 2.70 mmol) followed by acetic acid (77 µL, 1.34 mmol) were added. The resulting mixture was stirred at room temperature for 18 hours. $NaBH(OAc)_3$ (0.83 g, 3.93 mmol) was added and the reaction mixture was stirred at room temperature 24 hours. The mixture was diluted with DCM (10 mL) and washed with saturated aqueous $NaHCO_3$ solution (2×20 mL), brine (20 mL). The organic phase was filtered through a phase separator and the solvent was removed in vacuo. Purification by preparative HPLC gave the title compound (mixture of diastereoisomers) as an off-white solid (74 mg, 9.1%). $^1$H NMR (400 MHz, CD3CN): δ 8.19† or * (s, 2 H), 8.18† or * (s, 2 H), 7.70 (d, J=3.8 Hz, 1 H), 7.41 (d, J=4.3 Hz, 4 H), 7.39-7.34 (m, 1 H), 7.07-7.02 (m, 2 H), 6.97-6.94 (m, 2 H), 6.19 (dd, J=4.5, 9.6 Hz, 1 H), 4.45 (s, 1 H), 4.07-3.87 (m, 4 H), 3.84 (s, 3 H), 3.82 (s, 3 H), 3.67 (dd, J=9.9, 14.4 Hz, 1 H), 3.35 (dd, J=4.5, 13.9 Hz, 1 H), 2.86 (s, 1 H), 2.61-2.49 (m, 2 H), 2.10† or * (s, 3 H), 2.09† or * (s, 3 H), 1.84-1.78 (m, 2 H), 1.63-1.44 (m, 4 H), 0.95-0.86 (m, 1 H). † and * refer to different isomers (arbitrarily assigned). LCMS (Method 1): [MH+]=728 at 2.56 min.

The following compounds were synthesized via a similar method as a mixture of diastereoisomers using either $Na(OAc)_3BH$ or $NaCNBH_3$ as the reducing agent, in EtOH, or DCM as solvent, another possible solvent is trifluoroethanol used e.g. for examples 115 and 116.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-[[(2R)-1-methylpyrrolidin-2-yl]methoxy]-2-oxo-1-phenyl-ethyl]amino]methyl]thiophene-2-carboxylate | Example 15 | Intermediate 1 and Intermediate 56 | $^1$H NMR (400 MHz, CD$_3$CN): δ 8.19*$^{or†}$ (s, 2 H), 8.17*$^{or†}$ (s, 2 H), 7.69 (d, J = 3.8 Hz, 1 H), 7.42-7.35 (m, 5 H), 7.07-7.01 (m, 2 H), 6.97-6.92 (m, 2 H), 6.18 (dd, J = 4.5, 9.6 Hz, 1 H), 4.45-4.43 (m, 1 H), 4.12-3.93 (m, 4 H), 3.84*$^{or†}$ (s, 3 H), 3.83*$^{or†}$ (s, 3 H), 3.82 (s, 3 H), 3.71-3.63 (m, 1 H), 3.34 (dd, J = 4.5, 14.1 Hz, 1 H), 2.95-2.86 (m, 2 H), 2.37-2.31 (m, 1 H), 2.23*$^{or†}$ (s, 3 H), 2.22*$^{or†}$ (s, 3 H), 2.18-2.11 (m, 1 H), 1.83-1.75 (m, 1 H), 1.65-1.57 (m, 2 H), 1.49-1.40 (m, 1 H). * and † refer to different isomers LCMS (Method 1): [MH+] = 14 at 2.58 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-[[(2S)-1-methylpyrrolidin-2-yl]methoxy]-2-oxo-1-phenyl-ethyl]amino]methyl]thiophene-2-carboxylate 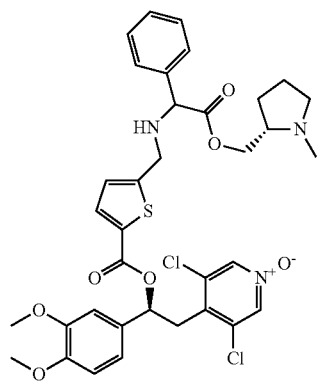 | Example 16 | Intermediate 1 and Intermediate 57 | $^1$H NMR (400 MHz, CD$_3$CN): δ 8.19*$^{or†}$ (s, 2 H), 8.17*$^{or†}$ (s, 2 H), 7.69 (d, J = 3.8 Hz, 1 H), 7.43-7.34 (m, 5 H), 7.07-7.00 (m, 2 H), 6.97-6.93 (m, 2 H), 6.19 (dd, J = 4.5, 9.6 Hz, 1 H), 4.44 (s, 1 H), 4.10-3.90 (m, 4 H), 3.83 (s, 3 H), 3.82 (s, 3 H), 3.67 (dd, J = 9.6, 14.1 Hz, 1 H), 3.37-3.31 (m, 1H), 2.95-2.84 (m, 2 H), 2.37-2.30 (m, 1 H), 2.22 (s, 3 H), 1.85-1.74 (m, 1 H), 1.65-1.57 (m, 2 H), 1.49-1.40 (m, 1 H). † and * refer to different isomers (arbitrarily assigned). NH not visible LCMS (Method 1): [MH+] = 714 at 2.58 min. |
| [(1S)-2-(3,5-dichloro-1-oxido-pyridin-1-ium-4-yl)-1-(3,4-dimethoxyphenyl)ethyl] 5-[[[2-[[(3R)-1-methylpyrrolidin-3-yl]methoxy]-2-oxo-1-phenyl-ethyl]amino]methyl]thiophene-2-carboxylate 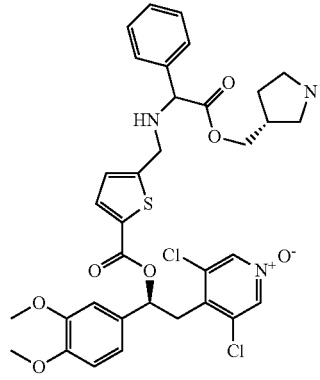 | Example 17 | Intermediate 1 and Intermediate 58 | $^1$H NMR (400 MHz, CD$_3$CN): δ 8.19*$^{or†}$ (s, 2 H), 8.18*$^{or†}$ (s, 2 H), 7.70 (d, J = 3.8 Hz, 1 H), 7.41-7.36 (m, 5 H), 7.07-7.01 (m, 2 H), 6.97-6.94 (m, 2 H), 6.19 (dd, J = 4.5, 9.3 Hz, 1 H), 4.43 (s, 1 H), 4.06-3.91 (m, 4 H), 3.84*$^{or†}$ (s, 3 H), 3.83*$^{or†}$ (s, 3 H), 3.82 (s, 3 H), 3.71-3.64 (m, 1 H), 3.37-3.32 (m, 1 H), 2.87 (s, 1 H), 2.42-2.33 (m, 3 H), 2.20 (s, 3 H), 2.12-2.11 (m, 2 H), 1.83-1.78 (m, 1 H), 1.42-1.30 (m, 1 H). † and * refer to different isomers (arbitrarily assigned). LCMS (Method 1): [MH+] = 714 at 2.52 min. |
| [(1S)-2-(3,5-dichloro-1-oxido-pyridin-1-ium-4-yl)-1-(3,4-dimethoxyphenyl)ethyl] 5-[[[2-[[(3S)-1-methylpyrrolidin-3-yl]methoxy]-2-oxo-1-phenyl-ethyl]amino]methyl]thiophene-2-carboxylate 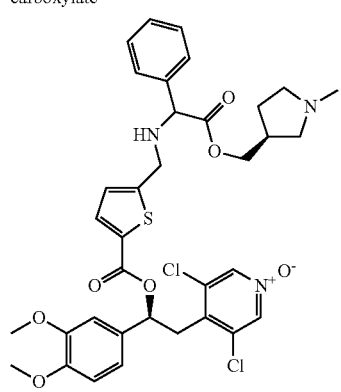 | Example 18 | Intermediate 1 and Intermediate 59 | $^1$H NMR (400 MHz, CD$_3$CN): δ 8.19*$^{or†}$ (s, 2 H), 8.18*$^{or†}$ (s, 2 H), 7.69 (d, J = 3.8 Hz, 1 H), 7.42-7.34 (m, 5 H), 7.07-7.01 (m, 2 H), 6.97-6.94 (m, 2 H), 6.19 (dd, J = 4.5, 9.6 Hz, 1 H), 4.44 (s, 1 H), 4.07-3.90 (m, 4 H), 3.84*$^{or†}$ (s, 3 H), 3.83*$^{or†}$ (s, 3 H), 3.82 (s, 3 H), 3.67 (dd, J = 9.3, 14.1 Hz, 1 H), 3.34 (dd, J = 4.4, 14.0 Hz, 1 H), 2.87-2.87 (m, 1 H), 2.42-2.34 (m, 4 H), 2.20 (s, 3 H), 2.16-2.10 (m, 1 H), 1.85-1.79 (m, 1 H), 1.41-1.31 (m, 1 H). † and * refer to different isomers (arbitrarily assigned). LCMS (Method 3): [MH+] = 714 at 2.66 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-[(1-ethyl-4-piperidyl)methoxy]-2-oxo-1-phenyl-ethyl]amino]methyl]thiophene-2-carboxylate | Example 19 | Intermediate 1 and Intermediate 60 | $^1$H NMR (400 MHz, CD$_3$CN): δ 8.19*$^{or†}$ (s, 2 H), 8.18*$^{or†}$ (s, 2 H), 7.69 (d, J = 3.8 Hz, 1 H), 7.42-7.32 (m, 5 H), 7.07-7.01 (m, 2 H), 6.97-6.93 (m, 2 H), 6.19 (dd, J = 4.5, 9.6 Hz, 1 H), 4.44 (s, 1 H), 3.94 (d, J = 6.8 Hz, 4 H), 3.84*$^{or†}$ (s, 3 H), 3.83*$^{or†}$ (s, 3 H), 3.82 (s, 3 H), 3.70-3.63 (m, 1 H), 3.38-3.32 (m, 1 H), 2.87-2.80 (m, 3 H), 2.30 (q, J = 7.2 Hz, 2 H), 1.84-1.75 (m, 2 H), 1.56-1.51 (m, 3 H), 1.20-1.10 (m, 2 H), 1.00 (t, J = 7.2 Hz, 3 H). † and * refer to different isomers (arbitrarily assigned). LCMS (Method 4): [MH+] = 742 at 3.33 min. |
| [(1S)-2-(3,5-dichloro-1-oxido-pyridin-1-ium-4-yl)-1-(3,4-dimethoxyphenyl)ethyl] 5-[[[2-[[1-(2-methoxyethyl)-4-piperidyl]methoxy]-2-oxo-1-phenyl-ethyl]amino]methyl]thiophene-2-carboxylate | Example 20 | Intermediate 1 and Intermediate 62 | $^1$H NMR (400 MHz, CD3CN): δ 8.19*$^{or†}$ (s, 2 H), 8.18*$^{or†}$ (s, 2 H), 7.69 (d, J = 3.8 Hz, 1 H), 7.42-7.39 (m, 4 H), 7.38-7.33 (m, 1 H), 7.07-7.02 (m, 2 H), 6.97-6.94 (m, 2 H), 6.19 (dd, J = 4.5, 9.6 Hz, 1 H), 4.45 (s, 1 H), 4.00-3.89 (m, 4 H), 3.84*$^{or†}$ (s, 3 H), 3.83*$^{or†}$ (s, 3 H), 3.82 (s, 3 H), 3.67 (ddd, J = 1.3, 9.6, 14.1 Hz, 1 H), 3.42 (t, J = 5.9 Hz, 2 H), 3.38-3.31 (m, 1 H), 3.27 (s, 3 H), 2.88-2.81 (m, 3 H), 2.44 (t, J = 6.0 Hz, 2 H), 1.93-1.85 (m, 2 H), 1.55-1.48 (m, 3 H), 1.20-1.09 (m, 2 H). † and * refer to different isomers (arbitrarily assigned). LCMS (Method 4): [MH+] = 772 at 3.35 min. |
| [(1S)-2-(3,5-dichloro-1-oxido-pyridin-1-ium-4-yl)-1-(3,4-dimethoxyphenyl)ethyl] 5-[[[2-oxo-1-phenyl-2-(2-pyrrolidin-1-ylethoxy)ethyl]amino]methyl]thiophene-2-carboxylate | Example 21 | Intermediate 1 and Intermediate 63 | $^1$H NMR (400 MHz, CDCl$_3$): δ 8.14*$^{or†}$ (s, 2 H), 8.13*$^{or†}$ (s, 2 H), 7.64 (d, J = 3.8 Hz, 1 H), 7.40-7.31 (m, 5 H), 7.00-6.97 (m, 2 H), 6.89-6.83 (m, 2 H), 6.22 (ddd, J = 1.8, 4.5, 9.8 Hz, 1 H), 4.45 (d, J = 2.5 Hz, 1 H), 4.30-4.23 (m, 2 H), 3.94 (dd, J = 6.6, 6.6 Hz, 2 H), 3.91*$^{or†}$ (s, 3 H), 3.90*$^{or†}$ (s, 3 H), 3.88 (s, 3 H), 3.75-3.63 (m, 1 H), 3.31 (ddd, J = 2.7, 4.5, 14.0 Hz, 1 H), 2.70-2.65 (m, 2H), 2.43 (s, 4 H), 1.70 (s, 4 H), 1.28-1.25 (m, 1 H). † and * refer to different isomers (arbitrarily assigned) LCMS (Method 1): [MH+] = 714 at 2.59 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-oxo-1-phenyl-2-[2-(1-piperidyl)ethoxyethyl]amino]methyl]thiophene-2-carboxylate 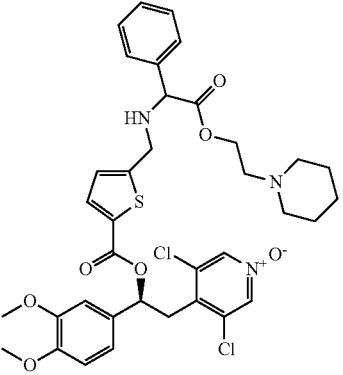 | Example 22 | Intermediate 1 and Intermediate 64 | $^1$H NMR (400 MHz, CDCl$_3$): δ 8.14*$^{or †}$ (s, 2 H), 8.13*$^{or †}$ (s, 2 H), 7.64 (d, J = 3.8 Hz, 1 H), 7.40-7.32 (m, 5 H), 6.98 (d, J = 2.8 Hz, 2 H), 6.89-6.83 (m, 2 H), 6.24-6.19 (m, 1 H), 4.44 (d, J = 2.5 Hz, 1 H), 4.28-4.21 (m, 2 H), 3.95 (d, J = 8.6 Hz, 2 H), 3.90*$^{or †}$ (s, 3 H), 3.89*$^{or †}$ (s, 3 H), 3.88 (s, 3 H), 3.66 (dd, J = 9.7, 14.0 Hz, 1 H), 3.31 (ddd, J = 2.7, 4.5, 14.0 Hz, 1 H), 2.51 (dd, J = 5.4, 5.4 Hz, 2 H), 2.28 (s, 4 H), 1.52-1.45 (m, 4 H), 1.40-1.36 (m, 2 H). † and * refer to different isomers (arbitrarily assigned). LCMS (Method 1): [MH+] = 728 at 2.62 min. |
| [(1S)-2-(3,5-dichloro-1-oxido-pyridin-1-ium-4-yl)-1-(3,4-dimethoxyphenyl)ethyl] 5-[[[2-[(1-methyl-4-piperidyl)methoxy]-2-oxo-1-phenyl-ethyl]amino]methyl]thiophene-2-carboxylate 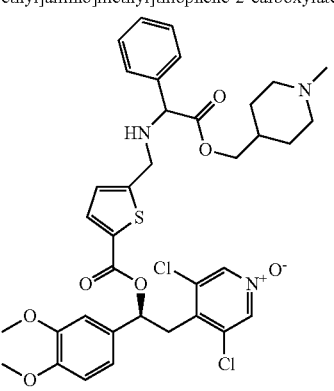 | Example 23 | Intermediate 1 and Intermediate 65 | $^1$H NMR (400 MHz, CDCl$_3$ + D$_2$O): δ 8.15*$^{or †}$ (s, 2 H), 8.14*$^{or †}$ (s, 2 H), 7.64 (d, J = 3.8 Hz, 1 H), 7.39-7.35 (m, 5 H), 7.01-6.96 (m, 2 H), 6.89-6.84 (m, 2 H), 6.24-6.20 (m, 1 H), 4.42 (d, J = 3.0 Hz, 1 H), 3.93-3.87 (m, 10 H), 3.67 (dd, J = 9.5, 13.3 Hz, 1 H), 3.34-3.28 (m, 1 H), 2.84-2.81 (m, 2 H), 2.26 (s, 3 H), 1.91-1.83 (m, 2 H), 1.54-1.54 (m, 3 H), 1.31-1.24 (m, 2 H). † and * refer to different isomers (arbitrarily assigned) LCMS (Method 2): [MH+] = 728 at 3.57 min. |
| [(1S)-2-(3,5-dichloro-1-oxido-pyridin-1-ium-4-yl)-1-(3,4-dimethoxyphenyl)ethyl] 5-[[[1-(2-fluorophenyl)-2-[(1-methyl-4-piperidyl)methoxy]-2-oxo-ethyl]amino]methyl]thiophene-2-carboxylate | Example 24 | Intermediate 1 and Intermediate 66 | $^1$H NMR (400 MHz, CDCl$_3$): δ 8.14*$^{or †}$ (s, 2 H), 8.13*$^{or †}$ (s, 2 H), 7.64 (d, J = 3.8 Hz, 1 H), 7.39-7.28 (m, 2 H), 7.18-7.05 (m, 2 H), 6.98 (d, J = 9.6 Hz, 2 H), 6.90-6.83 (m, 2 H), 6.22 (dd, J = 4.5, 9.6 Hz, 1 H), 4.74-4.70 (m, 1 H), 3.99-3.92 (m, 4 H), 3.90 (s, 3 H), 3.88*$^{or †}$ (s, 3 H), 3.87*$^{or †}$ (s, 3 H), 3.66 (ddd, J = 1.6, 9.9, 13.9 Hz, 1 H), 3.31 (ddd, J = 2.0, 4.6, 14.0 Hz, 1 H), 2.78 (d, J = 10.9 Hz, 2 H), 2.63-2.59 (m, 1 H), 2.23 (s, 3 H), 1.86-1.79 (m, 2 H), 1.51-1.48 (m, 2 H), 1.23-1.20 (m, 2 H). † and * refer to different isomers (arbitrarily assigned), NH not visible. LCMS (Method 1): [MH+] = 746 at 2.63 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-[(1-methylazetidin-3-yl)methoxy]-2-oxo-1-phenyl-ethyl]amino]methyl]thiophene-2-carboxylate | Example 25 | Intermediate 1 and Intermediate 67 | $^1$H NMR (400 MHz, CD$_3$CN): δ 8.20*$^{or\dagger}$ (s, 2 H), 8.19*$^{or\dagger}$ (s, 2 H), 7.69 (d, J = 3.8 Hz, 1 H), 7.41 (dd, J = 2.3, 4.3 Hz, 4 H), 7.39-7.34 (m, 1 H), 7.07-7.01 (m, 2 H), 6.97-6.93 (m, 2 H), 6.17 (dd, J = 4.5, 9.6 Hz, 1 H), 4.45 (s, 1 H), 4.19 (d, J = 6.6 Hz, 2 H), 3.99-3.88 (m, 2 H), 3.83 (s, 3 H), 3.82 (s, 3 H), 3.67 (dd, J = 9.9, 14.1 Hz, 1 H), 3.34 (dd, J = 4.7, 14.0 Hz, 1 H), 3.19 (q, J = 7.2 Hz, 2 H), 2.86-2.85 (m, 1 H), 2.82 (ddd, J = 6.9, 6.9, 6.9 Hz, 2 H), 2.62-2.52 (m, 1 H), 2.15 (s, 3 H). † and * refer to different isomers (arbitrarily assigned). LCMS (Method 1): [MH+] = 700 at 2.51 min. |
| [(1S)-2-(3,5-dichloro-1-oxido-pyridin-1-ium-4-yl)-1-(3,4-dimethoxyphenyl)ethyl] 5-[[[2-[[(3S)-1-methyl-3-piperidyl]methoxy]-2-oxo-1-phenyl-ethyl]amino]methyl]thiophene-2-carboxylate | Example 26 | Intermediate 1 and Intermediate 68 | $^1$H NMR (400 MHz, CDCl$_3$): δ 8.14*$^{or\dagger}$ (s, 2 H), 8.14*$^{or\dagger}$ (s, 2 H), 7.65 (d, J = 3.8 Hz, 1 H), 7.39-7.35 (m, 4 H), 7.35-7.31 (m, 1 H), 7.01-6.96 (m, 2 H), 6.89-6.84 (m, 2 H), 6.22 (ddd, J = 2.1, 4.4, 9.9 Hz, 1 H), 4.43 (d, J = 3.8 Hz, 1 H), 4.12-3.96 (m, 2 H), 3.95-3.92 (m, 2 H), 3.91*$^{or\dagger}$ (s, 3 H), 3.90*$^{or\dagger}$ (s, 3 H), 3.88 (s, 3 H), 3.67 (dd, J = 9.1, 13.6 Hz, 1 H), 3.31 (ddd, J = 2.6, 4.5, 14.0 Hz, 1 H), 2.71-2.68 (m, 1 H), 2.60 (s, 1 H), 2.17*$^{or\dagger}$ (s, 3 H), 2.15*$^{or\dagger}$ (s, 3 H), 1.90-1.76 (m, 2 H), 1.56-1.41 (m, 4 H), 0.86-0.78 (m, 1 H). † and * refer to different isomers (arbitrarily assigned). NH not visible LCMS (Method 1): [MH+] = 728 at 2.56 min. |
| [(1S)-2-(3,5-dichloro-1-oxido-pyridin-1-ium-4-yl)-1-(3,4-dimethoxyphenyl)ethyl] 5-[[[2-[[(2S)-1-methylazetidin-2-yl]methoxy]-2-oxo-1-phenyl-ethyl]amino]methyl]thiophene-2-carboxylate | Example 27 | Intermediate 1 and Intermediate 69 | $^1$H NMR (400 MHz, CD$_3$CN): δ 8.19*$^{or\dagger}$ (s, 2 H), 8.18*$^{or\dagger}$ (s, 2 H), 7.69 (d, J = 3.8 Hz, 1 H), 7.43-7.34 (m, 5 H), 7.07-7.02 (m, 2 H), 6.97-6.94 (m, 2 H), 6.19 (dd, J = 4.5, 9.6 Hz, 1 H), 4.46 (s, 1 H), 4.17 (ddd, J = 3.9, 11.4, 19.8 Hz, 1 H), 3.98 (ddd, J = 3.9, 11.8, 14.9 Hz, 3 H), 3.84*$^{or\dagger}$ ( (s, 3 H), 3.83*$^{or\dagger}$ (s, 3 H), 3.83 (s, 3 H), 3.68 (dd, J = 9.6, 14.1 Hz, 1 H), 3.38-3.32 (m, 1 H), 3.24-3.15 (m, 1 H), 3.12-3.01 (m, 1 H), 2.89 (s, 1 H), 2.73-2.64 (m, 1 H), 2.10*$^{or\dagger}$ (s, 3 H), 2.09*$^{or\dagger}$ (s, 3 H), 1.90-1.76 (m, 2 H). † and * refer to different isomers (arbitrarily assigned). LCMS (Method 1): [MH+] = 700 at 2.57 min. |

| Structure | Example number | Precursor | Analytical Data |
| --- | --- | --- | --- |
| [(1S)-2-(3,5-dichloro-1-oxido-pyridin-1-ium-4-yl)-1-(3,4-dimethoxyphenyl)ethyl] 5-[[[2-[[(2R)-1-methylazetidin-2-yl]methoxy]-2-oxo-1-phenyl-ethyl]amino]methyl]thiophene-2-carboxylate | Example 28 | Intermediate 1 and Intermediate 70 | $^1$H NMR (400 MHz, CD$_3$CN): δ 8.19*$^{or†}$ (s, 2 H), 8.18*$^{or†}$ (s, 2 H), 7.69 (d, J = 3.8 Hz, 1 H), 7.43-7.39 (m, 5 H), 7.07-7.01 (m, 2 H), 6.97-6.94 (m, 2 H), 6.18 (dd, J = 4.5, 9.6 Hz, 1 H), 4.45 (s, 1 H), 4.22-4.12 (m, 1 H), 4.00-3.93 (m, 3 H), 3.84*$^{or†}$ (s, 3 H), 3.83*$^{or†}$ (s, 3 H), 3.82 (s, 3 H), 3.71-3.64 (m, 1 H), 3.34 (dd, J = 4.5, 14.1 Hz, 1 H), 3.24-3.16 (m, 1 H), 3.11-3.02 (m, 1 H), 2.87 (s, 1 H), 2.73-2.64 (m, 1 H), 2.09*$^{or†}$ (s, 3 H), 2.09*$^{or†}$ (s, 3 H), 1.92-1.76 (m, 2 H). † and * refer to different isomers (arbitrarily assigned). LCMS (Method 2): [MH+] = 700 at 3.62 min. |
| [(1S)-2-(3,5-dichloro-1-oxido-pyridin-1-ium-4-yl)-1-(3,4-dimethoxyphenyl)ethyl] 5-[[[2-[[(2R)-1,4-dimethylpiperazin-2-yl]methoxy]-2-oxo-1-phenyl-ethyl]amino]methyl]thiophene-2-carboxylate | Example 29 | Intermediate 1 and Intermediate 71 | $^1$H NMR (400 MHz, CD$_3$CN): δ 8.19*$^{or†}$ (s, 2 H), 8.18*$^{or†}$ (s, 2 H), 7.69 (d, J = 3.8 Hz, 1 H), 7.42-7.36 (m, 5 H), 7.07-7.02 (m, 2 H), 6.97-6.93 (m, 2 H), 6.18 (dd, J = 4.5, 9.6 Hz, 1 H), 4.45 (d, J = 1.8 Hz, 1 H), 4.23-4.03 (m, 2 H), 4.01-3.90 (m, 2 H), 3.84*$^{or†}$ (s, 3 H), 3.83*$^{or†}$ (s, 3 H), 3.82 (s, 3 H), 3.67 (dd, J = 9.6, 14.1 Hz, 1 H), 3.34 (dd, J = 4.3, 14.1 Hz, 1 H), 2.68-2.62 (m, 1 H), 2.55-2.43 (m, 2 H), 2.30-2.18 (m, 2 H), 2.15 (s, 3 H), 2.10 (s, 3 H), 2.05-1.99 (m, 1 H), 1.80-1.74 (m, 1 H). * and † refer to different isomers. NH not observed. LCMS (Method 1): [MH+] = 743 at 2.51 min. |
| [(1S)-2-(3,5-dichloro-1-oxido-pyridin-1-ium-4-yl)-1-(3,4-dimethoxyphenyl)ethyl] 5-[[[2-[[(2R)-1-methyl-2-piperidyl]methoxy]-2-oxo-1-phenyl-ethyl]amino]methyl]thiophene-2-carboxylate | Example 30 | Intermediate 1 and Intermediate 72 | $^1$H NMR (400 MHz, CD$_3$CN): δ 8.19 *$^{or†}$ (s, 2 H), 8.18*$^{or†}$ (s, 2 H), 7.70 (d, J = 3.8 Hz, 1 H), 7.42-7.36 (m, 5 H), 7.07-7.02 (m, 2 H), 6.98-6.94 (m, 2 H), 6.19 (dd, J = 4.5, 9.6 Hz, 1 H), 4.45 (dd, J = 3.0, 8.1 Hz, 1 H), 4.13-4.09 (m, 2 H), 4.01-3.91 (m, 2 H), 3.84*$^{or†}$ (s, 3 H), 3.83*$^{or†}$ (s, 3.82 (s, 3 H), 3.67 (dd, J = 9.6, 14.1 Hz, 1 H), 3.38-3.32 (m, 1 H), 2.89-2.86 (m, 1 H), 2.76-2.69 (m, 1 H), 2.12*$^{or†}$ (s, 3 H), 2.11*$^{or†}$ (s, 3 H), 1.65-1.37 (m, 5 H), 1.26-1.16 (m, 2 H). NH not visible. * and † refer to different isomers. LCMS (Method 4): [MH+] = 728 at 3.4 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-[(1-methyl-2-piperidyl)methoxy]-2-oxo-1-phenyl-ethyl]amino]methyl]thiophene-2-carboxylate | Example 31 | Intermediate 1 and Intermediate 73 | $^1$H NMR (400 MHz, CD$_3$CN): δ 8.19*$^{or†}$ (s, 2 H), 8.18*$^{or†}$ (s, 2 H), 7.69 (d, J = 3.9 Hz, 1 H), 7.44-7.32 (m, 5 H), 7.04 (ddd, J = 6.0, 6.0, 6.0 Hz, 2 H), 6.95 (d, J = 8.1 Hz, 2 H), 6.19 (dd, J = 4.2, 10.0 Hz, 1 H), 4.45 (d, J = 7.1 Hz, 1 H), 4.11 (m, 2 H), 3.95 (m, 2 H), 3.84*$^{or†}$ (s, 3 H), 3.83*$^{or†}$ (s, 3 H), 3.83 (s, 3 H), 3.68 (dd, J = 9.7, 13.5 Hz, 1 H), 3.35 (dd, J = 5.2, 14.8 Hz, 1 H), 2.93-2.83 (m, 1 H), 2.78-2.67 (m, 1 H), 2.12*$^{or†}$ (s, 3 H), 2.11*$^{or†}$ (s, 3 H), 1.67-1.35 (m, 5 H), 1.24-1.14 (m, 2 H). NH not visible. * and † refer to different isomers. LCMS (Method 3): [MH+] = 728 at 2.74 min. |
| [(1S)-2-(3,5-dichloro-1-oxido-pyridin-1-ium-4-yl)-1-(3,4-dimethoxyphenyl)ethyl] 5-[[[2-[[(2S)-1,4-dimethylpiperazin-2-yl]methoxy]-2-oxo-1-phenyl-ethyl]amino]methyl]thiophene-2-carboxylate | Example 32 | Intermediate 1 and Intermediate 74 | $^1$H NMR (400 MHz, CD$_3$CN): δ 8.19*$^{or†}$ (s, 2 H), 8.18*$^{or†}$ (s, 2 H), 7.69 (d, J = 3.8 Hz, 1 H), 7.43-7.36 (m, 5 H), 7.07-7.01 (m, 2 H), 6.97-6.93 (m, 2 H), 6.18 (dd, J = 4.4, 9.5 Hz, 1 H), 4.45 (s, 1 H), 4.23-3.90 (m, 4 H), 3.83 (s, 3 H), 3.82 (s, 3 H), 3.67 (dd, J = 9.6, 14.1 Hz, 1 H), 3.38-3.31 (m, 1 H), 2.68-2.61 (m, 1 H), 2.54-2.42 (m, 2 H), 2.24-2.17 (m, 2 H), 2.16 (s, 3 H), 2.10 (s, 3 H), 2.04-1.99 (m, 1 H), 1.80-1.72 (m, 1 H). † and * refer to different isomers (arbitrarily assigned), NH not observed. LCMS (Method 4): [MH+] = 743 at 3.17 min. |
| [(1S)-2-(3,5-dichloro-1-oxido-pyridin-1-ium-4-yl)-1-(3,4-dimethoxyphenyl)ethyl] 5-[[[2-oxo-1-phenyl-2-(quinuclidin-4-ylmethoxy)ethyl]amino]methyl]thiophene-2-carboxylate | Example 33 | Intermediate 1 and Intermediate 77 | $^1$H NMR (400 MHz, CD$_3$CN): δ 8.19 (s, 2 H), 7.67 (d, J = 3.9 Hz, 1 H), 7.40-7.30 (m, 5 H), 7.04-6.99 (m, 2 H), 6.94-6.91 (m, 2 H), 6.15 (dd, J = 4.3, 9.7 Hz, 1 H), 4.43*$^{or†}$ (s, 1 H), 4.42*$^{or†}$ (s, 1 H), 3.93 (d, J = 15.1 Hz, 1 H), 3.88 (d, J = 15.3 Hz, 1 H), 3.81*$^{or†}$ (s, 3 H), 3.80*$^{or†}$ (s, 3 H), 3.79 (s, 3 H), 3.78-3.61 (m, 4 H), 3.32 (dd, J = 4.4, 14.0 Hz, 1 H), 2.70 (t, J = 7.9 Hz, 6 H), 1.28-1.18 (m, 6 H). † and * refer to different isomers (arbitrarily assigned). LCMS (Method 1): [MH+] = 740 at 2.56 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[1-methyl-2-[(1-methyl-4-piperidyl)methoxy]-2-oxo-1-phenyl-ethyl]amino]methyl]thiophene-2-carboxylate | Example 34 | Intermediate 1 and Intermediate 78 | $^1$H NMR (400 MHz, CD$_3$CN): δ 8.20*$^{or†}$ (s, 2 H), 8.19*$^{or†}$ (s, 2 H), 7.69 (d, J = 3.8 Hz, 1 H), 7.54-7.50 (m, 2 H), 7.43-7.37 (m, 2 H), 7.33 (dd, J = 7.2, 7.2 Hz, 1 H), 7.08-7.02 (m, 2 H), 6.95 (dd, J = 1.6, 5.4 Hz, 2 H), 6.17 (dd, J = 4.5, 9.6 Hz, 1 H), 4.00-3.96 (m, 2 H), 3.89-3.85 (m, 2 H), 3.84*$^{or†}$ (s, 3 H), 3.83*$^{or†}$ (s, 3 H), 3.82 (s, 3 H), 3.68 (dd, J = 9.7, 14.0 Hz, 1 H), 3.34 (dd, J = 4.5, 14.1 Hz, 1 H), 2.93-2.89 (m, 1 H), 2.75 (d, J = 11.4 Hz, 2 H), 2.16 (s, 3 H), 1.85-1.78 (m, 2 H), 1.67 (s, 3 H), 1.58-1.50 (m, 3 H), 1.27-1.17 (m, 2 H). † and * refer to different isomers (arbitrarily assigned). LCMS (Method 1): [MH+] = 742 at 2.59 min. |
| [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)methoxy]-2-oxo-1-phenyl-ethyl]amino]methyl]thiophene-2-carboxylate | Example 35 | Intermediate 1 and Intermediate 82 | $^1$H NMR (400 MHz, CDCl$_3$): δ 8.15 (d, J = 1.3 Hz, 2 H), 7.63 (dd, J = 1.5, 3.8 Hz, 1 H), 7.42-7.32 (m, 5 H), 7.03-6.97 (m, 2 H), 6.88-6.83 (m, 2 H), 6.22 (dd, J = 4.3, 9.6 Hz, 1 H), 4.30 (dd, J = 3.0, 10.4 Hz, 1 H), 4.10 (dd, J = 6.3, 10.9 Hz, 1 H), 3.99 (dd, J = 6.2, 10.7 Hz, 1 H), 3.93-3.85 (m, 8 H), 3.72-3.64 (m, 2 H), 3.33 (ddd, J = 2.8, 4.5, 13.9 Hz, 1 H), 3.07-2.95 (m, 2 H), 2.79 (d, J = 11.9 Hz, 2 H), 2.23 (s, 3 H), 1.89-1.81 (m, 2 H), 1.57-1.46 (m, 3 H), 1.31-1.22 (m, 2 H). LCMS (Method 1): [MH+] = 758 at 2.64 min. |
| [(1S)-2-(3,5-dichloro-1-oxido-pyridin-1-ium-4-yl)-1-(3,4-dimethoxyphenyl)ethyl] 5-[[[2-[(1-methyl-4-piperidyl)methoxy]-2-oxo-1-phenyl-ethyl]amino]methyl]thiophene-3-carboxylate | Example 36 | Intermediate 6 and Intermediate 65 | $^1$H NMR (400 MHz, DMSO): δ 8.61 (s, 2 H), 8.32 (s, 1 H), 7.47-7.30 (m, 6 H), 7.08 (s, 1 H), 7.05-7.02 (m, 2 H), 6.19 (dd, J = 4.4, 9.5 Hz, 1 H), 4.47-4.42 (m, 1 H), 3.96-3.85 (m, 4 H), 3.82 (d, J = 10.6 Hz, 6 H), 3.67-3.59 (m, 1 H), 3.53-3.47 (m, 1 H), 3.33 (d, J = 4.5 Hz, 1 H), 2.76 (d, J = 10.6 Hz, 2 H), 2.20 (s, 3 H), 1.86-1.86 (m, 2 H), 1.50 (s, 3 H), 1.26-1.11 (m, 2 H). LCMS (Method 3): [MH+] = 728 at 2.59 min. |

| Structure | Example number | Precursor | Analytical Data |
|---|---|---|---|
| [(1S)-2-(3,5-dichloro-1-oxido-pyridin-1-ium-4-yl)-1-[4-(difluoromethoxy)-3-(2-methoxyethoxy)phenyl]ethyl] 5-[[[2-[(1-methyl-4-piperidyl)methoxy]-2-oxo-1-phenyl-ethyl]amino]methyl]thiophene-2-carboxylate | Example 113 | Intermediate 65 and intermediate 95 | $^1$H NMR (400 MHz, CD$_3$CN): δ 8.19*$^{or†}$ (s, 2 H), 8.19*$^{or†}$ (s, 2 H), 7.72 (d, J = 3.8 Hz, 1 H), 7.42-7.39 (m, 4 H), 7.39-7.34 (m, 1 H), 7.23-7.17 (m, 2 H), 7.09 (dd, J = 1.9, 8.2 Hz, 1 H), 6.98-6.96 (m, 1 H), 6.79 (t, J = 75.4 Hz, 1 H), 6.19 (dd, J = 4.5, 9.3 Hz, 1 H), 4.45 (s, 1 H), 4.26-4.17 (m, 2 H), 3.97-3.92 (m, 4 H), 3.72 (t, J = 4.6 Hz, 2 H), 3.65 (dd, J = 8.9, 14.1 Hz, 1 H), 3.39-3.32 (m, 1 H), 3.37 (s, 3 H), 3.02-2.83 (m 1 H), 2.83-2.75 (m, 2 H), 2.20 (s, 3 H), 1.92-1.83 (m, 2 H), 1.57-1.50 (m, 3 H), 1.32-1.14 (m, 2 H), † and * refer to different isomers (arbitrarily assigned). LCMS [(Method 3)]: [MH+] = 808 at 2.83 min. |
| [(1S)-2-(3,5-dichloro-1-oxido-pyridin-1-ium-4-yl)-1-(3,4-dimethoxyphenyl)ethyl] 5-[[[2-[[(1R,5S)-8-methyl-8-azabicyclo[3.2.1]octan-3-yl]methoxy]-2-oxo-1-phenyl-ethyl]amino]methyl]thiophene-2-carboxylate | Example 114 | Intermediate 1 and intermediate 104 | $^1$H NMR (400 MHz, CD$_3$CN): δ 8.11*$^{or†}$ (s, 2 H), 8.10*$^{or†}$ (s, 2 H), 7.61 (d, J = 3.8 Hz, 1 H), 7.34-7.30 (m, 5 H), 6.99-6.94 (m, 2 H), 6.89-6.85 (m, 2 H), 6.10 (dd, J = 4.5, 9.6 Hz, 1 H), 4.35 (d, J = 7.1 Hz, 1 H), 3.88-3.83 (m, 2 H), 3.83-3.77 (m, 2 H), 3.76*$^{or†}$ (s, 3 H), 375*$^{or†}$ (s, 3 H), 3.74 (s, 3 H), 3.63-3.56 (m, 1 H), 3.29-3.23 (m, 1 H), 2.97-2.91 (m, 2 H), 2.78 (d, J = 5.8 Hz, 1 H), 2.07 (s, 3 H), 1.80-1.71 (m, 1 H), 1.40-1.32 (m, 3 H), 1.24-1.18 (m, 5 H). † and * refer to different isomers (arbitrarily assigned). LCMS [(Method 3)]: [MH+] = 754 at 2.69 min. |
| [(1S)-2-(3,5-dichloro-1-oxido-pyridin-1-ium-4-yl)-1-(3,4-dimethoxyphenyl)ethyl] 5-[[[1-(hydroxymethyl)-2-[[(3S)-1-methylpyrrolidin-3-yl]methoxy]-2-oxo-1-phenyl-ethyl]amino]methyl]thiophene-2-carboxylate | Example 115 | Intermediate 1 and intermediate 106 | $^1$H NMR (400 MHz, CD3CN): δ 8.21(s, 2 H), 7.69 (d, J = 3.8 Hz, 1 H), 7.51 (dd, J = 2.5, 7.7 Hz, 2 H), 7.43-7.39 (m, 2 H), 7.37-7.33 (m, 1 H), 7.10-7.04 (m, 2 H), 6.98-6.93 (m, 2 H), 6.19 (dd, J = 4.5, 9.7 Hz, 1 H), 4.49†or* (dd, J = 3.8, 11.5 Hz, 1 H), 4.33†or* (dd, J = 4.7, 11.8 Hz, 1 H), 4.20-3.98 (m, 3 H), 3.86 (s, 3 H), 3.84 (s, 3 H), 3.83-3.74 (m, 2 H), 3.73-3.66 (m, 1 H), 3.36 (dd, J = 4.4, 14.2 Hz, 1 H), 3.08 (br s, 1 H), 2.80-2.75†or* (m, 1 H), 2.72-2.66†or* (m, 1 H), 2.65-2.49 (m, 2H), 2.40-2.30 (m, 1 H), 2.26†or* (s, 3 H), 2.23†or* (s, 3 H), 2.08-1.81 (m, 2 H), 1.74-1.53 (m, 1 H). † and * refer to different isomers (arbitrarily assigned) NH not seenLCMS [(Method 3)]: [MH+] = 744 at 2.69 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[1-(hydroxymethyl)-2-[[(3R)-1-methylpyrrolidin-3-yl]methoxy]-2-oxo-1-phenyl-ethyl]amino]methyl]thiophene-2-carboxylate 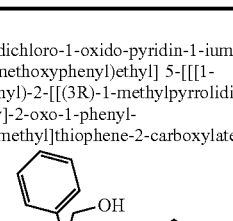 | Example 116 | Intermediate 1 and intermediate 107 | $^1$H NMR (400 MHz, CD$_3$CN): δ 8.21 (s, 2 H), 7.68 (dd, J = 2.1, 3.8 Hz, 1 H), 7.53-7.49 (m, 2 H), 7.44-7.35 (m, 3 H), 7.09-7.04 (m, 2 H), 6.98-6.93 (m, 2 H), 6.19 (dd, J = 4.5, 9.7 Hz, 1 H), 4.50-4.46$^{†or*}$ (m, 1 H), 4.31$^{†or*}$ (dd, J = 6.0, 11.3 Hz, 1 H), 4.20-3.98 (m, 3 H), 3.86 (s, 3 H), 3.84 (s, 3 H), 3.82-3.74 (m, 2 H), 3.69 (dd, J = 8.7, 13.9 Hz, 1 H), 3.37 (ddd, J = 1.6, 4.6, 14.1 Hz, 1H), 3.15 (hr s, 1 H), 2.87-2.77 (m, 1 H), 2.70-2.47 (m, 3 H), 2.39-2.35 (m, 2 H), 2.34$^{†or*}$ (s, 3 H), 2.30$^{†or*}$ (s, 3 H), 2.06-2.01 (m, 1 H), 1.76-1.68$^{†or*}$ (m, 1 H), 1.67-1.59$^{†or*}$ (m, 1 H), † and * refer to different isomers (arbitrarily assigned). LCMS [(Method 3)]: [MH+] = 744 at 2.69 min. |

Example 37

[(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-(2-thienyl)ethyl]amino]methyl]thiophene-2-carboxylate

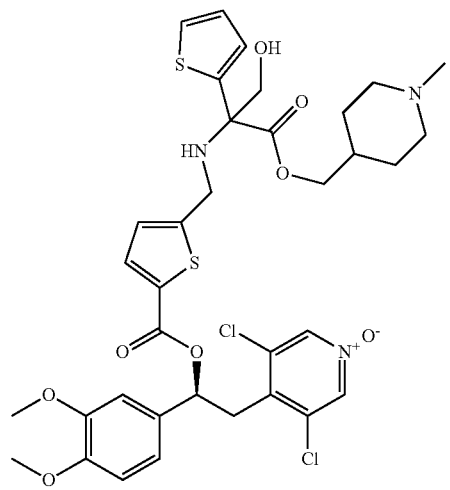

To a stirred solution of (1-methyl-4-piperidyl)methyl 2-amino-2-(2-thienyl)acetate bis hydrochloride (Intermediate 80, 1.2 g, 3.53 mmol) and Et$_3$N (0.98 mL, 7.06 mmol) in dry DCM (20 mL) was added MgSO$_4$ and the resulting mixture was stirred at room temperature for one hour. Benzaldehyde (0.36 mL, 3.53 mmol) was then added and the mixture was stirred at room temperature for 48 hours. The mixture was filtered and the solid was washed through with DCM. The filtrate was washed with water and the organic phase was filtered through a phase separator and the solvent was removed in vacuo. The residue was taken up into dry dioxane (18 mL) and para-formaldehyde (657 mg, 21.91 mmol) was added followed by the addition of DBU (654 μL, 4.38 mmol). The resulting mixture was stirred at room temperature for 18 hours. The solvent was removed in vacuo, the residue was dissolved in EtOAc (30 mL) and washed with water (3×30 mL). The aqueous phases were combined and back-extracted with EtOAc (3×30 mL). The organic extracts were combined, filtered through a phase separator and concentrated in vacuo. The residue was treated with 1 N HCl solution (15 mL) in THF (15 mL) and stirred at room temperature for 18 hours. The solvent was removed in vacuo, the residue was taken up in 1 N HCl solution (30 mL) and washed with EtOAc (3×30 mL). The combined organic phases were back-extracted with 1N HCl (3×30 mL). The combined aqueous extracts were concentrated in vacuo and co-evaporated with CH$_3$CN. To a solution of the residue in DCM (16 mL) was added [(1S)-2-(3,5-dichloro-1-oxido-pyridin-1-ium-4-yl)-1-(3,4-dimethoxyphenyl)ethyl]5-formylthiophene-2-carboxylate (Intermediate 1, 780 mg, 1.62 mmol), Et$_3$N (452 μL, 3.24 mmol) and AcOH (185 μL, 3.24 mmol). The resulting mixture was stirred at room temperature for 18 hours. NaBH(OAc)$_3$ (1.07 g, 4.86 mmol) was added and the mixture was stirred at room temperature for 18 hours. The reaction solution was diluted with H$_2$O (10 mL) and DCM (40 mL). The organic phase was filtered through a phase separator and was concentrated in vacuo. Purification of the crude material by preparative HPLC afforded the title compound (15 mg, 6%) as a white solid.

$^1$H NMR (400 MHz, CD$_3$CN): δ 8.18$^{*or†}$ (s, 2 H), 8.17$^{*or†}$ (s, 2 H), 7.67-7.65 (m, 1 H), 7.39-7.36 (m, 1 H), 7.14 (dd, J=1.1, 3.7 Hz, 1 H), 7.06-7.00 (m, 3 H), 6.95-6.92 (m, 2 H), 6.19-6.14 (m, 1 H), 4.14-3.96 (m, 4 H), 3.92-3.83 (m, 2 H), 3.82 (s, 3 H), 3.80 (s, 3 H), 3.66 (dd, J=9.6, 14.1 Hz, 1 H), 3.34 (ddd, J=1.9, 4.7, 14.3 Hz, 1 H), 3.19-3.13 (m, 1 H), 2.78 (d, J=11.9 Hz, 2 H), 2.17 (s, 3 H), 1.88-1.83 (m, 2 H), 1.63-1.60 (m, 3 H), 1.33-1.25 (m, 2 H). † and * refer to different isomers (arbitrarily assigned), NH or OH not observed. LCMS (Method 4): [MH+]=764 at 3.29 min.

Example 117

[(1S)-2-(3,5-dichloro-1-oxido-pyridin-1-ium-4-yl)-1-(3,4-dimethoxyphenyl)ethyl]5-[[[1-(hydroxymethyl)-2-oxo-1-phenyl-2-(quinuclidin-4-ylmethoxy)ethyl]amino]methyl]thiophene-2-carboxylate

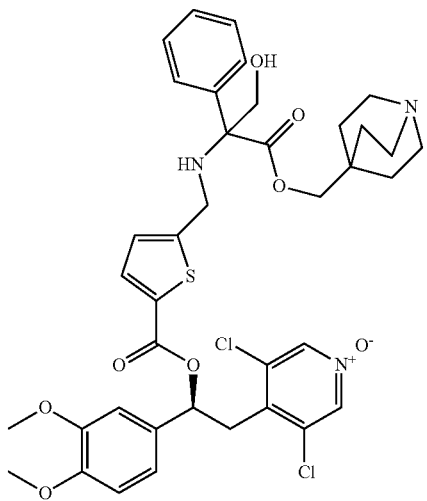

To a solution of quinuclidin-4-ylmethyl-2-amino-2-phenylacetate bis hydrochloride (Intermediate 77, 150 mg, 0.43 mmol) in TFE was added Et$_3$N (120 μL, 0.86 mmol) and the resulting mixture was stirred at room temperature for 20 minutes. [(1S)-2-(3,5-dichloro-1-oxido-pyridin-1-ium-4-yl)-1-(3,4-dimethoxyphenyl)ethyl]5-formylthiophene-2-carboxylate (Intermediate 1, 230 mg, 0.48 mmol) and acetic acid (49 μL, 0.86 mmol) were subsequently added and the mixture was stirred at room temperature for 18 hours. The reaction solvent was removed in vacuo and the residue was azeotroped with toluene. The residue was taken up into dioxane (5 mL) and paraformaldehyde (65 mg, 2.15 mmol) was added, followed by DBU (78 μL, 0.52 mmol). The resulting mixture was stirred at room temperature for 18 hours. The solvent was removed in vacuo and the residue partitioned between chloroform (15 mL) and H$_2$O (15 mL). The layers were separated and the organic phase was washed with H$_2$O (2×15 mL), passed through a phase separator and concentrated in vacuo to give a yellow oil (340 mg). The crude material was taken up into acetonitrile (5 mL) and NaBH(OAc)$_3$ (113 mg, 0.53 mmol) was added. The resultant mixture was stirred at room temperature for 18 hours. The solvent was removed in vacuo and the residue partitioned between 2N HCl (10 mL) and EtOAc (10 mL) the layers were separated and the aqueous phase was washed with EtOAc (2×15 mL). The aqueous phase was neutralized with solid NaHCO$_3$ and extracted with CHCl$_3$ (3×15 mL). The organic phases were combined, passed through a phase separator and concentrated in vacuo. Purification by preparative HPLC afforded the title compound (mixture of diastereoisomers) as a yellow solid (10 mg, 3%).

$^1$H NMR (400 MHz, CD$_3$CN): δ 8.20 (s, 2 H), 7.65 (d, J=3.8 Hz, 1 H), 7.49-7.44 (m, 2 H), 7.41-7.29 (m, 3 H), 7.06-7.00 (m, 2 H), 6.95-6.89 (m, 2 H), 6.14 (dd, J=4.4, 9.6 Hz, 1 H), 4.20-4.15 (m, 1 H), 3.96-3.83 (m, 3 H), 3.82 (s, 3 H), 3.80 (s, 3 H), 3.76-3.71 (m, 2 H), 3.67 (dd, J=9.7, 13.9 Hz, 1 H), 3.33 (dd, J=4.5, 13.9 Hz, 1 H), 2.75 (t, J=7.7 Hz, 6 H), 1.36-1.28 (m, 6 H), both NH and OH protons not observed.

LCMS (Method 3): [MH+]=770 at 2.70 min.

Example 38

[(1S)-2-(3,5-dichloro-1-oxido-pyridin-1-ium-4-yl)-1-(3,4-dimethoxyphenyl)ethyl]5-[[[1-[(1-methyl-4-piperidyl)methoxycarbonyl]indan-1-yl]amino]methyl]thiophene-2-carboxylate

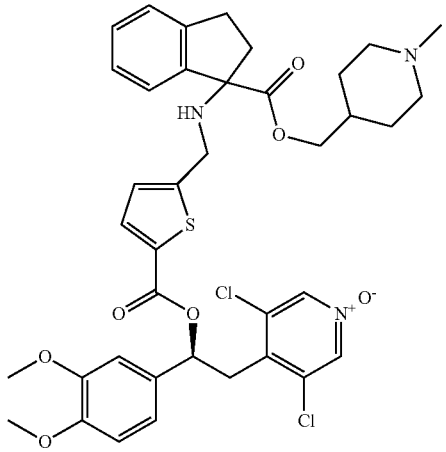

To a solution of (1-methyl-4-piperidyl)methyl-1-aminoindane-1-carboxylate bis hydrochloride (Intermediate 79, 360 mg, 1 mmol) in acetonitrile (5 mL) was added [(1S))-2-(3,5-dichloro-1-oxido-pyridin-1-ium-4-yl)-1-(3,4-dimethoxyphenyl)ethyl]5-formylthiophene-2-carboxylate (Intermediate 1, 481 mg, 1.0 mmol) and acetic acid (130 μL, 2.0 mmol). The mixture was stirred at room temperature for 18 hours. The solvent was removed in vacuo and the residue was azeotroped with toluene. The residue was taken up into acetonitrile (5 mL), and sodium triacetoxyborohydride (663 mg, 3.0 mmol) was added. The resultant solution was stirred at room temperature for 18 hours. Additional sodium triacetoxyborohydride (663 mg, 3.0 mmol) was added and the stirring was maintained at room temperature for 4 hours. The solvent was removed in vacuo and the residue was taken up in water (30 mL) and EtOAc (100 mL). The layers were separated and the aqueous phase was extracted with EtOAc (2×20 mL). The combined organic phases were filtered through a phase separator and the solvent was removed in vacuo. Purification of the crude material by preparative HPLC afforded the title compound (130 mg, 17%) as a white solid.

$^1$H NMR (400 MHz, CDCl$_3$): δ 8.14$^{*or†}$ (s, 2 H), 8.13$^{*or†}$ (s, 2 H), 7.62 (d, J=3.8 Hz, 1 H), 7.30-7.27 (m, 3 H), 7.25-7.20 (m, 1 H), 7.00-6.95 (m, 2 H), 6.89-6.83 (m, 2 H), 6.21 (dd, J=4.2, 9.7 Hz, 1 H), 3.96 (d, J=6.3 Hz, 2 H), 3.90$^{*or†}$ (s, 3 H), 3.90$^{*or†}$ (s, 3 H), 3.88 (s, 3 H), 3.89-3.80 (m, 2 H), 3.65 (dd, J=9.9, 13.9 Hz, 1 H), 3.30 (dd, J=4.5, 13.9 Hz, 1 H), 3.09 (t, J=6.9 Hz, 2 H), 2.84-2.81 (m, 2 H), 2.72 (td, J=6.6, 13.1 Hz, 1 H), 2.25 (s, 3 H), 2.24-2.18 (m, 1 H), 1.91-1.82 (m, 2 H), 1.59-1.50 (m, 3 H), 1.33-1.22 (m, 2 H). † and * refer to different isomers (arbitrarily assigned), NH not visible. LCMS (Method 1): [MH+]=754 at 2.52 min.

Example 39

[(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]-(oxetan-3-yl)amino]methyl]thiophene-2-carboxylate

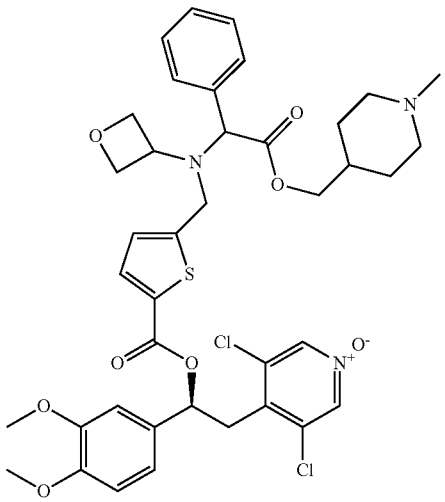

A mixture of [(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-2-carboxylate (Example 23, 118 mg, 0.16 mmol), oxetan-3-one (104 µL, 1.6 mmol) and AcOH (10 µL, 0.16 mmol) in dry DCM (5 mL) was stirred at room temperature for 2 hours and NaBH(OAc)$_3$ (0.12 g, 0.56 mmol) was added and the stirring was maintained at room temperature for 18 hours. Additional oxetan-3-one (0.1 mL, 1.6 mmol) and NaBH(OAc)$_3$ (0.1 g, 0.47 mmol) were added on three further occasions and the mixture was stirred at room temperature for a total of 7 days. The mixture was then diluted with DCM (10 mL) and washed with saturated aqueous NaHCO$_3$ solution (2×10 mL) and brine (10 mL). The organic phase was filtered through a phase separator and the solvent was removed in vacuo. Purification by preparative HPLC gave the title compound (mixture of diastereoisomers) as an off-white solid (17 mg, 13%).

$^1$H NMR (400 MHz, CD$_3$CN): δ 8.19$^{*or†}$ (s, 2 H), 8.18$^{*or†}$ (s, 2 H), 7.67 (d, J=3.8 Hz, 1 H), 7.41-7.32 (m, 5 H), 7.08-7.02 (m, 2 H), 7.01-6.94 (m, 2 H), 6.22-6.16 (m, 1 H), 4.69-4.65 (m, 2 H), 4.53 (dd, J=6.8, 6.8 Hz, 1 H), 4.40-4.33 (m, 4 H), 4.20 (d, J=16.2 Hz, 1 H), 4.08-3.97 (m, 2 H), 3.84$^{*or†}$ (s, 3 H), 3.84$^{*or†}$ (s, 3 H), 3.83 (s, 3 H), 3.72-3.64 (m, 1 H), 3.35 (dd, J=3.8, 14.1 Hz, 1 H), 2.77-2.72 (m, 2 H), 2.16 (s, 3 H), 1.87-1.79 (m, 2 H), 1.61-1.54 (m, 3 H), 1.31-1.18 (m, 2 H). † and * refer to different isomers (arbitrarily assigned). LCMS (Method 4): [MH+]=784 at 3.37 min.

Example 40 and Example 41

Single Diastereoisomers of [(1S)-2-(3,5-dichloro-1-oxido-pyridin-1-ium-4-yl)-1-(3,4-dimethoxyphenyl)ethyl]5-[[[1-(3-hydroxyphenyl)-2-[(1-methyl-4-piperidyl)methoxy]-2-oxo-ethyl]amino]methyl]thiophene-2-carboxylate (Diastereoisomers 1 and 2)

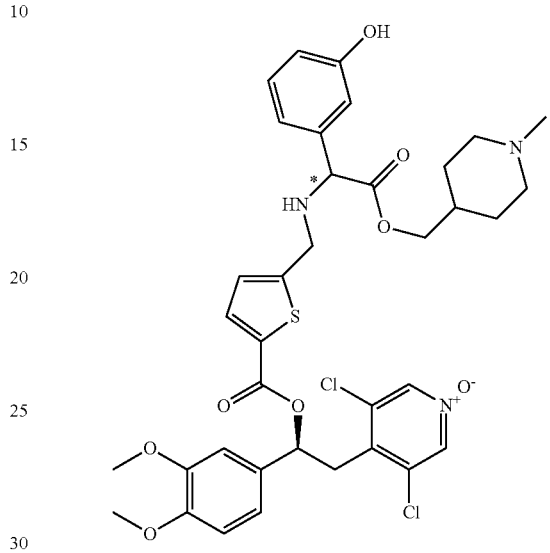

A solution of [(1S)-2-(3,5-dichloro-1-oxido-pyridin-1-ium-4-yl)-1-(3,4-dimethoxyphenyl)ethyl]5-formylthiophene-2-carboxylate (Intermediate 1, 300 mg, 0.62 mmol), (1-methyl-4-piperidyl)methyl 2-amino-2-(3-hydroxyphenyl)acetate (Intermediate 88, 208 mg, 0.75 mmol) and acetic acid (0.08 mL, 1.24 mmol) in EtOH (7 mL) was stirred at room temperature for 10 minutes. NaBH$_3$CN (78 mg, 1.24 mmol) was then added and the stirring was maintained for 18 hours. Additional NaBH$_3$CN (78 mg, 1.24 mmol) was added and the mixture was stirred for 2 hours. The solvent was concentrated in vacuo and the residue was partitioned between H$_2$O (10 mL) and iso-butanol (20 ml). The aqueous phase was extracted with iso-butanol (3×20 mL). The combined organic layers were concentrated in vacuo. Purification of the crude material by preparative HPLC afforded the product as a mixture of diastereoisomers (65 mg, 14%) as a pale yellow solid.

Purification of the mixture of diastereoisomers by chiral preparative SFC afforded the single diastereoisomers.

Title compound (Example 40, single diastereoisomer 1) was obtained as a beige solid (25 mg, 11%).

$^1$H NMR (400 MHz, DMSO): δ 9.47 (s, 1 H), 8.60 (s, 2 H), 7.74 (d, J=3.8 Hz, 1 H), 7.19 (dd, J=8.1, 8.1 Hz, 1 H), 7.08-7.03 (m, 4 H), 6.86-6.82 (m, 2 H), 6.77-6.73 (m, 1 H), 6.20 (dd, J=4.3, 9.6 Hz, 1 H), 4.36 (d, J=9.3 Hz, 1 H), 3.96-3.88 (m, 4 H), 3.82 (s, 3 H), 3.81 (s, 3 H), 3.63 (dd, J=9.8, 14.3 Hz, 1 H), 3.45 (td, J=6.0, 9.2 Hz, 1 H), 3.37 (dd, J=12.2, 16.2 Hz, 1 H), 2.75-2.70 (m, 2 H), 2.62-2.58 (m, 1 H), 2.14 (s, 3 H), 1.83-1.74 (m, 2 H), 1.54-1.46 (m, 2 H), 1.21-1.09 (m, 2 H). LCMS (Method 2): [MH+]=744 at 3.30 min. Chiral analysis (Method 7) at 13.69 min.

Title compound (Example 41, single diastereoisomer 2) was obtained as a light yellow solid (9 mg, 4%).

$^1$H NMR (400 MHz, CD$_3$CN): δ 8.21 (s, 2 H), 7.67 (d, J=3.5 Hz, 1 H), 7.22 (dd, J=7.8, 7.8 Hz, 1 H), 7.08-7.01 (m, 2 H), 6.97-6.92 (m, 2 H), 6.91-6.85 (m, 2 H), 6.79-6.75 (m,

1 H), 6.18 (dd, J=4.5, 9.9 Hz, 1 H), 4.34 (s, 1 H), 3.98-3.91 (m, 4 H), 3.83 (s, 3 H), 3.82 (s, 3 H), 3.83-3.80 (m, 1 H), 3.68 (dd, J=9.9, 14.1 Hz, 1 H), 3.35 (dd, J=4.5, 14.1 Hz, 1 H), 2.83-2.82 (m, 2 H), 2.20 (s, 3 H), 1.98-1.92 (m, 2 H), 1.57-1.49 (m, 3 H), 1.34-1.24 (m, 2 H), NH not visible. LCMS (Method 2): [MH+]=744 at 2.73 min.

Chiral analysis (Method 7) at 15.28 min.

Example 42 and Example 43

Single Diastereoisomers of [(1S)-2-(3,5-dichloro-1-oxido-pyridin-1-ium-4-yl)-1-(3,4-dimethoxyphenyl)ethyl]5-[[[2-[(1-isopropyl-4-piperidyl)methoxy]-2-oxo-1-phenyl-ethyl]amino]methyl]-thiophene-2-carboxylate (Diastereoisomers 1 and 2)

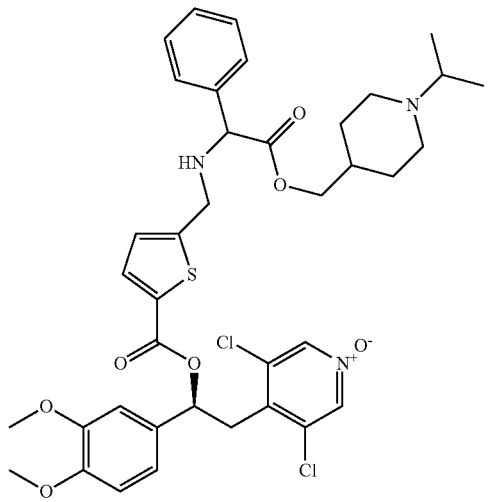

To a stirred solution of [(1S)-2-(3,5-dichloro-1-oxido-pyridin-1-ium-4-yl)-1-(3,4-dimethoxyphenyl)ethyl]5-formylthiophene-2-carboxylate (Intermediate 1, 0.40 g, 0.83 mmol) and (Intermediate 61, 1-isopropyl-4-piperidyl)methyl 2-amino-2-phenyl-acetate bis-hydrochloride (0.36 g, 1.0 mmol) in DCM (10 mL) was added successively added Et$_3$N (0.28 mL, 2.0 mmol) and acetic acid (50 mL, 0.83 mmol). The mixture was stirred at room temperature for 72 hours. NaBH(OAc)$_3$ (0.52 g, 2.5 mmol) was added and the reaction mixture was stirred at room temperature five hours.

The mixture was diluted with DCM (20 mL) and washed with NaHCO$_3$ (2×25 mL). The organic phase was then washed with 1N aqueous HCl (3×25 mL). The acidic extracts were combined, basified with solid NaHCO$_3$ and extracted with EtOAc (3×25 mL). The combined EtOAc extracts were filtered through a phase separator and the solvent was removed in vacuo. Purification by preparative HPLC gave the product as a mixture of diastereoisomers as an off-white solid (176 mg, 28%). LCMS (Method 3): [MH+]=756 at 2.73 min.

Purification of the mixture of diastereoisomers by chiral preparative SFC afforded the single diastereoisomers.

Title compound (Example 42, single diastereoisomer 1) was obtained as an off-white solid (58 mg, 19%).

$^1$H NMR (400 MHz, CD$_3$CN): δ 8.19 (s, 2 H), 7.70 (d, J=3.8 Hz, 1 H), 7.42-7.39 (m, 4 H), 7.38-7.33 (m, 1 H), 7.08-7.02 (m, 2 H), 6.97-6.94 (m, 2 H), 6.19 (dd, J=4.8, 9.6 Hz, 1 H), 4.45 (br s, 1 H), 4.00-3.89 (m, 4 H), 3.84 (s, 3 H), 3.83 (s, 3 H), 3.71-3.64 (m, 1 H), 3.35 (dd, J=4.5, 14.1 Hz, 1 H), 2.88 (s, 1 H), 2.81-2.74 (m, 2 H), 2.70-2.63 (m, 1 H), 2.11-2.02 (m, 2 H), 1.57-1.48 (m, 3 H), 1.16-1.08 (m, 2 H), 0.97 (d, J=6.6 Hz, 6 H).

LCMS (Method 3): [MH+]=756 at 2.71 min.

Chiral analysis (Method 16) at 7.94 min.

Title compound (Example 43, single diastereoisomer 2) was obtained as an off-white solid (53 mg, 17%).

$^1$H NMR (400 MHz, CD$_3$CN): δ 8.18 (s, 2 H), 7.69 (d, J=3.8 Hz, 1 H), 7.42-7.39 (m, 4 H), 7.39-7.32 (m, 1 H), 7.07-7.02 (m, 2 H), 6.97-6.94 (m, 2 H), 6.18 (dd, J=4.5, 9.6 Hz, 1 H), 4.45 (br s, 1 H), 4.00-3.89 (m, 4 H), 3.84 (s, 3 H), 3.82 (s, 3 H), 3.67 (dd, J=9.6, 14.1 Hz, 1 H), 3.34 (dd, J=4.5, 14.1 Hz, 1 H), 2.88 (br s, 1 H), 2.80-2.73 (m, 2 H), 2.70-2.62 (m, 1 H), 2.10-2.01 (m, 2 H), 1.56-1.43 (m, 3 H), 1.17-1.05 (m, 2 H), 0.97 (d, J=6.6 Hz, 6 H). LCMS (Method 3): [MH+]=756 at 2.71 min.

Chiral analysis (Method 16) at 9.33 min.

Example 44 and Example 45

Single Diastereoisomers of [(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl]thiophene-2-carboxylate (Diastereoisomers 1 and 2)

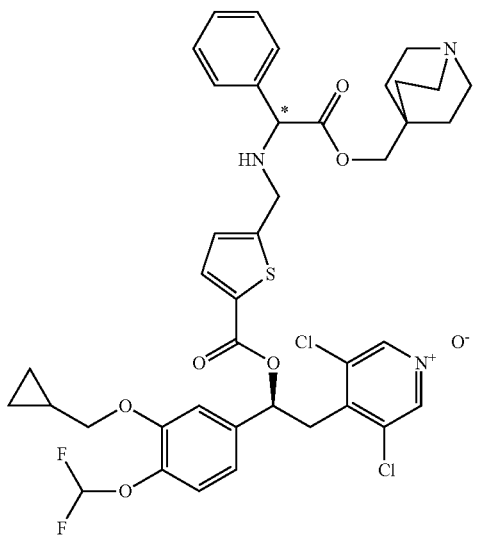

To a solution of quinuclidin-4-ylmethyl 2-amino-2-phenyl-acetate bis hydrochloride (Intermediate 77, 300 mg, 0.86 mmol) in EtOH (10 mL) was added [(1S)-1-[3-(cyclopropylmethoxy)-4-(difluoromethoxy)phenyl]-2-(3,5-dichloro-1-oxido-pyridin-1-ium-4-yl)ethyl]5-formylthiophene-2-carboxylate (Intermediate 5, 482 mg, 0.86 mmol) and pyridine (70 μL, 0.86 mmol). The solution was heated to 60° C. then NaBH$_3$CN (54 mg, 0.86 mmol) was added. The resultant mixture was stirred at 60° C. for one hour. The reaction solvent was removed in vacuo and the residue was partitioned between EtOAc and 2 N HCl solution. The aqueous phase was neutralised with solid NaHCO$_3$ and was extracted with EtOAc (3×30 mL). The combined organic phases were acidified with 2 N HCl solution to pH~2 and extracted with H$_2$O (2×20 mL). The combined aqueous phases were extracted with CHCl$_3$ (3×30 mL) and the combined organic phases were washed with saturated aqueous NaHCO$_3$ (30 mL). The organic phase was filtered through a phase separator and concentrated in vacuo to give the product as a mixture of diastereoisomers as a yellow solid (400 mg, 57%).

Purification of the mixture of diastereoisomers by chiral preparative SFC afforded the single diastereoisomers.

Title compound (Example 44, single diastereoisomer 1) was obtained as an yellow solid (60 mg, 17%).

$^1$H NMR (400 MHz, CD$_3$CN): δ 8.16 (s, 2 H), 7.69 (d, J=3.8 Hz, 1 H), 7.40-7.37 (m, 3 H), 7.36-7.30 (m, 2 H), 7.18-7.11 (m, 2 H), 7.04 (dd, J=2.0, 8.5 Hz, 1 H), 6.75 (t, J=72.6 Hz, 1 H), 6.14 (dd, J=4.7, 9.3 Hz, 1 H), 4.42 (s, 1 H), 3.95-3.86 (m, 4 H), 3.74 (dd, J=10.6, 30.0 Hz, 2 H), 3.61 (dd, J=9.5, 14.1 Hz, 1 H), 3.32 (dd, J=5.1, 14.3 Hz, 1 H), 2.88 (s, 1 H), 2.70 (t, J=7.6 Hz, 6 H), 1.26-1.18 (m, 8 H), 0.63-0.56 (m, 2 H), 0.37-0.31 (m, 2 H).

LCMS (Method 3): [MH+]=816 at 2.98 min.

Chiral analysis (Method 8) at 4.92 min.

Title compound (Example 45, single diastereoisomer 2) was obtained as an off-white solid (91 mg, 26%).

$^1$H NMR (400 MHz, CD$_3$CN): δ 8.16 (s, 2 H), 7.69 (d, J=3.8 Hz, 1 H), 7.42-7.38 (m, 4 H), 7.38-7.32 (m, 1 H), 7.18-7.12 (m, 2 H), 7.05 (dd, J=2.2, 8.2 Hz, 1 H), 6.95-6.93 (m, 1 H), 6.77 (t, J=75.3 Hz, 1 H), 6.15 (dd, J=4.6, 9.3 Hz, 1 H), 4.46 (s, 1 H), 3.99-3.81 (m, 7 H), 3.62 (dd, J=9.5, 14.2 Hz, 1 H), 3.33 (dd, J=4.7, 14.1 Hz, 1 H), 3.00 (t, J=7.6 Hz, 6 H), 1.56-1.44 (m, 6 H), 1.29-1.18 (m, 1 H), 0.63-0.56 (m, 2 H), 0.37-0.32 (m, 2 H).

LCMS (Method 3): [MH+]=816 at 2.97 min.

Chiral analysis (Method 8) at 5.65 min.

Example 46

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(3-hydroxyphenyl)-2-[(1-methyl-4-piperidyl)methoxy]-2-oxo-ethyl]amino]methyl]thiophene-2-carboxylate

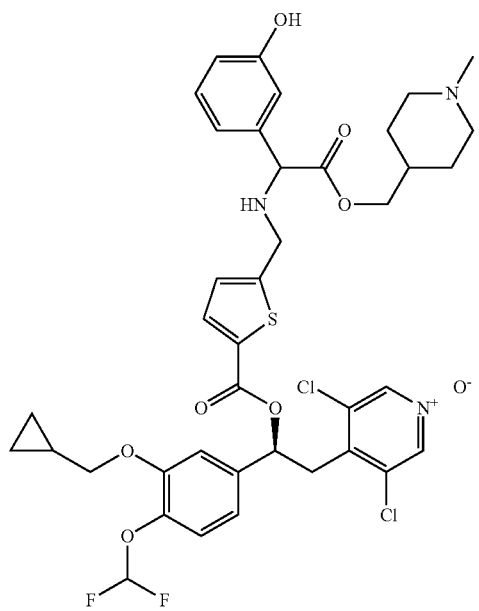

A mixture of [(1S)-1-[3-(cyclopropylmethoxy)-4-(difluoromethoxy)phenyl]-2-(3,5-dichloro-1-oxido-pyridin-1-ium-4-yl)ethyl]5-formylthiophene-2-carboxylate (Intermediate 5, 500 mg, 0.89 mmol), (1-methyl-4-piperidyl)methyl 2-amino-2-(3-hydroxyphenyl)acetate his hydrobromide (Intermediate 89, 280 mg, 0.64 mmol) and pyridine (79 mg, 1.00 mmol) in EtOH (10 mL) was heated at 60° C. After one hour, NaBH$_3$CN (55 mg, 0.87 mmol) was added and the mixture was stirred for one more hour. The solvent was removed in vacuo and the residue was partitioned between H$_2$O (10 mL) and iso-butanol (20 mL). The aqueous phase was extracted with isobutanol (3×20 mL). The combined organic layers were combined and concentrated in vacuo. Purification of the crude material by preparative HPLC afforded the product as a mixture of diastereoisomers as a pale yellow solid (79 mg, 15%).

$^1$H NMR (400 MHz, CD$_3$CN): δ 8.19$^{*or\dagger}$ (s, 2 H), 8.19$^{*or\dagger}$ (s, 2 H), 7.67 (dd, J=3.9, 3.9 Hz, 1 H), 7.22-7.12 (m, 3 H), 7.05 (dd, J=1.9, 8.2 Hz, 1 H), 6.95-6.92 (m, 1 H), 6.87-6.82 (m, 2 H), 6.77-6.74 (m, 1 H), 6.76 (t, J=75.4 Hz, 1 H), 6.18-6.11 (m, 1 H), 4.35" (s, 1 H), 4.32$^{*or\dagger}$ (s, 1 H), 3.95-3.88 (m, 6 H), 3.66-3.58 (m, 1 H), 3.37-3.31 (m, 1 H), 2.85-2.79 (m, 1 H), 2.76-2.69 (m, 2 H), 2.14 (s, 3 H), 1.84-1.76 (m, 2 H), 1.52-1.46 (m, 3 H), 1.27-1.13 (m, 3 H), 0.62-0.56 (m, 2 H), 0.37-0.31 (m, 2 H), OH not visible, † and * refer to different isomers (arbitrarily assigned). LCMS (Method 3): [MH+]=820 at 2.86 min.

The following compounds were synthesized via a similar method as a mixture of diastereoisomers.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[1-(2-methoxyphenyl)-2-[(1-methyl-4-piperidyl)methoxy]-2-oxo-ethyl]amino]methyl]thiophene-2-carboxylate 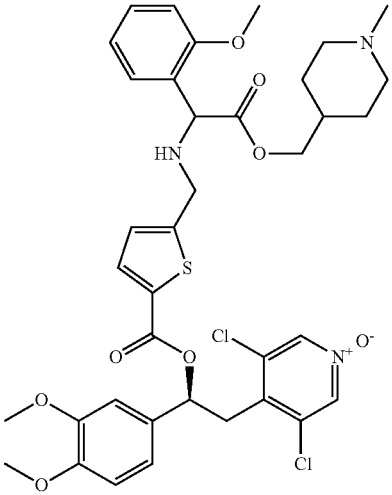 | Example 118 | Intermediate 1 and Intermediate 97 | $^1$H NMR (400 MHz, CDCl$_3$): δ 8.14*$^{or†}$ (s, 2 H), 8.13*$^{or†}$ (s, 2 H), 7.65-7.62 (m, 1 H), 7.32-7.28 (m, 1 H), 7.24-7.19 (m, 1 H), 7.01-6.93 (m, 3 H), 6.91-6.82 (m, 3 H), 6.25-6.19 (m, 1H), 4.66-4.63 (m, 1 H), 4.01-3.91 (m, 4 H), 3.90*$^{or†}$ (s, 3 H), 3.89*$^{or†}$ (s, 3 H), 3.88*$^{or†}$ (s, 3 H), 3.87*$^{or†}$ (s, 3 H), 3.81-3.77 (m, 3 H), 3.70-3.62 (m, 1 H), 3.33-3.29 (m, 1 H), 2.76 (d, J = 11.5 Hz, 2 H), 2.22*$^{or†}$ (s, 3 H), 2.20*$^{or†}$ (s, 3 H), 1.87-1.79 (m, 2 H), 1.54-1.44 (m, 3 H), 1.24-1.14 (m, 2 H), NH not observed, † and * refer to different isomers (arbitrarily assigned). LCMS [(Method 3)]: [MH+] = 758 at 2.53 min. |
| [(1S)-2-(3,5-dichloro-1-oxido-pyridin-1-ium-4-yl)-1-(3,4-dimethoxyphenyl)ethyl] 5-[[[1-(3-methoxyphenyl)-2-[(1-methyl-4-piperidyl)methoxy]-2-oxo-ethyl]amino]methyl]thiophene-2-carboxylate 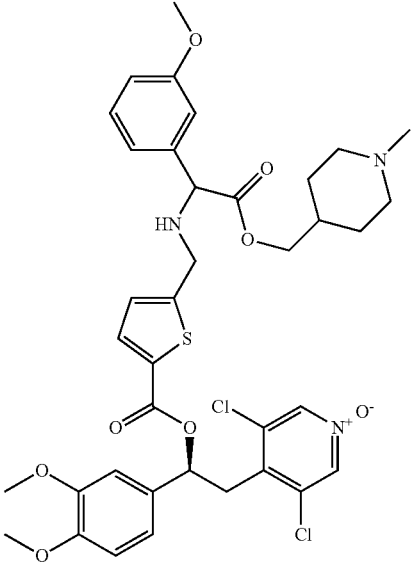 | Example 119 | Intermediate 1 and Intermediate 54 | $^1$H NMR (400 MHz, CD$_3$CN): δ 8.16 (s, 2 H), 7.67 (d, J = 3.8 Hz, 1 H), 7.31-7.25 (m, 1 H), 7.05-6.99 (m, 2 H), 6.97-6.91 (m, 4 H), 6.88 (d, J = 8.3 Hz, 1 H), 6.16 (dd, J = 4.5, 9.6 Hz, 1 H), 4.39 (s, 1 H), 3.94-3.88 (m, 4 H), 3.82-3.77 (m, 9 H), 3.69-3.61 (m, 1 H), 3.32 (dd, J = 4.5, 14.1 Hz, 1 H), 2.72 (d, J = 11.4 Hz, 2 H), 2.15 (s, 3 H), 1.84-1.76 (m, 2 H), 1.52-1.45 (m, 3 H), 1.23-1.13 (m, 2 H), NH not observed. LCMS [(Method 4)]: [MH+] = 758 at 2.69 min. |

| Structure | Example number | Precursor | Analytical Data |
|---|---|---|---|
| Epimeric mixture 2 of [2-(3,5-dichloro-1-oxido-pyridin-1-ium-4-yl)-1-(3-ethoxy-4-methoxy-phenyl)ethyl] 5-[[[1-(3-hydroxyphenyl)-2-[(1-methyl-4-piperidyl)methoxy]-2-oxo-ethyl]amino]methyl]thiophene-2-carboxylate 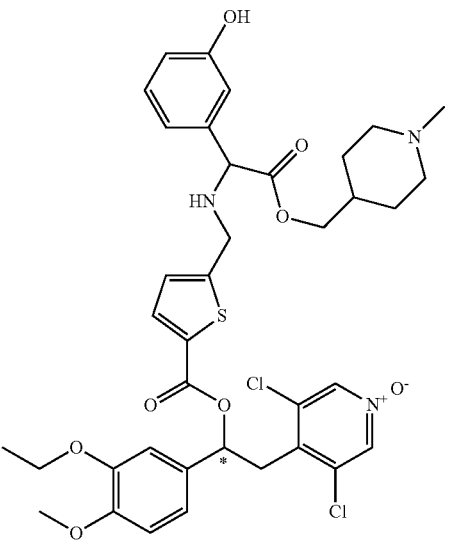 | Example 120 | Intermediate 8 and Intermediate 89 | $^1$H NMR (400 MHz, CD$_3$CN): δ 8.18*$^{or†}$ (s, 2 H), 8.18*$^{or†}$ (s, 2 H), 7.65*$^{or†}$ (d, J = 3.5 Hz, 1 H), 7.63*$^{or†}$ (d, J = 3.5 Hz, 1 H), 7.21-7.15 (m, 1 H), 7.02-6.98 (m, 2 H), 6.94-6.90 (m, 2 H), 6.86-6.81 (m, 2 H), 6.76-6.72 (m, 1 H), 6.18-6.10 (m, 1 H), 4.33*$^{or†}$ (s, 1 H), 4.31*$^{or†}$ (s, 1 H), 4.11-4.00 (m, 2 H), 3.95-3.87 (m, 4 H), 3.79 (s, 3 H), 3.68-3.59 (m, 1 H), 3.35-3.28 (m, 1 H), 2.81-2.77 (m, 1 H), 2.76-2.68 (m, 2 H), 2.14 (s, 3 H), 1.82-1.75 (m, 2 H), 1.52-1.46 (m, 3 H), 1.35 (t, J = 7.1 Hz, 3 H), 1.32-1.13 (m, 2 H), OH not observed, † and * refer to different isomers (arbitrarily assigned). LCMS [(Method 4)]: [MH+] = 758 at 2.63 min. |

Example 47 and Example 48

Single Diastereoisomers of Epimeric Mixture 2 of [1-[3-(cyclopropylmethoxy)-4-methoxy-phenyl]-2-(3,5-dichloro-1-oxido-pyridin-1-ium-4-yl)ethyl]5-[[[1-(3-hydroxyphenyl)-2-[(1-methyl-4-piperidyl)methoxy]-2-oxo-ethyl]amino]methyl]thiophene-2-carboxylate (Diastereoisomer 1 and 2)

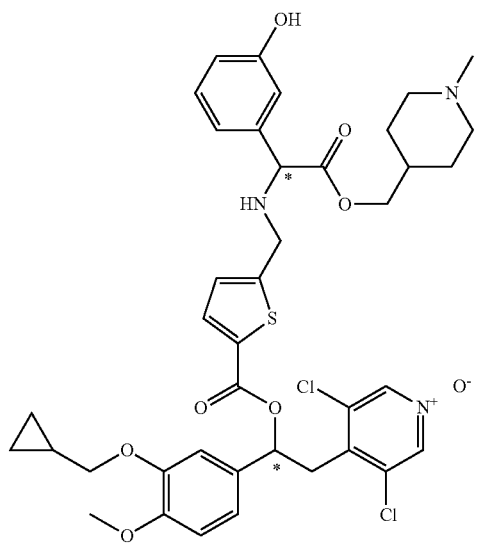

A mixture of enantiomer 2 of [1-[3-(cyclopropylmethoxy)-4-methoxy-phenyl]-2-(3,5-dichloro-1-oxido-pyridin-1-ium-4-yl)ethyl]5-formylthiophene-2-carboxylate (Intermediate 12, 350 mg, 0.67 mmol), (Intermediate 89, 1-methyl-4-piperidyl)methyl 2-amino-2-(3-hydroxyphenyl) acetate bis hydrobromide (170 mg, 0.38 mmol) and pyridine (48 mg, 0.61 mmol) in EtOH (10 mL) was heated at 60° C. After one hour, NaBH$_3$CN (45 mg, 0.71 mmol) was added and the mixture was stirred for one hour. The solvent was removed in vacuo and the residue was partitioned between H$_2$O (10 mL) and isobutanol (20 mL). The aqueous phase was extracted with isobutanol (3×20 mL). The combined organic layers were combined and concentrated in vacuo. Purification of the crude material by preparative HPLC afforded the product as a mixture of diastereoisomers (epimeric mixture 2 obtained from enantiomer 2 above) as a pale yellow solid (87 mg, 29%) that was submitted directly to chiral preparative SFC to afford the single diastereoisomers.

Title compound (Example 47, single diastereoisomer 1) was obtained as pale yellow solid (16 mg, 11%).

NMR (400 MHz, CD$_3$CN): δ 8.18 (s, 2 H), 7.65 (d, J=3.8 Hz, 1 H), 7.18 (dd, J=7.8, 7.8 Hz, 1 H), 7.03-6.98 (m, 2 H), 6.95-6.91 (m, 2 H), 6.88-6.87 (m, 1 H), 6.84 (d, J=7.6 Hz, 1 H), 6.74 (dd, J=2.1, 7.7 Hz, 1 H), 6.14 (dd, J=4.5, 9.6 Hz, 1 H), 4.34 (s, 1 H), 3.99-3.88 (m, 4 H), 3.87-3.77 (m, 2 H), 3.81 (s, 3 H), 3.63 (dd, J=9.9, 14.1 Hz, 1 H), 3.31 (dd, J=4.5, 14.1 Hz, 1 H), 2.88-2.77 (m, 2 H), 2.22 (s, 3 H), 1.97-1.84 (m, 2 H), 1.56-1.48 (m, 3 H), 1.31-1.19 (m, 3 H), 0.61-0.55 (m, 2 H), 0.33-0.29 (m, 2 H), OH and NH not visible. LCMS (Method 2): [MH+]=785 at 2.71 min.

Chiral analysis (Method 23) at 12.63 min.

Title compound (Example 48, single diastereoisomer 2) was obtained as white solid (11 mg, 8%).

$^1$H NMR (400 MHz, CD$_3$CN): δ 8.18 (s, 2 H), 7.65 (d, J=3.8 Hz, 1 H), 7.18 (dd, J=8.1, 8.1 Hz, 1 H), 7.03-6.98 (m,

2 H), 6.95-6.90 (m, 2 H), 6.86-6.82 (m, 2 H), 6.76-6.73 (m, 1 H), 6.14 (dd, J=4.7, 9.7 Hz, 1 H), 4.33 (s, 1 H), 3.82-3.80 (m, 6 H), 3.81 (s, 3 H), 3.63 (dd, J=9.6, 14.1 Hz, 1 H), 3.31 (dd, J=4.7, 14.0 Hz, 1 H), 2.78-2.71 (m, 3 H), 2.16 (s, 3 H), 1.92-1.76 (m, 2 H), 1.55-1.46 (m, 3 H), 1.28-1.16 (m, 3 H), 0.61-0.55 (m, 2 H), 0.33-0.28 (m, 2 H), OH not visible. LCMS (Method 2): [MH+]=785 at 2.71 min.
Chiral analysis (Method 23) at 14.54 min.

Example 49 and Example 50

Single Diastereoisomers of [(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]methoxy]-2-oxo-1-phenyl-ethyl]amino]methyl]thiophene-2-carboxylate (Diastereoisomers 1 and 2)

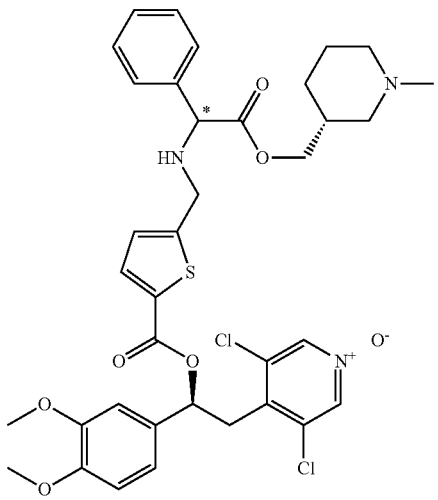

Purification of the mixture of diastereoisomers of Example 14 by chiral preparative SFC afforded the single diastereoisomers.

Title compound (Example 49, single diastereoisomer 1) was obtained as white solid (18 mg, 4%).

$^1$H NMR (400 MHz, CD$_3$CN): δ 8.20 (s, 2 H), 7.70 (d, J=3.8 Hz, 1 H), 7.41 (d, J=4.3 Hz, 4 H), 7.39-7.34 (m, 1 H), 7.08-7.01 (m, 2 H), 6.97-6.93 (m, 2 H), 6.17 (dd, J=4.5, 9.6 Hz, 1 H), 4.45 (s, 1 H), 3.95 (dd, J=6.7, 11.5 Hz, 4 H), 3.83 (s, 3 H), 3.82 (s, 3 H), 3.67 (dd, J=9.7, 14.0 Hz, 1 H), 3.34 (dd, J=4.5, 14.1 Hz, 1 H), 2.94-2.93 (m, 1 H), 2.62-2.56 (m, 1 H), 2.48 (dd, J=1.4, 10.2 Hz, 1 H), 2.08 (s, 3 H), 1.86-1.75 (m, 2 H), 1.62-1.42 (m, 4 H), 0.92-0.83 (m, 1 H). LCMS (Method 1): [MH+]=728 at 2.56 min.

Chiral analysis (Method 13) at 3.68 min.

Title compound (Example 50, single diastereoisomer 2) was obtained as light brown solid (20 mg, 5%).

$^1$H NMR (400 MHz, CD$_3$CN): δ 8.19 (s, 2 H), 7.69 (d, J=3.8 Hz, 1 H), 7.41 (d, J=4.5 Hz, 5 H), 7.07-7.01 (m, 2 H), 6.96-6.93 (m, 2 H), 6.17 (dd, J=4.5, 9.6 Hz, 1 H), 4.44 (s, 1 H), 4.07-3.85 (m, 4 H), 3.84 (s, 3 H), 3.82 (s, 3 H), 3.67 (dd, J=9.9, 14.1 Hz, 1 H), 3.33 (dd, J=4.3, 14.1 Hz, 1 H), 2.95-2.88 (m, 1 H), 2.59-2.47 (m, 2 H), 2.09 (s, 3 H), 1.82-1.74 (m, 2 H), 1.60-1.42 (m, 4 H), 0.92-0.83 (m, 1 H). LCMS (Method 1): [MH+]=728 at 2.55 min.

Chiral analysis (Method 13) at 4.72 min.

Compounds reported in the table herebelow were obtained as single diastereoisomers according to the procedure described in Examples 49 and 50 by chiral preparative SFC or chiral preparative HPLC.

| Structure | Reference | Precursor | Analytical Data |
|---|---|---|---|
| Single diastereomer 1 of [(1S)-2-(3,5-dichloro-1-oxido-pyridin-1-ium-4-yl)-1-(3,4-dimethoxyphenyl)ethyl] 5-[[[2-[(1,4-dimethyl-4-piperidyl)methoxy]-2-oxo-1-phenyl-ethyl]amino]methyl]thiophene-2-carboxylate 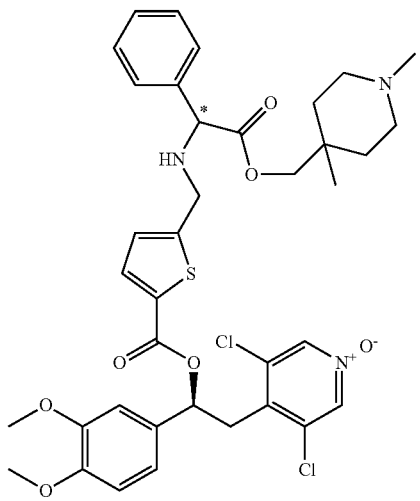 | Example 51 (diastereoisomer 1) | Example 2 | $^1$H NMR (400 MHz, CD$_3$CN): δ 8.21 (s, 2 H), 7.69 (d, J = 3.7 Hz, 1 H), 7.43-7.32 (m, 5 H), 7.07-7.01 (m, 2 H), 6.97-6.93 (m, 2 H), 6.18 (dd, J = 4.6, 9.8 Hz, 1 H), 4.47 (s, 1 H), 3.99-3.85 (m, 4 H), 3.83 (s, 3 H), 3.82 (s, 3 H), 3.68 (dd, J = 9.8, 14.8 Hz, 1 H), 3.35 (dd, J = 5.0, 14.5 Hz, 1 H), 2.24-2.18 (m, 2 H), 2.17 (s, 3 H), 2.16-2.09 (m, 2 H), 1.50-1.35 (m, 2 H), 1.32-1.18 (m, 2 H), 0.81 (s, 3 H). Note: NH not visible LCMS (Method 1): [MH+] = 742 at 2.61 min. Chiral analysis (Method 14) at 2.65 min |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-[(1,4-dimethyl-4-piperidyl)methoxy]-2-oxo-1-phenyl-ethyl]amino]methyl]thiophene-2-carboxylate | Example 52 (diastereoisomer 2) | Example 2 | $^1$H NMR (400 MHz, CD$_3$CN): δ 8.21 (s, 2 H), 7.69 (d, J = 3.7 Hz, 1 H), 7.43-7.32 (m, 5 H), 7.07-7.01 (m, 2 H), 6.97-6.93 (m, 2 H), 6.18 (dd, J = 4.6, 9.8 Hz, 1 H), 4.47 (s, 1 H), 3.99-3.85 (m, 4 H), 3.83 (s, 3 H), 3.82 (s, 3 H), 3.68 (dd, J = 9.8, 14.8 Hz, 1 H), 3.35 (dd, J = 5.0, 14.5 Hz, 1 H), 2.24-2.18 (m, 2 H), 2.17 (s, 3 H), 2.16-2.09 (m, 2 H), 1.50-1.35 (m, 2 H), 1.32-1.18 (m, 2 H), 0.81 (s, 3 H). Note: NH not visible LCMS (Method 1): [MH+] = 742 at 2.61 min. Chiral analysis (Method 14) at 3.37 min. |
| Single diastereomer 1 of [(1S)-2-(3,5-dichloro-1-oxido-pyridin-1-ium-4-yl)-1-(3,4-dimethoxyphenyl)ethyl] 5-[[[2-[(4-fluoro-1-methyl-4-piperidyl)methoxy]-2-oxo-1-phenyl-ethyl]amino]methyl]thiophene-2-carboxylate | Example 53 (diastereoisomer 1) | Example 3 | $^1$H NMR (400 MHz, CD$_3$CN): δ 8.17 (s, 2 H), 7.66 (d, J = 4.1 Hz, 1 H), 7.39-7.34 (m, 5 H), 7.04-6.99 (m, 2 H), 6.94-6.91 (m, 2 H), 6.16 (dd, J = 4.3, 9.5 Hz, 1 H), 4.48 (s, 1 H), 4.19-4.13 (m, 1 H), 4.12-4.06 (m, 1 H), 3.95 (d, J = 14.6 Hz, 1 H), 3.89 (d, J = 15.0 Hz, 1 H), 3.80 (s, 3 H), 3.79 (s, 3 H), 3.65 (dd, J = 9.5, 14.3 Hz, 1 H), 3.32 (dd, J = 4.4, 14.2 Hz, 1 H), 2.55-2.47 (m, 2 H), 2.17 (s, 3 H), 2.15-2.07 (m, 3 H), 1.78-1.49 (m, 4 H). LCMS (Method 2): [MH+] = 746 at 3.19 min. Chiral analysis (Method 14) at 2.68 min. |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-[(4-fluoro-1-methyl-4-piperidyl)methoxy]-2-oxo-1-phenyl-ethyl]amino]methyl]thiophene-2-carboxylate 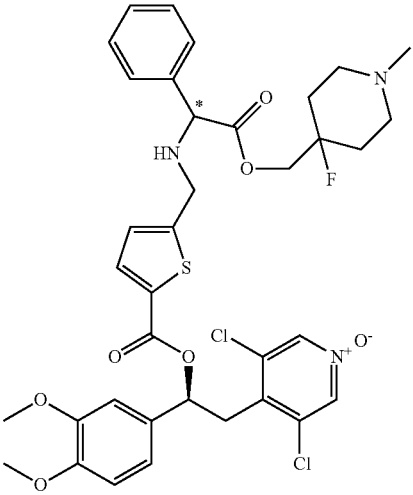 | Example 54 (diastereoisomer 2) | Example 3 | ¹H NMR (400 MHz, CD₃CN): δ 8.18 (s, 2 H), 7.66 (d, J = 3.8 Hz, 1 H), 7.40-7.31 (m, 5 H), 7.04-6.99 (m, 2 H), 6.94-6.91 (m, 2 H), 6.15 (dd, J = 4.5, 9.6 Hz, 1 H), 4.47 (s, 1 H), 4.19-4.12 (m, 1 H), 4.12-4.06 (m, 1 H), 3.95 (d, J = 15.8 Hz, 1 H), 3.88 (d, J = 14.4 Hz, 1 H), 3.80 (s, 3 H), 3.79 (s, 3 H), 3.65 (dd, J = 9.6, 14.1 Hz, 1 H), 3.32 (dd, J = 4.5, 14.1 Hz, 1 H), 2.56-2.47 (m, 2 H), 2.17 (s, (s, 3 H), 2.16-2.07 (m, 3 H), 1.73-1.49 (m, 4 H). LCMS (Method 2): [MH+] = 746 at 3.18 min. Chiral analysis (Method 14) at 3.35 min. |
| Single diastereomer 1 of epimeric mixture 2 of [1-[3-(cyclopropylmethoxy)-4-methoxy-phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate 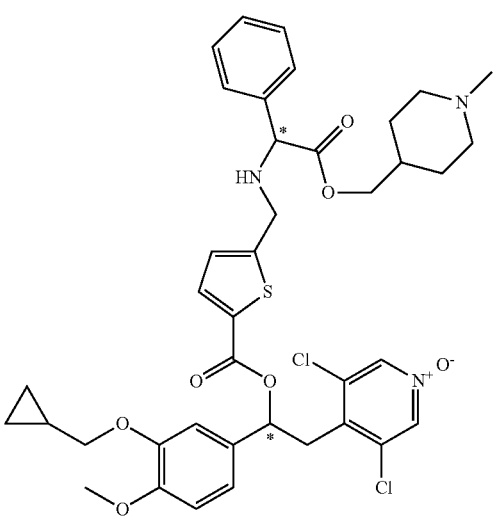 | Example 55 (diastereoisomer 1) | Example 4 | ¹H NMR (400 MHz, CD₃CN): δ 8.19 (s, 2 H), 7.66-7.63 (m, 1 H), 7.38-7.30 (m, 5 H), 7.02-6.97 (m, 2 H), 6.94-6.90 (m, 2 H), 6.12 (dd, J = 4.7, 9.5 Hz, 1 H), 4.41 (s, 1 H), 3.95-3.81 (m, 6 H), 3.80 (s, 3 H), 3.63 (dd, J = 9.6, 13.9 Hz, 1 H), 3.30 (dd, J = 4.5, 14.1 Hz, 1 H), 2.71 (d, J = 11.1 Hz, 2 H), 2.13 (s, 3 H), 1.85-1.77 (m, 2 H), 1.52-1.43 (m, 3 H), 1.27-1.10 (m, 4 H), 0.60-0.54 (m, 2 H), 0.32-0.27 (m, 2H). LCMS (Method 3): [MH+] = 768 at 2.86 min. Chiral analysis (Method 10) at 2.61 min. |

| Structure | Reference | Precursor | Analytical Data |
|---|---|---|---|
| Single diasteromer 2 of epimeric mixture 2 of [1-[3-(cyclopropylmethoxy)-4-methoxy-phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate | Example 56 (diastereoisomer 2) | Example 4 | $^1$H NMR (400 MHz, CD$_3$CN): δ 8.18 (s, 2 H), 7.65 (d, J = 3.5 Hz, 1 H), 7.38-7.35 (m, 4 H), 7.35-7.30 (m, 1 H), 7.02-6.98 (m, 2 H), 6.94-6.91 (m, 2 H), 6.12 (dd, J = 4.5, 9.6 Hz, 1 H), 4.41 (s, 1 H), 3.96-3.81 (m, 6 H), 3.80 (s, 3 H), 3.63 (dd, J = 9.6, 14.1 Hz, 1 H), 3.30 (dd, J = 4.5, 14.1 Hz, 1 H), 2.70 (d, J = 11.4 Hz, 2 H), 2.12 (s, 3 H), 1.83-1.74 (m, 2 H), 1.51-1.43 (m, 3 H), 1.27-1.09 (m, 4 H), 0.60-0.54 (m, 2 H), 0.33-0.27 (m, 2 H). LCMS (Method 3): [MH+] = 768 at 2.87 min. Chiral analysis (Method 10) at 3.17 min. |
| Single diasteromer 1 of epimeric mixture 2 of [1-[3-(cyclopentoxy)-4-methoxy-phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate | Example 57 (diastereoisomer 1) | Example 6 | $^1$H NMR (400 MHz, CD$_3$CN): δ 8.21 (s, 2 H), 7.69 (d, J = 3.8 Hz, 1 H), 7.41-7.35 (m, 5 H), 7.00 (dd, J = 2.0, 5.8 Hz, 2 H), 6.97-6.91 (m, 2 H), 6.15 (dd, J = 4.8, 9.1 Hz, 1 H), 4.84-4.79 (m, 1 H), 4.43 (s, 1 H), 3.95-3.90 (m, 4 H), 3.79 (s, 3 H), 3.65 (dd, J = 9.2, 14.0 Hz, 1 H), 3.35 (dd, J = 4.8, 14.1 Hz, 1 H), 2.73 (d, J = 11.1 Hz, 2 H), 2.14 (s, 3 H), 1.86-1.68 (m, 9 H), 1.64-1.59 (m, 2 H), 1.54-1.45 (m, 3 H), 1.24-1.13 (m, 2 H). LCMS (Method 1): [MH+] = 782 at 2.79 min. Chiral analysis (Method 20) at 15.57 min. |

-continued

| Structure | Reference | Precursor | Analytical Data |
|---|---|---|---|
| Single diasteromer 2 of epimeric mixture 2 of [1-[3-(cyclopentoxy)-4-methoxy-phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate | Example 58 (diastereoisomer 2) | Example 6 | H NMR (400 MHz, CD$_3$CN): δ 8.21 (s, 2 H), 7.69 (d, J = 3.8 Hz, 1 H), 7.41-7.33 (m, 5 H), 7.00 (dd, J = 2.0, 6.1 Hz, 2 H), 6.97-6.92 (m, 2 H), 6.15 (dd, J = 4.8, 9.3 Hz, 1 H), 4.84-4.78 (m, 1 H), 4.43 (s, 1 H), 3.95-3.90 (m, 4 H), 3.79 (s, 3 H), 3.65 (dd, J = 9.3, 14.1 Hz, 1 H), 3.35 (dd, J = 4.8, 14.1 Hz, 1 H), 2.73 (d, J = 11.4 Hz, 2 H), 2.14 (s, 3 H), 1.91-1.69 (m, 9 H), 1.67-1.59 (m, 2 H), 1.53-1.46 (m, 3 H), 1.24-1.12 (m, 2 H). LCMS (Method 1): [MH+] = 782 at 2.8 min. Chiral analysis (Method 20) at 20.22 min. |
| Single diasteromer 1 of epimeric mixture 2 of [1-[3-(cylcopropylmethoxy)-4-methoxy-phenyl]-2-(3,5-dichloro-1-oxido-pyridin-1-ium-4-yl)ethyl] 5-[[[2-oxo-1-phenyl-2-(quinuclidin-4-ylmethoxy)ethyl]amino]methyl]thiophene-2-carboxylate | Example 59 (diastereoisomer 1) | Example 8 | $^1$H NMR (400 MHz, CD$_3$CN): δ 8.15 (s, 2 H), 7.66 (d, J = 3.9 Hz, 1 H), 7.40-7.37 (m, 4 H), 7.37-7.30 (m, 1 H), 7.02-6.98 (m, 2 H), 6.95-6.91 (m, 2 H), 6.13 (dd, J = 4.6, 9.6 Hz, 1 H), 4.45-4.41 (m, 1 H), 3.96-3.86 (m, 2 H), 3.83-3.82 (m, 1 H), 3.81 (s, 3 H), 3.80-3.79 (m, 1 H), 3.73 (dd, J = 10.9, 29.9 Hz, 2 H), 3.63 (dd, J = 9.5, 14.0 Hz, 1 H), 3.30 (dd, J = 4.4, 14.1 Hz, 1 H), 2.70 (t, J = 7.6 Hz, 6 H), 1.27-1.15 (m, 8 H), 0.61-0.55 (m, 2 H), 0.34-0.28 (m, 2 H). LCMS (Method 3): [MH+] = 780 at 2.85 min. Chiral analysis (Method 15) at 2.80 min. |

-continued

| Structure | Reference | Precursor | Analytical Data |
|---|---|---|---|
| Single diastereomer 2 of epimeric mixture 2 of [1-[3-(cyclopropylmethoxy)-4-methoxy-phenyl]-2-(3,5-dichloro-1-oxido-pyridin-1-ium-4-yl)ethyl] 5-[[[2-oxo-1-phenyl-2-(quinuclidin-4-ylmethoxy)ethyl]amino]methyl]thiophene-2-carboxylate | Example 60 (diastereoisomer 2) | Example 8 | $^1$H NMR (400 MHz, CD$_3$CN): δ 8.15 (s, 2 H), 7.66 (d, J = 3.6 Hz, 1 H), 7.39 (d, J = 5.6 Hz, 4 H), 7.37-7.30 (m, 1 H), 7.03-6.98 (m, 2 H), 6.95-6.91 (m, 2 H), 6.13 (dd, J = 4.6, 9.6 Hz, 1 H), 4.44 (s, 1 H), 3.98-3.87 (m, 2 H), 3.84-3.82 (m, 2 H), 3.81 (s, 3 H), 3.73 (dd, J = 10.9, 27.2 Hz, 2 H), 3.63 (dd, J = 9.7, 14.2 Hz, 1 H), 3.30 (dd, J = 4.5, 14.0 Hz, 1 H), 2.71 (t, J = 7.5 Hz, 6 H), 1.29-1.16 (m, 8 H), 0.62-0.55 (m, 2 H), 0.34-0.29 (m, 2 H). LCMS (Method 3): [MH+] = 780 at 2.85 min. Chiral analysis (Method 15) at 4.04 min. |
| Single diasteromer 1 of [(1S)-2-(3,5-dichloro-1-oxido-pyridin-1-ium-4-yl)-1-(3,4-dimethoxyphenyl)ethyl] 5-[[[1-cyclohexyl-2-[(1-methyl-4-piperidyl)methoxy]-2-oxo-ethyl]amino]methyl]thiophene-2-carboxylate | Example 61 (diastereoisomer 1) | Example 9 | $^1$H NMR (400 MHz, DMSO): δ 8.54 (s, 2 H), 7.66 (d, J = 3.8 Hz, 1 H), 7.01-6.95 (m, 4 H), 6.12 (dd, J = 4.3, 9.6 Hz, 1 H), 4.00 (dd, J = 4.7, 15.5 Hz, 1 H), 3.89 (d, J = 6.1 Hz, 2 H), 3.77 (s, 3 H), 3.74 (s, 3 H), 3.73-3.66 (m, 1 H), 3.56 (dd, J = 9.7, 14.0 Hz, 1 H), 3.33-3.27 (m, 1 H), 2.98 (dd, J = 6.6, 11.1 Hz, 1 H), 2.81 (dd, J = 5.3, 11.1 Hz, 1 H), 2.71 (d, J = 11.4 Hz, 2 H), 2.11 (s, 3 H), 1.82-1.73 (m, 3 H), 1.69-1.62 (m, 2 H), 1.60-1.43 (m, 6 H), 1.23-0.99 (m, 7 H). LCMS (Method 3): [MH+] = 734 at 2.7 min. Chiral analysis (Method 13) at 2.47 min. |

-continued

| Structure | Reference | Precursor | Analytical Data |
|---|---|---|---|
| Single diasteromer 2 of [(1S)-2-(3,5-dichloro-1-oxido-pyridin-1-ium-4-yl)-1-(3,4-dimethoxyphenyl)ethyl] 5-[[[1-cyclohexyl-2-[(1-methyl-4-piperidyl)methoxy]-2-oxo-ethyl]amino]methyl]thiophene-2-carboxylate | Example 62 (diastereoisomer 2) | Example 9 | ¹H NMR (400 MHz, DMSO): δ 8.53 (s, 2 H), 7.66 (d, J = 3.8 Hz, 1 H), 7.02 (s, 1 H), 6.99-6.97 (m, 3 H), 6.13 (dd, J = 4.2, 9.7 Hz, 1 H), 4.00 (d, J = 15.4 Hz, 1 H), 3.90 (d, J = 6.3 Hz, 2 H), 3.77 (s, 3 H), 3.75 (s, 3 H), 3.73-3.66 (m, 1 H), 3.58 (dd, J = 9.7, 14.0 Hz, 1 H), 3.35-3.27 (m, 1 H), 3.01-2.93 (m, 1 H), 2.83-2.80 (m, 1 H), 2.77-2.69 (m, 2 H), 2.12 (s, 3 H), 1.85-1.75 (m, 3 H), 1.73-1.63 (m, 2 H), 1.54-1.43 (m, 6 H), 1.21-0.94 (m, 7 H). LCMS (Method 3): [MH+] = 734 at 2.7 min. Chiral analysis (Method 13) at 3.28 min. |
| Single diasteromer 1 of [(1S)-2-(3,5-dichloro-1-oxido-pyridin-1-ium-4-yl)-1-(3,4-dimethoxyphenyl)ethyl] 5-[[[2-oxo-1-phenyl-2-[[(3S)-quinuclidin-3-yl]methoxy]ethyl]amino]methyl]thiophene-2-carboxylate | Example 63 (diastereoisomer 1) | Example 10 | ¹H NMR (400 MHz, CD₃CN): δ 8.16 (s, 2 H), 7.67 (d, J = 3.8 Hz, 1 H), 7.38-7.30 (m, 5 H), 7.05-6.99 (m, 2 H), 6.94-6.91 (m, 2 H), 6.16 (dd, J = 4.5, 9.6 Hz, 1 H), 4.41 (s, 1 H), 4.13-4.00 (m, 2 H), 3.97-3.87 (m, 2 H), 3.81 (s, 3 H), 3.80 (s, 3 H), 3.65 (dd, J = 9.5, 14.0 Hz, 1 H), 3.32 (dd, J = 4.7, 14.0 Hz, 1 H), 2.85-2.78 (m, 1 H), 2.71-2.62 (m, 4 H), 2.28-2.17 (m, 1 H), 1.91-1.84 (m, 1 H), 1.54-1.49 (m, 2 H), 1.41-1.39 (m, 1 H), 1.29-1.24 (m, 2 H), NH not observed. LCMS (Method 3): [MH+] = 740 at 2.74 min. Chiral analysis (Method 12) at 9.36 min. |

-continued

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-oxo-1-phenyl-2-[[(3S)-quinuclidin-3-yl]methoxy]ethyl]amino]methyl]thiophene-2-carboxylate 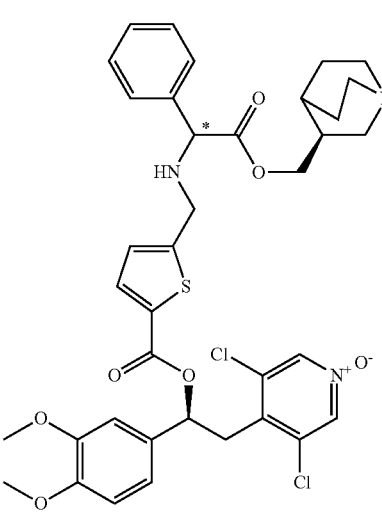 | Example 64 (diastereoisomer 2) | Example 10 | $^1$H NMR (400 MHz, CD$_3$CN): δ 8.19 (s, 2 H), 7.70 (d, J = 3.8 Hz, 1 H), 7.42-7.39 (m, 4 H), 7.39-7.34 (m, 1 H), 7.08-7.02 (m, 2 H), 6.97-6.94 (m, 2 H), 6.19 (dd, J = 4.5, 9.6 Hz, 1 H), 4.44 (s, 1 H), 4.11-4.07 (m, 2 H), 4.00-3.90 (m, 2 H), 3.84 (s, 3 H), 3.82 (s, 3 H), 3.68 (dd, J = 9.6, 14.1 Hz, 1 H), 3.34 (dd, J = 4.5, 14.1 Hz, 1 H), 2.90-2.67 (m, 6 H), 1.92-1.86 (m, 2 H), 1.62-1.52 (m, 3 H), 1.45-1.39 (m, 1 H), 1.34-1.29 (m, 1 H). LCMS (Method 3): [MH+] = 740 at 2.69 min. Chiral analysis (Method 12) at 10.77 min. |
| Single diastereomer 1 of [(1S)-2-(3,5-dichloro-1-oxido-pyridin-1-ium-4-yl)-1-(3,4-dimethoxyphenyl)ethyl] 5-[[[2-oxo-1-phenyl-2-[[(3R)-quinuclidin-3-yl]methoxy]ethyl]amino]methyl]thiophene-2-carboxylate 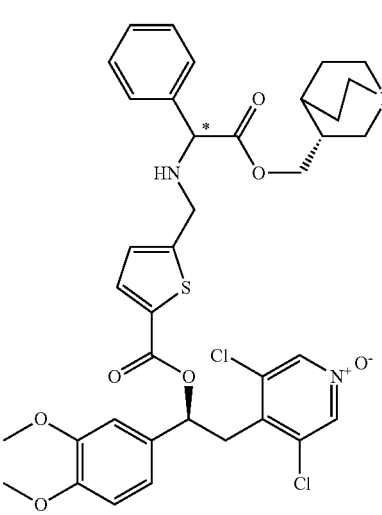 | Example 65 (diastereoisomer 1) | Example 11 | $^1$H NMR (400 MHz, CD$_3$CN): δ 8.19 (s, 2 H), 7.69 (d, J = 3.8 Hz, 1 H), 7.41-7.32 (m, 5 H), 7.08-7.02 (m, 2 H), 6.97-6.94 (m, 2 H), 6.19 (dd, J = 4.5, 9.6 Hz, 1 H), 4.44 (s, 1 H), 4.11-4.08 (m, 2 H), 4.00-3.90 (m, 2 H), 3.84 (s, 3 H), 3.83 (s, 3 H), 3.71-3.64 (m, 1 H), 3.35 (dd, J = 4.5, 14.1 Hz, 1 H), 2.84 (dd, J = 9.9, 13.6 Hz, 2 H), 2.76-2.64 (m, 4 H), 2.26-2.19 (m, 1 H), 1.90-1.81 (m, 1 H), 1.61-1.50 (m, 3 H), 1.44-1.25 (m, 2 H). LCMS (Method 4): [MH+] = 740 at 3.22 min. Chiral analysis (Method 13) at 6.31 min. |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-oxo-1-phenyl-2-[[(3R)-quinuclidin-3-yl]methoxy]ethyl]amino]methyl]thiophene-2-carboxylate | Example 66 (diastereoisomer 2) | Example 11 | $^1$H NMR (400 MHz, CD$_3$CN): δ 8.18 (s, 2 H), 7.69 (d, J = 3.8 Hz, 1 H), 7.43-7.34 (m, 5 H), 7.09-7.01 (m, 2 H), 6.98-6.94 (m, 2 H), 6.19 (dd, J = 4.4, 9.7 Hz, 1 H), 4.45 (s, 1 H), 4.15-4.04 (m, 2 H), 4.00-3.89 (m, 2 H), 3.85 (s, 3 H), 3.82 (s, 3 H), 3.71-3.64 (m, 1 H), 3.35 (dd, J = 4.4, 14.0 Hz, 1 H), 2.89-2.65 (m, 5 H), 2.31-2.23 (m, 1 H), 1.90 (dd, J = 8.4, 20.4 Hz, 1 H), 1.61-1.44 (m, 3 H), 1.34-1.26 (m, 2 H), NH not observed. LCMS (Method 4): [MH+] = 740 at 3.22 min. Chiral analysis (Method 13) at 7.51 min. |
| Single diastereoisomer 1 of epimeric mixture 2 of [2-(3,5-dichloro-1-oxido-pyridin-1-ium-4-yl)-1-(3-ethoxy-4-methoxy-phenyl)ethyl] 5-[[[2-[(1-methyl-4-piperidyl)methoxy]-2-oxo-1-phenyl-ethyl]amino]methyl]thiophene-2-carboxylate | Example 67 (diastereoisomer 1) | Example 12 | $^1$H NMR (400 MHz, CD$_3$CN): δ 8.15 (s, 2 H), 7.66 (d, J = 3.8 Hz, 1 H), 7.38-7.29 (m, 5 H), 7.03-6.97 (m, 2 H), 6.94-6.90 (m, 2 H), 6.14 (dd, J = 4.7, 9.5 Hz, 1 H), 4.42 (s, 1 H), 4.10-3.95 (m, 2 H), 3.97-3.85 (m, 4 H), 3.79 (s, 3 H), 3.63 (dd, J = 9.6, 14.1 Hz, 1 H), 3.31 (dd, J = 4.8, 14.1 Hz, 1 H), 2.77 (d, J = 11.6 Hz, 2 H), 2.18 (s, 3 H), 1.92-1.83 (m, 2 H), 1.54-1.46 (m, 3 H), 1.35 (t, J = 6.9 Hz, 3 H), 1.29-1.08 (m, 2 H). NH not observed. LCMS (Method 4): [MH+] = 742 at 3.38 min. Chiral analysis (Method 13) at 3.71 min. |

| Structure | Reference | Precursor | Analytical Data |
|---|---|---|---|
| Single diasteroisomer 2 of epimeric mixture 2 of [2-(3,5-dichloro-1-oxido-pyridin-1-ium-4-yl)-1-(3-ethoxy-4-methoxy-phenyl)ethyl] 5-[[[2-[(1-methyl-4-piperidyl)methyl]-2-oxo-1-phenyl-ethyl]amino]methyl]thiophene-2-carboxylate | Example 68 (diastereoisomer 2) | Example 12 | $^1$H NMR (400 MHz, CD$_3$CN): δ 8.14 (s, 2 H), 7.65 (d, J = 3.8 Hz, 1 H), 7.38-7.30 (m, 5 H), 7.02-6.97 (m, 2 H), 6.93-6.89 (m, 2 H), 6.13 (dd, J = 4.5, 9.6 Hz, 1 H), 4.41 (s, 1 H), 4.09-3.95 (m, 2 H), 3.93-3.88 (m, 4 H), 3.79 (s, 3 H), 3.62 (dd, J = 9.6, 14.1 Hz, 1 H), 3.30 (dd, J = 4.5, 14.1 Hz, 1 H), 2.89-2.80 (m, 2 H), 2.24 (s, 3 H), 2.06-1.96 (m, 2 H), 1.57-1.48 (m, 3 H), 1.34 (t, J = 6.9 Hz, 3 H), 1.31-1.18 (m, 2 H), NH not observed. LCMS (Method 4): [MH+] = 742 at 3.38 min. Chiral analysis (Method 13) at 4.43 min. |
| Single diastereomer 1 of [(1S)-1-[3-(cyclopropylmethoxy)-4-(difluoromethoxy)phenyl]-2-(3,5-dichloro-1-oxido-pyridin-1-ium-4-yl)ethyl] 5-[[[2-[(1-methyl-4-piperidyl)methoxy]-2-oxo-1-phenyl-ethyl]amino]methyl]thiophene-2-carboxylate | Example 69 (diastereoisomer 1) | Example 13 | $^1$H NMR (400 MHz, CD$_3$CN): δ 8.19 (s, 2 H), 7.71 (d, J = 3.8 Hz, 1 H), 7.42-7.33 (m, 5 H), 7.20-7.14 (m, 2 H), 7.07 (dd, J = 2.0, 8.3 Hz, 1 H), 6.96 (d, J = 3.6 Hz, 1 H), 6.78 (t, J = 75.3 Hz, 1 H), 6.17 (dd, J = 4.5, 9.3 Hz, 1 H), 4.45 (s, 1 H), 4.01-3.88 (m, 6 H), 3.64 (dd, J = 9.6, 14.1 Hz, 1 H), 3.34 (dd, J = 4.7, 14.0 Hz, 1 H), 2.88 (br s, 1 H), 2.76-2.69 (m, 2 H), 2.15 (s, 3 H), 1.83-1.74 (m, 2 H), 1.55-1.46 (m, 3 H), 1.30-1.11 (m, 3 H), 0.65-0.60 (m, 2 H), 0.39-0.34 (m, 2 H). LCMS (Method 3): [MH+] = 804 at 2.99 min. Chiral analysis (Method 22) at 9.65 min. |

| Structure | Reference | Precursor | Analytical Data |
|---|---|---|---|
| Single diasteromer 2 of [(1S)-1-[3-(cyclopropylmethoxy)-4-(difluoromethoxy)phenyl]-2-(3,5-dichloro-1-oxido-pyridin-1-ium-4-yl)ethyl] 5-[[[2-[(1-methyl-4-piperidnyl)methoxy]-2-oxo-1-phenyl-ethyl]amino]methyl]thiophene-2-carboxylate | Example 70 (diastereoisomer 2) | Example 13 | $^1$H NMR (400 MHz, CD$_3$CN): δ 8.19 (s, 2 H), 7.71 (d, J = 3.8 Hz, 1 H), 7.42-7.32 (m, 5 H), 7.20-7.14 (m, 2 H), 7.07 (dd, J = 1.9, 8.2 Hz, 1 H), 6.96 (d, J = 4.2 Hz, 1 H), 6.78 (t, J = 75.3 Hz, 1 H), 6.17 (dd, J = 4.8, 9.3 Hz, 1 H), 4.45 (s, 1 H), 4.00-3.88 (m, 6 H), 3.64 (dd, J = 9.3, 14.1 Hz, 1 H), 3.35 (dd, J = 4.8, 14.1 Hz, 1 H), 2.89 (br s, 1 H), 2.75-2.69 (m, 2 H), 2.15 (s, 3 H), 1.83- 1.74 (m, 2 H), 1.54-1.45 (m, 3 H), 1.30-1.11 (m, 3 H), 0.65-0.60 (m, 2 H), 0.39-0.34 (m, 2 H). LCMS (Method 3): [MH+] = 804 at 2.98 min. Chiral analysis (Method 22) at 11.10 min. |
| Single diastereomer 1 of [(1S)-2-(3,5-dichloro-1-oxido-pyridin-1-ium-4-yl)-1-(3,4-dimethoxyphenyl)ethyl] 5-[[[2-[[(2R)-1-methylpyrrolidin-2-yl]methoxy]-2-oxo-1-phenyl-ethyl]amino]methyl]thiophene-2-carboxylate | Example 71 (diastereoisomer 1) | Example 15 | $^1$H NMR (400 MHz, CD$_3$CN): δ 8.18 (s, 2 H), 7.69 (dd, J = 4.2, 4.2 Hz, 1 H), 7.42-7.34 (m, 5 H), 7.07-7.01 (m, 2 H), 6.97-6.93 (m, 2 H), 6.19 (dd, J = 4.7, 9.5 Hz, 1 H), 4.45 (s, 1 H), 4.12-3.90 (m, 4 H), 3.83 (s, 3 H), 3.82 (s, 3 H), 3.71-3.63 (m, 1 H), 3.35 (dd, J = 4.5, 14.1 Hz, 1 H), 2.93-2.87 (m, 1 H), 2.35 (dd, J = 6.6, 8.6 Hz, 1 H), 2.22 (s, 3 H), 2.19-2.10 (m, 1 H), 1.84-1.75 (m, 1 H), 1.64-1.57 (m, 2 H), 1.48-1.40 (m, 1 H). NH not visible LCMS (Method 3): [MH+] = 714 at 2.72 min. Chiral analysis (Method 9) at 4.04 min. |

| Structure | Reference | Precursor | Analytical Data |
|---|---|---|---|
| Single diastereomer 1 of [(1S)-2-(3,5-dichloro-1-oxido-pyridin-1-ium-4-yl)-1-(3,4-dimethoxyphenyl)ethyl] 5-[[[2-[[(2R)-1-methylpyrrolidin-2-yl]methoxy]-2-oxo-1-phenyl-ethyl]amino]methyl]thiophene-2-carboxylate | Example 72 (diasteroisomer 2) | Example 15 | $^1$H NMR (400 MHz, CD$_3$CN): δ 8.18 (s, 2 H), 7.69 (d, J = 3.8 Hz, 1 H), 7.41-7.33 (m, 5 H), 7.07-7.02 (m, 2 H), 6.97-6.93 (m, 2 H), 6.19 (dd, J = 4.5, 9.6 Hz, 1 H), 4.44 (s, 1 H), 4.10-3.95 (m, 4 H), 3.84 (s, 3 H), 3.82 (s, 3 H), 3.68 (dd, J = 9.7, 14.0 Hz, 1 H), 3.34 (dd, J = 4.5, 14.1 Hz, 1 H), 2.96-2.90 (m, 1 H), 2.36 (ddd,J = 5.1, 8.6, 11.6 Hz, 1 H), 2.23 (s, 3 H), 2.21-2.11 (m, 1 H), 1.84-1.74 (m, 1 H), 1.66-1.58 (m, 2 H), 1.49-1.40 (m, 1 H). NH not visible LCMS (Method 3): [MH+] = 714 at 2.68 min. Chiral analysis (Method 9) at 5.65 min. |
| Single diasteromer 1 of [(1S)-2-(3,5-dichloro-1-oxido-pyridin-1-ium-4-yl)-1-(3,4-dimethoxyphenyl)ethyl] 5-[[[2-[[(2S)-1-methypyrrolidin-2-yl]methoxy]-2-oxo-1-phenyl-ethyl]amino]methyl]thiophene-2-carboxylate | Example 73 (diastereoisomer 1) | Example 16 | $^1$H NMR (400 MHz, CD$_3$CN): δ 8.18 (s, 2 H), 7.69 (d, J = 3.8 Hz, 1 H), 7.42-7.36 (m, 5 H), 7.07-7.01 (m, 2 H), 6.96-6.92 (m, 2 H), 6.18 (dd, J = 4.7, 9.5 Hz, 1 H), 4.44 (s, 1 H), 4.11-4.00 (m, 2 H), 3.95 (dd, J = 15.2, 24.4 Hz, 2 H), 3.83 (s, 3 H), 3.82 (s, 3 H), 3.71-3.63 (m, 1 H), 3.34 (dd, J = 4.5, 14.1 Hz, 1 H), 2.97-2.90 (m, 1 H), 2.43-2.34 (m, 1 H), 2.23 (s, 3 H), 2.22-2.11 (m, 1 H), 1.85-1.74 (m, 1H), 1.67-1.58 (m, 2 H), 1.50-1.40 (m, 1 H). NH not visible LCMS (Method 2): [MH+] = 714 at 3.67 min. Chiral analysis (Method 10) at 2.18 min. |

-continued

| Structure | Reference | Precursor | Analytical Data |
|---|---|---|---|
| Single diasteromer 2 of [(1S)-2-(3,5-dichloro-1-oxido-pyridin-1-ium-4-yl)-1-(3,4-dimethoxyphenyl)ethyl] 5-[[[2-[[(2S)-1-methylpyrrolidin-2-yl]methoxy]-2-oxo-1-phenyl-ethyl]amino]methyl]thiophene-2-carboxylate | Example 74 (diastereoisomer 2) | Example 16 | ¹H NMR (400 MHz, CD₃CN): δ 8.18 (s, 2 H), 7.69 (d, J = 3.8 Hz, 1 H), 7.43-7.33 (m, 5 H), 7.07-7.02 (m, 2 H), 6.97-6.93 (m, 2 H), 6.19 (dd, J = 4.5, 9.6 Hz, 1 H), 4.44 (s, 1 H), 4.12-4.02 (m, 2 H), 3.95 (dd, J = 15.6, 27.8 Hz, 2 H), 3.84 (s, 3 H), 3.82 (s, 3 H), 3.71-3.64 (m, 1 H), 3.34 (dd, J = 4.5, 14.1 Hz, 1 H), 2.94-2.87 (m, 1 H), 2.40-2.28 (m, 1 H), 2.23 (s, 3 H), 2.20-2.09 (m, 1 H), 1.86-1.76 (m, 1 H), 1.65-1.55 (m, 2 H), 1.49-1.40 (m, 1 H). NH not visible LCMS (Method 1): [MH+] = 714 at 2.6 min. Ciral analysis (Method 10) at 3.08 min. |
| Single diasteromer 1 of [(1S)-2-(3,5-dichloro-1-oxido-pyridin-1-ium-4-yl)-1-(,34-dimethoxyphenyl)ethyl] 5-[[[2-[[(3R)-1-methypyrrolidin-3-yl]methoxy]-2-oxo-1-phenyl-ethyl]amino]methyl]thiophene-2-carboxylate | Example 75 (diastereoisomer 1) | Example 17 | ¹H NMR (400 MHz, CD₃CN): δ 8.19 (s, 2 H), 7.69 (d, J = 3.8 Hz, 1 H), 7.42-7.36 (m, 5 H), 7.07-7.01 (m, 2 H), 6.97-6.93 (m, 2 H), 6.18 (dd, J = 4.5, 9.6 Hz, 1 H), 4.44 (s, 1 H), 4.02-3.98 (m, 2 H), 3.97-3.90 (m, 2 H), 3.83 (s, 3 H), 3.82 (s, 3 H), 3.67 (dd, J = 9.7, 14.0 Hz, 1 H), 3.35 (dd, J = 4.5, 14.1 Hz, 1 H), 2.45-2.33 (m, 4 H), 2.22 (s, 3 H), 2.14-2.10 (m, 1 H), 1.86-1.79 (m, 1 H), 1.42-1.29 (m, 1 H). NH not visible LCMS (Method 1): [MH+] = 714 at 2.52 min. Chiral analysis (Method 13) at 3.57 min. |

-continued

| Structure | Reference | Precursor | Analytical Data |
|---|---|---|---|
| Single diasteromer 2 of [(1S)-2-(3,5-dichloro-1-oxido-pyridin-1-ium-4-yl)-1-(3,4-dimethoxyphenyl)ethyl] 5-[[[2-[[(3R)-1-methylpyrrolidin-3-yl]methoxy]-2-oxo-1-phenyl-ethyl]amino]methyl]thiophene-2-carboxylate | Example 76 (diastereoisomer 2) | Example 17 | $^1$H NMR (400 MHz, CD$_3$CN): δ 8.18 (s, 2 H), 7.69 (d, J = 4.6 Hz, 1 H), 7.42-7.34 (m, 5 H), 7.07-7.02 (m, 2 H), 6.97-6.93 (m, 2 H), 6.19 (dd, J = 4.3, 10.0 Hz, 1 H), 4.45 (s, 1 H), 4.06-3.89 (m, 4 H), 3.84 (s, 3 H), 3.81 (s, 3 H), 3.68 (dd, J = 9.6, 14.1 Hz, 1 H), 3.35 (dd, J = 4.4, 14.0 Hz, 1 H), 2.48-2.38 (m, 4 H), 2.23 (s, 3 H), 2.22-2.14 (m, 1 H), 1.88-1.78 (m, 1 H), 1.43-1.34 (m, 1 H). NH not visible LCMS (Method 1): [MH+] = 714 at 2.53 min. Chiral analysis (Method 13) at 4.54 min. |
| Single diasteromer 1 of [(1S)-2-(3,5-dichloro-1-oxido-pyridin-1-ium-4-yl)-1-(3,4-dimethoxyphenyl)ethyl] 5-[[[2-[[(3S)-1-methylpyrrolidin-3-yl]methoxy]-2-oxo-1-phenyl-ethyl]amino]methyl]thiophene-2-carboxylate | Example 77 (diastereoisomer 1) | Example 18 | $^1$H NMR (400 MHz, CD$_3$CN): δ 8.18 (s, 2 H), 7.69 (d, J = 3.8 Hz, 1 H), 7.41-7.34 (m, 5 H), 7.07-7.01 (m, 2 H), 6.97-6.93 (m, 2 H), 6.19 (dd, J = 4.7, 9.7 Hz, 1 H), 4.44 (s, 1 H), 4.08-3.90 (m, 4 H), 3.83 (s, 3 H), 3.82 (s, 3 H), 3.71-3.63 (m, 1 H), 3.35 (dd, J = 4.5, 14.1 Hz, 1 H), 2.74-2.35 (m, 5 H), 2.23 (s, 3 H), 2.21-2.13 (m, 1 H), 1.90-1.79 (m, 1 H), 1.43-1.34 (m, 1 H). LCMS (Method 3): [MH+] = 714 at 2.7 min. Chiral analysis (Method 14) at 2.64 min. |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyhenyl)ethyl] 5-[[[2-[[(3S)-1-methylpyrrolidin-3-yl]methoxy]-2-oxo-1-phenyl-ethyl]amino]methyl]thiophene-2-carboxylate | Example 78 (diastereoisomer 2) | Example 18 | $^1$H NMR (400 MHz, CD$_3$CN): δ 8.18 (s, 2 H), 7.69 (d, J = 3.8 Hz, 1 H), 7.42-7.33 (m, 5 H), 7.07-7.02 (m, 2 H), 6.97-6.94 (m, 2 H), 6.19 (dd, J = 4.5, 9.6 Hz, 1 H), 4.44 (s, 1 H), 4.03-3.89 (m, 4 H), 3.84 (s, 3 H), 3.82 (s, 3 H), 3.67 (dd, J = 9.6, 14.1 Hz, 1 H), 3.35 (dd, J = 4.5, 14.1 Hz, 1 H), 2.73-2.35 (m, 5 H), 2.23 (s, 3 H), 2.18-2.11 (m, 1 H), 1.89-1.79 (m, 1 H), 1.43-1.34 (m, 1 H). LCMS (Method 3): [MH+] = 714 at 2.71 min. Chiral analysis (Method 14) at 3.73 min. |
| Single diastereomer 1 of [(1S)-2-(3,5-dichloro-1-oxido-pyridin-1-ium-4-yl)-1-(3,4-dimethoxyphenyl)ethyl] 5-[[[2-[(1-ethyl-4-piperidyl)methoxy]-2-oxo-1-phenyl-ethyl]amino]methyl]thiophene-2-carboxylate | Example 79 (diastereoisomer 1) | Example 19 | $^1$H NMR (400 MHz, CD$_3$CN): δ 8.19 (s, 2 H), 7.69 (d, J = 3.8 Hz, 1 H), 7.40-7.34 (m, 5 H), 7.07-7.01 (m, 2 H), 6.96-6.94 (m, 2 H), 6.18 (dd, J = 4.5, 9.6 Hz, 1 H), 4.45 (d, J = 4.0 Hz, 1 H), 3.99-3.89 (m, 4 H), 3.83 (s, 3 H), 3.82 (s, 3 H), 3.67 (dd, J = 9.6, 14.1 Hz, 1 H), 3.35 (dd, J = 4.7, 14.0 Hz, 1 H), 2.87-2.80 (m, 3 H), 2.29 (q, J = 7.2 Hz, 2 H), 1.83-1.74 (m, 2 H), 1.56-1.51 (m, 3 H), 1.19-1.11 (m, 2 H), 1.00 (t, J = 7.2 Hz, 3 H). LCMS (Method 3): [MH+] = 742 at 2.7 min. Chiral analysis (Method 12) at 7.16 min |

-continued

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-[(1-ethyl-4-piperidyl)methoxy]-2-oxo-1-phenyl-ethyl]amino]methyl]thiophene-2-carboxylate | Example 80 (diastereoisomer 2) | Example 19 | $^1$H NMR (400 MHz, CD$_3$CN): δ 8.18 (s, 2 H), 7.69 (d, J = 3.8 Hz, 1 H), 7.40 (d, J = 4.5 Hz, 4 H), 7.38-7.34 (m, 1 H), 7.07-7.02 (m, 2 H), 6.96-6.93 (m, 2 H), 6.18 (dd, J = 4.5, 9.6 Hz, 1 H), 4.45 (s, 1 H), 3.94 (d, J = 6.1 Hz, 4 H), 3.84 (s, 3 H), 3.82 (s, 3 H), 3.67 (dd, J = 9.6, 14.1 Hz, 1 H), 3.34 (dd, J = 4.5, 14.1 Hz, 1 H), 2.89-2.78 (m, 3 H), 2.30 (q, J = 7.2 Hz, 2 H), 1.85-1.75 (m, 2 H), 1.57-1.51 (m, 3 H), 1.21-1.11 (m, 2 H), 1.01 (t, J = 7.0 Hz, 3 H). LCMS (Method 3): [MH+] = 742 at 2.71 min. Chiral analysis (Method 12) at 8.45 min. |
| Single diastereomer 1 of [(1S)-2-(3,5-dichloro-1-oxido-pyridin-1-ium-4-yl)-1-(3,4-dimethoxyphenyl)ethyl] 5-[[[2-[[1-(2-methoxyethyl)-4-piperidyl]methoxy]-2-oxo-1-phenyl-ethyl]amino]methyl]thiophene-2-carboxylate | Example 81 (diastereoisomer 1) | Example 20 | $^1$H NMR (400 MHz, CD$_3$CN): δ 8.19 (s, 2 H), 7.70 (d, J = 3.8 Hz, 1 H), 7.42-7.39 (m, 4 H), 7.38-7.34 (m, 1 H), 7.08-7.02 (m, 2 H), 6.97-6.94 (m, 2 H), 6.19 (dd, J = 4.5, 9.6 Hz, 1 H), 4.45 (s, 1 H), 4.00-3.89 (m, 4 H), 3.84 (s, 3 H), 3.83 (s, 3 H), 3.67 (dd, J = 9.6, 14.1 Hz, 1 H), 3.42 (t, J = 6.3 Hz, 2 H), 3.35 (dd, J = 5.2, 14.7 Hz, 1 H), 3.27 (s, 3 H), 2.91-2.79 (m, 3 H), 2.44 (t, J = 6.3 Hz, 2 H), 1.94-1.85 (m, 2 H), 1.54-1.48 (m, 3 H), 1.21-1.10 (m, 2 H). LCMS (Method 3): [MH+] = 772 at 2.73 min. Chiral analysis (Method 12) at 6.75 min. |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-[[1-(2-methoxyethyl)-4-piperidyl]methoxy]-2-oxo-1-phenyl-ethyl]amino]methyl]thiophene-2-carboxylate | Example 82 (diastereoisomer 2) | Example 20 | $^1$H NMR (400 MHz, CD$_3$CN): δ 8.19 (s, 2 H), 7.69 (d, J = 3.8 Hz, 1 H), 7.42-7.34 (m, 5 H), 7.07-7.02 (m, 2 H), 6.97-6.94 (m, 2 H), 6.18 (dd, J = 4.5, 9.6 Hz, 1 H), 4.45 (s, 1 H), 4.00-3.89 (m, 4 H), 3.84 (s, 3 H), 3.82 (s, 3 H), 3.67 (dd, J = 9.7, 14.0 Hz, 1 H), 3.42 (t, J = 6.3 Hz, 2 H), 3.34 (dd, J = 5.0, 14.5 Hz, 1 H), 3.27 (s, 3 H), 2.88-2.82 (m, 3 H), 2.44 (t, J = 5.8 Hz, 2 H), 195-1.84 (m, 2 H), 1.54-1.47 (m, 3 H), 1.20-1.08 (m, 2 H). LCMS (Method 3): [MH+] = 772 at 2.73 min. Chiral analysis (Method 12) at 8.35 min. |
| Single diastereomer 1 of [(1S)-2-(3,5-dichloro-1-oxido-pyridin-1-ium-4-yl)-1-(3,4-dimethoxyphenyl)ethyl] 5-[[[2-oxo-1-phenyl-2-(2-pyrrolidin-1-ylethoxy)ethyl]amino]methyl]thiophene-2-carboxylate | Example 83 (diastereoisomer 1) | Example 21 | $^1$H NMR (400 MHz, CD$_3$CN): δ 8.20 (s, 2 H), 7.69 (d, J = 3.8 Hz, 1 H), 7.42-7.36 (m, 5 H), 7.07-7.01 (m, 2 H), 6.97-6.93 (m, 2 H), 6.17 (dd, J = 4.5, 9.9 Hz, 1 H), 4.43 (s, 1 H), 4.23-4.17 (m, 2 H), 4.01-3.89 (m, 2 H), 3.83 (s, 3 H), 3.82 (s, 3 H), 3.67 (dd, J = 9.7, 14.0 Hz, 1 H), 3.34 (dd, J = 4.5, 14.1 Hz, 1 H), 2.64 (dd, J = 5.7, 5.7 Hz, 2 H), 2.45-2.40 (m, 4 H), 1.70-1.65 (m, 4 H). LCMS (Method 1): [MH+] = 714 at 2.58 min. Chiral analysis (Method 10) at 2.50 min. |

| Structure | Reference | Precursor | Analytical Data |
|---|---|---|---|
| Single diasteromer 2 of [(1S)-2-(3,5-dichloro-1-oxido-pyridin-1-ium-4-yl)-1-(3,4-dimethoxyphenyl)ethyl] 5-[[[2-oxo-1-phenyl-2-(2-pyrrolidin-1-ylethoxy)ethyl]amino]methyl]thiophene-2-carboxylate 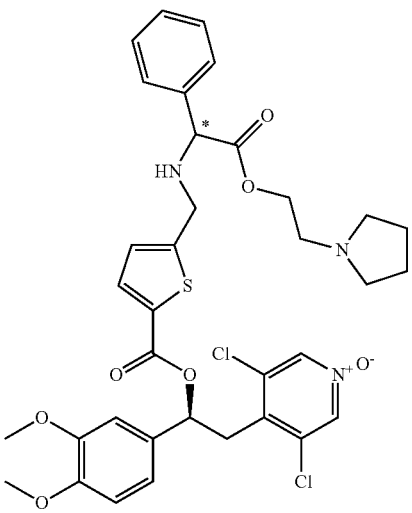 | Example 84 (diastereoisomer 2) | Example 21 | $^1$H NMR (400 MHz, CD$_3$CN): δ 8.19 (s, 2 H), 7.69 (d, J = 3.8 Hz, 1 H), 7.43-7.36 (m, 5 H), 7.07-7.01 (m, 2 H), 6.98-6.93 (m, 2 H), 6.17 (dd, J = 4.4, 9.7 Hz, 1 H), 4.43 (s, 1 H), 4.24-4.15 (m, 2 H), 4.02-3.89 (m, 2 H), 3.83 (s, 3 H), 3.82 (s, 3 H), 3.67 (dd, J = 9.6, 14.1 Hz, 1 H), 3.33 (dd, J = 4.3, 14.1 Hz, 1 H), 2.63 (dd, J = 57, 5.7 Hz, 2 H), 2.45-2.40 (m, 4 H), 1.70-1.65 (m, 4 H). LCMS (Method 1): [MH+] = 714 at 2.58 min. Chiral analysis (Method 10) at 3.34 min. |
| Single diastereomer 2 of [(1S)-2-(3,5-dichloro-1-oxido-pyridin-1-ium-4-yl)-1-(3,4-dimethoxyphenyl)ethyl] 5-[[[2-oxo-1-phenyl-2-[2-(1-piperidyl)ethoxy]ethyl]amino]methyl]thiophene-2-carboxylate 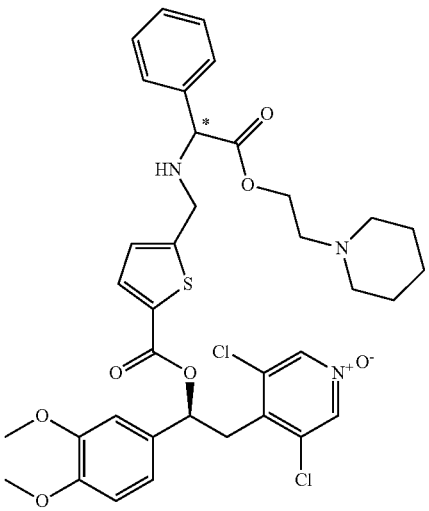 | Example 85 (diastereoisomer 2) The corresponding diastereoisomer 1, chiral analysis (Method 14) at 3.19 min. was not isolated | Example 22 | $^1$H NMR (400 MHz, CD$_3$CN): δ 8.18 (s, 2 H), 7.70 (d, J = 3.8 Hz, 1 H), 7.42-7.36 (m, 5 H), 7.07-7.02 (m, 2 H), 6.98-6.94 (m, 2 H), 6.18 (dd, J = 4.5, 9.6 Hz, 1 H), 4.43 (s, 1 H), 4.19 (dd, J = 5.6, 5.6 Hz, 2 H), 4.03-3.91 (m, 2 H), 3.84 (s, 3 H), 3.82 (s, 3 H), 3.68 (dd, J = 9.9, 14.1 Hz, 1 H), 3.34 (dd, J = 4.5, 14.1 Hz, 1 H), 2.48 (dd, J = 5.6, 5.6 Hz, 2 H), 2.35-2.25 (m, 4 H), 1.51-1.36 (m, 6 H). NH not observed LCMS (Method 1): [MH+] = 728 at 2.67 min. Chiral analysis (Method 14) at 3.84 min. |

| Structure | Reference | Precursor | Analytical Data |
|---|---|---|---|
| Single diastereomer 1 of [(1S)-2-(3,5-dichloro-1-oxido-pyridin-1-ium-4-yl)-1-(3,4-dimethoxyphenyl)ethyl] 5-[[[2-[(1-methyl-4-piperidyl)methoxy]-2-oxo-1-phenyl-ethyl]amino]methyl]thiophene-2-carboxylate 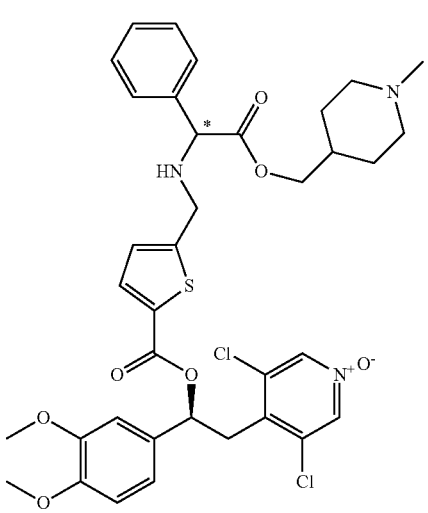 | Example 86 (diastereoisomer 1) | Example 23 | ¹H NMR (400 MHz, CDCl₃): δ 8.14 (s, 2 H), 7.64 (d, J = 3.8 Hz, 1 H), 7.37-7.35 (m, 5 H), 7.01-6.97 (m, 2 H), 6.89-6.84 (m, 2 H), 6.22 (dd, J = 4.5, 9.9 Hz, 1 H), 4.43 (s, 1 H), 3.98-3.91 (m, 4 H), 3.90 (s, 3 H), 3.88 (s, 3 H), 3.67 (dd, J = 9.7, 14.0 Hz, 1 H), 3.31 (dd, J = 4.5, 13.9 Hz, 1 H), 2.81 (d, J = 10.6 Hz, 2 H), 2.25 (s, 3 H), 1.89-1.82 (m, 2 H), 1.53-1.52 (m, 3 H), 1.29-1.20 (m, 2 H). LCMS (Method 1): [MH+] = 728 at 2.55 min. Chiral analysis (Method 12) at 6.14 min. |
| Single diaster 2 of [(1S)-2-(3,5-dichloro-1-oxido-pyridin-1-ium-4-yl)-1-(3,4-dimethoxyphenyl)ethyl] 5-[[[2-[(1-methyl-4-piperidyl)methoxy]-2-oxo-1-phenyl-ethyl]amino]methyl]thiophene-2-carboxylate 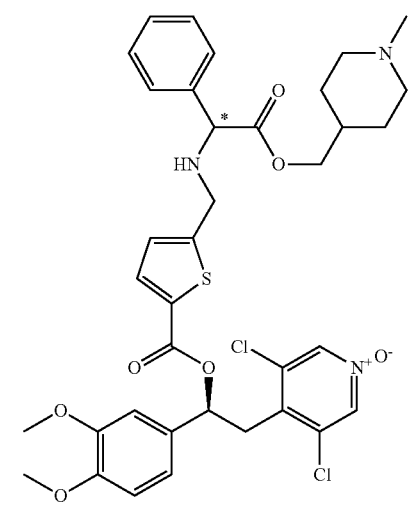 | Example 87 (diastereoisomer 2) | Example 23 | ¹H NMR (400 MHz, CDCl₃): δ 8.13 (s, 2 H), 7.64 (d, J = 3.8 Hz, 1 H), 7.38-7.36 (m, 5 H), 7.02-6.96 (m, 2 H), 6.88-6.84 (m, 2 H), 6.22 (dd, J = 4.5, 9.9 Hz, 1 H), 4.42 (s, 1 H), 3.99-3.92 (m, 4 H), 3.91 (s, 3 H), 3.88 (s, 3 H), 3.67 (dd, J = 9.9, 13.9 Hz, 1 H), 3.31 (dd, J = 4.4, 14.0 Hz, 1 H), 2.86 (d, J = 8.8 Hz, 2 H), 2.29 (s, 3 H), 1.92-1.87 (m, 2 H), 1.54-1.54 (m, 3 H), 1.35-1.20 (m, 2 H). LCMS (Method 1): [MH+] = 728 at 2.57 min. Chiral analysis (Method 12) at 7.21 min. |

| Structure | Reference | Precursor | Analytical Data |
|---|---|---|---|
| Single diastereoisomer 1 of [(1S)-2-(3,5-dichloro-1-oxido-pyridin-1-ium-4-yl)-1-(3,4-dimethoxyphenyl)ethyl] 5-[[[1-(2-fluorophenyl)-2-[(1-methyl-4-piperidyl)methoxy]-2-oxo-ethyl]amino]methyl]thiophene-2-carboxylate 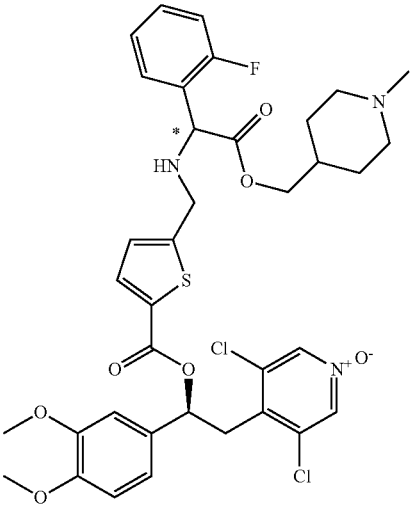 | Example 88 (diastereoisomer 1) | Example 24 | $^1$H NMR (400 MHz, CDCl$_3$): δ 8.14 (s, 2 H), 7.64 (d, J = 3.8 Hz, 1 H), 7.38-7.28 (m, 2 H), 7.15 (dd, J = 7.5, 7.5 Hz, 1 H), 7.08 (dd, J = 8.8, 8.8 Hz, 1 H), 7.01-6.97 (m, 2 H), 6.89 (d, J = 3.2 Hz, 1H), 6.85 (d, J = 7.8 Hz, 1 H), 6.21 (dd, J = 4.5, 9.9 Hz, 1 H), 4.73 (s, 1 H), 3.99-3.93 (m, 4 H), 3.91 (s, 3 H), 3.88 (s, 3 H), 3.66 (dd, J = 9.9, 13.9 Hz, 1 H), 3.31 (dd, J = 4.5, 13.9 Hz, 1 H), 2.83-2.75 (m, 2 H), 2.64-2.62 (m, 1 H), 2.23 (s, 3 H), 1.87-1.78 (m, 2 H), 1.57-1.50 (m, 2 H), 1.25-1.19 (m, 2 H), NH not visible. LCMS (Method 1): [MH+] = 746 at 2.65 min. Chiral analysis (Method 11) at 9.19 min. |
| Single diastereoisomer 2 of [(1S)-2-(3,5-dichloro-1-oxido-pyridin-1-ium-4-yl)-1-(3,4-dimethoxyphenyl)ethyl] 5-[[[1-(2-fluorophenyl)-2-[(1-methyl-4-piperidyl)methoxy]-2-oxo-ethyl]amino]methyl]thiophene-2-carboxylate 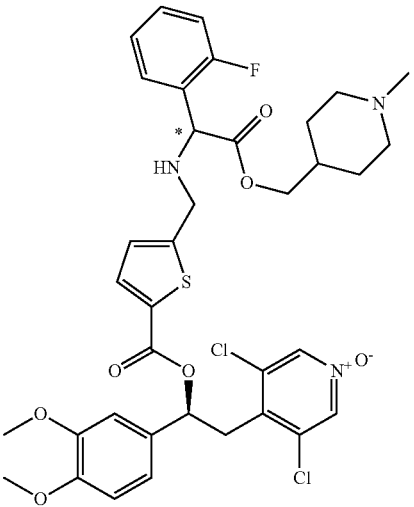 | Example 89 (diastereoisomer 2) | Example 24 | $^1$H NMR (400 MHz, CD$_3$CN): δ 8.16 (s, 2 H), 7.66 (d, J = 3.8 Hz, 1 H), 7.42 (ddd, J = 7.5, 7.5, 1.9 Hz, 1 H), 7.39-7.31 (m, 1 H), 7.20 (ddd, J = 3.7, 3.7, 7.5 Hz, 1 H), 7.16-7.09 (m, 1 H), 7.04-6.98 (m, 2 H), 6.94-6.91 (m, 2 H), 6.15 (dd, J = 4.5, 9.6 Hz, 1 H), 4.69 (s, 1 H), 3.97-3.90 (m, 4 H), 3.80 (s, 3 H), 3.80 (s, 3 H), 3.64 (dd, J = 9.9, 14.1 Hz, 1 H), 3.31 (dd, J = 4.5, 14.1 Hz, 1 H), 3.08-2.78 (m, 1 H) 2.82-2.74 (m, 2 H), 2.20 (s, 3 H), 1.91-1.86 (m, 2 H), 1.51-1.45 (m, 2 H), 1.27-1.15 (m, 2 H), NH not visible. LCMS (Method 2): [MH+] = 746 at 3.65 min. Chiral analysis (Method 11) at 11.13 min. |

-continued

| Structure | Reference | Precursor | Analytical Data |
|---|---|---|---|
| Single diastereomer 1 of [(1S)-2-(3,5-dichloro-1-oxido-pyridin-1-ium-4-yl)-1-(3,4-dimethoxyphenyl)ethyl] 5-[[[2-[[(3S)-1-methyl-3-piperidyl]methoxy]-2-oxo-1-phenyl-ethyl]amino]methyl]thiophene-2-carboxylate | Example 90 (diastereoisomer 1) | Example 26 | $^1$H NMR (400 MHz, CD$_3$CN): δ 8.18 (s, 2 H), 7.69 (d, J = 3.8 Hz, 1 H), 7.42-7.37 (m, 5 H), 7.07-7.01 (m, 2 H), 6.97-6.93 (m, 2 H), 6.18 (dd, J = 4.5, 9.3 Hz, 1 H), 4.45 (s, 1 H), 4.07-3.98 (m, 1 H), 3.96-3.87 (m, 3 H), 3.83 (s, 3 H), 3.82 (s, 3 H), 3.67 (dd, J = 9.9, 14.1 Hz, 1 H), 3.35 (dd, J = 4.7, 14.0 Hz, 1 H), 2.86 (br s, 1 H), 2.60-2.48 (m, 2 H), 2.09 (s, 3 H), 1.84-1.76 (m, 2 H), 1.62-1.43 (m, 4 H), 0.94-0.85 (m, 1 H). LCMS (Method 2): [MH+] = 728 at 1.19 min. Chiral analysis (Method 15) at 1.64 min. |
| Single diastereomer 2 of [(1S)-2-(3,5-dichloro-1-oxido-pyridin-1-ium-4-yl)-1-(3,4-dimethoxyphenyl)ethyl] 5-[[[2-[[(3S)-1-methyl-3-piperidyl]methoxy]-2-oxo-1-phenyl-ethyl]amino]methyl]thiophene-2-carboxylate | Example 91 (diastereoisomer 2) | Example 26 | $^1$H NMR (400 MHz, CD$_3$CN): δ 8.18 (s, 2 H), 7.70 (d, J = 3.6 Hz, 1 H), 7.41 (d, J = 4.3 Hz, 5 H), 7.07-7.02 (m, 2 H), 6.97-6.93 (m, 2 H), 6.19 (dd, J = 4.8, 10.0 Hz, 1 H), 4.45 (s, 1 H), 4.00-3.89 (m, 4 H), 3.84 (s, 3 H), 3.83 (s, 3 H), 3.68 (dd, J = 9.1, 13.9 Hz, 1 H), 3.35 (dd, J = 6.7, 15.1 Hz, 1 H), 2.82 (s, 1 H), 2.58 (d, J = 8.5 Hz, 1 H), 2.49 (dd, J = 4.2, 7.9 Hz, 1 H), 2.09 (s, 3 H), 1.86-1.77 (m, 2 H), 1.62-1.43 (m, 4 H), 0.96-0.83 (m, 1 H). LCMS (Method 2): [MH+] = 728 at 3.18 min. Chiral analysis (Method 15) at 2.28 min. |

-continued

| Structure | Reference | Precursor | Analytical Data |
|---|---|---|---|
| Single diastereomer 1 of [(1S)-2-(3,5-dichloro-1-oxido-pyridin-1-ium-4-yl)-1-(3,4-dimethoxyphenyl)ethyl] 5-[[[2-[[(2S)-1-methylazetidin-2-yl]methoxy]-2-oxo-1-phenyl-ethyl]amino]methyl]thiophene-2-carboxylate | Example 92 (diastereoisomer 1) | Example 27 | $^1$H NMR (400 MHz, CD$_3$CN): δ 8.19 (s, 2 H), 7.69 (d, J = 3.8 Hz, 1 H), 7.42-7.34 (m, 5 H), 7.07-7.01 (m, 2 H), 6.97-6.93 (m, 2 H), 6.19 (dd, J = 4.7, 9.7 Hz, 1 H), 4.46 (s, 1 H), 4.14 (dd, J = 3.9, 11.5 Hz, 1 H), 4.01-3.90 (m, 3 H), 3.83 (s, 3 H), 3.82 (s, 3 H), 3.67 (dd, J = 9.5, 14.0 Hz, 1 H), 3.35 (dd, J = 4.7, 14.0 Hz, 1 H), 3.25-3.19 (m, 1 H), 3.14-3.08 (m, 1 H), 2.74-2.67 (m, 1 H), 2.10 (s, 3 H), 1.91-1.77 (m, 2 H). NH not visible. LCMS (Method 1): [MH+] = 700 at 2.58 min. Chiral analysis (Method 21) at 12.85 min. |
| Single diastereomer 2 of [(1S)-2-(3,5-dichloro-1-oxido-pyridin-1-ium-4-yl)-1-(3,4-dimethoxyphenyl)ethyl] 5-[[[2-[[(2S)-1-methylazetidin-2-yl]methoxy]-2-oxo-1-phenyl-ehtyl]amino]methyl]thiophene-2-carboxylate | Example 93 (diastereoisomer 2) | Example 27 | $^1$H NMR (400 MHz, CD$_3$CN): δ 8.18 (s, 2 H), 7.69 (d, J = 3.8 Hz, 1 H), 7.44-7.34 (m, 5 H), 7.07-7.02 (m, 2 H), 6.97-6.93 (m, 2 H), 6.19 (dd, J = 4.5, 9.6 Hz, 1 H), 4.46 (s, 1 H), 4.19 (dd, J = 3.9, 11.5 Hz, 1 H), 4.02-3.90 (m, 3 H), 3.83 (s, 3 H), 3.82 (s, 3 H), 3.71-3.63 (m, 1 H), 3.35 (dd, J = 4.4, 14.3 Hz, 1 H), 3.21-3.16 (m, 1 H), 3.09-3.00 (m, 1 H), 2.72-2.65 (m, 1 H), 2.08 (s, 3 H), 1.88-1.76 (m, 2 H). NH not visible LCMS (Method 1): [MH+] = 700 at 2.59 min. Chiral analysis (Method 21) at 16.73 min. |

| Structure | Reference | Precursor | Analytical Data |
|---|---|---|---|
| Single diastereomer 1 of [(1S)-2-(3,5-dichloro-1-oxido-pyridin-1-ium-4-yl)-1-(3,4-dimethoxyphenyl)ethyl] 5-[[[2-[[(2R)-1-methylazetidin-2-yl]methoxy]-2-oxo-1-phenyl-ethyl]amino]methyl]thiophene-2-carboxylate | Example 94 (diastereoisomer 1) | Example 28 | $^1$H NMR (400 MHz, CD$_3$CN): δ 8.19 (s, 2 H), 7.69 (d, J = 3.8 Hz, 1 H), 7.44-7.34 (m, 5 H), 7.07-7.01 (m, 2 H), 6.97-6.93 (m, 2 H), 6.19 (dd, J = 4.5, 9.6 Hz, 1 H), 4.46 (s, 1 H), 4.20 (dd, J = 3.8, 11.4 Hz, 1 H), 4.02-3.90 (m, 3 H), 3.83 (s, 3 H), 3.82 (s, 3 H), 3.67 (dd, J = 9.6, 14.1 Hz, 1 H), 3.35 (dd, J = 4.5, 14.1 Hz, 1 H), 3.22-3.16 (m, 1 H), 3.09-3.01 (m, 1 H), 2.69 (ddd, J = 6.6, 8.0, 9.3 Hz, 1 H), 2.09 (s, 3 H), 1.91-1.76 (m, 2 H). Note: NH not visible LCMS (Method 1): [MH+] = 700 at 2.56 min. Chiral analysis (Method 13) at 3.44 min. |
| Single diastereomer 2 of [(1S)-2-(3,5-dichloro-1-oxido-pyridin-1-ium-4-yl)-1-(3,4-dimethoxyphenyl)ethyl] 5-[[[2-[[(2R)-1-methylazetidin-2-yl]methoxy]-2-oxo-1-phenyl-ethyl]amino]methyl]thiophene-2-carboxylate | Example 95 (diastereoisomer2) | Example 28 | $^1$H NMR (400 MHz, CD$_3$CN): δ 8.18 (s, 2 H), 7.69 (d, J = 3.8 Hz, 1 H), 7.43-7.40 (m, 5 H), 7.07-7.02 (m, 2 H), 6.97-6.94 (m, 2 H), 6.19 (dd, J = 4.5, 9.9 Hz, 1 H), 4.46 (s, 1 H), 4.19-4.12 (m, 1 H), 4.01-3.89 (m, 3 H), 3.83 (s, 3 H), 3.82 (s, 3 H), 3.71-3.63 (m, 1 H), 3.34 (dd, J = 4.5, 14.1 Hz, 1 H), 3.25-3.20 (m, 1 H), 3.15-3.07 (m, 1 H), 2.74-2.67 (m, 1 H), 2.10 (s, 3 H), 1.91-1.76 (m, 2 H). NH not visible LCMS (Method 1): [MH+] = 700 at 2.56 min. Chiral analysis (Method 13) at 4.30 min. |

-continued

| Structure | Reference | Precursor | Analytical Data |
|---|---|---|---|
| Single diastereomer 1 of [(1S)-2-(3,5-dichloro-1-oxido-pyridin-1-ium-4-yl)-1-(3,4-dimethoxyphenyl)ethyl] 5-[[[2-[[(2R)-1,4-dimethylpiperazin-2-yl]methoxy]-2-oxo-1-phenyl-ethyl]amino]methyl]thiophene-2-carboxylate | Example 96 (diastereoisomer 1) The corresponding diastereoisomer 2, chiral analysis (Method 7) at 8.00 min. was not isolated | Example 29 | $^1$H NMR (400 MHz, CD$_3$CN): δ 8.07 (s, 2 H), 7.57 (d, J = 3.5 Hz, 1 H), 7.31-7.25 (m, 5 H), 6.96-6.89 (m, 2 H), 6.86-6.81 (m, 2 H), 6.07 (dd, J = 4.5, 9.6 Hz, 1 H), 4.33 (s, 1 H), 4.08-3.95 (m, 2 H), 3.90-3.78 (m, 2 H), 3.72 (s, 3H), 3.70 (s, 3 H), 3.59-3.51 (m, 1 H), 3.23 (dd, J = 4.5, 14.1 Hz, 1 H), 2.73 (s, 1 H), 2.56-2.48 (m, 1 H), 2.42-2.31 (m, 2 H), 2.17-2.07 (m, 2 H) 2.02 (s, 3 H), 1.98 (s, 3 H), 1.93-1.89 (m, 1 H), 1.68-1.60 (m, 1 H). LCMS (Method 3): [MH+] = 743 at 2.66 min. Chiral analysis (Method 7) at 6.67 min. |
| Single diastereomer 1 of [(1S)-2-(3,5-dichloro-1-oxido-pyridin-1-ium-4-yl)-1-(3,4-dimethoxphenyl)ethyl] 5-[[[2-[[(2R)-1-methyl-2-piperidyl]methoxy]-2-oxo-1-phenyl-ethyl]amino]methyl]thiophene-2-carboxylate | Example 97 (diastereoisomer 1) Single diastereoisomer 1 of Example 30 obtainable also as Single diastereoisomer 1 (1$^{st}$ eluted) below from Example 31 | Example 30 or Example 31 | $^1$H NMR (400 MHz, CD$_3$CN): δ 8.18 (s, 2 H), 7.70 (d, J = 3.8 Hz, 1 H), 7.43-7.32 (m, 5 H), 7.07-7.02 (m, 2 H), 6.98-6.94 (m, 2 H), 6.19 (dd, J = 4.5, 9.6 Hz, 1 H), 4.44 (s, 1 H), 4.15-4.07 (m, 2 H), 4.01-3.90 (m, 2 H), 3.84 (s, 3 H), 3.82 (s, 3 H), 3.68 (dd, J = 9.7, 14.0 Hz, 1 H), 3.34 (dd, J = 4.5, 14.1 Hz, 1 H), 2.77-2.71 (m, 1 H), 2.12 (s, 3 H), 2.03-1.99 (m, 1 H), 1.66-1.61 (m, 1 H), 1.56-1.40 (m, 3 H), 1.32-1.25 (m, 1 H), 1.24-1.16 (m, 2 H), NH not visible. LCMS (Method 3): [MH+] = 728 at 2.77 min. Chiral analysis (Method 6) at 6.09 min. |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-[[(2R)-1-methyl-2-piperidyl]methoxy]-2-oxo-1-phenyl-ethyl]amino]methyl]thiophene-2-carboxylate | Example 98 (diastereoisomer 2) Single diastereoisomer 2 of Example 30 obtainable also as Single diastereoisomer 4 (4th eluted) below from Example 31) | Example 30 or Example 31 | 1H NMR (400 MHz, CD3CN): δ 8.18 (s, 2 H), 7.69 (d, J = 3.8 Hz, 1 H), 7.42-7.36 (m, 5 H), 7.07-7.01 (m, 2 H), 6.97-6.93 (m, 2 H), 6.19 (dd, J = 4.8, 9.6 Hz, 1 H), 4.45 (s, 1 H), 4.12 (d, J = 4.5 Hz, 2 H), 4.02-3.90 (m, 2 H), 3.83 (s, 3 H), 3.82 (s, 3H), 3.67 (dd, J = 9.6, 14.1 Hz, 1 H), 3.35 (dd, J = 4.5, 14.1 Hz, 1 H), 2.75-2.70 (m, 1 H), 2.12 (s, 3 H), 1.70-1.61 (m, 1 H), 1.56-1.49 (m, 2 H), 1.47-1.17 (m, 4 H), 0.97-0.89 (m, 1 H), NH not visible. LCMS (Method 3): [MH+] = 728 at 2.74 min. Chiral analysis (Method 6) at 8.21 min. |
| Single diastereomer 1 of [(1S)-2-(3,5-dichloro-1-oxido-pyridin-1-ium-4-yl)-1-(3,4-dimethoxyphenyl)ethyl] 5-[[[2-[[(2S)-1-methyl-2-piperidyl]methoxy]-2-oxo-1-phenyl-ethyl]amino]methyl]thiophene-2-carboxylate<br><br>Second eluted Songle diastereoisomer of Example 31 | Example 99 (diastereoisomer 1) | Example 31 | 1H NMR (400 MHz, CD3CN): δ 8.17 (s, 2 H), 7.69 (d, J = 3.8 Hz, 1 H), 7.42-7.36 (m, 5 H), 7.07-7.01 (m, 2 H), 6.97-6.92 (m, 2 H), 6.19 (dd, J = 4.5, 9.6 Hz, 1 H), 4.44 (s, 1 H), 4.12 (d, J = 4.5 Hz, 2 H), 4.03-3.90 (m, 2 H), 3.83 (s, 3 H), 3.82 (s, 3 H), 3.71-3.64 (m, 1 H), 3.34 (dd, J = 4.5, 14.1 Hz, 1 H), 2.75-2.69 (m, 1 H), 2.12 (s, 3 H), 2.03-2.01 (m, 2 H), 1.67-1.62 (m, 1 H), 1.56-1.51 (m, 2 H), 1.48-1.37 (m, 1 H), 1.26-1.18 (m, 2 H), NH not visible. LCMS (Method 3): [MH+] = 728 at 2.77 min. Chiral analysis (Method 6) at 6.11 min.<br>Two further compounds were detected during the chiral separation of compounds 99 and 100 from example 31, corresponding to examples 97 and 98 eluting in chiral analysis at 6.09 and 8.21 min (Method 6) |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-[[(2S)-1-methyl-2-piperidyl]methoxy]-2-oxo-1-phenyl-ethyl]amino]methyl]thiophene-2-carboxylate<br>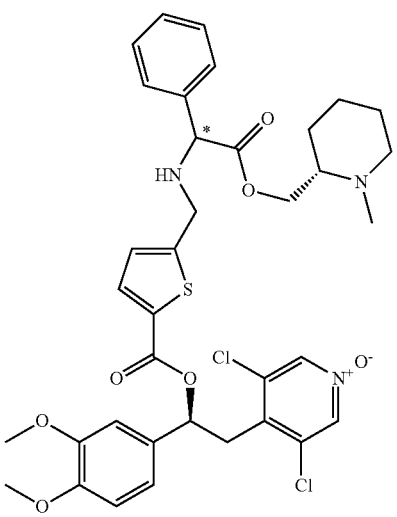<br>Third eluted Single diastereoisomer of Example 31 | Example 100 (diastereoisomer 2) Two further compounds were detected during the chiral separation of compounds 99 and 100 from example 31, corresponding to examples 97 and 98 eluting in chiral analysis.at 6.09 and 8.21 min (Method 6) | Example 31 | ¹H NMR (400 MHz, CD₃CN): δ 8.19 (s, 2 H), 7.70 (d, J = 3.8 Hz, 1 H), 7.41-7.37 (m, 5 H), 7.07-7.02 (m, 2 H), 6.98-6.94 (m, 2 H), 6.19 (dd, J = 4.4, 9.5 Hz, 1 H), 4.45 (s, 1 H), 4.16-4.08 (m, 2 H), 4.01-3.91 (m, 2 H), 3.83 (s, 3 H), 3.82 (s, 3 H), 3.67 (dd, J = 9.6, 14.1 Hz, 1 H), 3.35 (dd, J = 4.7, 14.0 Hz, Hz, 1 H), 2.78-2.73 (m, 1 H), 2.13 (s, 3 H), 2.05-1.98 (m, 2 H), 1.65-1.63 (m, 1 H), 1.56-1.42 (m, 3 H), 1.26-1.17 (m, 2 H), NH not observed. LCMS (Method 3): [MH+] = 728 at 2.74 min. Chiral analysis (Method 6) at 6.63 min. |
| Single diastereomer 1 of [(1S)-2-(3,5-dichloro-1-oxido-pyridin-1-ium-4-yl)-1-(3,4-dimethoxyphenyl)ethyl] 5-[[[2-oxo-1-phenyl-2-(quinuclidin-4-ylmethoxy)ethyl]amino]methyl]thiophene-2-carboxylate<br>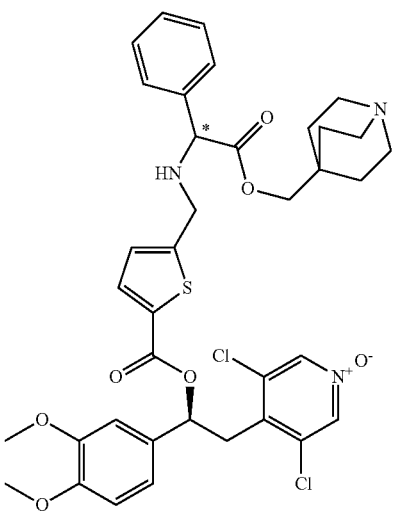 | Example 101 (diastereoisomer 1) | Example 33 | ¹H NMR (400 MHz, CD₃CN): δ 8.18 (s, 2 H), 7.67 (d, J = 3.8 Hz, 1 H), 7.41-7.30 (m, 5 H), 7.04-6.98 (m, 2 H), 6.94-6.90 (m, 2 H), 6.15 (dd, J = 4.4, 9.4 Hz, 1 H), 4.43 (s, 1 H), 3.93 (d, J = 15.0 Hz, 1 H), 3.88 (d, J = 15.0 Hz, 1 H), 3.80 (s, 3 H), 3.79 (s, 3 H), 3.77-3.61 (m, 4 H), 3.32 (dd, J = 4.6, 14.2 Hz, 1 H), 2.72 (t, J = 7.4 Hz, 6 H), 1.28-1.20 (m, 6 H). LCMS (Method 1): [MH+] = 740 at 2.57 min. Chiral analysis (Method 15) at 2.36 min. |

-continued

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-oxo-1-phenyl-2-(quinuclidin-4-ylmethoxy)ethyl]amino]methyl]thiophene-2-carboxylate<br />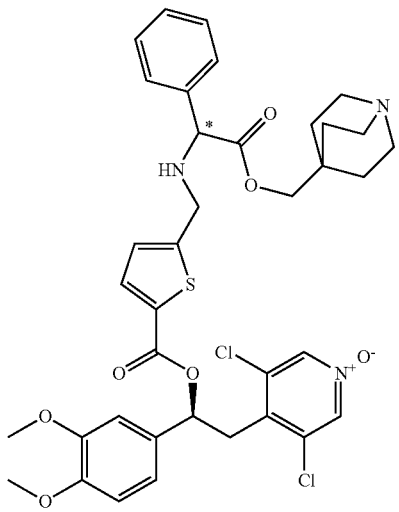 | Example 102 (diastereoisomer 2) | Example 33 | $^1$H NMR (400 MHz, CD$_3$CN): δ 8.17 (s, 2 H), 7.67 (d, J = 4.8 Hz, 1 H), 7.40-7.31 (m, 5 H), 7.04-6.98 (m, 2 H), 6.94-6.89 (m, 2 H), 6.18-6.13 (m, 1 H), 4.42 (s, 1 H), 3.94 (d, J = 13.9 Hz, 1 H), 3.88 (d, J = 14.3 Hz, 1 H), 3.80 (s, 3 H), 3.78 (s, 3 H), 3.77-3.62 (m, 4 H), 3.32 (dd, J = 4.6, 14.5 Hz, 1 H), 2.72 (t, J = 7.9 Hz, 6 H), 1.28-1.21 (m, 6 H). LCMS (Method 1): [MH+] = 740 2.56 min. Chiral analysis (Method 15) at 3.14 min. |
| Single diastereomer 1 of [(1S)-2-(3,5-dichloro-1-oxido-pyridin-1-ium-4-yl)-1-(3,4-dimethoxyphenyl)ethyl] 5-[[[1-methyl-2-[(1-methyl-4-piperidyl)methoxy]-2-oxo-1-phenyl-ethyl]amino]methyl]thiophene-2-carboxylate<br />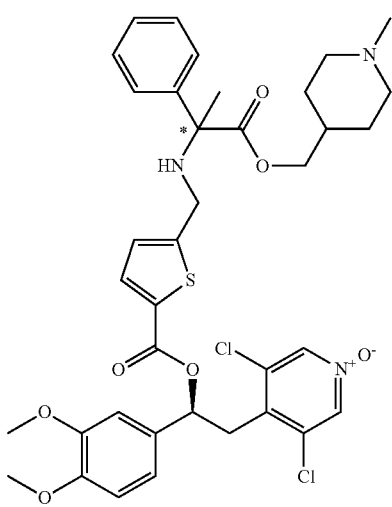 | Example 103 (diastereoisomer 1) | Example 34 | $^1$H NMR (400 MHz, CD$_3$CN): δ 8.19 (s, 2 H), 7.69 (d, J = 3.8 Hz, 1 H), 7.55-7.51 (m, 2 H), 7.43-7.38 (m, 2 H), 7.34-7.30 (m, 1 H), 7.08-7.02 (m, 2 H), 6.97-6.94 (m, 2 H), 6.18 (dd, J = 4.5, 9.6 Hz, 1 H), 3.99 (dd, J = 3.3, 6.1 Hz, 2 H), 3.87 (s, 2 H), 3.84 (s, 3 H), 3.82 (s, 3 H), 3.68 (dd, J = 9.6, 14.1 Hz, 1 H), 3.35 (dd, J = 4.5, 14.1 Hz, 1 H), 2.95-2.89 (m, 1 H), 2.77 (d, J = 11.4 Hz, 2 H), 2.17 (s, 3 H), 1.89-1.81 (m, 2 H), 1.68 (s, 3 H), 1.61-1.53 (m, 3 H), 1.31-1.18 (m, 2 H). LCMS (Method 1): [MH+] = 742 at 2.64 min. Chiral analysis (Method 15) at 1.62 min. |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[1-methyl-2-[(1-methyl-4-piperidyl)methoxy]-2-oxo-1-phenyl-ethyl]amino]methyl]thiophene-2-carboxylate | Example 104 (diastereoisomer 2) | Example 34 | $^1$H NMR (400 MHz, CD$_3$CN): δ 8.18 (s, 2 H), 7.68 (d, J = 3.8 Hz, 1 H), 7.52 (d, J = 7.8 Hz, 2 H), 7.40 (dd, J = 7.5, 7.5 Hz, 2 H), 7.32 (dd, J = 7.3, 7.3 Hz, 1 H), 7.08-7.02 (m, 2 H), 6.95 (dd, J = 2.1, 5.9 Hz, 2 H), 6.18 (dd, J = 4.5, 9.6 Hz, 1 H), 4.01-3.95 (m, 2 H), 3.87 (s, 2 H), 3.85 (s, 3 H), 3.82 (s, 3 H), 3.68 (dd, J = 9.7, 14.0 Hz, 1 H), 3.35 (dd, J = 4.4, 14.0 Hz, 1 H), 2.91 (s, 1 H), 2.76 (d, J = 11.1 Hz, 2 H), 2.17 (s, 3 H), 1.89-1.81 (m, 2 H), 1.68 (s, 3 H), 1.56 (dd, J = 10.7, 10.7 Hz, 3 H), 1.31-1.18 (m, 2 H), LCMS (Method 1): [MH+] = 742 at 2.64 min. Chiral analysis (Method 15) at 2.81 min. |
| Single diastereomer 1 of [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)methoxy]-2-oxo-1-phenyl-ethyl]amino]methyl]thiophene-2-carboxylate | Example 105 (diastereoisomer 1) | Example 35 | $^1$H NMR (400 MHz, CD$_3$CN): δ 8.21 (s, 2 H), 7.68 (dd, J = 3.0, 3.0 Hz, 1 H), 7.49 (dd, J = 1.4, 7.2 Hz, 2 H), 7.42-7.34 (m, 3 H), 7.09-7.02 (m, 2 H), 6.98-6.92 (m, 2 H), 6.18 (dd, J = 4.7, 9.5 Hz, 1 H), 4.17 (d, J = 10.6 Hz, 1 H), 4.05-3.89 (m, 4 H), 3.85 (s, 3 H), 3.83 (s, 3 H), 3.77-3.65 (m, 2 H), 3.38-3.33 (m, 1 H), 3.26-3.09 (m, 2 H), 2.76 (d, J = 10.1 Hz, 2 H), 2.19 (s, 3H), 1.87-1.79 (m, 2 H), 1.59-1.57 (m, 3 H), 1.26-1.22 (m, 2 H). LCMS (Method 1): [MH+] = 758 at 2.45 min. Chiral analysis (Method 14) at 3.38 min. |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxphenyl)ethyl] 5-[[[1-(hydroxymethyl)-2-[(1-methyl-4-piperidyl)methoxy]-2-oxo-1-phenyl-ethyl]amino]methyl]thiophene-2-carboxylate | Example 106 (diastereoisomer 2) | Example 35 | ¹H NMR (400 MHz, CD₃CN): δ 8.20 (s, 2 H), 7.67 (d, J = 3.8 Hz, 1 H), 7.49 (d, J = 7.3 Hz, 2 H), 7.43-7.34 (m, 3 H), 7.08-7.03 (m, 2 H), 6.98-6.92 (m, 2 H), 6.18 (dd, J = 4.4, 9.7 Hz, 1 H), 4.18 (d, J = 11.1 Hz, 1 H), 4.07-3.87 (m, 5 H), 3.85 (s, 3 H), 3.83 (s, 3 H), 3.75-3.65 (m, 1 H), 3.36 (dd, J = 4.7, 14.3 Hz, 1 H), 3.16 (dd, J = 20.6, 64.4 Hz, 2 H), 2.75 (d, J = 11.1 Hz, 2 H), 2.15 (s, 3H), 1.82 (dd, J = 11.4, 11.4 Hz, 2 H), 1.59-1.52 (m, 3 H), 1.28-1.17 (m, 2 H). LCMS (Method 1): [MH+] = 758 at 2.58 min. Chiral analysis (Method 14) at 4.17 min. |
| Single diastereomer 1 of [(1S)-2-(3,5-dichloro-1-oxido-pyridin-1-ium-4-yl)-1-(3,4-dimethoxyphenyl)ethyl] 5-[[[2-[(1-methyl-4-piperidyl)methoxy]-2-oxo-1-phenyl-ethyl]amino]methyl]thiophene-3-carboxylate | Example 107 (diastereoisomer 1) | Example 36 | ¹H NMR (400 MHz, DMSO): δ 8.56 (s, 2 H), 8.27 (s, 1 H), 7.40-7.35 (m, 6 H), 7.26 (s, 1 H), 7.06-6.98 (m, 3 H), 6.15 (dd, J = 4.3, 9.3 Hz, 1 H), 4.39 (s, 1 H), 3.91-3.81 (m, 3 H), 3.80 (s, 3 H), 3.77 (s, 3 H), 3.59 (dd, J = 9.6, 13.9 Hz, 1 H), 3.41 (s, 1 H), 3.32 (dd, J = 4.3, 13.9 Hz, 1 H), 2.66 (d, J = 11.1 Hz, 2 H), 2.10 (s, 3 H), 1.77-1.69 (m, 2 H), 1.51-1.40 (m, J = 3.5, 6.8 Hz, 3 H), 1.15-1.05 (m, 2 H). LCMS (Method 4): [MH+] = 728 at 3.29 min. Chiral analysis (Method 10) at 3.00 min. |

| Structure | Reference | Precursor | Analytical Data |
|---|---|---|---|
| Single diastereomer 2 of [(1S)-2-(3,5-dichloro-1-oxido-pyridin-1-ium-4-yl)-1-(3,4-dimethoxyphenyl)ethyl] 5-[[[2-[(1-methyl-4-piperidyl)methoxy]-2-oxo-1-phenyl-ethyl]amino]methyl]thiophene-3-carboxylate 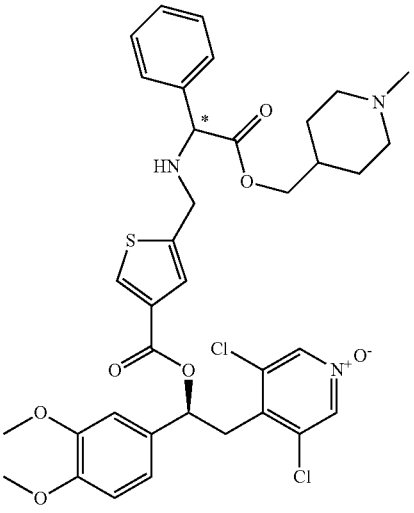 | Example 108 (diastereoisomer 2) | Example 36 | $^1$H NMR (400 MHz, DMSO): δ 8.57 (s, 2 H), 8.28 (s, 1 H), 7.41-7.35 (m, 6 H), 7.25 (s, 1H), 7.04-6.98 (m, 3H), 6.15 (dd, J = 4.4, 9.5 Hz, 1 H), 4.40 (s, 1 H), 3.91-3.81 (m, 4H), 3.79 (s, 3 H), 3.77 (s, 3 H), 3.60 (dd, J = 9.6, 14.1 Hz, 1 H), 3.32 (dd, J = 4.4, 14.3 Hz, 1 H), 2.77-2.69 (m, 2 H), 2.17 (s, 3 H), 1.86-1.85 (m, 2 H), 1.49-1.42 (m, 3 H), 1.18-1.05 (m, 2 H). LCMS (Method 4): [MH+] = 728 at 3.29 min. Chiral analysis (Method 10) at 7.45 min. |
| Single diastereomer 1 [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)methoxy]-2-oxo-1-(2-thienyl)ethyl]amino]methyl]thiophene-2-carboxylate formate salt 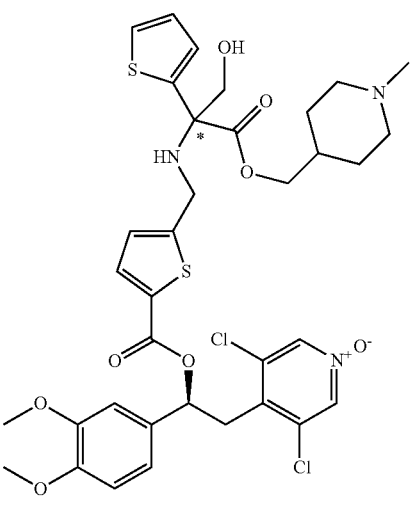 | Example 109 (diastereoisomer 1) | Example 37 | $^1$H NMR (400 MHz, CD$_3$CN): δ 8.36 (s, 1H), 8.17 (s, 2 H), 7.64 (d, J = 3.8 Hz, 1 H), 7.36 (dd, J = 1.2, 5.1 Hz, 1 H), 7.13 (dd, J = 1.3, 3.5 Hz, 1 H), 7.06-6.96 (m, 3 H), 6.95-6.89 (m, 2 H), 6.15 (dd, J = 5.1, 10.0 Hz, 1 H), 4.23 (dd, J = 4.9, 10.9 Hz, 1 H), 4.13 (d, J = 10.3 Hz, 1 H), 4.06-3.98 (m, 2 H), 3.90-3.85 (m, 2 H), 3.81 (s, 3 H), 3.79 (s, 3 H), 3.66 (dd, J = 10.2, 13.8 Hz, 1 H), 3.33 (dd, J = 5.2, 14.5 Hz, 1 H), 3.11-3.02 (m, 2 H), 2.40 (s, 3 H), 2.35-2.25 (m, 2 H), 1.79-1.52 (m, 6 H), NH or OH, not observed. LCMS (Method 3): [MH+] = 764 at 2.74 min. Chiral analysis (Method 13) at 4.48 min. |

-continued

| Structure | Reference | Precursor | Analytical Data |
|---|---|---|---|
| Single diastereomer 2 [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)methoxy]-2-oxo-1-(2-thienyl)ethyl]amino]methyl]thiophene-2-carboxylate formate salt | Example 110 (diastereoisomer 2) | Example 37 | $^1$H NMR (400 MHz, CD$_3$CN): δ 8.39 (s, 1H), 8.18 (s, 2 H), 7.65 (d, J = 3.7 Hz, 1 H), 7.37 (dd, J = 1.1, 5.1 Hz, 1 H), 7.14 (dd, J = 1.2, 3.6 Hz, 1 H), 7.05-6.98 (m, 3 H), 6.95-6.92 (m, 2 H), 6.16 (dd, J = 4.3, 10.1 Hz, 1 H), 4.23 (dd, J = 4.7, 11.5 Hz, 1 H), 4.15 (d, J = 10.3 Hz, 1 H), 4.04-3.97 (m, 2 H), 3.91-3.84 (m, 2 H), 3.82 (s, 3 H), 3.80 (s, 3 H), 3.66 (dd, J = 10.0, 14.4 Hz, 1 H), 3.34 (dd, J = 4.7, 14.0 Hz, 1 H), 3.11-3.02 (m, 2 H), 2.40 (s, 3 H), 2.30 (t, J = 13.4 Hz, 2 H), 1.75-1.51 (m, 6 H), NH or OH not observed. LCMS (Method 3): [MH+] = 764 at 2.74 min. Chiral analysis (Method 13) at 623 min. |
| Single diastereoisomer 1 of [(1S)-2-(3,5-dichloro-1-oxido-pyridin-1-ium-4-yl)-1-(3,4-dimethoxyphenyl)ethyl] 5-[[[1-[(1-methyl-4-piperidyl)methoxycarbonyl]indan-1-yl]amino]methyl]thiophene-2-carboxylate | Example 111 (diastereoisomer 1) | Example 38 | $^1$H NMR (400 MHz, CDCl$_3$): δ 8.12 (s, 2 H), 7.61 (d, J = 3.8 Hz, 1 H), 7.29-7.26 (m, 3 H), 7.23-7.19 (m, 1 H), 6.99-6.95 (m, 2 H), 6.88-6.82 (m, 2 H), 6.21 (dd, J = 4.7, 9.7 Hz, 1 H), 3.99-3.93 (m, 2 H), 3.91-3.86 (m, 2 H), 3.90 (s, 3 H), 3.87 (s, 3 H), 3.64 (dd, J = 9.6, 13.9 Hz, 1 H), 3.31 (dd, J = 4.5, 13.9 Hz, 1 H), 3.12-3.06 (m, 2 H), 2.98-2.85 (m, 2 H), 2.72 (dt, J = 6.6, 13.3 Hz, 1 H),), 2.34 (s, 3 H), 2.22 (dt, J = 7.7, 13.1 Hz, 1 H), 2.07-1.96 (m, 2 H), 1.67-1.33 (m, 5 H), NH not visible. LCMS (Method 1): [MH+] = 754 at 2.54 min. Chiral analysis (Method 11) at 11.17 min. |

| Structure | Reference | Precursor | Analytical Data |
|---|---|---|---|
| Single diastereoisomer 2 of [(1S)-2-(3,5-dichloro-1-oxido-pyridin-1-ium-4-yl)-1-(3,4-dimethoxyphenyl)ethyl] 5-[[[1-[(1-methyl-4-piperidyl)methoxycarbonyl]indan-1-yl]amino]methyl]thiophene-2-carboxylate | Example 112 (diastereoisomer 2) | Example 38 | $^1$H NMR (400 MHz, CDCl$_3$): δ 8.12 (s, 2 H), 7.61 (d, J = 3.8 Hz, 1 H), 7.29-7.27 (m, 3 H), 7.23-7.19 (m, 1 H), 7.00-6.95 (m, 2 H), 6.87 (d, J = 3.3 Hz, 1 H), 6.84 (d, J = 7.8 Hz, 1 H), 6.21 (dd, J = 4.4, 9.7 Hz, 1 H), 3.97 (d, J = 6.3 Hz, 2 H), 3.91-3.80 (m, 2 H), 3.89 (s, 3 H), 3.87 (s, 3 H), 3.65 (dd, J = 9.6, 13.9 Hz, 1 H), 3.30 (dd, J = 4.7, 14.0 Hz, 1 H), 3.09 (dd, J = 7.2, 7.2 Hz, 2 H), 2.83-2.78 (m, 2 H), 2.75 (dt, J = 6.6, 13.5 Hz, 1 H), 2.26-2.17 (m, 1 H), 2.24 (s, 3 H), 1.90-1.81 (m, 2 H), 1.62-1.50 (m, 3 H), 1.32-1.24 (m, 2 H), NH not visible. LCMS (Method 1): [MH+] = 754 at 2.55 min. Chiral analysis (Method 11) at 12.30 Min. |
| Single diastereoisomer 1 of [(1S)-2-(3,5-dichloro-1-oxido-pyridin-1-ium-4-yl)-1-(3,4-dimethoxyphenyl)ethyl] 5-[[[1-(3-methoxyphenyl)-2-[(1-methyl-4-piperidyl)methoxy]-2-oxo-ethyl]amino]methyl]thiophene-2-carboxylate | Example 121 (diastereoisomer 1) | Example 119 | $^1$H NMR (400 MHz, CD$_3$CN): δ 8.16 (s, 2 H), 7.66 (d, J = 3.8 Hz, 1 H), 7.27 (dd, J = 8.1, 8.1 Hz, 1 H), 7.04-6.98 (m, 2 H), 6.96-6.90 (m, 3 H), 6.87 (dd, J = 2.6, 8.2 Hz, 2 H), 6.15 (dd, J = 4.5, 9.6 Hz, 1 H), 4.39 (s, 1 H), 3.93-3.88 (m, 4 H), 3.80 (s, 3 H), 3.79 (s, 3 H), 3.77 (s, 3 H), 3.64 (dd, J = 9.7, 14.0 Hz, 1 H), 3.31 (dd, J = 4.8, 14.1 Hz, 1 H), 2.93-2.86 (m, 1 H), 2.73-2.67 (m, 2 H), 2.12 (s, 3 H), 1.81-1.71 (m, 2 H), 1.51-1.44 (m, 3 H), 1.21-1.08 (m, 2 H). LCMS [(Method 3)]: [MH+] = 758 at 2.78 min. Chiral analysis [(Method 11)] at 10.19 min. |

-continued

| Structure | Reference | Precursor | Analytical Data |
|---|---|---|---|
| Single diastereoisomer 2 of [(1S)-2-(3,5-dichloro-1-oxido-pyridin-1-ium-4-yl)-1-(3,4-dimethoxyphenyl)ethyl] 5-[[[1-(3-methoxyphenyl)-2-[(1-methyl-4-piperidyl)methoxy]-2-oxo-ethyl]amino]methyl]thiophene-2-carboxylate 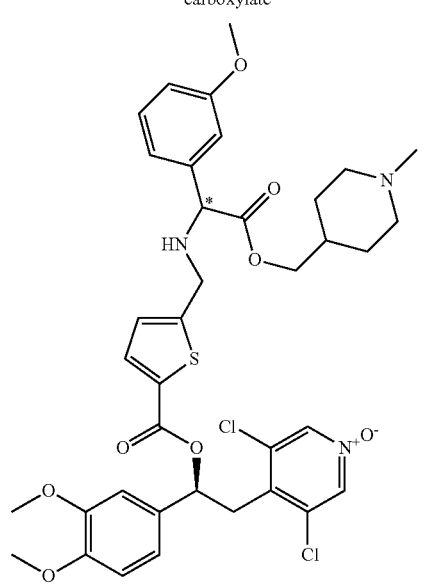 | Example 122 (diastereoisomer 2) | Example 119 | $^1$H NMR (400 MHz, CD$_3$CN): δ 8.16 (s, 2 H), 7.66 (d, J = 3.8 Hz, 1 H), 7.28 (dd, J = 8.1, 8.1 Hz, 1 H), 7.05-6.99 (m, 2 H), 6.96-6.90 (m, 4 H), 6.90-6.86 (m, 1 H), 6.15 (dd, J = 4.5, 9.6 Hz, 1 H), 4.39 (s, 1 H), 3.94-3.88 (m, 4 H), 3.81 (s, 3 H), 3.80 (s, 3 H), 3.78 (s, 3 H), 3.65 (dd, J = 9.6, 14.1 Hz, 1 H), 3.32 (dd, J = 4.7, 14.0 Hz, 1 H), 2.89-2.89 (m, 1 H), 2.74-2.68 (m, 2 H), 2.13 (s, 3 H), 1.80-1.72 (m, 2 H), 1.52-1.45 (m, 3 H), 1.21-1.12 (m, 2 H). LCMS [(Method 3)]: [MH+] = 758 at 2.77 min. Chiral analysis [(Method 11)] at 12.38 min. |
| Single diastereoisomer 1 of [(1S)-2-(3,5-dichloro-1-oxido-pyridin-1-ium-4-yl)-1-[4-(difluoromethoxy)-3-(2-methoxyethoxy)phenyl]ethyl] 5-[[[2-[(1-methyl-4-piperidyl)methoxy]-2-oxo-1-phenyl-ethyl]amino]methyl]thiophene-2-carboxylate 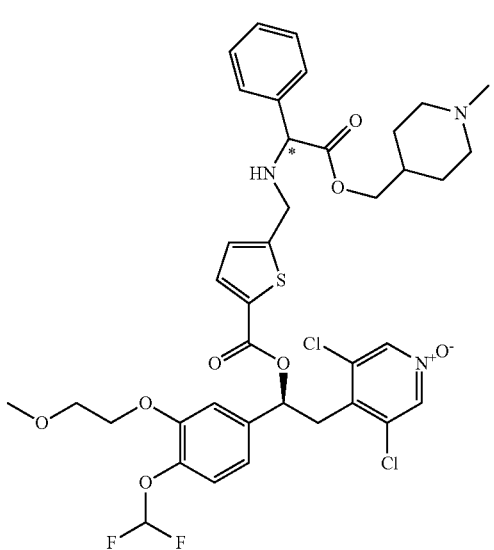 | Example 123 (diastereoisomer 1) | Example 113 | $^1$H NMR (400 MHz, CD3CN): δ 8.17 (s, 2 H), 7.69 (d, J = 3.8 Hz, 1 H), 7.39-7.36 (m, 4 H), 7.36-7.31 (m, 1 H), 7.20-7.14 (m, 2 H), 7.06 (dd, J = 2.0, 8.3 Hz, 1 H), 6.94 (d, J = 3.7 Hz, 1 H), 6.76 (t, J = 75.4 Hz, 1 H), 6.16 (dd, J = 4.8, 9.4 Hz, 1 H), 4.42 (s, 1 H), 4.23-4.14 (m, 2 H), 3.94 (d, J = 15.2 Hz, 2 H), 3.89 (d, J = 17.6 Hz, 2 H), 3.69 (t, J = 4.5 Hz, 2 H), 3.62 (dd, J = 9.3, 14.3 Hz, 1 H), 3.36-3.30 (m, 1 H), 3.34 (s, 3 H), 2.96-2.78 (m, 1 H), 2.73-2.66 (m, 2 H), 2.18 (s, 3 H), 1.81-1.71 (m, 2 H), 1.51-1.43 (m, 3 H), 1.21-1.08 (m, 2 H). LCMS [(Method 3)]: [MH+] = 808 at 2.90 min. Chiral analysis [(Method 11)] at 2.46 min. |

-continued

| Structure | Reference | Precursor | Analytical Data |
|---|---|---|---|
| Single diastereoisomer 2 of [(1S)-2-(3,5-dichloro-1-oxido-pyridin-1-ium-4-yl)-1-[4-(difluoromethoxy)-3-(2-methoxyethoxy)phenyl]ethyl] 5-[[[2-[(1-methyl-4-piperidyl)methoxy]-2-oxo-1-phenyl-ethyl]amino]methyl]thiophene-2-carboxylate | Example 124 (diastereisomer 2) | Example 113 | $^1$H NMR (400 MHz, CD$_3$CN): δ 8.17 (s, 2 H), 7.69 (d, J = 3.8 Hz, 1 H), 7.42-7.29 (m, 5 H), 7.18 (d, J = 1.5 Hz, 1 H), 7.16 (d, J = 9.2 Hz, 1 H), 7.06 (dd, J = 2.0, 8.3 Hz, 1 H), 6.96-6.93 (m, 1 H), 6.76 (t, J = 75.9 Hz, 1 H), 6.16 (dd, J = 4.5, 9.3 Hz, 1 H), 4.42 (s, 1 H), 4.23-4.14 (m, 2 H), 3.99-3.85 (m, 4 H), 3.69 (t, J = 4.6 Hz, 2 H), 3.62 (dd, J = 9.7, 14.2 Hz, 2 H), 3.34 (s, 3 H), 3.33 (dd, J = 5.2, 13.5 Hz, 1 H), 2.75-2.68 (m, 2 H), 2.13 (s, 3 H), 1.83-1.74 (m, 2 H), 1.53-1.44 (m, 3 H), 1.22-1.09 (m, 2 H). LCMS [(Method 4)]: [MH+] = 808 at 3.64 min. Chiral analysis [(Method 11)] at 3.59 min. |
| Single diastereoisomer 1 of epimeric mixture 2 of [2-(3,5-dichloro-1-oxido-pyridin-1-ium-4-yl)-1-(3-ethoxy-4-methoxy-phenyl)ethyl] 5-[[[1-(3-hydroxyphenyl)-2-[(1-methyl-4-piperidyl)methoxy]-2-oxo-ethyl]amino]methyl]thiophene-2-carboxylate | Example 125 (diastereoisomer 1) | Example 120 | $^1$H NMR (400 MHz, CD$_3$CN): δ 8.18 (s, 2 H), 7.65 (d, J = 3.8 Hz, 1 H), 7.18 (dd, J = 8.0, 8.0 Hz, 1 H), 7.02-6.99 (m, 2 H), 6.95-6.92 (m, 2 H), 6.86-6.82 (m, 2 H), 6.76-6.73 (m, 1 H), 6.15 (dd, J = 4.5, 9.6 Hz, 1 H), 4.34 (s, 1 H), 4.11-4.00 (m, 2 H), 3.97-3.88 (m, 4 H), 3.80 (s, 3 H), 3.63 (dd, J = 9.6, 14.1 Hz, 1 H), 3.32 (dd, J = 4.5, 14.1 Hz, 1 H), 2.89-2.70 (m, 1 H), 2.77-2.72 (m, 2 H), 2.14 (s, 3 H), 1.84-1.76 (m, 2 H), 1.54-1.46 (m, 3 H), 1.35 (dd, J = 6.9, 6.9 Hz, 3 H), 1.29-1.14 (m, 2 H), OH not observed. LCMS [(Method 3)]: [MH+] = 758 at 2.62 min. Chiral analysis [(Method 11)] at 10.87 min. |

-continued

| Structure | Reference | Precursor | Analytical Data |
|---|---|---|---|
| Single diastereoisomer 1 of [(1S)-2-(3,5-dichloro-1-oxido-pyridin-1-ium-4-yl)-1-(3,4-dimethoxyphenyl)ethyl] 5-[[[1-(hydroxymethyl)-2-[[(3)S-1-methylpyrrolidin-3-yl]methoxy]-2-oxo-1-phenyl-ethyl]amino]methyl]thiophene-2-carboxylate | Example 126 (diastereoisomer 1) | Example 115 | $^1$H NMR (400 MHz, CD$_3$CN): δ 8.08 (s, 2 H), 7.56 (d, J = 3.8 Hz, 1 H), 7.41-7.38 (m, 2 H), 7.31-7.26 (m, 2 H), 7.24-7.20 (m, 1 H), 6.97-6.91 (m, 2 H), 6.86-6.81 (m, 2 H), 6.07 (dd, J = 4.5, 9.6 Hz, 1 H), 4.21 (dd, J = 4.9, 10.7 Hz, 1 H), 4.03-3.99 (m, 2 H), 3.94 (d, J = 16.1 Hz, 1 H), 3.73 (s, 3 H), 3.71 (s, 3 H), 3.69-3.62 (m, 2 H), 3.57 (dd, J = 8.8, 14.6 Hz, 1 H), 3.24 (dd, J = 4.4, 14.0 Hz, 1 H), 2.96-2.96 (br m, 1 H), 2.59-2.46 (m, 2 H), 2.44-2.36 (m, 1 H), 2.23 (dd, J = 8.7, 8.7 Hz, 1 H), 2.12 (s, 3 H), 1.90-1.78 (m, 2 H), 1.52-1.42 (m, 1 H). NH not observed. LCMS [(Method 3)]: [MH+] = 744 at 2.71 min. Chiral analysis [(Method 14)] at 2.84 min. |
| Single diastereoisomer 2 of [(1S)-2-(3,5-dichloro-1-oxido-pyridin-1-ium-4-yl)-1-(3,4-dimethoxyphenyl)ethyl] 5-[[[1-(hydroxymethyl)-2-[[(3S)-1-methylpyrrolidin-3-yl]methoxy]-2-oxo-1-phenyl-ethyl]amino]methyl]thiophene-2-carboxylate | Example 127 (diastereoisomer 2) | Example 115 | $^1$H NMR (400 MHz, CD$_3$CN): δ 8.11 (s, 2 H), 7.59 (d, J = 3.8 Hz, 1 H), 7.43-7.40 (m, 2 H), 7.34-7.25 (m, 3 H), 7.00-6.94 (m, 2 H), 6.89-6.84 (m, 2 H), 6.09 (dd, J = 4.5, 9.6 Hz, 1 H), 4.39 (dd, J = 4.0, 10.9 Hz, 1 H), 4.08 (d, J = 11.1 Hz, 1 H), 4.00-3.91 (m, 1 H), 3.88 (dd, J = 4.7, 10.7 Hz, 1 H), 3.77 (s, 3 H), 3.74 (s, 3 H), 3.73-3.63 (m, 2 H), 3.60 (dd, J = 9.9, 13.6 Hz, 1 H), 3.27 (dd, J = 4.5, 14.1 Hz, 1 H), 3.07-3.00 (m, 1 H), 2.70-2.63 (m, 1 H), 2.49-2.40 (m, 2 H), 2.28-2.15 (m, 2 H), 2.13 (s, 3 H), 1.94-1.83 (m, 2 H), 1.64-1.54 (m, 1 H). LCMS [(Method 3)]: [MH+] = 744 at 2.71 min. Chiral analysis [(Method 14)] at 3.82 min. |

| Structure | Reference | Precursor | Analytical Data |
|---|---|---|---|
| Single diastereoisomer 1 of [(1S)-2-(3,5-dichloro-1-oxido-pyridin-1-ium-4-yl)-1-(3,4-dimethoxyphenyl)ethyl] 5-[[[1-(hydroxymethyl)-2-[[(3R)-1-methylpyrrolidin-3-yl]methoxy]-2-oxo-1-phenyl-ethyl]amino]methyl]thiophene-2-carboxylate | Example 128 (diastereoisomer 1) | Example 116 | $^1$H NMR (400 MHz, CD$_3$CN): δ 8.21 (s, 2 H), 7.68 (d, J = 3.8 Hz, 1 H), 7.51 (d, J = 7.3 Hz, 2 H), 7.43-7.34 (m, 3 H), 7.09-7.04 (m, 2 H), 6.98-6.93 (m, 2 H), 6.19 (dd, J = 4.5, 9.7 Hz, 1 H), 4.51 (dd, J = 3.6, 10.9 Hz, 1 H), 4.18 (d, J = 11.2 Hz, 1 H), 4.11 (d, J = 16.0 Hz, 1 H), 3.98 (dd, J = 4.7, 10.9 Hz, 1 H), 3.86 (s, 3 H), 3.84 (s, 3 H), 3.82-3.73 (m, 2 H), 3.69 (dd, J = 9.7, 14.1 Hz, 1 H), 3.36 (dd, J = 4.5, 14.2 Hz, 1 H), 3.14 (s, 1 H), 2.80-2.74 (m, 1 H), 2.60-2.51 (m, 2 H), 2.34 (dd, J = 8.7, 8.7 Hz, 1 H), 2.29-2.24 (m, 1 H), 2.28-2.20 (m, 2 H), 2.23 (s, 3 H), 1.74-1.65 (m, 1 H). LCMS [(Method 3)]: [MH+] = 744 at 2.69 min. Chiral analysis [(Method 14)] at 3.04 min. |
| Single diastereoisomer 2 of [(1S)-2-(3,5-dichloro-1-oxido-pyridin-1-ium-4-yl)-1-(3,4-dimethoxyphenyl)ethyl] 5-[[[1-(hydroxymethyl)-2-[[(3R)-1-methypyrrolidin-3-yl]methoxy]-2-oxo-1-phenyl-ethyl]amino]methyl]thiophene-2-carboxylate | Example 129 (diastereoisomer 2) | Example 116 | $^1$H NMR (400 MHz, CD$_3$CN): δ 8.21 (s, 2 H), 7.69 (d, J = 3.8 Hz, 1 H), 7.52 (d, J = 7.4 Hz, 2 H), 7.43-7.34 (m, 3 H), 7.09-7.04 (m, 2 H), 6.98-6.94 (m, 2 H), 6.19 (dd, J = 4.6, 9.6 Hz, 1 H), 4.33 (dd, J = 4.9, 10.7 Hz, 1 H), 4.16-4.11 (m, 2 H), 4.06 (d, J = 14.5 Hz, 1 H), 3.86 (s, 3 H), 3.83 (s, 3 H), 3.81-3.75 (m, 2 H), 3.69 (dd, J = 9.0, 13.7 Hz, 1 H), 3.37 (dd, J = 4.6, 14.2 Hz, 1 H), 3.11 (s, 1 H), 2.71-2.65 (m, 1 H), 2.62-2.58 (m, 1 H), 2.57-2.47 (m, 1 H), 2.38-2.33 (m, 1 H), 2.24 (s, 3 H), 2.22-2.20 (m, 2 H), 1.64-1.54 (m, 1 H). NH not observed. LCMS [(Method 3)]: [MH+] = 744 at 2.69 min. Chiral analysis [(Method 14)] at 4.13 min. |

Duration of Action (DoA)

Comparison of the DoA of compounds of examples 87 and 78 with comparative compounds of examples 87c and 78c, that are, respectively, example 146 and 142, disclosed in co-pending application PCT/EP2014/076572, which is incorporated herein by reference in its entirety, and herewith replicated; and compound of example 105 with compound of example 105c, that is example 29 disclosed in co-pending PCT/EP2015/062417, which is incorporated herein by reference in its entirety, and herewith replicated, demonstrating the superiority of examples 87 and 78 and 105 in terms of DoA as antibronchospastic agents.

| Compound | Chemical structure | M3 Ki*** (nM) | M3 IC₅₀*** (nM) | sub-maximal inhibition Dose* (nmol/kg) | inhibition at 16 h** |
|---|---|---|---|---|---|
| Example 87 Single diastereoisomer 2 of [(1S)-2-(3,5-dichloro-1-oxido-pyridin-1-ium-4-yl)-1-(3,4-dimethoxyphenyl)ethyl] 5-[[[2-[(1-methyl-4-piperidyl)methoxy]-2-oxo-1-phenyl-ethyl]amino]methyl]thiophene-2-carboxylate | 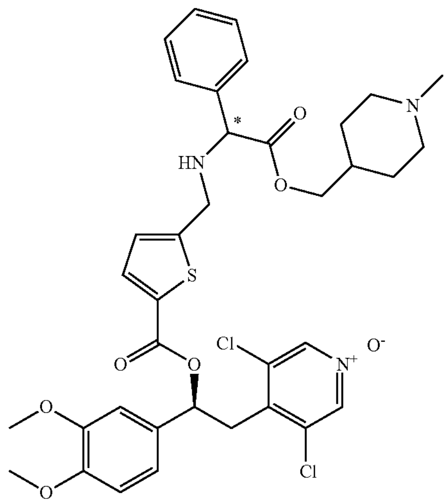 | 0.7 | 1.3 | 10 | >90% |
| Example 87c (Example 146 PCT/EP2014/076572) Single diastereoisomer 2 of [(1S)-2-(3,5-dichloro-1-oxido-pyridin-1-ium-4-yl)-1-(3,4-dimethoxyphenyl)ethyl] 5-[[[2-[(1-methyl-4-piperidyl)oxy]-2-oxo-1-phenyl-ethyl]amino]methyl]thiophene-2-carboxylate | 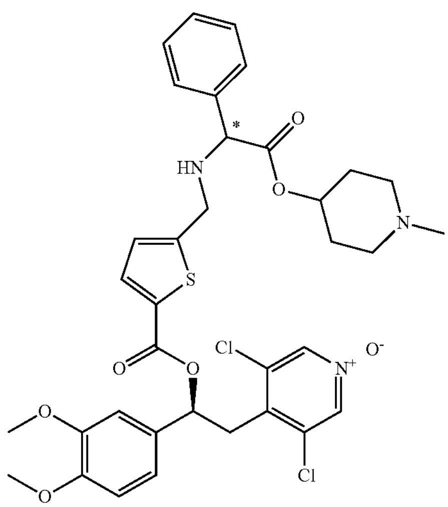 | 0.3 | 0.5 | 30 | <10% |
| Example 78 Single diastereoisomer 2 of [(1S)-2-(3,5-dichloro-1-oxido-pyridin-1-ium-4-yl)-1-(3,4-dimethoxyphenyl)ethyl] 5-[[[2-[[(3S)-1-methylpyrrolidin-3-yl]methoxy]-2-oxo-1-phenyl-ethyl]amino]methyl]thiophene-2-carboxylate | 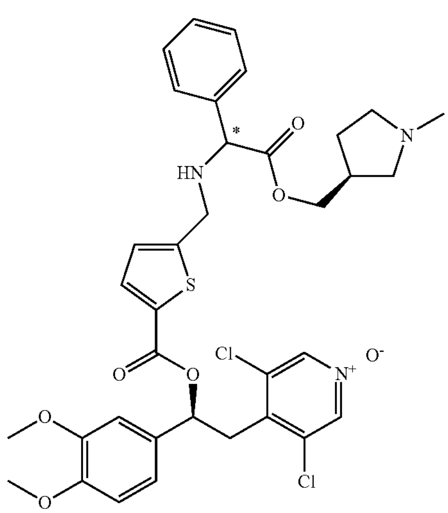 | 0.59 | 1.19 | 30 nmol/kg | 51% |

| Compound | Chemical structure | M3 Ki* (nM) | M3 IC₅₀* (nM) | sub-maximal inhibition Dose* (nmol/kg) | inhibition at 16 h** |
|---|---|---|---|---|---|
| Example 78c (Example 142 PCT/EP2014/076572) Single diastereoisomer 2 of [(1S)-2-(3,5-dichloro-1-oxido-pyridin-1-ium-4-yl)-1-(3,4-dimethoxyphenyl)ethyl] 5-[[[2-[(3S)-1-methylpyrrolidin-3-yl]oxy-2-oxo-1-phenyl-ethyl]amino]methyl]thiophene-2-carboxylate | 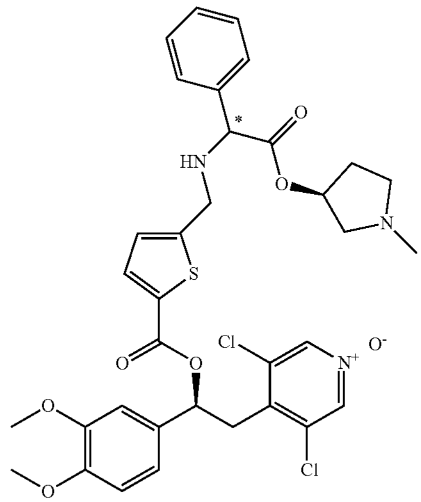 | 0.54 | 1.08 | 100 nmol/kg | 26% |
| Example 105 Single diastereomer 1 of [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)methoxy]-2-oxo-1-phenyl-ethyl]amino]methyl]thiophene-2-carboxylate | 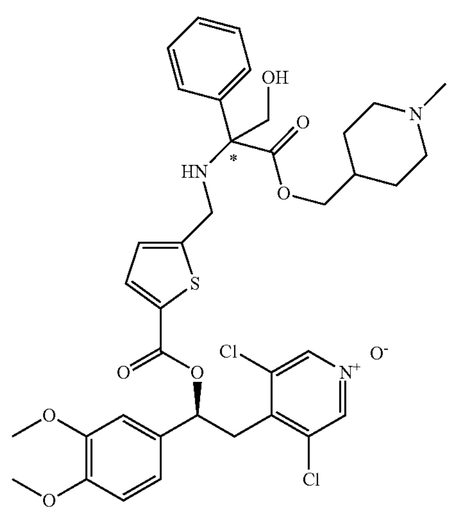 | 0.85 | 1.7 | 30 | 88% |

| Compound | Chemical structure | M3 Ki* (nM) | M3 IC$_{50}$* (nM) | sub-maximal inhibition Dose* (nmol/kg) | inhibition at 16 h** |
|---|---|---|---|---|---|
| Example 105c (Example 29 PCT/EP2015/062417) Single diastereomer 1 of [(1S)-2-(3,5-dichloro-1-oxido-pyridin-1-ium-4-yl)-1-(3,4-dimethoxyphenyl)ethyl] 5-[[[1-(hydroxymethyl)-2-[(1-methyl-4-piperidyl)oxy]-2-oxo-1-phenyl-ethyl]amino]methyl]thiophene-2-carboxylate | 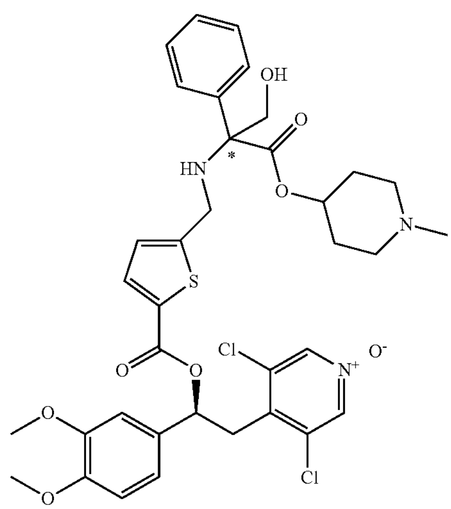 | 0.23 | 0.45 | 10 | 35% |

*Dose producing about 80% (sub- maximal) inhibition of the bronchospasm after 1 h
**16 h after administration of the sub-maximal inhibition dose as indicated in the column here on the left side.
***determined according to the M3 Receptor radioligand binding assay protocol below

Example 87c (Comparative)

Single Diastereomer 2 of [(1S)-2-(3,5-dichloro-1-oxido-pyridin-1-ium-4-yl)-1-(3,4-dimethoxyphenyl)ethyl]5-[[[2-[(1-methyl-4-piperidyl)oxy]-2-oxo-1-phenyl-ethyl]amino]methyl]thiophene-2-carboxylate The title compound was obtained as single diastereoisomer, via a similar method as for example 87; starting from 1-methyl-piperidin-4-ol as precursor instead of (1-methyl-4-piperidyl)-methanol.

$^1$H NMR (400 MHz, CD$_3$CN): δ 8.18 (s, 2 H), 7.69 (d, J=4.3 Hz, 1 H), 7.44-7.32 (m, 5H), 7.07-7.01 (m, 2 H), 6.97-6.91 (m, 2 H), 6.18 (dd, J=4.4, 9.7 Hz, 1 H), 4.81-4.73 (m, 1 H), 4.41 (s, 1 H), 3.95 (dd, J=14.9, 25.1 Hz, 2 H), 3.83 (s, 3 H), 3.82 (s, 3 H), 3.67 (dd, J=9.6, 14.1 Hz, 1 H), 3.33 (dd, J=4.5, 14.1 Hz, 1 H), 2.56-2.11 (m, 4 H), 2.16 (s, 3 H), 1.89-1.81 (m, 1 H), 1.77-1.59 (m, 2 H), 1.55-1.45 (m, 1 H), NH not observed. LCMS (Method 2): [MH+]=714 at 3.61 min.

Chiral analysis (Method 15) at 2.50 min.

Example 78c (Comparative)

Single Diastereoisomer 2 of [(1S)-2-(3,5-dichloro-1-oxido-pyridin-1-ium-4-yl)-1-(3,4-dimethoxyphenyl)ethyl]5-[[[2-[(3S)-1-methylpyrrolidin-3-yl]oxy-2-oxo-1-phenyl-ethyl]amino]methyl]thiophene-2-carboxylate The title compound was here obtained as single diastereoisomer, via a similar method as for example 78, starting from (3S)-1-methylpyrrolidin-3-ol instead of [(3S)-1-methylpyrrolidin-3-yl]-methanol.

$^1$H NMR (400 MHz, DMSO): δ 8.62 (s, 2 H), 7.74 (d, J=3.8 Hz, 1 H), 7.45-7.42 (m, 4 H), 7.42-7.36 (m, 1 H), 7.08-7.06 (m, 2 H), 7.04-7.00 (m, 2 H), 6.19 (dd, J=4.3, 9.9 Hz, 1 H), 5.17-5.10 (m, 1 H), 4.42 (d, J=9.3 Hz, 1 H), 3.97-3.85 (m, 2 H), 3.82 (s, 3 H), 3.80 (s, 3 H), 3.67-3.56 (m, 2 H), 3.34 (dd, J=4.3, 14.1 Hz, 1 H), 2.75-2.60 (m, 3 H), 2.36-2.23 (m, 1 H), 2.30 (s, 3 H), 2.21-2.10 (m, 1 H), 1.56-1.47 (m, 1 H). LCMS (Method 1): [MH+]=700 at 2.59 min.

Chiral analysis (Method 15) at 1.90 min.

Example 105c (Comparative)

Single Diastereomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-phenyl-ethyl]amino]methyl]thiophene-2-carboxylate The title compound was here obtained as single diastereoisomer, via a similar method as for example 105, starting from 1-methyl-piperidin-4-ol as precursor instead of (1-methyl-4-piperidyl)-methanol.

$^1$H NMR (400 MHz, CD$_3$CN): δ 8.20 (s, 2 H), 7.67 (d, J=3.8 Hz, 1 H), 7.52-7.48 (m, 2 H), 7.43-7.37 (m, 2 H), 7.36-7.32 (m, 1 H), 7.08-7.02 (m, 2 H), 6.97-6.91 (m, 2 H), 6.18 (dd, J=4.5, 9.6 Hz, 1 H), 4.92-4.85 (m, 1 H), 4.17 (d, J=10.9 Hz, 1 H), 4.00-3.90 (m, 2 H), 3.84 (s, 3 H), 3.83 (s, 3 H), 3.79-3.64 (m, 2 H), 3.35 (dd, J=4.5, 14.1 Hz, 1 H), 3.11-3.11 (m, 2 H), 2.51-2.44 (m, 1 H), 2.32 (s, 1 H), 2.23 (d, J=10.9 Hz, 2 H), 2.14 (s, 3 H), 1.90-1.79 (m, 2 H), 1.72-1.58 (m, 2 H). LCMS (Method 2): [MH+]=744 at 3.13 min.

Chiral analysis (Method 8) at 2.28 min.

Protocol of Bronchospasm—Percentage of Inhibition

Animals

Male CD Sprague Dawley rats (220-250 g) were purchased from Charles River Laboratories Italy (Calco, Lecco). Prior to use animals were acclimated for at least 5 days to the local vivarium conditions (room temperature: 20-24° C.; relative humidity: 40-70%), having free access to standard rat chow and softened tap water. All the procedures were performed in animal operating rooms according to ethical guidelines for the conduct of animal research (D. L.vo 116/92).

Treatment with Test Compounds

For the evaluation of potency test compounds were administered intratracheally (i.t.), at different doses in the range 1 nmol/kg-100 nmol/kg, at 1 hour before the induction of experimental bronchospasm. For the assessment of duration of action test compounds were administered intratracheally (i.t.) at 16 hours before the induction of experimental bronchospasm, at the dose showing at 1 h the 80% of inhibition of bronchospasm. Animals were anaesthetised with Urethane (1.2 g/kg, i.p.) and a laryngoscope was moved forward into the mouth to visualize the trachea and guide the insertion of the tip of a custom made small diameter cannula directly into the trachea and located 1-2 mm above the bifurcation. Test compounds were dissolved in 100% dimethyl sulphoxide (DMSO) at $10^{-2}$ M. The target concentration was obtained by dilution of the DMSO stock in saline. Test compounds were instilled locally into the trachea in a volume of 125 μl.

Experimental Procedure

In order to assess the residual inhibitory activity of test compounds at 1-16 hours after their administration, rats were surgically prepared. In order to assess the Cch-induced bronchoconstriction in rats, the infusion of physiological solution was stopped and the bronchospastic agent injected into the jugular vein using the same cannula. Soon after washing the cannula with saline to ensure the complete administration of the bronchoconstrictor agent, the saline infusion was started again. Body temperature was kept constant at 37° C. by a heated blanket.

The trachea was cannulated and the lungs were ventilated artificially with a small animal constant volume ventilator (rodent ventilator mod. 7025, Ugo Basile, Comerio, Varese, Italy) at a frequency of 80 strokes/min and at a tidal volume of 2.5 ml/kg. To avoid spontaneous breathing, the animals were injected intravenously (i.v.) with pancuronium bromide (2 mg/kg). Bronchoconstriction was induced by the i.v. injection of Cch 50 μg/kg. In control experiments, repeated injections of this dose produced reproducible short-lasting (1-2 min duration) bronchospasms. Bronchoconstriction, quantified as a reduction of tidal volume, was evaluated according to the method described by Konzett & Roessler in Konzett H. and Roessler R., Versuchanornungzu untersuchungen ande bronchialmuskulatur. Arch. Exp. Path. Pharmak.; 195:71-74 (1940), which is incorporated herein by reference in its entirety.

Systemic blood pressure and changes in airway resistance were monitored with a digital pressure transducer connected to a bridge amplifier (PowerLab; Ugo Basile, Italy) and recorded using Chart 5 software (Ugo Basile, Italy).

After stabilization of artificial breathing and blood pressure, animals were injected (i.v.) with Cch every 3 min, until 3 stable and reproducible basal responses were obtained. Challenges did not ever exceed the number of 10. The effect of test compounds was expressed as % inhibition of Cch-evoked bronchoconstriction in time-matched, vehicle-treated, animals (controls).

In Vitro Determination of PDE4 Inhibitory Activity

In vitro determination of PDE4 inhibitory activity for compounds of the invention may be determined according to one of the protocols herebelow reported:

PDE4B2 HTRF Assay:

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl. Human recombinant PDE4B2 (80 pM) is incubated for 2 h with 3 nM cAMP in buffer containing 1×HBSS, 5 mM HEPES, 3 mM $MgCl_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. $IC_{50}$ values are determined from competition curves using a non-linear curve fitting program.

PDE4 Cell Free Assay Protocol

PDE4 activity is determined in U937 human monocytic supernatants cells lysate. Cells are cultured, harvested and supernatant fraction prepared essentially as described in Torphy T J et al J. Pharmacol. Exp. Ther. 1992; 263:1195-1205, which is incorporated herein by reference in its entirety.

U937 cells are grown at 37° C., 5% $CO_2$ in RPMI 1640 with GlutaMAX™-I medium supplemented with 10% fetal bovine serum and 100 μg/mL Pen-strep (Gibco).

Cells are harvested and washed twice by centrifugation (150×g, 8 min) in cold PBS. Washed cells are re-suspended in cold Krebs-Ringer-Henseleit buffer at a final concentration 20×$10^6$ cells/mL and sonicated. After centrifugation at 15000×g for 20 min, the supernatants are pooled, divided in aliquots and stored at −80° C. PDE4 activity is determined in cells supernatants by assaying cAMP disappearance from the incubation mixtures.

The concentration of the test compounds ranges between $10^{-12}$ M and $10^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance ($IC_{50}$). Percentage of inhibition of PDE4 activity is calculated, assuming cAMP disappearance in the absence of inhibitors as 100% and cAMP disappearance in heat inactivated samples as 0%. The compounds of the invention, tested in one of the above reported protocols, displayed an $IC_{50}$ lower than 100 nM.

In vitro Determination of M3 Antagonism

In vitro determination of M3 antagonism for compounds of the invention may be determined according to one of the protocols herebelow reported:

M3 Receptor Radioligand Binding Assay:

Human $M_3$ receptor membranes (15 μg/well) from Perkin Elmer are incubated with 0.52 nM Scopolamine Methyl Chloride, [N-methyl-3H] with or without test compounds, or a saturating concentration of Atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 h at room temperature on an orbital shaker (slow speed). Membranes are harvested onto 96-well unifilter GF/C filter plates pre-treated with 0.5% polyethyleneimine (v/v), using a filter manifold, washed four times with 200 µl of assay buffer. The plates are dried before addition of 50 µl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

M3 Binding Assay:

CHO-K1 clone cells expressing the human M3-receptor (Swissprot P20309) were harvested in $Ca^{++}/Mg^{++}$ free phosphate-buffered saline and collected by centrifugation at 1500 rpm for 3 min. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non selective muscarinic radioligand [$^3$H]—N-methyl scopolamine (*Mol. Pharmacol.* 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 µM. Samples (final volume 0.75 mL) were incubated at room temperature for 90 min. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

The Compounds of the invention, tested in one of the above reported protocols, displayed an $IC_{50}$ lower than 100 nM. The Compounds of the invention displayed an $IC_{50}$ lower than 100 nM, preferred even less than 10 nM or even less than 1 nM, in both PDE4 cell free and M3 binding assays. Compounds having lower activity, compared with more active compounds, might be preferred for development having consideration of their pharmacological profile in vivo and specifically when showing the above said improved duration of action.

In the following table $IC_{50}$ data are reported for the compounds tested in the above methods, classified according to the following ranges:

+: M3 IC50 in the range 10-100 nM
++: M3 IC50 in the range 1-10 nM
+++: M3 IC50<=1 nM
+: PDE4B2 IC50 in the range 10-100 nM
++: PDE4B2 IC50 in the range 1-10 nM
+++: PDE4B2 IC50<=1 nM

| Example No. | M3 IC50 activity | PDE4B2 IC50 activity |
| --- | --- | --- |
| 1 | + | ++ |
| 2 | + | ++ |
| 3 | ++ | ++ |
| 4 | ++ | +++ |
| 5 | ++ | ++ |
| 6 | ++ | +++ |
| 7 | + | ++ |
| 8 | +++ | +++ |
| 9 | + | ++ |
| 10 | ++ | +++ |
| 11 | ++ | +++ |
| 12 | ++ | +++ |
| 13 | ++ | ++ |
| 14 | ++ | ++ |
| 15 | ++ | ++ |
| 16 | ++ | ++ |
| 17 | ++ | ++ |
| 18 | ++ | ++ |
| 19 | + | +++ |
| 21 | + | ++ |
| 22 | + | ++ |
| 23 | ++ | ++ |
| 24 | ++ | ++ |
| 25 | ++ | ++ |
| 26 | ++ | ++ |
| 27 | ++ | ++ |
| 28 | +++ | ++ |
| 29 | + | ++ |
| 30 | + | ++ |
| 31 | + | ++ |
| 32 | + | ++ |
| 33 | +++ | +++ |
| 34 | ++ | ++ |
| 35 | ++ | +++ |
| 36 | ++ | ++ |
| 37 | ++ | +++ |
| 38 | ++ | ++ |
| 41 | ++ | +++ |
| 42 | + | ++ |
| 44 | ++ | ++ |
| 45 | +++ | ++ |
| 46 | ++ | ++ |
| 47 | ++ | ++ |
| 48 | + | +++ |
| 49 | + | ++ |
| 50 | ++ | +++ |
| 52 | + | ++ |
| 53 | + | ++ |
| 54 | +++ | ++ |
| 55 | + | +++ |
| 56 | +++ | +++ |
| 57 | + | ++ |
| 58 | ++ | +++ |
| 59 | ++ | +++ |
| 60 | +++ | +++ |
| 62 | + | +++ |
| 63 | + | ++ |
| 64 | +++ | +++ |
| 65 | + | ++ |
| 66 | ++ | ++ |
| 67 | + | +++ |
| 68 | ++ | +++ |
| 69 | ++ | +++ |
| 70 | + | ++ |
| 71 | ++ | ++ |
| 72 | +++ | ++ |
| 73 | + | ++ |
| 74 | +++ | ++ |
| 75 | + | ++ |
| 76 | ++ | ++ |
| 77 | + | ++ |
| 78 | ++ | +++ |
| 79 | + | +++ |
| 80 | ++ | +++ |
| 82 | + | ++ |
| 83 | + | ++ |
| 84 | ++ | ++ |
| 85 | ++ | ++ |
| 86 | + | ++ |
| 87 | ++ | ++ |

215
-continued

| Example No. | M3 IC50 activity | PDE4B2 IC50 activity |
|---|---|---|
| 88 | + | +++ |
| 89 | ++ | +++ |
| 90 | + | +++ |
| 91 | ++ | +++ |
| 92 | + | ++ |
| 93 | +++ | ++ |
| 94 | ++ | ++ |
| 95 | +++ | ++ |
| 97 | ++ | +++ |
| 99 | ++ | +++ |
| 101 | ++ | ++ |
| 102 | +++ | +++ |
| 103 | ++ | ++ |
| 104 | + | +++ |
| 105 | ++ | ++ |
| 106 | + | ++ |
| 107 | + | +++ |
| 108 | +++ | +++ |
| 109 | ++ | +++ |
| 111 | + | +++ |
| 112 | ++ | +++ |
| 113 | ++ | ++ |
| 114 | + | ++ |
| 115 | ++ | ++ |
| 116 | ++ | ++ |
| 117 | +++ | ++ |
| 118 | + | +++ |
| 119 | ++ | ++ |
| 120 | + | +++ |
| 121 | + | ++ |
| 122 | ++ | +++ |
| 123 | + | ++ |
| 124 | ++ | ++ |
| 125 | + | +++ |
| 126 | +++ | ++ |
| 127 | + | +++ |
| 128 | +++ | ++ |
| 129 | + | ++ |

\* M3 Receptor radioligand binding assay
\*\* PDE4B2 HTRF assay

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

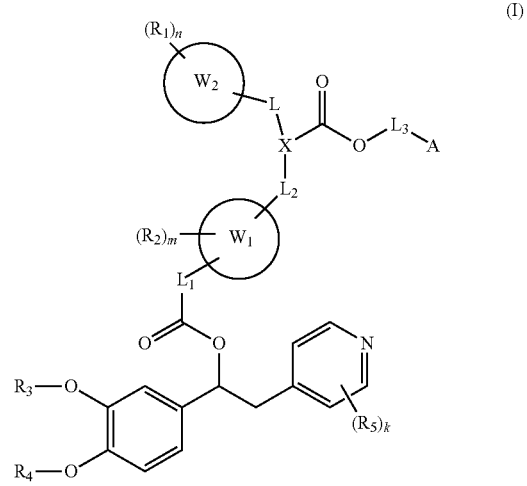

wherein
each $R_1$ is hydrogen, halogen, $(C_1-C_4)$ alkyl, $(C_1-C_4)$ alkoxy, $(C_1-C_4)$ haloalkyl, hydroxy, $-SO_2NR_6R_7$, $-CN$, $-NR_8SO_2R_9$, $-NR_6R_7$, $-CONR_6R_7$, or $-NR_8COR_9$, wherein said $(C_1-C_4)$ alkyl is optionally substituted by one or more groups selected from $(C_3-C_7)$ cycloalkyl, hydroxyl, and $-NR_6R_7$ and wherein said $(C_1-C_4)$ alkoxy is optionally substituted by one or more halogens or $(C_3-C_7)$ cycloalkyl groups, wherein
$R_6$ is hydrogen or $(C_1-C_6)$ alkyl;
$R_7$ is hydrogen or $(C_1-C_6)$ alkyl;
$R_8$ is hydrogen or $(C_1-C_6)$ alkyl;
$R_9$ is hydrogen or $(C_1-C_6)$ alkyl;
n is an integer ranging from 1 to 3;
each $R_2$ is hydrogen, halogen, $(C_1-C_4)$ alkyl, $(C_1-C_4)$ alkoxy, $(C_1-C_4)$haloalkyl, hydroxy, $-SO_2NR_{10}R_{11}$, $-CN$, or $-NR_{12}SO_2R_{13}$, wherein said $(C_1-C_4)$ alkyl and said $(C_1-C_4)$ alkoxy are optionally substituted by one or more $(C_3-C_7)$ cycloalkyl groups, wherein
$R_{10}$ is hydrogen or $(C_1-C_6)$ alkyl;
$R_{11}$ is hydrogen or $(C_1-C_6)$ alkyl;
$R_{12}$ is hydrogen or $(C_1-C_6)$ alkyl;
$R_{13}$ is hydrogen or $(C_1-C_6)$ alkyl;
m is an integer ranging from 1 to 3;
$R_3$ and $R_4$ are the same or different and are independently:
H;
$(C_3-C_7)$ cycloalkylcarbonyl;
$(C_1-C_6)$ alkyl optionally substituted by one or more substituents selected from the group consisting of $(C_1-C_4)$ alkoxy, $(C_3-C_7)$ cycloalkyl, and $(C_5-C_7)$ cycloalkenyl;
$(C_1-C_6)$ haloalkyl;
$(C_3-C_7)$ cycloalkyl;
$(C_5-C_7)$ cycloalkenyl;
$(C_2-C_6)$ alkenyl; or
$(C_2-C_6)$ alkynyl;
each $R_5$, whenever present, is CN, $NO_2$, $CF_3$, or halogen;
k is 0 or an integer ranging from 1 to 3;
$W_1$ is a divalent heteroarylene group;
$W_2$ is an aryl group, a heteroaryl group, or $(C_3-C_7)$ cycloalkyl;
L is a bond or a $-(CH_2)-$ group;

L₁ is:
a bond,
—(CH₂)ₚ—,
[3]-(CH₂)ₚ—O-[4],
[3]-(CH₂)ₚ—NR₁₀—(CH₂)-[4],
[3]-(CH₂)ₚ—OC(O)-[4],
[3]-(CH₂)ₚ—NR₁₀C(O)-[4],
[3]-(CH₂)ₚ—NR₁₀S(O₂)-[4], or
[3]-(CH₂)ₚ—S(O₂)—N(R₁₀)-[4],
wherein [3] and [4] represent, respectively the point of attachment of group L₁ to the carbonyl group and to the ring W₁ and wherein
R₁₀ is as described above,
p is an integer ranging from 1 to 4 and
t is an integer ranging from 1 to 4;
L₂ is —(CH₂)_q— wherein q is an integer ranging from 1 to 4;
L₃ is a (C₁-C₄) alkylene;
X is a group X₁, X₂, or X₃:

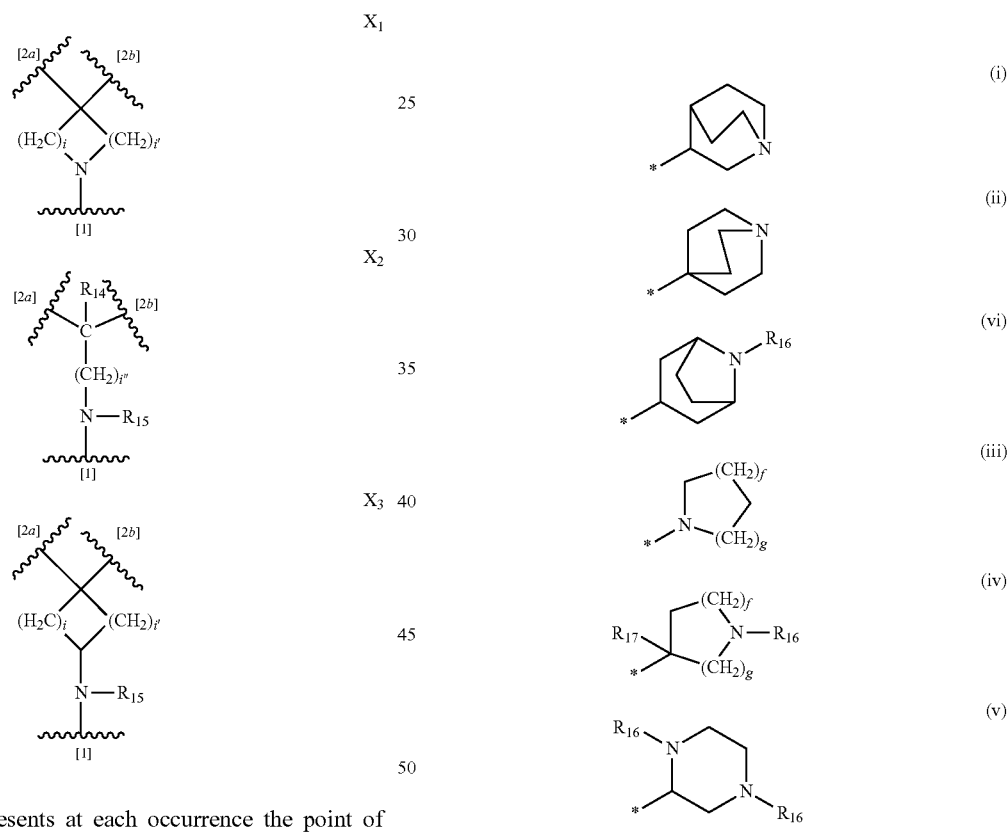

wherein [1] represents at each occurrence the point of attachment of the group X to L2, [2a] represents at each occurrence the point of attachment to L-W₂ and [2b] represents at each occurrence the point of attachment to the carbonyl group —CO₂A;
and wherein
R₁₄ is H, OH, (C₁-C₄) alkyl, (C₁-C₄) alkoxy, (C₁-C₄) haloalkyl, or —CN, wherein said (C₁-C₄) alkyl is optionally substituted by one or more groups selected from (C₃-C₇) cycloalkyl and hydroxyl, or, in the alternative, when R₁₄ is (C₁-C₄) alkyl, W₂ is a phenyl ring, one of R₁ is an alkyl in ortho position with respect to L, both R₁ and R₁₄ may be connected to form with W₂ a condensed ring radical selected from at least 1H-cyclopropabenzene-1,1-diyl, indane-1,1-diyl (also named as 2,3-dihydro-1H-in-dene-1,1-diyl), indane-2,2-diyl (also named as 2,3-dihydro-1H-indene-2,2-diyl), 1,2,3,4-tetrahydronaphthalene-1,1-diyl, and 1,2,3,4-tetrahydronaphthalene-2,2-diyl;

R₁₅ is hydrogen, (C₁-C₆) alkyl, (C₃-C₇) cycloalkyl, (C₃-C₇) heterocycloalkyl or benzyl; wherein said (C₁-C₆) alkyl is optionally substituted by hydroxyl or NR₁₈R₁₉; said R₁₈ and R₁₉ being independently hydrogen or (C₁-C₄) alkyl, or, taken together with the nitrogen atom to which they are attached, form a nitrogen containing, saturated heterocycloalkyl group, optionally containing an additional heteroatom selected from O, S and NH;

and wherein i is 1 or 2;

i' is 1 or 2;

i" is an integer ranging from 0 to 3;

A is a group of formula (i) to (vi):

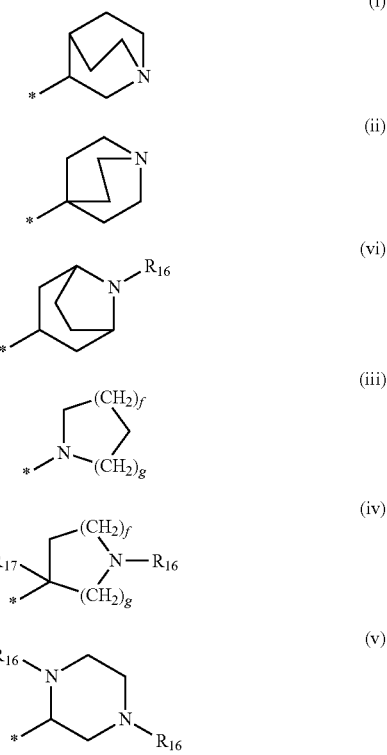

wherein R₁₆ is in each occurrence independently (C₁-C₄) alkyl optionally substituted by one or more (C₁-C₄) alkoxy groups; R₁₇ is hydrogen, halogen or (C₁-C₄) alkyl; f=0, 1, 2 or 3; g=0, 1, 2 or 3; and the asterisk (*) represents the point of attachment to the group L₃ in formula (I), an N-oxide on the pyridine ring, a deuterated derivative, or a pharmaceutically acceptable salt thereof.

2. A compound, N-oxide, deuterated derivative, or a pharmaceutically acceptable salt according to claim 1, of formula (I)':

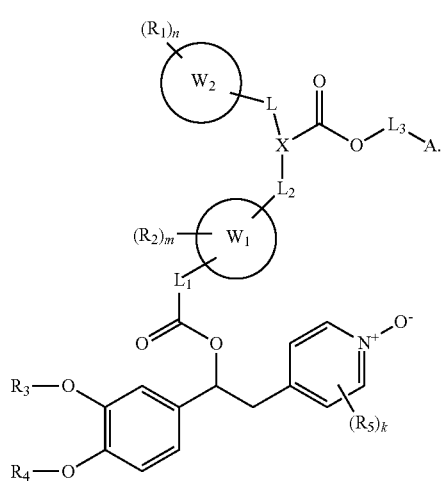

(I)′

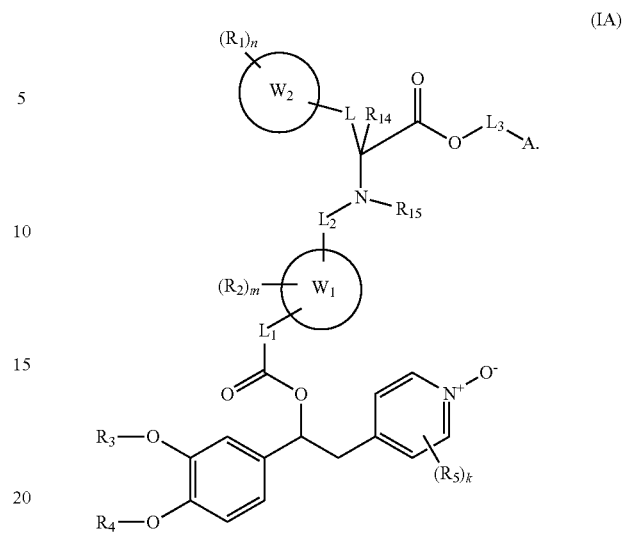

(IA)

5. A compound, N-oxide, deuterated derivative, or a pharmaceutically acceptable salt according to claim 4, wherein k is 2 and $R_5$ are halogen atoms.

6. A compound, N-oxide, deuterated derivative, or a pharmaceutically acceptable salt according to claim 5, wherein $R_5$ are two chlorine atoms at positions 3 and 5 of the pyridine ring.

3. A compound, N-oxide, deuterated derivative, or a pharmaceutically acceptable salt according to claim 1, wherein A is represented by a group of formula (i), (ii) or (iv):

7. A compound, N-oxide, deuterated derivative, or a pharmaceutically acceptable salt according to claim 4, wherein $R_4$ is $(C_1-C_6)$ alkyl and $R_3$ is $(C_3-C_7)$ cycloalkyl or $(C_1-C_6)$ alkyl; wherein said $(C_1-C_6)$ alkyl is optionally substituted by one or more halogens or $(C_3-C_7)$ cycloalkyl groups.

8. A compound, N-oxide, deuterated derivative, or a pharmaceutically acceptable salt according to claim 1, of formula (IC):

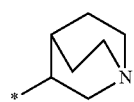

(i)

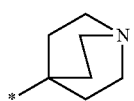

(ii)

(IC)

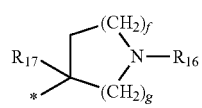

(iv)

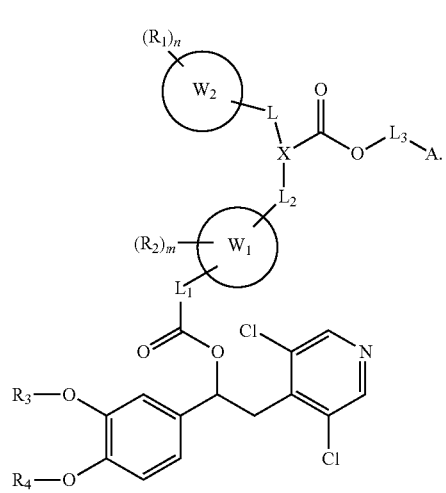

wherein f=0, 1, 2, 3; g=0, 1, 2; $R_{17}$ is hydrogen, methyl, or fluorine; $R_{16}$ is methyl or ethyl and the asterisk (*) represents the point of attachment to $L_3$ in formula (I).

4. A compound, N-oxide, deuterated derivative, or a pharmaceutically acceptable salt according to claim 1, wherein X is the group $X_2$ and i″ is 0, of formula (IA):

9. A compound, N-oxide, deuterated derivative, or a pharmaceutically acceptable salt according to claim 8, of general (ID):

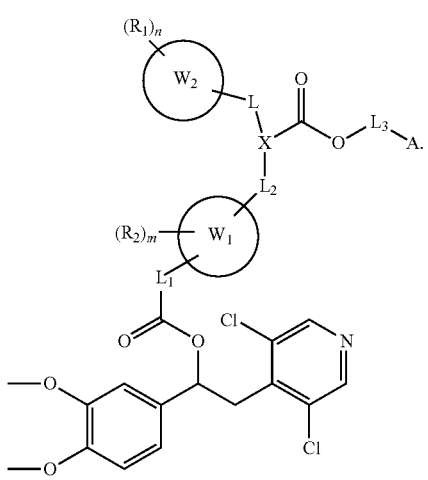

(ID)

10. A compound, N-oxide, deuterated derivative, or a pharmaceutically acceptable salt according to claim 8, wherein:
each $R_1$ is hydrogen, fluorine, methoxy, or hydroxyl;
each $R_2$ is hydrogen;
$R_4$ is methyl or difluoromethyl and $R_3$ is methyl, ethyl, pentyl cyclopropylmethyl, or 2-methoxyethyl
$L_1$ is a bond and $L_2$ and $L_3$ are both methylene;
m is 0;
$W_1$ is thienylene-2,5-diyl or thienylene-2,4-diyl;
n is 0;
$W_2$ is phenyl, thienyl, or cyclohexyl;
X is a group of formula $X_1$ wherein both i and i' are 1 or 2; or X is a group of formula $X_2$ wherein i" is 0 or 1 and $R_{14}$ is H, methyl, hydroxyl, or hydroxymethyl; or $R_1$ and $R_{14}$ are connected to form with $W_2$ a condensed ring radical which is indane-1,1-diyl; or X is a group of formula $X_3$ wherein both i and i' are 1; $R_{15}$ is H or oxetan-3-yl;
A is a group of formula (i), (ii) or (iv):

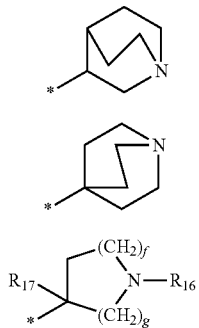

wherein f=0, 1, 2 or 3; g=0, 1, 2 or 3; $R_{17}$ is hydrogen, fluoro, or methyl; $R_{16}$ is methyl, ethyl, or 2-metoxyethyl and the asterisk (*) represents the point of attachment to $L_3$.

11. A compound, N-oxide, deuterated derivative, or a pharmaceutically acceptable salt according to claim 1, which is selected from the group consisting of:
[(1S)-2-(3,5-dichloro-1-oxido-pyridin-1-ium-4-yl)-1-(3,4-dimethoxyphenyl)ethyl]5-[[[2-hydroxy-3-[(1-methyl-4-piperidyl)methoxy]-3-oxo-2-(2-thienyl)propyl]amino]methyl]-thiophene-2-carboxylate;
[(1S)-2-(3,5-dichloro-1-oxido-pyridin-1-ium-4-yl)-1-(3,4-dimethoxyphenyl)ethyl]5-[[[2-[(1,4-dimethyl-4-piperidyl)methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[2-[(4-fluoro-1-methyl-4-piperidyl)methoxy]-2-oxo-1-phenyl-ethyl]amino]methyl]thiophene-2-carboxylate;
Epimeric mixture 2 of [1-[3-(cyclopropylmethoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;
Epimeric mixture 1 of [1-[3-(cyclopentoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;
Epimeric mixture 2 of [1-[3-(cyclopentoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[3-[(1-methyl-4-piperidyl)methoxy]-3-oxo-2-phenyl-propyl]amino]methyl]thiophene-2-carboxylate;
Epimeric mixture 2 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[1-cyclohexyl-2-[(1-methyl-4-piperidyl)methoxy]-2-oxo-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[2-oxo-1-phenyl-2-[[(3S)-quinuclidin-3-yl]methoxy]ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[2-oxo-1-phenyl-2-[[(3R)-quinuclidin-3-yl]methoxy]ethyl]amino]methyl]thiophene-2-carboxylate;
Epimeric mixture 2 of [2-(3,5-dichloro-1-oxido-pyridin-1-ium-4-yl)-1-(3-ethoxy-4-methoxy-phenyl)ethyl]5-[[[2-[(1-methyl-4-piperidyl)methoxy]-2-oxo-1-phenyl-ethyl]amino]methyl]thiophene-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[2-[[(2R)-1-methylpyrrolidin-2-yl]methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[2-[[(2S)-1-methylpyrrolidin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3R)-1-methylpyrrolidin-3-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3S)-1-methylpyrrolidin-3-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-ethyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[1-(2-methoxyethyl)-4-piperidyl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-(2-pyrrolidin-1-ylethoxy)ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-[2-(1-piperidyl)ethoxy]ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)methoxy]-2-oxo-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methylazetidin-3-yl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3S)-1-methyl-3-piperidyl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2S)-1-methylazetidin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2R)-1-methylazetidin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2R)-1,4-dimethylpiperazin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2R)-1-methyl-2-piperidyl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-2-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(2S)-1,4-dimethylpiperazin-2-yl]methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-(quinuclidin-4-ylmethoxy)ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-methyl-2-[(1-methyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-3-carboxylate;

[(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-(2-thienyl)ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-[(1-methyl-4-piperidyl)methoxycarbonyl]indan-1-yl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]-(oxetan-3-yl)amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-(3-hydroxyphenyl)-2-[(1-methyl-4-piperidyl)methoxy]-2-oxo-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-(3-hydroxyphenyl)-2-[(1-methyl-4-piperidyl)methoxy]-2-oxo-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(1-isopropyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(1-isopropyl-4-piperidyl)methoxy]-2-oxo-1-phenyl-ethyl]amino]methyl]thiophene-2-carboxylate;

Single diastereoisomer 1 of [(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl]thiophene-2-carboxylate;

Single diastereoisomer 2 of [(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(3-hydroxyphenyl)-2-[(1-methyl-4-piperidyl)methoxy]-2-oxo-ethyl]amino]methyl]thiophene-2-carboxylate;

Single diastereoisomer 1 of epimeric mixture 2 of [1-[3-(cyclopropylmethoxy)-4-methoxy-phenyl]-2-(3,5-dichloro-1-oxido-pyridin-1-ium-4-yl)ethyl]5-[[[1-(3-hydroxyphenyl)-2-[(1-methyl-4-piperidyl)methoxy]-2-oxo-ethyl]amino]methyl]thiophene-2-carboxylate;

Single diastereoisomer 2 of epimeric mixture 2 of [1-[3-(cyclopropylmethoxy)-4-methoxy-phenyl]-2-(3,5-dichloro-1-oxido-pyridin-1-ium-4-yl)ethyl]5-[[[1-(3-hydroxyphenyl)-2-[(1-methyl-4-piperidyl)methoxy]-2-oxo-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(1,4-dimethyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(1,4-dimethyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[(4-fluoro-1-methyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[(4-fluoro-1-methyl-4-piperidyl)methoxy]-2-oxo-1-phenyl-ethyl]amino]methyl]thiophene-2-carboxylate;

Single diastereoisomer 1 of epimeric mixture 2 of [1-[3-(cyclopropylmethoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Single diastereoisomer 2 of epimeric mixture 2 of [1-[3-(cyclopropylmethoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Single diastereoisomer 1 of epimeric mixture 2 of [1-[3-(cyclopentoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Single diastereoisomer 2 of epimeric mixture 2 of [1-[3-(cyclopentoxy)-4-methoxy-phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Single diastereoisomer 1 of epimeric mixture 2 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl]thiophene-2-carboxylate;

Single diastereoisomer 2 of epimeric mixture 2 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-(quinuclidin-4-ylmethoxy)ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[1-cyclohexyl-2-[(1-methyl-4-piperidyl)methoxy]-2-oxo-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[1-cyclohexyl-2-[(1-methyl-4-piperidyl)methoxy]-2-oxo-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-oxo-1-phenyl-2-[[(3S)-quinuclidin-3-yl]methoxy]ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-oxo-1-phenyl-2-[[(3S)-quinuclidin-3-yl]methoxy]ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-oxo-1-phenyl-2-[[(3R)-quinuclidin-3-yl]methoxy]ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-oxo-1-phenyl-2-[[(3R)-quinuclidin-3-yl]methoxy]ethyl]amino]methyl]thiophene-2-carboxylate;

Single diastereoisomer 1 of epimeric mixture 2 of [2-(3,5-dichloro-1-oxido-pyridin-1-ium-4-yl)-1-(3-ethoxy-4-methoxy-phenyl)ethyl]5-[[[2-[(1-methyl-4-piperidyl)methoxy]-2-oxo-1-phenyl-ethyl]amino]methyl]thiophene-2-carboxylate;

Single diastereoisomer 2 of epimeric mixture 2 of [2-(3,5-dichloro-1-oxido-pyridin-1-ium-4-yl)-1-(3-ethoxy-4-methoxy-phenyl)ethyl]5-[[[2-[(1-methyl-4-piperidyl)methoxy]-2-oxo-1-phenyl-ethyl]amino]methyl]thiophene-2-carboxylate;

Single diastereoisomer 1 of [(1S)-1-[3-(cyclopropylmethoxy)-4-(difluoromethoxy)phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Single diastereoisomer 2 of [(1S)-1-[3-(cyclopropylmethoxy)-4-(difluoromethoxy)phenyl]-2-(3,5-dichloro-1-oxido-pyridin-1-ium-4-yl)ethyl]5-[[[2-[(1-methyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2R)-1-methylpyrrolidin-2-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl]5-[[[2-[[(2R)-1-methylpyrrolidin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]5-[[[2-[[(2S)-1-methylpyrrolidin-2-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)

ethyl]5-[[[2-[[(2S)-1-methylpyrrolidin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[(3R)-1-methylpyrrolidin-3-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[[(3R)-1-methylpyrrolidin-3-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[(3S)-1-methylpyrrolidin-3-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[[(3S)-1-methylpyrrolidin-3-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[(1-ethyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[(1-ethyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[1-(2-methoxyethyl)-4-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[[1-(2-methoxyethyl)-4-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-oxo-1-phenyl-2-(2-pyrrolidin-1-ylethoxy)ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-oxo-1-phenyl-2-(2-pyrrolidin-1-ylethoxy)ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-oxo-1-phenyl-2-[2-(1-piperidyl)ethoxy]ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[(1-methyl-4-piperidyl)methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[(1-methyl-4-piperidyl)methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[1-(2-fluorophenyl)-2-[(1-methyl-4-piperidyl)methoxy]-2-oxo-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[1-(2-fluorophenyl)-2-[(1-methyl-4-piperidyl)methoxy]-2-oxo-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[(3S)-1-methyl-3-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[[(3S)-1-methyl-3-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[(2S)-1-methylazetidin-2-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[[(2S)-1-methylazetidin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[(2R)-1-methylazetidin-2-yl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[[(2R)-1-methylazetidin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[(2R)-1,4-dimethylpiperazin-2-yl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[(2R)-1-methyl-2-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[[(2R)-1-methyl-2-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl) ethyl]5-[[[2-[[(2S)-1-methyl-2-piperidyl]methoxy]-2-oxo-1-phenyl-ethyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl) ethyl]5-[[[2-[[(2S)-1-methyl-2-piperidyl]methoxy]-2-oxo-1-phenyl-ethyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)

ethyl]5-[[[2-oxo-1-phenyl-2-(quinuclidin-4-yl-methoxy)ethyl]amino]methyl]thiophene-2-carboxylate;
Single diastereoisomer 2 of [(1S)-2-(3,5-dichloro-1-oxido-pyridin-1-ium-4-yl)-1-(3,4-dimethoxyphenyl)ethyl]5-[[[2-oxo-1-phenyl-2-(quinuclidin-4-yl-methoxy)ethyl]amino]methyl]thiophene-2-carboxylate;
Single diastereoisomer 1 of [(1S)-2-(3,5-dichloro-1-oxido-pyridin-1-ium-4-yl)-1-(3,4-dimethoxyphenyl)ethyl]5-[[[1-methyl-2-[(1-methyl-4-piperidyl)methoxy]-2-oxo-1-phenyl-ethyl]amino]methyl]thiophene-2-carboxylate;
Single diastereoisomer 2 of [(1S)-2-(3,5-dichloro-1-oxido-pyridin-1-ium-4-yl)-1-(3,4-dimethoxyphenyl)ethyl]5-[[[1-methyl-2-[(1-methyl-4-piperidyl)methoxy]-2-oxo-1-phenyl-ethyl]amino]methyl]thiophene-2-carboxylate;
Single diastereoisomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-phenyl-ethyl]amino]methyl]thiophene-2-carboxylate;
Single diastereoisomer 2 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-phenyl-ethyl]amino]methyl]thiophene-2-carboxylate;
Single diastereoisomer 1 of [(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-3-carboxylate;
Single diastereoisomer 2 of [(1S)-2-(3,5-dichloro-1-oxido-pyridin-1-ium-4-yl)-1-(3,4-dimethoxyphenyl)ethyl]5-[[[2-[(1-methyl-4-piperidyl)methoxy]-2-oxo-1-phenyl-ethyl]amino]methyl]thiophene-3-carboxylate;
Single diastereoisomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-(2-thienyl)ethyl]amino]methyl]thiophene-2-carboxylate;
Single diastereoisomer 2 of [(1S)-2-(3,5-dichloro-1-oxido-pyridin-1-ium-4-yl)-1-(3,4-dimethoxyphenyl)ethyl]5-[[[1-(hydroxymethyl)-2-[(1-methyl-4-piperidyl)methoxy]-2-oxo-1-(2-thienyl)ethyl]amino]methyl]thiophene-2-carboxylate;
Single diastereoisomer 1 of [(1S)-2-(3,5-dichloro-1-oxido-pyridin-1-ium-4-yl)-1-(3,4-dimethoxyphenyl)ethyl]5-[[[1-[(1-methyl-4-piperidyl)methoxycarbonyl]indan-1-yl]amino]methyl]thiophene-2-carboxylate;
Single diastereoisomer 2 of [(1S)-2-(3,5-dichloro-1-oxido-pyridin-1-ium-4-yl)-1-(3,4-dimethoxyphenyl)ethyl]5-[[[1-[(1-methyl-4-piperidyl)methoxycarbonyl]indan-1-yl]amino]methyl]thiophene-2-carboxylate;
[(1S)-2-(3,5-dichloro-1-oxido-pyridin-1-ium-4-yl)-1-[4-(difluoromethoxy)-3-(2-methoxyethoxy)phenyl]ethyl]5-[[[2-[(1-methyl-4-piperidyl)methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[2-[[(1R,5S)-8-methyl-8-azabicyclo[3.2.1]octan-3-yl]methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[1-(hydroxymethyl)-2-[[(3S)-1-methylpyrrolidin-3-yl]methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[1-(hydroxymethyl)-2-[[(3R)-1-methylpyrrolidin-3-yl]methoxy]-2-oxo-1-phenyl-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[1-(hydroxymethyl)-2-oxo-1-phenyl-2-(quinuclidin-4-ylmethoxy)ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[1-(2-methoxyphenyl)-2-[(1-methyl-4-piperidyl)methoxy]-2-oxo-ethyl]amino]methyl]thiophene-2-carboxylate;
[(1S)-2-(3,5-dichloro-1-oxido-pyridin-1-ium-4-yl)-1-(3,4-dimethoxyphenyl)ethyl]5-[[[1-(3-methoxyphenyl)-2-[(1-methyl-4-piperidyl)methoxy]-2-oxo-ethyl]amino]methyl]thiophene-2-carboxylate;
Epimeric mixture 2 of [2-(3,5-dichloro-1-oxido-pyridin-1-ium-4-yl)-1-(3-ethoxy-4-methoxy-phenyl)ethyl]5-[[[1-(3-hydroxyphenyl)-2-[(1-methyl-4-piperidyl)methoxy]-2-oxo-ethyl]amino]methyl]thiophene-2-carboxylate;
Diastereoisomer 1 of [(1S)-2-(3,5-dichloro-1-oxido-pyridin-1-ium-4-yl)-1-(3,4-dimethoxyphenyl)ethyl]5-[[[1-(3-methoxyphenyl)-2-[(1-methyl-4-piperidyl)methoxy]-2-oxo-ethyl]amino]methyl]thiophene-2-carboxylate;
Diastereoisomer 2 of [(1S)-2-(3,5-dichloro-1-oxido-pyridin-1-ium-4-yl)-1-(3,4-dimethoxyphenyl)ethyl]5-[[[1-(3-methoxyphenyl)-2-[(1-methyl-4-piperidyl)methoxy]-2-oxo-ethyl]amino]methyl]thiophene-2-carboxylate;
Diastereoisomer 1 of [(1S)-2-(3,5-dichloro-1-oxido-pyridin-1-ium-4-yl)-1-[4-(difluoromethoxy)-3-(2-methoxyethoxy)phenyl]ethyl]5-[[[2-[(1-methyl-4-piperidyl)methoxy]-2-oxo-1-phenyl-ethyl]amino]methyl]thiophene-2-carboxylate;
Diastereoisomer 2 of [(1S)-2-(3,5-dichloro-1-oxido-pyridin-1-ium-4-yl)-1-[4-(difluoromethoxy)-3-(2-methoxyethoxy)phenyl]ethyl]5-[[[2-[(1-methyl-4-piperidyl)methoxy]-2-oxo-1-phenyl-ethyl]amino]methyl]thiophene-2-carboxylate;
Diastereoisomer 1 of Epimeric mixture 2 of [2-(3,5-dichloro-1-oxido-pyridin-1-ium-4-yl)-1-(3-ethoxy-4-methoxy-phenyl)ethyl]5-[[[1-(3-hydroxyphenyl)-2-[(1-methyl-4-piperidyl)methoxy]-2-oxo-ethyl]amino]methyl]thiophene-2-carboxylate;
Diastereoisomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[[(3S)-1-methylpyrrolidin-3-yl]methoxy]-2-oxo-1-phenyl-ethyl]amino]methyl]thiophene-2-carboxylate;
Diastereoisomer 2 of [(1S)-2-(3,5-dichloro-1-oxido-pyridin-1-ium-4-yl)-1-(3,4-dimethoxyphenyl)ethyl]5-[[[1-(hydroxymethyl)-2-[[(3S)-1-methylpyrrolidin-3-yl]methoxy]-2-oxo-1-phenyl-ethyl]amino]methyl]thiophene-2-carboxylate;
Diastereoisomer 1 of [(1S)-2-(3,5-dichloro-1-oxido-pyridin-1-ium-4-yl)-1-(3,4-dimethoxyphenyl)ethyl]5-[[[1-(hydroxymethyl)-2-[[(3R)-1-methylpyrrolidin-3-yl]methoxy]-2-oxo-1-phenyl-ethyl]amino]methyl]thiophene-2-carboxylate; and
Diastereoisomer 2 of [(1S)-2-(3,5-dichloro-1-oxido-pyridin-1-ium-4-yl)-1-(3,4-dimethoxyphenyl)ethyl]5-[[[1-

(hydroxymethyl)-2-[[(3R)-1-methylpyrrolidin-3-yl]methoxy]-2-oxo-1-phenyl-ethyl]amino]methyl]thiophene-2-carboxylate.

12. A compound, N-oxide, deuterated derivative, or a pharmaceutically acceptable salt according to claim 11, represented by formula (I)″ wherein the absolute configuration of carbon (1) is as in formula (I)″:

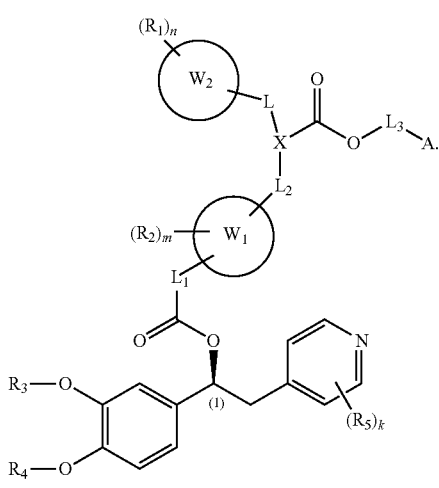

13. A pharmaceutical composition, comprising a compound, N-oxide, deuterated derivative, or a pharmaceutically acceptable salt as defined in claim 1, in admixture with one or more pharmaceutically acceptable carriers.

14. A pharmaceutical composition according to claim 13, further comprising another active ingredient selected from the group consisting of a beta2-agonist, an antimuscarinic agent, a corticosteroid, a mitogen-activated protein kinase inhibitor, a nuclear factor kappa-B kinase subunit beta inhibitor, a human neutrophil elastase inhibitor, a phosphodiesterase 4 inhibitor, a leukotriene modulator, a non-steroidal anti-inflammatory agent, and a mucus regulator.

15. A method for the treatment of a disease of the respiratory tract selected from the group consisting of asthmas and COPD, comprising administering to a subject in need thereof an effective amount of a compound, N-oxide, deuterated derivative, or a pharmaceutically acceptable salt according to claim 1.

16. A method according to claim 15, wherein said disease of the respiratory tract is COPD.

17. A method according to claim 15, wherein said disease of the respiratory tract is asthma.

* * * * *

UNITED STATES PATENT AND TRADEMARK OFFICE
CERTIFICATE OF CORRECTION

PATENT NO. : 9,636,336 B2  
APPLICATION NO. : 15/168425  
DATED : May 2, 2017  
INVENTOR(S) : Gabriele Amari et al.

Page 1 of 3

It is certified that error appears in the above-identified patent and that said Letters Patent is hereby corrected as shown below:

In the Specification

Column 2, Line 16, "(Atrovent)" should read --(Atrovent®)--

Column 2, Line 16, "(Oxivent d" should read --(Oxivent®) and--

Column 4, Line 8, "hydroxy" should read --hydroxy, -$SO_2NR_{10}R_{11}$--

Column 4, Line 41, "[3]-$(CH_2)_p$-$NR_{10}$-$(CH_2)_t$[4]," should read --[3]-$(CH_2)_p$-$NR_{10}$-$(CH_2)_t$-[4],--

Column 39, " 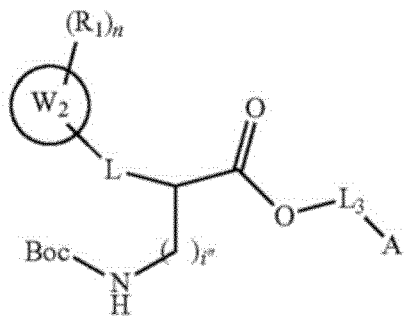 "

Signed and Sealed this  
Twenty-eighth Day of May, 2019

Andrei Iancu  
*Director of the United States Patent and Trademark Office*

CERTIFICATE OF CORRECTION (continued)
U.S. Pat. No. 9,636,336 B2

Page 2 of 3 should read -- 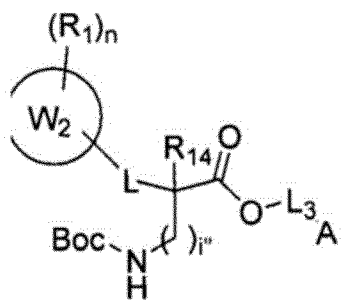 --

Column 71, Line 19-20, "his hydrochloride" should read --bis hydrochloride--

Column 90, Line 42, Analytical Data column of the table, "3.96*or†" should read --3.90*or†--

Column 97, the structure of Example 11, " 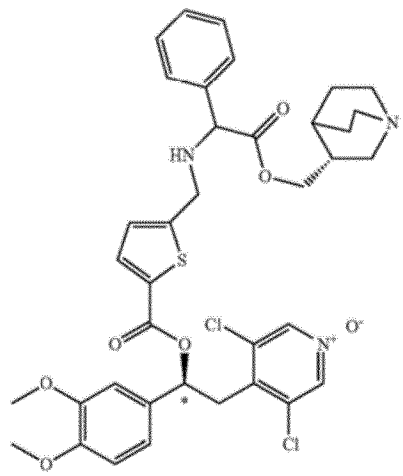 "

should read -- 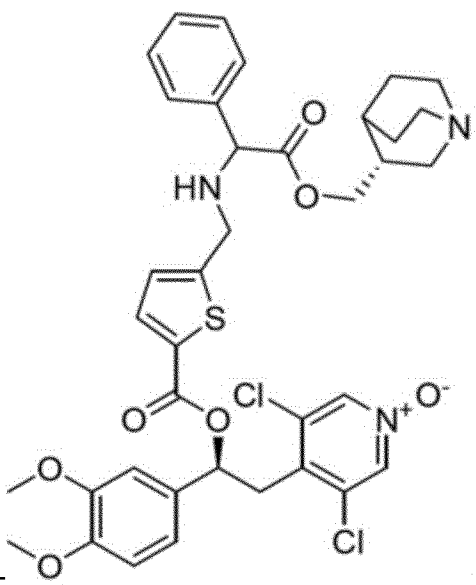 --

CERTIFICATE OF CORRECTION (continued)
U.S. Pat. No. 9,636,336 B2

Column 102, Line 53, Analytic Data column of table, "[MH+] = 14 at 2.58 min." should read --[MH+] = 714 at 2.58 min.--

Column 106, Line 9 of Example 21, "Hz, 1 H), 2.70-2.65 (m, 211), 2.43 (s, 4 H)," should read --Hz, 1 H), 2.70-2.65 (m, 2 H), 2.43 (s, 4 H),--

Column 112, Line 7 of Example 30, "3.83*or† (s, 3.82 (s, 3 H), 3.67 (dd, J = 9.6," should read --3.83*or† (s, 3 H), 3.82 (s, 3 H), 3.67 (dd, J = 9.6,--